US008242256B2

(12) United States Patent
Thompson et al.

(10) Patent No.: US 8,242,256 B2
(45) Date of Patent: Aug. 14, 2012

(54) SIRNA USEFUL TO SUPRESS EXPRESSION OF EIF-5A1

(75) Inventors: John E. Thompson, Waterloo (CA); Bruce C. Galton, Madison, NJ (US); Catherine Taylor, Waterloo (CA); Adrienne Boone, Waterloo (CA); Elizabeth Heikkila, Waterloo (CA); Dominic Cliche, Kitchner (CA); Shelley Culp-Stewart, Brandford (CA); John Gerard Flanagan, Waterloo (CA); Michelle Senchyna, Fort Worth, TX (US)

(73) Assignee: Senesco Technologies, Inc., New Brunswick, NJ (US)

( * ) Notice: Subject to any disclaimer, the term of this patent is extended or adjusted under 35 U.S.C. 154(b) by 0 days.

(21) Appl. No.: 12/640,148

(22) Filed: Dec. 17, 2009

(65) Prior Publication Data

US 2011/0098460 A1    Apr. 28, 2011

Related U.S. Application Data

(60) Division of application No. 11/287,460, filed on Nov. 28, 2005, now Pat. No. 7,662,796, which is a continuation of application No. 11/078,526, filed on Mar. 14, 2005, now abandoned, which is a continuation of application No. 10/792,893, filed on Mar. 5, 2004, now abandoned.

(60) Provisional application No. 60/476,194, filed on Jun. 6, 2003, provisional application No. 60/504,731, filed on Sep. 22, 2003.

(51) Int. Cl.
   *C07H 21/04* (2006.01)
(52) U.S. Cl. ...................................... 536/24.5
(58) Field of Classification Search ............ 536/24.5
   See application file for complete search history.

(56) References Cited

U.S. PATENT DOCUMENTS

| 6,506,559 B1 * | 1/2003 | Fire et al. ................ 435/6.16 |
| 2003/0225022 A1 | 12/2003 | Taylor et al. |
| 2004/0259247 A1 * | 12/2004 | Tuschl et al. ............. 435/375 |

FOREIGN PATENT DOCUMENTS

| WO | 96/25492 | 8/1996 |
| WO | 99/01551 | 1/1999 |
| WO | 01/10906 | 2/2001 |
| WO | 03/010286 | 2/2003 |
| WO | 2004/078940 A2 | 9/2004 |
| WO | 2004/113528 | 12/2004 |
| WO | 2005/007853 A2 | 1/2005 |

OTHER PUBLICATIONS

Harborth et al. (2001) J. Cell Science 114:4557-4565.
Holen et al. (2002) Nucleic Acids Res. 30:1757-1766.
Boese et al., "Mechanical Insights Aid Computational Short Interfering RNA Design," Methods in Enzymology 392:73-96, (2005).
Reynolds et al., "Rational siRNA design for RNA interference," Nature Biotechnology 22:326-330, (2004).
Jen et al. (Stem Cells 2000, vol. 18, p. 307-319).
Opalinska et al. (nature Reviews Drug Discovery, 2002, vol. 1, p. 503-514).
Jin, Bao-Feng et al., "Proteomic analysis of ubiquitin-proteasome effects: insight into the future of eukaryotic initiation factor 5A," Oncogene, Jul. 31, 2003, pp. 4819-4830, vol. 22, No. 31, Nature Publishing Group, XP-002388453, ISSN: 0950-9232.
Annexes to Form PCT/ISA/206, Invitation to Pay Additional Fees, Communication Relating to the Results of the Partial International Search, PCT/US2005/044266, Aug. 11, 2006, comprised of the Annex first, continuation and 4th of 5 extra sheets and the Patent Family Annex, European Patent Office, International Searching Authority, Rijswijk, NL.
Hayashizaki et al., "Analysis of the mouse transcriptome based on functional annotation of 60,770 full-length cDNAs," Nature, United Kingdom, vol. 420, No. 6915, pp. 563-573, ISSN: 0028-0836, SP 002965277, Dec. 5, 2002.
Ruhl, M. et al., "Eukaryotic initiation factor 5A is a cellular target of teh human immunodeficiency virus type 1 rev activation domain mediating trans-activation," Journal of cell biology, Dec. 1, 1993, pp. 1309-1320, vol. 123, No. 6, XP 000571505, ISSN: 0021-9525, Rockfeller University Press, New York, US.
Chen, K.Y. et al., "RNA interference analysis of the function of hypusine-containing eukaryotic initiaition factor 5A in *C. elegans*," FASEB Journal (Federation of American Societies for Experimental Biology), Mar. 20, 2002, p. A162, vol. 16, No. 4, XP 008033807, ISSN: 0892-6638, Bethesda, US.
Zhang, X. eta l., "Small interfering Rna targeting heme oxygenase-1 enhances ischemia-reperfusion-induced lung apoptosis," Journal of Biological Chemistry, American Society of Biochemical Biologists, Mar. 12, 2003, pp. 10677-10684, vol. 279, No. 11, XP002343181, ISSN: 0021-9258, Birmaingham, US.
International Search Report, PCT/US2005/025766, Mar. 17, 2006, comprised of Form PCT/ISA/220 and Form PCT/ISA/210, first & continuation sheets, second sheet: pp. 1-3, and patent family annex, European Patent Office, International Searching Authority, Rijswik, NL.
M. Caraglia et al.: "The Role of Eukaryotic Initiation Factor 5A in the Control of Cell Proliferation and Apoptosis", Amino Acids, vol. 20, No. 2, Jan. 1, 2001, pp. 91-104, XP002291822, ISSN: 0939-4451.

* cited by examiner

*Primary Examiner* — J. E. Angell

(74) *Attorney, Agent, or Firm* — Morgan Lewis & Bockius LLP

(57) ABSTRACT

The present invention relates to apoptosis specific eucaryotic initiation factor 5A (eIF-5A), referred to as apoptosis factor 5A1 or simply factor 5A1, apoptosis factor 5A1 nucleic acids and polypeptides and methods for inhibiting or suppressing apoptosis in cells using antisense nucleotides or siRNAs to inhibit expression of factor 5A1. The invention also relates to suppressing or inhibiting expression of pro-inflammatory cytokines by inhibiting expression of apoptosis factor 5A.

11 Claims, 101 Drawing Sheets

```
TCGAAGACCGGTAAGCACGGCCATGCCAAGGTCCATCTGGTTGGTATTGATATTTTTACTGGGAAGAAATAT
 S   K   T   G   K   H   G   H   A   K   V   H   L   V   G   I   D   I   F   T   G   K   K   Y
GAAGATATCTGCCCGTCGACTCATAACATGGATGTCCCCAACATCAAAAGGAATGATTTCCAGCTGATTGGC
 E   D   I   C   P   S   T   H   N   M   D   V   P   N   I   K   R   N   D   F   Q   L   I   G
ATCCAGGATGGGTACCTATCCCTGCTCCAGGACAGTGGGGAGGTACGAGAGGACCTTCGTCTGCCTGAGGGA
 I   Q   D   G   Y   L   S   L   L   Q   D   S   G   E   V   R   E   D   L   R   L   P   E   G
GACCTTGGCAAGGAGATTGAGCAGAAGTATGACTGTGGAGAAGAGATCCTGATCACAGTGCTGTCCGCCATG
 D   L   G   K   E   I   E   Q   K   Y   D   C   G   E   E   I   L   I   T   V   L   S   A   M
ACAGAGGAGGCAGCTGTTGCAATCAAGGCCATGGCAAAATAACTGGCTTCCAGGGTGGCGGTGGTGGCAGCA
 T   E   E   A   A   V   A   I   K   A   M   A   K
GTGATCCATGAGCCTACAGAGGCCCCTCCCCCAGCTCTGGCTGGGCCCTTGGCTGGACTCCTATCCAATTTA
TTTGACGTTTTATTTTGGTTTTCCTCACCCCTTCAAACTGTCGGGGAGACCCTGCCCTTCACCTAGCTCCCT
TGGCCAGGCATGAGGGAGCCATGGCCTTGGTGAAGCTACCTGCCTCTTCTCTCGCAGCCCTGATGGGGGAAA
GGGAGTGGGTACTGCCTGTGGTTTAGGTTCCCCTCTCCCTTTTTCTTTTTAATTCAATTTGGAATCAGAAAG
CTGTGGATTCTGGCAAATGGTCTTGTGTCCTTTATCCCACTCAAACCCATCTGGTCCCCTGTTCTCCATAGT
CCTTCACCCCCAAGCACCACTGACAGACTGGGGACCAGCCCCCTTCCCTGCCTGTGTCTCTTCCCAAACCCC
TCTATAGGGGTGACAAGAAGAGGAGGGGGGAGGGGACACGATCCCTCCTCAGGCATCTGGGAAGGCCTTGC
CCCCATGGGCTTTACCCTTTCCTGTGGGCTTTCTCCCTGACACATTTGTTAAAAATCAAACCTGAATAAAAC
TACAAGTTTAATATGAAAAAAAAAAAAAAAAAAAAAAA
(972 NT, 109 aa)
```

FIG.1

```
CAGGTCTAGAGTTGGAATCGAAGCCTCTTAAAATGGCAGATGATTTGGACTTCGAGACAGGAGATGCAGGGG
                                 M   A   D   D   L   D   F   E   T   G   D   A   G
CCTCAGCCACCTTCCCAATGCAGTGCTCAGCATTACGTAAGAATGGTTTTGTGGTGCTCAAGGGCCGGCCAT
 A   S   A   T   F   P   M   Q   C   S   A   L   R   K   N   G   F   V   V   L   K   G   R   P
GTAAGATCGTCGAGATGTCTACTTCGAAGACTGGCAAGCATGGCCATGCCAAGGTCCATCTGGTTGGTATTG
 C   K   I   V   E   M   S   T   S   K   T   G   K   H   G   H   A   K   V   H   L   V   G   I
ATATTTTTACTGGGAAGAAATATGAAGATATCTGCCCGTCGACTCATAACATGGATGTCCCCAACATCAAAA
 D   I   F   T   G   K   K   Y   E   D   I   C   P   S   T   H   N   M   D   V   P   N   I   K
GGAATGATTTCCAGCTGATTGGCATCCAGGATGGGTACCTATCCCTGCTCCAGGACAGTGGGGAGGTACGAG
 R   N   D   F   Q   L   I   G   I   Q   D   G   Y   L   S   L   L   Q   D   S   G   E   V   R
AGGACCTTCGTCTGCCTGAGGGAGACCTTGGCAAGGAGATTGAGCAGAAGTATGACTGTGGAGAAGAGATCC
 E   D   L   R   L   P   E   G   D   L   G   K   E   I   E   Q   K   Y   D   C   G   E   E   I
TGATCACAGTGCTGTCCGCCATGACAGAGGAGGCAGCTGTTGCAATCAAGGCTCGAG
 L   I   T   V   L   S   A   M   T   E   E   A   A   V   A   I   K   A
```

```
CAGGTCTAGAGTTGGAATCGAAGCCTCTTAAAATGGCAGATGATTTGGACTTCGAGACAGGAGATGCAGGGG
                             M   A   D   D   L   D   F   E   T   G   D   A   G        13
CCTCAGCCACCTTCCCAATGCAGTGCTCAGCATTACGTAAGAATGGTTTTGTGGTGCTCAAGGGCCGGCCAT      144
 A   S   A   T   F   P   M   Q   C   S   A   L   R   K   N   G   F   V   V   L   K   G   R   P
GTAAGATCGTCGAGATGTCTACTTCGAAGACTGGCAAGCATGGCCATGCCAAGGTCCATCTGGTTGGTATTG
 C   K   I   V   E   M   S   T   S   K   T   G   K   H   G   H   A   K   V   H   L   V   G   I       61
ATATTTTTACTGGGAAGAAATATGAAGATATCTGCCCGTCGACTCATAACATGGATGTCCCCAACATCAAAA      288
 D   I   F   T   G   K   K   Y   E   D   I   C   P   S   T   H   N   M   D   V   P   N   I   K
GGAATGATTTCCAGCTGATTGGCATCCAGGATGGGTACCTATCCCTGCTCCAGGACAGTGGGGAGGTACGAG
 R   N   D   F   Q   L   I   G   I   Q   D   G   Y   L   S   L   L   Q   D   S   G   E   V   R      109
AGGACCTTCGTCTGCCTGAGGGAGACCTTGGCAAGGAGATTGAGCAGAAGTATGACTGTGGAGAAGAGATCC      432
 E   D   L   R   L   P   E   G   D   L   G   K   E   I   E   Q   K   Y   D   C   G   E   E   I
TGATCACAGTGCTGTCCGCCATGACAGAGGAGGCAGCTGTTGCAATCAAGGCCATGGCAAAATAACTGGCTT
 L   I   T   V   L   S   A   M   T   E   E   A   A   V   A   I   K   A   M   A   K   *            154
CCAGGGTGGCGGTGGTGGCAGCAGTGATCCATGAGCCTACAGAGGCCCCTCCCCCAGCTCTGGCTGGGCCCT      576
TGGCTGGACTCCTATCCAATTTATTTGACGTTTTATTTTGGTTTTCCTCACCCCTTCAAACTGTCGGGGAGA
CCCTGCCCTTCACCTAGCTCCCTTGGCCAGGCATGAGGGAGCCATGGCCTTGGTGAAGCTACCTGCCTCTTC      720
TCTCGCAGCCCTGATGGGGGAAAGGGAGTGGGTACTGCCTGTGGTTTAGGTTCCCCTCTCCCTTTTTCTTTT
TAATTCAATTTGGAATCAGAAAGCTGTGGATTCTGGCAAATGGTCTTGTGTCCTTTATCCCACTCAAACCCA      864
TCTGGTCCCCTGTTCTCCATAGTCCTTCACCCCCAAGCACCACTGACAGACTGGGGACCAGCCCCCTTCCCT
GCCTGTGTCTCTTCCCAAACCCCTCTATAGGGGTGACAAGAAGAGGAGGGGGGAGGGGACACGATCCCTCC     1008
TCAGGCATCTGGGAAGGCCTTGCCCCCATGGGCTTTACCCTTTCCTGTGGGCTTTCTCCCTGACACATTTGT
TAAAAATCAAACCTGAATAAAACTACAAGTTTAATATGAAAAAAAAAAAAAAAAAAAAAA                 1139
```

```
GCTGTGTATTATTGGGCCCATAAGAACCACATACCTGTGCTGAGTCCTGCACTCACAGACGGCTCACTGGGT
  A  V  Y  Y  W  A  H  K  N  H  I  P  V  L  S  P  A  L  T  D  G  S  L  G
GACATGATCTTTTTCCATTCCTATAAAAACCCAGGCTTGGTCCTGGACATCGTTGAAGACCTGCGGCTCATC
  D  M  I  F  F  H  S  Y  K  N  P  G  L  V  L  D  I  V  E  D  L  R  L  I
AACATGCAGGCCATTTTCGCCAAGCGCACTGGGATGATCATCCTGGGTGGAGGCGTGGTCAAGCACCACATC
  N  M  Q  A  I  F  A  K  R  T  G  M  I  I  L  G  G  G  V  V  K  H  H  I
GCCAATGCTAACCTCATGCGGAATGGAGCTGACTACGCTGTTTATATCAACACAGCCCAGGAGTTTGATGGC
  A  N  A  N  L  M  R  N  G  A  D  Y  A  V  Y  I  N  T  A  Q  E  F  D  G
TCAGACTCAGGAGCCCGGCCAGATGAGGCTGTCTCCTGGGGCAAGATCCGGATGGATGCACAGCCAGTAAAG
  S  D  S  G  A  R  P  D  E  A  V  S  W  G  K  I  R  M  D  A  Q  P  V  K
GTCTATGCTGATGCATCTCTGGTTTTCCCCTTGCTGGTGGCTGAGACATTCGCCCAAAAGGCAGATGCCTTC
  V  Y  A  D  A  S  L  V  F  P  L  L  V  A  E  T  F  A  Q  K  A  D  A  F
AGAGCTGAGAAGAATGAGGACTGAGCAGATGGGTAAAGACGGAGGCTTCTGCCACACCTTTATTTATTATTT
  R  A  E  K  N  E  D
GCATACCAACCCCTCCTGGGCCCTCTCCTTGGTCAGCAGCATCTTGAGAATAAATGGCCTTTTTGTTGGTTT
CTGTAAAAAAAGGACTTTAAAAAAAAAAAAA
```

(606 NT, 151 aa)

FIG.4 rat vs. human(BC000751 or NM_001970) 96.5% identity (coding)

```
                 10         20         30         40         50         60
rat     ATGGCAGATGATTTGGACTTCGAGACAGGAGATGCAGGGGCCTCAGCCACCTTCCCAATG
        :::::::::: ::::::::::::::::::::::::::::::::::::::::::::::::
human   ATGGCAGATGACTTGGACTTCGAGACAGGAGATGCAGGGGCCTCAGCCACCTTCCCAATG
                 10         20         30         40         50         60

70         80         90        100        110        120
rat     CAGTGCTCAGCATTACGTAAGAATGGTTTTGTGGTGCTCAAGGGCCGGCCATGTAAGATC
        ::::::::::::::::::::::::::::: :::::::::::::: :::::::::::::::
human   CAGTGCTCAGCATTACGTAAGAATGGCTTTGTGGTGCTCAAAGGCCGGCCATGTAAGATC
                 70         80         90        100        110        120

130        140        150        160        170        180
rat     GTCGAGATGTCTACTTCGAAGACTGGCAAGCATGGCCATGCCAAGGTCCATCTGGTTGGT
        :::::::::::::::::::::::::::::::::: :::::: ::::::::::::::::::
human   GTCGAGATGTCTACTTCGAAGACTGGCAAGCACGGCCACGCCAAGGTCCATCTGGTTGGT
                130        140        150        160        170        180

190        200        210        220        230        240
rat     ATTGATATTTTTACTGGGAAGAAATATGAAGATATCTGCCCGTCGACTCATAACATGGAT
        :::: :: :::::::::::::::::::::::::::::::::::: :::::::: ::::::
human   ATTGACATCTTTACTGGGAAGAAATATGAAGATATCTGCCCGTCAACTCATAATATGGAT
                190        200        210        220        230        240

250        260        270        280        290        300
rat     GTCCCCAACATCAAAAGGAATGATTTCCAGCTGATTGGCATCCAGGATGGGTACCTATCC
        ::::::::::::::::::::::::: :::::::::::::::::::::::::::::::::
human   GTCCCCAACATCAAAAGGAATGACTTCCAGCTGATTGGCATCCAGGATGGGTACCTATCA
                250        260        270        280        290        300

310        320        330        340        350        360
rat     CTGCTCCAGGACAGTGGGGAGGTACGAGAGGACCTTCGTCTGCCTGAGGGAGACCTTGGC
        ::::::::::::::: :::::::::::::::::::::::::: ::::::::::::::::
human   CTGCTCCAGGACAGCGGGGAGGTACGAGAGGACCTTCGTCTCCCTGAGGGAGACCTTGGC
                310        320        330        340        350        360

370        380        390        400        410        420
rat     AAGGAGATTGAGCAGAAGTATGACTGTGGAGAAGAGATCCTGATCACAGTGCTGTCCGCC
        :::::::::::::::::::: :::::::::::::::::::::::::::: ::::: :::
human   AAGGAGATTGAGCAGAAGTACGACTGTGGAGAAGAGATCCTGATCACGGTGCTGTCTGCC
                370        380        390        400        410        420

430        440        450        460
rat     ATGACAGAGGAGGCAGCTGTTGCAATCAAGGCCATGGCAAAA
        :::::::::::::::::::::::::::::::::::::::::
human   ATGACAGAGGAGGCAGCTGTTGCAATCAAGGCCATGGCAAAA
                430        440        450        460
```

FIG.5 rat vs. human(NM_020390) 72.5% identity (coding)

```
              10        20        30        40        50        60
rat    ATGGCAGATGATTTGGACTTCGAGACAGGAGATGCAGGGGCCTCAGCCACCTTCCCAATG
       ::::::::: ::  :    :  ::  :::     ::  ::::::  :::::  ::   :::  :  :::   :::
human  ATGGCAGACGAAATTGATTTCACTACTGGAGATGCCGGGGCTTCCAGCACTTACCCTATG
              10        20        30        40        50        60

70        80        90       100       110       120
rat    CAGTGCTCAGCATTACGTAAGAATGGTTTTGTGGTGCTCAAGGGCCGGCCATGTAAGATC
       :::::::::: ::  :: ::   ::   ::  ::  :: :::::::::::: :: ::::: :: ::
human  CAGTGCTCGGCCTTGCGCAAAAACGGCTTCGTGGTGCTCAAAGGACGACCATGCAAAATA
              70        80        90       100       110       120

130       140       150       160       170       180
rat    GTCGAGATGTCTACTTCGAAGACTGGCAAGCATGGCCATGCCAAGGTCCATCTGGTTGGT
       ::  ::::::::  :: ::  :::::   :::: :::::::::: :::::::::::::::  :::::  ::
human  GTGGAGATGTCAACTTCCAAAACTGGAAAGCATGGTCATGCCAAGGTTCACCTTGTTGGA
             130       140       150       160       170       180

190       200       210       220       230       240
rat    ATTGATATTTTTACTGGGAAGAAATATGAAGATATCTGCCCCGTCGACTCATAACATGGAT
       ::::::::::::    ::  ::   :::::::::::::::::  ::   :: :::::   :::::::::::
human  ATTGATATTTTTCACGGGCAAAAAATATGAAGATATTTGTCCTTCTACTCACAACATGGAT
             190       200       210       220       230       240

250       260       270       280       290       300
rat    GTCCCCAACATCAAAAGGAATGATTTCCAGCTGATTGGCATCCAGGATGGGTACCTATCC
       ::  ::  :: ::  ::  :: ::::::::  ::  :::::   ::::  ::  :::::  :::::  :::
human  GTTCCAAATATTAAGAGAAAATGATTATCAACTGATATGCATTCAAGATGGTTACCTTTCC
             250       260       270       280       290       300

310       320       330       340       350       360
rat    CTGCTCCAGGACAGTGGGGAGGTACGAGAGGACCTTCGTCTGCCTGAGGGAGACCTTGGC
       :::::        ::  ::  ::  ::  :: :::::    :::::: :: :: :: :::  ::::
human  CTGCTGACAGAAACTGGTGAAGTTCGTGAGGATCTTAAACTGCCAGAAGGTGAACTAGGC
             310       320       330       340       350       360

370       380       390       400       410       420
rat    AAGGAGATTGAGCAGAAGTATGACTGTGGAGAAGAGATCCTGATCACAGTGCTGTCCGCC
       ::  ::  :: :::    ::  ::  :     ::  ::::::  :  ::  :   :   :  :: ::: ::
human  AAAGAAATAGAGGGAAAATACAATGCAGGTGAAGATGTACAGGTGTCTGTCATGTGTGCA
             370       380       390       400       410       420

430       440       450       460
rat    ATGACAGAGGAGGCAGCTGTTGCAATCAAGGCCATGGCAAAA
       ::::  ::  ::     ::::: ::  :: ::     ::::::
human  ATGAGTGAAGAATATGCTGTAGCCATAAAACCCT--GCAAAT
             430       440       450       460
```

FIG.6 rat vs. mouse (BC003889) 98.3% identity (coding)

```
              10        20        30        40        50        60
rat    ATGGCAGATGATTTGGACTTCGAGACAGGAGATGCAGGGGCCTCAGCCACCTTCCCAATG
       ::::::::::::::::::::::::::::::::::::::::::::::::::::::::::::
mouse  ATGGCAGATGATTTGGACTTCGAGACAGGAGATGCAGGGGCCTCAGCCACCTTCCCAATG
              10        20        30        40        50        60

70        80        90       100       110       120
rat    CAGTGCTCAGCATTACGTAAGAATGGTTTTGTGGTGCTCAAGGGCCGGCCATGTAAGATC
       ::::::::::::::::::::::::::::::::::::::: ::::::::::::::::::::
mouse  CAGTGCTCAGCATTACGTAAGAATGGTTTTGTGGTGCTCAAAGGCCGGCCATGTAAGATC
              70        80        90       100       110       120

130       140       150       160       170       180
rat    GTCGAGATGTCTACTTCGAAGACTGGCAAGCATGGCCATGCCAAGGTCCATCTGGTTGGT
       :::::::::::::::::::::::::::::::::::::::::::::::::::::::::::
mouse  GTCGAGATGTCTACTTCGAAGACTGGCAAGCATGGCCATGCCAAGGTCCATCTGGTTGGC
             130       140       150       160       170       180

190       200       210       220       230       240
rat    ATTGATATTTTTACTGGGAAGAAATATGAAGATATCTGCCCGTCGACTCATAACATGGAT
       ::::: :::::::::::::::::::::::::::::::::::::::::::::::: :::::
mouse  ATTGACATTTTTACTGGGAAGAAATATGAAGATATCTGCCCGTCGACTCATAATATGGAT
             190       200       210       220       230       240

250       260       270       280       290       300
rat    GTCCCCAACATCAAAAGGAATGATTTCCAGCTGATTGGCATCCAGGATGGGTACCTATCC
       :::::::::::::::: :::::::: ::::::::::::::::::::::::::::::::::
mouse  GTCCCCAACATCAAACGGAATGACTTCCAGCTGATTGGCATCCAGGATGGGTACCTATCC
             250       260       270       280       290       300

310       320       330       340       350       360
rat    CTGCTCCAGGACAGTGGGGAGGTACGAGAGGACCTTCGTCTGCCTGAGGGAGACCTTGGC
       :::::::::::::::::::::::::::::::::::::::::::::::: :::::::::::
mouse  CTGCTCCAGGACAGTGGGGAGGTACGAGAGGACCTTCGTCTGCCTGAAGGAGACCTTGGC
             310       320       330       340       350       360

370       380       390       400       410       420
rat    AAGGAGATTGAGCAGAAGTATGACTGTGGAGAAGAGATCCTGATCACAGTGCTGTCCGCC
       :::::::::::::::::::::::::::::::::::::::::::::::::::::: :::::
mouse  AAGGAGATTGAGCAGAAGTATGACTGTGGAGAAGAGATCCTGATCACAGTGCTGTCTGCC
             370       380       390       400       410       420

430       440       450       460
rat    ATGACAGAGGAGGCAGCTGTTGCAATCAAGGCCATGGCAAAA
       :::::::::::::::::::::::::::::::::::::::::
mouse  ATGACAGAGGAGGCAGCTGTTGCAATCAAGGCCATGGCAAAA
             430       440       450       460
```

FIG. 7 rat vs. human(BC000751 or NM_001970) 100.0% identity

```
              10        20        30        40        50        60
rat    MADDLDFETGDAGASATFPMQCSALRKNGFVVLKGRPCKIVEMSTSKTGKHGHAKVHLVG
       ::::::::::::::::::::::::::::::::::::::::::::::::::::::::::::
human  MADDLDFETGDAGASATFPMQCSALRKNGFVVLKGRPCKIVEMSTSKTGKHGHAKVHLVG
              10        20        30        40        50        60

70        80        90       100       110       120
rat    IDIFTGKKYEDICPSTHNMDVPNIKRNDFQLIGIQDGYLSLLQDSGEVREDLRLPEGDLG
       ::::::::::::::::::::::::::::::::::::::::::::::::::::::::::::
human  IDIFTGKKYEDICPSTHNMDVPNIKRNDFQLIGIQDGYLSLLQDSGEVREDLRLPEGDLG
              70        80        90       100       110       120

130       140       150
rat    KEIEQKYDCGEEILITVLSAMTEEAAVAIKAMAK
       :::::::::::::::::::::::::::::::::
human  KEIEQKYDCGEEILITVLSAMTEEAAVAIKAMAK
             130       140       150
```

FIG.8 rat vs. human(NM_020390) 82.5% identity

```
            10         20         30         40         50         60
rat    MADDLDFETGDAGASATFPMQCSALRKNGFVVLKGRPCKIVEMSTSKTGKHGHAKVHLVG
       :::..::  :::::::::..:::::::::::::::::::::::::::::::::::::::
human  MADEIDFTTGDAGASSTYPMQCSALRKNGFVVLKGRPCKIVEMSTSKTGKHGHAKVHLVG
            10         20         30         40         50         60

70         80         90        100        110        120
rat    IDIFTGKKYEDICPSTHNMDVPNIKRNDFQLIGIQDGYLSLLQDSGEVREDLRLPEGDLG
       :::::::::::::::::::::::::::::.:::  :::::::::..:::::::.:::.::
human  IDIFTGKKYEDICPSTHNMDVPNIKRNDYQLICIQDGYLSLLTETGEVREDLKLPEGELG
            70         80         90        100        110        120

130        140        150
rat    KEIEQKYDCGEEILITVLSAMTEEAAVAIKAMAK
       ::::  ::. ::..  ...  ::.:: :::::  :
human  KEIEGKYNAGEDVQVSVMCAMSEEYAVAIKP-CK
            130        140        150
```

FIG.9 rat vs. mouse (BC003889)100.0% identity

```
           10        20        30        40        50        60
rat    MADDLDFETGDAGASATFPMQCSALRKNGFVVLKGRPCKIVEMSTSKTGKHGHAKVHLVG
       ::::::::::::::::::::::::::::::::::::::::::::::::::::::::::::
mouse  MADDLDFETGDAGASATFPMQCSALRKNGFVVLKGRPCKIVEMSTSKTGKHGHAKVHLVG
           10        20        30        40        50        60

70        80        90       100       110       120
rat    IDIFTGKKYEDICPSTHNMDVPNIKRNDFQLIGIQDGYLSLLQDSGEVREDLRLPEGDLG
       ::::::::::::::::::::::::::::::::::::::::::::::::::::::::::::
mouse  IDIFTGKKYEDICPSTHNMDVPNIKRNDFQLIGIQDGYLSLLQDSGEVREDLRLPEGDLG
           70        80        90       100       110       120

130       140       150
rat    KEIEQKYDCGEEILITVLSAMTEEAAVAIKAMAK
       :::::::::::::::::::::::::::::::::
mouse  KEIEQKYDCGEEILITVLSAMTEEAAVAIKAMAK
          130       140       150
```

FIG.10 rat vs. human (BC000333) 87.4% identity (coding)

```
              10        20        30        40        50        60
rat    GCTGTGTATTATTGGGCCCATAAGAACCACATACCTGTGCTGAGTCCTGCACTCACAGAC
        : :::::::: ::::::::: :::::::::::: :::::: : ::::: ::::: :::::::
human  TCCGTGTATTACTGGGCCCAGAAGAACCACATCCCTGTGTTTAGTCCCGCACTTACAGAC
              10        20        30        40        50        60

70        80        90       100       110       120
rat    GGCTCACTGGGTGACATGATCTTTTTCCATTCCTATAAAAACCCAGGCTTGGTCCTGGAC
       ::::: :::::: :::::::::::: :: :::::::::: :::: ::: ::::::::::::
human  GGCTCGCTGGGCGACATGATCTTCTTCCATTCCTACAAGAACCCGGGCCTGGTCCTGGAC
              70        80        90       100       110       120

130       140       150       160       170       180
rat    ATCGTTGAAGACCTGCGGCTCATCAACATGCAGGCCATTTTCGCCAAGCGCACTGGGATG
       :::::::: :::::: :::::::::::::::  ::::::::: :::::: ::::::::::
human  ATCGTTGAGGACCTGAGGCTCATCAACACACAGGCCATCTTTGCCAAGTGCACTGGGATG
             130       140       150       160       170       180

190       200       210       220       230       240
rat    ATCATCCTGGGTGGAGGCGTGGTCAAGCACCACATCGCCAATGCTAACCTCATGCGGAAT
       :::: : ::::: :: ::::::::::::::::::::  ::::::::  :::::::::::::
human  ATCATTCTGGGCGGGGGCGTGGTCAAGCACCACATTGCCAATGCCAACCTCATGCGGAAC
             190       200       210       220       230       240

250       260       270       280       290       300
rat    GGAGCTGACTACGCTGTTTATATCAACACAGCCCAGGAGTTTGATGGCTCAGACTCAGGA
       :: :: ::::::::::::::: :::::::::::::::::::::::::::::: :::::: 
human  GGGGCCGACTACGCTGTTTACATCAACACAGCCCAGGAGTTTGATGGCTCTGACTCAGGT
             250       260       270       280       290       300

310       320       330       340       350       360
rat    GCCCGGCCAGATGAGGCTGTCTCCTGGGGCAAGATCCGGATGGATGCACAGCCAGTAAAG
       ::::: :::::: :::::::::::::::::::::::::::: :::::::::::::: :::
human  GCCCGACCAGACGAGGCTGTCTCCTGGGGCAAGATCCGGGTGGATGCACAGCCCGTCAAG
             310       320       330       340       350       360

370       380       390       400       410       420
rat    GTCTATGCTGATGCATCTCTGGTTTTTCCCCTTGCTGGTGGCTGAGACATTCGCCCAAAAG
       :::::::::::: :: :: ::::: :: :::: :::::: :::::::::  :: :::: :::
human  GTCTATGCTGACGCCTCCCTGGTCTTCCCCCCTGCTTGTGGCTGAAACCTTTGCCCAGAAG
             370       380       390       400       410       420

430       440       450
rat    GCAGATGCCTTCAGAGCTGAGAAGAATGAGGAC
       :::::::::: ::   :::::::::::: ::::::
human  ATGGATGCCTTCATGCATGAGAAGAACGAGGAC
             430       440       450
```

FIG.11

Hoescht Staining of Transformed
COS-7 Cells Deprived of Serum
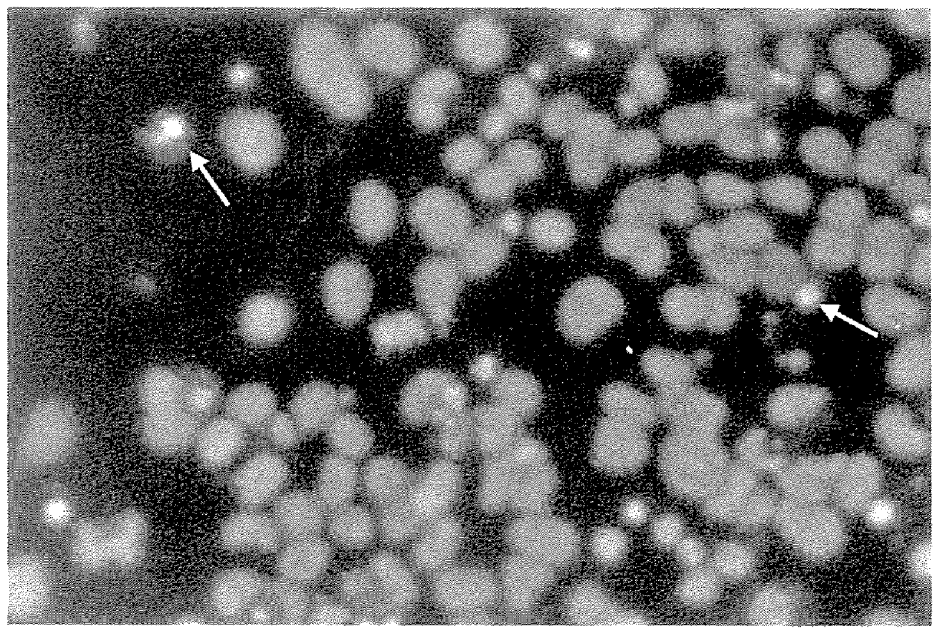
Mock Transformed
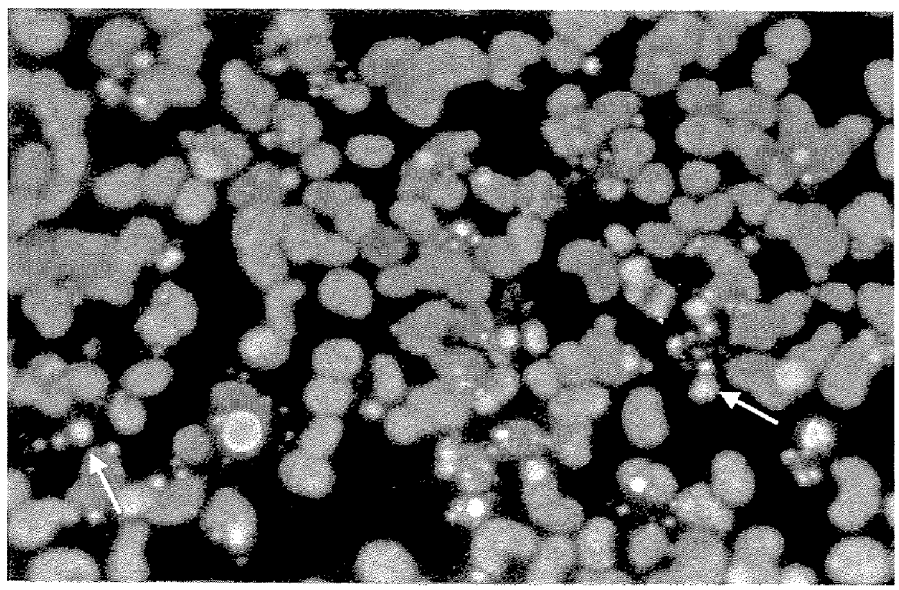
pHm6-Sense rat F5A
FIG.27

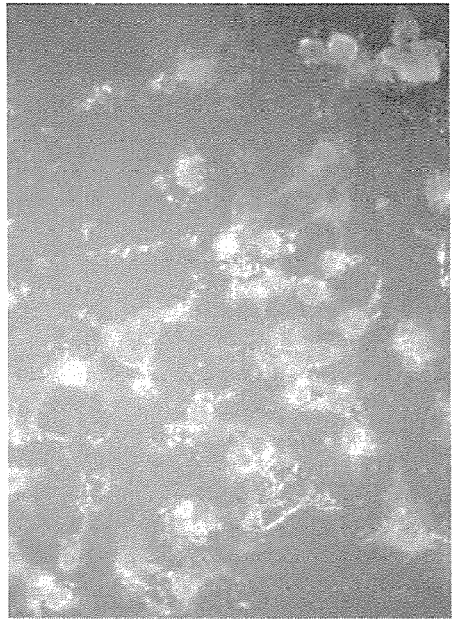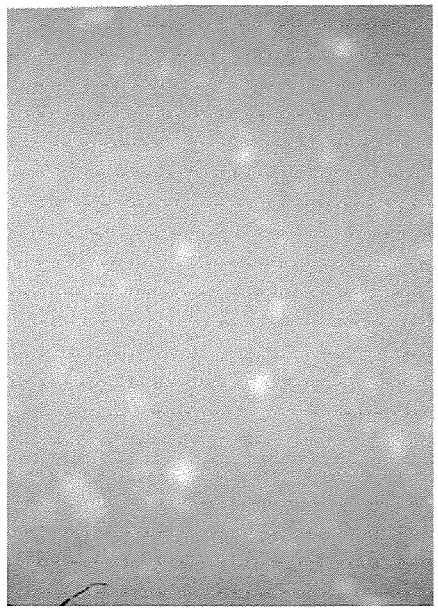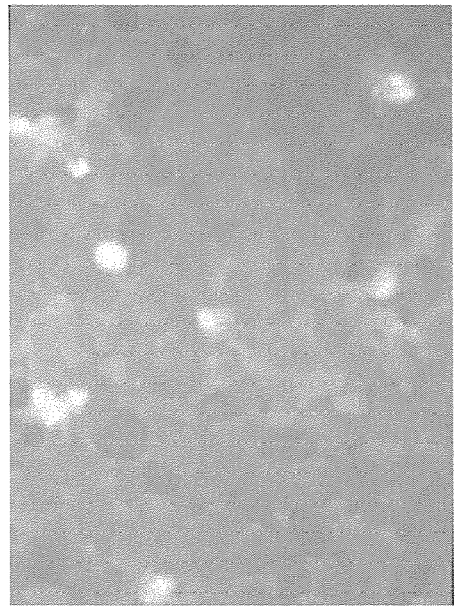
FIG. 29

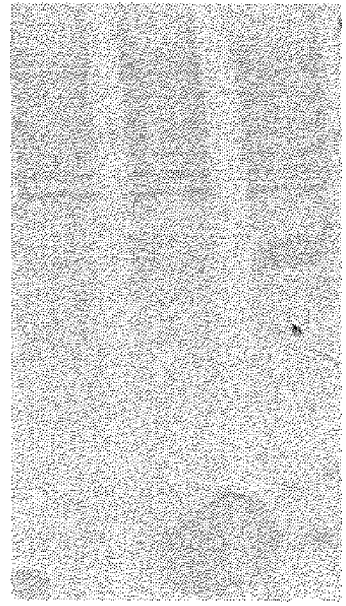
FIG.37A

Sequence and Alignment of human eIF5A2 isolated from RKO cells with sequence of human eIF5A2 in Genbank (ACCESSION XM_113401)

```
XM_113401  MADEIDFTTG DAGASSTYPM QCSALRKNGF VVLKGRPCKI VEMSTSKTGK
      PCR  MADEIDFTTG DAGASSTYPM QCSALRKNGF VVLKGRPCKI VEMSTSKTGK
Consensus  MADEIDFTTG DAGASSTYPM QCSALRKNGF VVLKGRPCKI VEMSTSKTGK 51                                                100
XM_113401  HGHAKVHLVG IDIFTGKKYE DICPSTHNMD VPNIKRNDYQ LICIQDGYLS
      PCR  HGHAKVHLVG IDIFTGKKYE DICPSTHNMD VPNIKRNDYQ LICIQDGCLS
Consensus  HGHAKVHLVG IDIFTGKKYE DICPSTHNMD VPNIKRNDYQ LICIQDGcLS 101                                               150
XM_113401  LLTETGEVRE DLKLPEGELG KEIEGKYNAG EDVQVSVMCA MSEEYAVAIK
      PCR  LLTETGEVRE DLKLPEGELG KEIEGKYNAG EDVQVSVMCA MSEEYAVAIK
Consensus  LLTETGEVRE DLKLPEGELG KEIEGKYNAG EDVQVSVMCA MSEEYAVAIK 151
XM_113401  PCK
      PCR  PCK
Consensus  PCK
``` eIF5A2 = proliferating eIF-5A

FIG.38

| TRANSFECTED PLASMID | PERCENT APOPTOSIS |
|---|---|
| UNTRANSFECTED | 21.2% |
| pHM6-Lac Z | 21.7% |
| pHM6-eIF5A1 | 60.7% (80%)* |
| pHM6-eIF5A2 | 20.5% |
| pHM6-TRUNCATED eIF5A1 | 24.1% |

*CORRECTED FOR BACKGROUND APOPTOSIS IN UNTRANSFECTED CELLS AND FOR TRANSFECTION EFFICIENCY

| PATIENT | Ds | IF5a1 pg/ng rRNA | IF5a2 pg/ng rRNA | 0.5 | 2.0 | IL-18 pg/ng rRNA | IL-1b pg/ng rRNA |
|---|---|---|---|---|---|---|---|
| 207 | CABG | 9.0 | 2.4 | 3.8 | 0.3 | 10.1 | 7.2 |
| 21 | CABG | 123.2 | 81.6 | 1.5 | 0.7 | 405.9 | 41.5 |
| 23 | CABG | 0.1 | 0.0 | 11.0 | 0.1 | 0.0 | 0.0 |
| 26 | CABG | | | | | | |
| 28 | CABG | 200.4 | 294.6 | 0.7 | 1.5 | 894.1 | 49.7 |
| 30 | CABG | 279.4 | 921.2 | 0.3 | 3.3 | 669.8 | 71.0 |
| 33 | CABG | 260.1 | 723.9 | 0.4 | 2.8 | 545.6 | 105.1 |
| 34 | CABG | 263.4 | 309.3 | 0.9 | 1.2 | 520.0 | 19.9 |
| 65 | CABG | 82.9 | 43.1 | 1.9 | 0.5 | 98.2 | 20.2 |
| 139 | CABG | 23.9 | 7.0 | 3.4 | 0.3 | 22.7 | 57.3 |
| 140 | CABG | 0.9 | 0.0 | #DIV/0! | 0.0 | 0.1 | 0.0 |
| 143 | CABG | 137.7 | 169.5 | 0.8 | 1.2 | 338.7 | 77.9 |

FIG.50A

| PATIENT | Ds | IF5a1 pg/ng rRNA | IF5a2 pg/ng rRNA | 0.5 | 2.0 | IL-18 pg/ng rRNA | IL-1b pg/ng rRNA |
|---|---|---|---|---|---|---|---|
| 206 | VALVE | 44.4 | 33.1 | 1.3 | 0.7 | 50.0 | 67.2 |
| 330 | VALVE | | | | | | |
| 331 | VALVE | 11.3 | 0.2 | 68.9 | 0.0 | 0.1 | 0.0 |
| 332 | VALVE | 224.5 | 194.0 | 1.2 | 0.9 | 510.5 | 37.2 |
| 289 | VALVE | 286.3 | 674.1 | 0.4 | 2.4 | 888.0 | 167.5 |
| 290 | VALVE | 303.9 | 540.4 | 0.6 | 1.8 | 545.8 | 20.6 |
| 291 | VALVE | 148.1 | 311.8 | 0.5 | 2.1 | 229.2 | 31.1 |
| 292 | VALVE | 221.1 | 367.2 | 0.6 | 1.7 | 280.8 | 55.0 |
| 312 | VALVE | 361.1 | 262.5 | 1.4 | 0.7 | 198.0 | 44.2 |
| 314 | VALVE | 6.5 | 1.6 | 4.0 | 0.2 | 74.7 | 18.6 |
| 318 | VALVE | 83.3 | 48.5 | 1.7 | 0.6 | 69.3 | 13.3 |
| 324 | VALVE | 485.9 | 414.1 | 1.2 | 0.9 | 584.9 | 98.6 |

FIG.50B

| Expt # | Age | Sex | DM | Unstable engine | Operation | Misc..... | date RNA |
|---|---|---|---|---|---|---|---|
| 19 | 61 | M | Y | N | CABG | Metoprolol, Lovastatin, NTG | |
| 20 | 72 | M | Y | N | CABG | Metoprolol, Lipitor | |
| 21 | 55 | M | N | N | CABG | CYA, Imuran, Prednisone, Lasix, INS, Metoprolol | 7/30/02 |
| 23 | 71 | M | N | N | CABG | Imipramine, Isordil, NTG, Metoprolol | 7/30/02 |
| 24 | 75 | M | Y | Y | CABG | Lisinopril, Glipizide, Metoprolol, NTG | |
| ? | 61 | M | N | N | CABG | Lisinopril, digoxin, Lasix, NTG, ASA | 7/30/02 |
| 26 | 57 | M | N | N | CABG | Atenolol, Norvasc, HCTZ, NTG, ASA | |
| 28 | 48 | F | N | N | MVR | Atenolol, INS, Lisinopril | 9-Aug |
| 29 | 64 | M | N | N | CABG | Lasix, Lisinopril | |
| 30 | 76 | M | N | N | CABG | | 9-Aug |
| 31 | 65 | M | Y | N | CABG | Simvastatin, metoprolol | |
| 33 | 54 | M | N | N | CABG | Lisinopril, Felodipoine, NTG | 9-Aug |
| 34 | 63 | M | N | N | CABG | Amlodipine, Glyburide, Prazosin | 9-Aug |
| 35 | 74 | M | Y | N | CABG | Simvastatin, INS, Felodipine, Spironolactone, Metoprtolol, Lisinopril | |
| 36 | 62 | M | Y | N | CABG | Famotidine, Atenolol, Fosinopril, Procardia, Zocor, NTG | |
| 37 | 63 | M | N | N | CABG | A-fib, Dig, Atenolol, Zocor, Coumadin | |
| 38 | 63 | M | N | N | CABG | | |

CONT'D FROM FIG.51

| | | | | | | |
|---|---|---|---|---|---|---|
| 39 | 77 | M | N | N | CABG | Coumadin, Cozar, Zocor, HCTZ, Cortioarone |
| 41 | 74 | F | N | Y | AVR/CABG | Dig, Zestril |
| 42 | 59 | M | Y | N | CABG | Statin, Atenolol, Glucotrol, Lisinopril |
| 44 | 64 | M | Y | N | CABG | Atenolol, NTG, Lisinopril, Simvastatin, Verapamil |
| 47 | 64 | M | N | N | CABG | NTG, Lisinopril, Synthroid, simvastatin |
| 48 | 56 | M | Y | Y | CABG | NTG, Metoprolol, Glipizide, Simvastatin |
| 52 | 70 | M | Y | N | CABG | Fosinopril, Glipizide, HCTZ, Felodipine, Metoprolol, |
| 53 | 55 | M | Y | N | CABG | Lasix, Lisinopril, Glyburide, Nifedipine |
| 54 | 48 | M | Y | Y | CABG | Lisinopril, Metoprolol, NTG, Lasiz, ASA<Simvastatin, INS |
| 55 | 67 | M | N | N | CABG | ASA, prednisone, Atenolol |
| 56 | 71 | M | Y | N | CABG | ASA, Simvastatin, Atenolol, Lisinopril, NTG |
| 58 | 70 | M | Y | N | CABG | Coumadin, Synthroid, NTG, Glyburide |
| 59 | 55 | M | Y | N | CABG | Lisinopril, NTG, Glyburide, metoprolol, Simvastatin |
| 60 | 55 | M | Y | N | CABG | Metformin, Glyburide, ASA, Atenolol, Lisinopril, Simvastatin |
| 61 | 68 | M | Y | N | CABG | Atenolol, Lasix, Fosinopril, Simvastatin, Glyburide |
| 61 | 68 | M | Y | N | CABG | Atenolol, Lasix, Fosinopril, Simvastatin, Glyburide |
| 62 | 76 | M | N | N | CABG | Gemfibrozil, ASA, Metoprolol, NTG |
| 64 | 61 | M | | N | MVR | |

CONT'D FROM FIG.51A

| | | | | | | | |
|---|---|---|---|---|---|---|---|
| 64 | 61 | M | N | N | MVR | | |
| 65 | 72 | M | N | Y | CABG | ASA, NTG | 12-Sep |
| 67 | 69 | M | Y | N | CABG | | |
| 138 | 75 | M | Y | N | CABG | Lisinopril, Simvastatin, metoprolol, Metformin, glyburide | |
| 139 | 71 | M | N | Y | CABG | Metoprolol, Dyazide, Lipitor, Cardura, Lotrel | 12-Sep |
| 140 | 86 | M | N | Y | CABG | Metoprolol, Amlodipine, NTG, Heparin | 12-Sep |
| 141 | 65 | M | Y | N | CABG | ASA, Clopidogril, Glipizide, Lisinopril, INS, | |
| 142 | 75 | F | Y | N | CABG | Glyburide, Atenolol, Lisinopril, Maxide, Methyldopa | |
| 141 | 44 | M | N | N | CABG | Atenolol, Lisinopril, Simvastatin, | 12-Sep |
| 144 | 57 | M | N | N | AVR | Allopurinol, Colchicine, Minoxidil, Atenol, Lasix, Prednisone, Simvastatin | |
| 145 | 67 | M | N | N | CABG | Lipitor, Metoprolol, NTG, ASA | |
| 146 | 42 | M | N | N | CABG | Atenolol, Norvasc, NTG | |
| 147 | 71 | M | N | N | MVR | Dig, Verapamil, Coumadin | |
| 148 | 71 | F | N | N | CABG | | |
| 150 | 70 | M | Y | N | CABG | Felodipine, HCTZ, INS, Synthroid, Losartin, Simvastatin, Atenolol, | |
| 151 | 78 | F | Y | N | CABG | Dig, NTG, Lisinopril, Cavedolol, INS | |

CONT'D FROM FIG.51B

| | | | | | |
|---|---|---|---|---|---|
| 152 | 50 | M | N | N | CABG | Lisinopril, NTG, Lasix, Metoprolol |
| 153 | 48 | M | N | N | AVR | |
| 154 | 67 | M | N | N | CABG | Simvastatin, Lisinopril, Atenolol |
| 155 | 59 | M | N | N | CABG | Lisinopril, ASA, Metoprolol, Simvastatin |
| 156 | 62 | M | Y | N | CABG | NTG, Glyburide, Atorvastatin, Atenolol |
| 161 | 56 | M | Y | N | MVR | INS, Metoprolol, NTG, Simvastatin, Lisinopril |
| 162 | 23 | F | N | N | MVR | |
| 163 | 72 | M | N | N | AVR | Simvastatin, Felodipine, Cimetidine |
| 164 | 65 | F | N | N | MVR | Multi valve Dz. A-fib Metoprolol, DIG, Coumadin |
| 166 | 57 | F | N | N | MVR | Synthroid |
| 173 | 60 | M | N | N | AVR | |
| 177 | 66 | F | N | N | MVR | Severe MR, Lisinopril |
| 184 | 46 | M | N | N | MVR | Vasotec |
| 185 | 75 | M | N | Y | CABG, MVR | Tropolol, Capoten, Plavix, Synthroid |
| 201 | 50 | M | N | N | AVR | Lasix, Incubated in ICE prior to D/C |

CONT'D FROM FIG.51C

| | | | | | |
|---|---|---|---|---|---|
| 206 | 58 | M | N | AVR | |
| 207 | 68 | M | N | CABG | Vasotec |
| 211 | 51 | M | N | AVR | Simvastatin, Atenolol |
| 289 | 45 | M | N | AVR | EF<20% |
| 290 | 77 | M | N | MVR | |
| 291 | 55 | F | N | AVR | |
| 292 | 39 | M | N | MVR | |
| 310 | 67 | F | N | AVR/MVY | |
| 312 | 72 | F | N | AVR | |
| 314 | 75 | F | N | AVR | |
| 318 | 62 | M | N | AVR | |
| 329 | 70 | M | N | AVR | |
| 330 | 67 | M | N | AVR | |
| 331 | 58 | M | N | AVR | |
| 339 | 69 | M | N | AVR | |

| | |
|---|---|
| | |
| | |
| | |
| 9-Aug | |
| 9-Aug | |
| 9-Aug | |
| 9-Aug | |
| | |
| 12-Sep | |
| 12-Sep | |
| 12-Sep | |
| 12-Sep | |
| 7/30/02 | |
| 7/30/02 | |
| 7/30/02 | |

FIG.51D

+ serum

- serum

```
siRNA #1    target 5' AA(AGGAATGACTTCCAGCTGA)TT 3' SEQ ID NO:30
siRNA #2    target 5' AA(GATCGTCGAGATGTCTACT)TC 3' SEQ ID NO:31
siRNA #3    target 5' AA(GGTCCATCTGGTTGGTATT)GA 3' SEQ ID NO:32
siRNA #4    target 5' AA(GCTGGACTCCTCCTACACA)AT 3' SEQ ID NO:33
siRNA #5    REVERSE OF siRNA #1 5' AA(AGTCGACCTTCAGTAAGGA)TT 3' SEQ ID NO:34

1 ggcacgaggg tagaggcggc ggcggcggcg gcagcgggct cggaggcagc ggttgggctc
   61 gcggcgagcg gacggggtcg agtcagtgcg ttcgcgcgag ttggaatcga agcctcttaa
  121 aatggcagat gacttggact tcgagacagg agatgcaggg gcctcagcca ccttcccaat
  181 gcagtgctca gcattacgta agaatggctt tgtggtgctc aaaggccggc catgtaagat
  241 cgtcgagatg tctacttcga agactggcaa gcacggccac gccaaggtcc atctggttgg
  301 tattgacatc tttactggga agaaatatga agatatctgc ccgtcaactc ataatatgga
  361 tgtccccaac atcaaaagga atgacttcca gctgattggc atccaggatg ggtacctatc
  421 actgctccag gacagcgggg aggtacgaga ggaccttcgt ctccctgagg gagaccttgg
  481 caaggagatt gagcagaagt acgactgtgg agaagagatc ctgatcacgg tgctgtctgc
  541 catgacagag gaggcagctg ttgcaatcaa ggccatggca aaataactgg ctcccaggat
  601 ggcggtggtg gcagcagtga tcctctgaac ctgcagaggc cccctccccg agcctggcct
  661 ggctctggcc cggtcctaag ctggactcct cctacacaat ttatttgacg ttttattttg
  721 gttttcccca ccccctcaat ctgtcgggga gcccctgccc ttcacctagc tcccttggcc
  781 aggagcgagc gaagctgtgg ccttggtgaa gctgccctcc tcttctcccc tcacactaca
  841 gccctggtgg gggagaaggg ggtgggtgct gcttgtggtt tagtctttttt tttttttttt
  901 tttttttttt aaattcaatc tggaatcaga aagcggtgga ttctggcaaa tggtccttgt
  961 gccctcccca ctcatccctg gtctggtccc ctgttgccca tagccccttta ccctgagcac
 1021 cacccccaaca gactggggac cagccccctc gcctgcctgt gtctctcccc aaaccccttt
 1081 agatggggag ggaagaggag gagaggggag gggacctgcc ccctcctcag gcatctggga
 1141 gggccctgcc cccatgggct ttacccttcc ctgcgggctc tctccccgac acatttgtta
 1201 aaatcaaacc tgaataaaac tacaagttta atatgaaaaa aaaaaaaaaa aaaaaaaaa
 1261 aaaaaaaaaa aaaaaaaaaa aaaaaaaaaa aaaaaaaaaa aaaaaaaa   SEQ ID No:29
```

FIG. 70

| | |
|---|---|
| ANTISENSE OLIGO #1 | 5'- CCT GTC TCG AAG TCC AAG TC-3' (SEQ ID NO:63) |
| TARGET | 5'- GACTTGGACTTCGAGACA GG-3' |
| ANTISENSE OLIGO #2 | 5'- GGA CCT TGG CGT GGC CGT GC-3' (SEQ ID NO:64) |
| TARGET | 5'- GCACGGCC ACGCCAAGGTCC-3' |
| ANTISENSE OLIGO #3 | 5'- CTC GTA CCT CCC CGC TCT CC 3' (SEQ ID NO:65) |
| TARGET | 5'- GGACAGCGG GGAGGTACGA-3' |

```
   1 ggcacgaggg tagaggcggc ggcggcggcg gcagcgggct cggaggcagc ggttgggctc
  61 gcggcgagcg gacggggtcg agtcagtgcg ttcgcgcgag ttggaatcga agcctcttaa
 121 aatggcagat gacttggact tcgagacagg agatgcaggg gcctcagcca ccttcccaat
 181 gcagtgctca gcattacgta agaatggctt tgtggtgctc aaaggccggc catgtaagat
 241 cgtcgagatg tctacttcga agactggcaa gcacggccac gccaaggtcc atctggttgg
 301 tattgacatc tttactggga agaaatatga agatatctgc ccgtcaactc ataatatgga
 361 tgtccccaac atcaaaagga atgacttcca gctgattggc atccaggatg ggtacctatc
 421 actgctccag gacagcgggg aggtacgaga ggaccttcgt ctccctgagg gagaccttgg
 481 caaggagatt gagcagaagt acgactgtgg agaagagatc ctgatcacgg tgctgtctgc
 541 catgacagag gaggcagctg ttgcaatcaa ggccatggca aaataactgg ctcccaggat
 601 ggcggtggtg gcagcagtga tcctctgaac ctgcagaggc cccctccccg agcctggcct
 661 ggctctggcc cggtcctaag ctggactcct cctacacaat ttatttgacg ttttattttg
 721 gttttcccca ccccctcaat ctgtcgggga gccctgcc ttcacctagc tcccttggcc
 781 aggagcgagc gaagctgtgg ccttggtgaa gctgccctcc tcttctcccc tcacactaca
 841 gccctggtgg gggagaaggg ggtgggtgct gcttgtggtt tagtcttttt ttttttttt
 901 ttttttttt aaattcaatc tggaatcaga aagcggtgga ttctggcaaa tggtccttgt
 961 gccctcccca ctcatccctg gtctggtccc ctgttgccca tagccctta ccctgagcac
1021 caccccaaca gactggggac cagcccctc gcctgccgt gtctctcccc aaacccctt
1081 agatggggag ggaagaggag gagaggggag gggacctgcc ccctcctcag gcatctggga
1141 gggccctgcc cccatgggct ttacccttcc ctgcgggctc tctccccgac acatttgtta
1201 aaatcaaacc tgaataaaac tacaagtta atatgaaaaa aaaaaaaaa aaaaaaaaa
1261 aaaaaaaaa aaaaaaaaa aaaaaaaaa aaaaaaaa aaaaaaa
```

FIG.71

POSITION OF ANTISENSE OLIGONUCLEOTIDES WITHIN NUCLEOTIDE SEQUENCE OF HUMAN eIF5A1 (ACCESSION NM_001970; TRANSLATION START AND STOP IN BOLD)

*ANTISENSE eIF5A1 # 1 (SEQ ID NO:25)* - BINDS TO *GACTTGGACTTCGAGACAGG*
*ANTISENSE eIF5A1 # 2 (SEQ ID NO:26)* - BINDS TO *GCACGGCCACGCCAAGGTC*
ANTISENSE eIF5A1 # 3 (SEQ ID NO:27) - BINDS TO GGACAGCAGGGAGGTACGAG

GGCAGAGGGCGGCGGCGGCGGTAGAGGCGGCGGGCGGCTCGGAGGCAGCGGTTGGGCTCGGGGAGGGAGCGGGTCGAGTCAGTGCGTTCG
CGCGAGTTGGAATCGAAGCTCTTAAAATGGCAGAGCTTGAGACTTCGAGACAGGAGATGCAGAGGGCCACCTTCCCAATGCAGTCGCTCAGCATTACGTA
AGAATGGCTTTGTGGTGCTCAAAGGCCGGCCATGTAAGATCGTGAGATGTCTACTTGAGAGACTGACTTCCAGCTGATTGGCATCCAGGATGGG
CATCTTTACTGGGAAGAAATATGAAGATATCTGCCGTCAACTCATAATGCAAGGAATGACTTCCAGCTGATTGGCATCCAGGATGGG
TACCTATCACTGCTCTGCCATGACAGGAGGCAGCTGTTGCAATCAAGGCCATGGCAAAATAACTGGCTCCTACACAATTTATTTGACGTTTATTTGGTTTTCCCCA
TCCTGATCACGGTCGTGTCTGCCATGACAGGAGGCAGCTGTTGCAATCAAGGCCATGGCAAAATAACTGGCTCCTACACAATTTATTTGACGTTTATTTGGTTTTCCCCA
CTGAACCTGACAGGCCCCTCCCCGGAGCCCTGCCTTCACCTAGCTCCCTTGGCCAGGAGCGAGCGAAGCTGTGGCCTTGGTGAAGCTGCCCTTCTCCCCTCACAC
CCCCCTCAATCTGTCGGGGAGAAAGGGGTGGGTGCTGCTGTGGTTAGTCTTTTTTTTTTTTTTTAAATTCAATCGGAATCAGAAAGCGGTGGAT
TACAGCCCTGGTGGGGGAGAAAGGGGTGGGTGCCCTCCCCACTCATCCCTGGTCTGGTCTCCCCTGTTGCCCATAGCCCTTACCCTGAGCACCACCCGAGCACCACCCAACAGACTGGGGACCAGCCCC
TCTGGCAAATGTCCTTGTGCCTCCCCAAACCCCTTTAGATGGGAGGGAAGGAGGAGGAGGAGGGGACCTGCCCCCCTGCCCCCTCCTCAGGCATCTGGGAGGGCCCTGCCCCC
CTCGCCTGCCTGTGTCTCTCCCCTGCGGGCTCTCCCCCGACACATTGTTAAAATCAAAACCTGAATAAAACTACAAGTTAATATGAAAAAAAAAAAAAAAAAA
ATGGGCTTTACCCTTCCCTGCGGGCTCTCCCCCGACACATTGTTAAAATCAAAACCTGAATAAAACTACAAGTTAATATGAAAAAAAAAAAAAAAAAA
AAAAAAAAAAAAAAAAAAAAAAAA

FIG.72

NUCLEOTIDE ALIGNMENT OF HUMAN eIF5A1 (ACC. NM_001970) AND HUMAN eIF5A2 (ACC. NM_020390)

```
eIF5a1    1  ATGGCAGATG ACTTGGACTT CGAGACAGGA GATGCAGGGG CCTCAGCCAC
eIF5a2    1  ATGGCAGACG AAATTGATTT CACTACTGGA GATGCCGGGG CTTCCAGCAC eIF5a1   51  CTTCCCAATG CAGTGCTCAG CATTACGtAA GAATGGCTTT GTGGTGCTCA
eIF5a2   51  TTACCCTATG CAGTGCTCGG CCTTGGCcAA AAACGGCTTC GTGGTGCTCA eIF5a1  101  AAGGCCGGCC ATGtAAGATC GTCGAGATGT CTACTTCGAA GACTGGCAAG
eIF5a2  101  AAGGACGACC ATGCAAAATA GTGGAGATGT CAACTTCCAA AACTGGAAAG eIF5a1  151  CACGGCCACG CCAAGGTCCA TCTGGTTGGT ATTGACATCT TtACTGGGAA
eIF5a2  151  CAtGGTCATG CCAAGGTTCA CCTTGTTGGA ATTGATATTT TCACGGGCAA eIF5a1  201  GAAATATGAA GATATCTGCC CGTCAACTCA tAATATGGAT GTCCCCAACA
eIF5a2  201  AAAATATGAA GATATTTGTC CTTCTACTCA CAACATGGAT GTTCCAAATA eIF5a1  251  TCAAAAGGAA TGACTtcCAG CTGATTGGCA TCCAGGATGG GTACCTATCA
eIF5a2  251  TTAAGAGAAA TGATTAtCAA CTGATATGCA TTCAAGATGG TTACTTTCC eIF5a1  301  CTGCTccagG ACAGCGGGGA AACTGGTGA GGTACGAGAG GACCTTCGTC TcCCTGAGGG
eIF5a2  301  CTGCTgacaG AAACTGGTGA AGTTCGTGAG GATCTTAAAC TgCCAGAAGG eIF5a1  351  AGACCTTGGC AAGGAGATTG AGcagAAGTA CGACTGTGGA GAAGAGATCC
eIF5a2  351  TGAACTAGGC AAAGAAATAG AGggaAAATA CAATGCAGGT GAAGATGTAC eIF5a1  401  TGATCACGGT GCTGTcTGCC ATGACAGAGG AGGCAGCTGT TGCAATCAAG
eIF5a2  401  AGGTGTCTGT CATGTGTGCA ATGAGTGAAG AATATGCTGT AGCCATAAAA eIF5a1  451  GCCatgGCAA AATAa
eIF5a2  451  CCCt--GCAA ATAA-
```

FIG. 73A

AMINO ACID ALIGNMENT OF HUMAN eIF5A1 (ACC. NM_001970) AND HUMAN eIF5A2 (ACC. NM_020390)

```
eIF5a1         MADDLDFETG DAGASATFPM QCSALRKNGF VVLKGwPCKI VEMSASKTGK
eIF5a2    1    MADEIDFTTG DAGASSTYPM QCSALRKNGF VVLKGrPCKI VEMSTSKTGK eIF5a1   51    HGHAKVHLVG IDIFTGKKYE DICPSTHNMD VPNIKRNDFQ LIGIQDGYLS
eIF5a2   51    HGHAKVHLVG IDIFTGKKYE DICPSTHNMD VPNIKRNDYQ LICIQDGYLS eIF5a1  101    LLQDSGEVPE DLRLPEGDLG KEIEQKYDCG EEILITLLSA MTEEAAVAIK
eIF5a2  101    LLTETGEVRE DLKLPEGELG KEIEGKYNAG EDVQVSVMCA MSEEYAVAIK eIF5a1  151    amak
eIF5a2  151    pck-
```

FIG. 73B

Time course of U-937 differentiation experiment.

WESTERN BLOT OF HT-29 CELLS TREATED WITH
IFN GAMMA FOR 8 OR 24 HOURS

IFN    -    +    +

HOURS  8    8   24 eIF5A

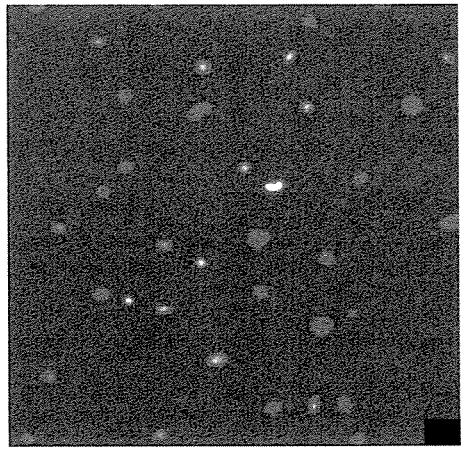
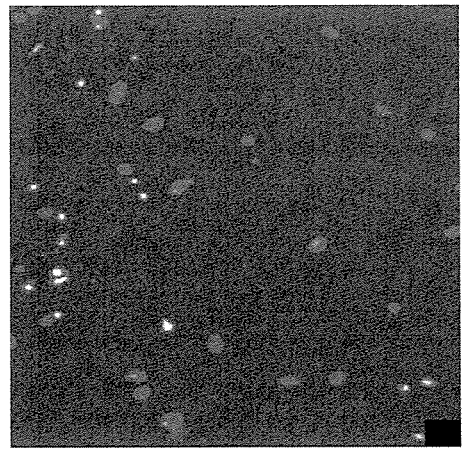
FIG.88B
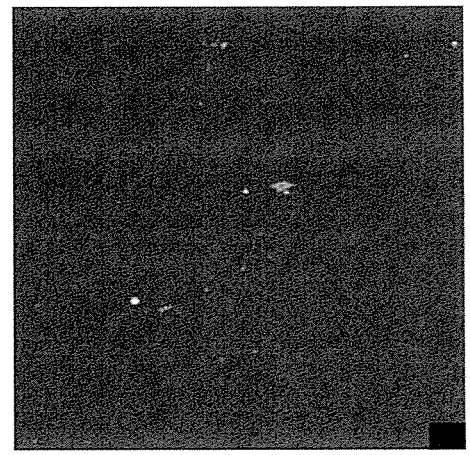
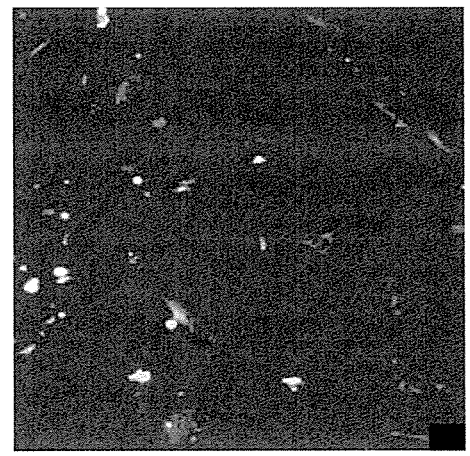
FIG.88A

DESIGN OF siRNAs AGAINST eIF5A1

POSITION OF siRNAs WITHIN eIF5AI mRNA
* TRANSLATION START AND STOP ARE BOLD AND UNDERLINED

```
   1 ggcacgaggg tagaggcggc ggcggcggcg gcagcgggct cggaggcagc ggttgggctc
  61 gcggcgagcg gacggggtcg agtcagtgcg ttcgcgcgag ttggaatcga agcctcttaa
 121 aatggcagat gacttggact tcgagacagg agatgcaggg gcctcagcca ccttcccaat
 181 gcagtgctca gcattacgta agaatggctt tgtggtgctc aaaggccggc catgtaagat
 241 cgtcgagatg tctacttcga agactggcaa gcacggccac gccaaggtcc atctggttgg
 301 tattgacatc tttactggga agaaatatga agatatctgc ccgtcaactc ataatatgga
 361 tgtccccaac atcaaaagga atgacttcca gctgattggc atccaggatg ggtacctatc
 421 actgctccag gacagcgggg aggtacgaga ggaccttcgt ctccctgagg gagaccttgg
 481 caaggagatt gagcagaagt acgactgtgg agaagagatc ctgatcacgg tgctgtctgc
 541 catgacagag gaggcagctg ttgcaatcaa ggccatggca aataactgg ctcccaggat
 601 ggcggtggtg gcagcagtga tcctctgaac ctgcagaggc ccctccccg agcctggcct
 661 ggctctggcc cggtcctaag ctggactcct cctacacaat ttatttgacg ttttattttg
 721 gttttcccca cccctcaat ctgtcgggga gccctgccc ttcacctagc tcccttggcc
 781 aggagcgagc gaagctgtgg ccttggtgaa gctgccctcc tcttctcccc tcacactaca
 841 gccctggtgg gggagaaggg ggtgggtgct gcttgtggtt tagtcttttt ttttttttt
 901 tttttttttt aaattcaatc tggaatcaga aagcggtgga ttctggcaaa tggtccttgt
 961 gccctcccca ctcatccctg gtctggtccc ctgttgccca tagccccttta ccctgagcac
1021 caccccaaca gactggggac cagcccctc gcctgcctgt gtctctcccc aaacccctt
1081 agatggggag ggaagaggag gagaggggag gggacctgcc ccctcctcag gcatctggga
1141 gggccctgcc cccatgggct ttacccttcc ctgcgggctc tctccccgac acatttgtta
1201 aaatcaaacc tgaataaaac tacaagttta atatgaaaaa aaaaaaaaaa aaaaaaaaaa
1261 aaaaaaaaaa aaaaaaaaaa aaaaaaaaaa aaaaaaaaaa aaaaaaaa
```

<u>siRNA # 1 TARGET</u>
<u>siRNA # 2 TARGET</u>
<u>siRNA # 3 TARGET</u>
<u>siRNA # 4 TARGET</u>

POSITION OF siRNA TARGETS AND SEQUENCES AND BLAST RESULTS
siRNA # 1 TARGET POSITION 375 TO 395 bp (POSITION 254 TO 274 bp RELATIVE TO START) % G/C = 39.1 BLAST = NONE BUT eIF5A

TARGET     5' AA(AGGAATGACTTCCAGCTGA) 3'  SEQ ID NO:44 siRNA      5'     AAAGGAAUGACUUCCAGCUGAdTdT 3'  SEQ ID NO:45
           3' dTdTUUUCCUUACUGAAGGUCGACU 5'  SEQ ID NO:46

FIG.89A siRNA # 2 TARGET POSITION 236 TO 256 (115 TO 135 bp RELATIVE TO START) % G/C = 43.4 BLAST = IDENTICAL TO HYPOTHETICAL PROTEIN IN RAT

TARGET    5' AA(GATCGTCGAGATGTCTACT) 3' SEQ ID NO:47 siRNA    5'    AAGAUCGUCGAGAUGUCUACUdTdT 3' SEQ ID NO:48
         3' dTdTUUCUAGCAGCUCUACAGAUGA 5' SEQ ID NO:49 siRNA # 3 TARGET POSITION 284 TO 304 (163 TO 183 bp RELATIVE TO START) % G/C = 43.4 BLAST = NONE BUT eIF5A

TARGET    5' AA(GGTCCATCTGGTTGGTATT) 3' SEQ ID NO:50 siRNA    5'    AAGGUCCAUCUGGUUGGUAUUdTdT 3' SEQ ID NO:51
         3' dTdTUUCCAGGUAGACCAACCAUAA 3' SEQ ID NO:52 siRNA # 4 TARGET POSITION 678 TO 698 (3'UTR;POSITION 557 TO 577 bp RELATIVE TO START) % G/C = 48 BLAST = NONE BUT eIF5A

TARGET    5' AA(GCTGGACTCCTCCTACACA) 3' SEQ ID NO:53 siRNA    5'    AAGCUGGACUCCUCCUACACAdTdT 3' SEQ ID NO:54
         3' dTdTUUCGACCUGAGGAGGAUGUGU 5' SEQ ID NO:55 siRNA # 5 CONTROL;REVERSE SEQUENCE OF siRNA # 1

% G/C = 39.1 BLAST = GOOD, NO MORE THAN 17/23 % IDENTITY

TARGET    5' AA(AGTCGACCTTCAGTAAGGA) 3' SEQ ID NO:56 siRNA    5'    AAAGUCGACCUUCAGUAAGGAdTdT 3' SEQ ID NO:57
         3' dTdTUUUCAGCUGGAAGUCAUUCCU 5' SEQ ID NO:58

FIG.89B

SIRNA USEFUL TO SUPRESS EXPRESSION OF EIF-5A1

RELATED APPLICATIONS

This application is a divisional application of Ser. No. 11/287,460, filed on Nov. 28, 2005 now U.S. Pat. No. 7,662,796, which is a continuation of U.S. application Ser. No. 11/078,526, filed on Mar. 14, 2005 now abandoned, which is a continuation of U.S. application Ser. No. 10/792,893, filed on Mar. 5, 2004 now abandoned, and also claims priority to U.S. provisional 60/476,194, filed on Jun. 6, 2003; and U.S. provisional 60/504,731, filed on Sep. 22, 2003, all of which are herein incorporated in their entirety.

SEQUENCE LISTING SUBMISSION VIA EFS-WEB

A computer readable text file, entitled "061945-5008-03-SequenceListing.txt" created on or about 3 Nov. 2011 with a file size of about 46 kb contains the sequence listing for this application and is hereby incorporated by reference in its entirety.

FIELD OF THE INVENTION

The present invention relates to apoptosis-specific eucaryotic initiation Factor-5A (eIF-5A) or referred to as apoptosis Factor 5A or Factor 5A1 and deoxyhypusine synthase (DHS). The present invention relates to apoptosis Factor 5A and DHS nucleic acids and polypeptides and methods for inhibiting expression of apoptosis Factor 5A and DHS.

BACKGROUND OF THE INVENTION

Apoptosis is a genetically programmed cellular event that is characterized by well-defined morphological features, such as cell shrinkage, chromatin condensation, nuclear fragmentation, and membrane blebbing. Kerr et al. (1972) Br. J. Cancer, 26, 239-257; Wyllie et al. (1980) Int. Rev. Cytol., 68, 251-306. It plays an important role in normal tissue development and homeostasis, and defects in the apoptotic program are thought to contribute to a wide range of human disorders ranging from neurodegenerative and autoimmunity disorders to neoplasms. Thompson (1995) Science, 267, 1456-1462; Mullauer et al. (2001) Mutat. Res, 488, 211-231. Although the morphological characteristics of apoptotic cells are well characterized, the molecular pathways that regulate this process have only begun to be elucidated.

One group of proteins that is thought to play a key role in apoptosis is a family of cysteine proteases, termed caspases, which appear to be required for most pathways of apoptosis. Creagh & Martin (2001) Biochem. Soc. Trans, 29, 696-701; Dales et al. (2001) Leuk. Lymphoma, 41, 247-253. Caspases trigger apoptosis in response to apoptotic stimuli by cleaving various cellular proteins, which results in classic manifestations of apoptosis, including cell shrinkage, membrane blebbing and DNA fragmentation. Chang & Yang (2000) Microbiol. Mol. Biol. Rev., 64, 821-846.

Pro-apoptotic proteins, such as Bax or Bak, also play a key role in the apoptotic pathway by releasing caspase-activating molecules, such as mitochondrial cytochrome c, thereby promoting cell death through apoptosis. Martinou & Green (2001) Nat. Rev. Mol. Cell. Biol., 2, 63-67; Zou et al. (1997) Cell, 90, 405-413. Anti-apoptotic proteins, such as Bcl-2, promote cell survival by antagonizing the activity of the pro-apoptotic proteins, Bax and Bak. Tsujimoto (1998) Genes Cells, 3, 697-707; Kroemer (1997) Nature Med., 3, 614-620. The ratio of Bax:Bcl-2 is thought to be one way in which cell fate is determined; an excess of Bax promotes apoptosis and an excess of Bcl-2 promotes cell survival. Salomons et al. (1997) Int. J. Cancer, 71, 959-965; Wallace-Brodeur & Lowe (1999) Cell Mol. Life. Sci., 55, 64-75.

Another key protein involved in apoptosis is that encoded by the tumor suppressor gene p53. This protein is a transcription factor that regulates cell growth and induces apoptosis in cells that are damaged and genetically unstable, presumably through up-regulation of Bax. Bold et al. (1997) Surgical Oncology, 6, 133-142; Ronen et al., 1996; Schuler & Green (2001) Biochem. Soc. Trans., 29, 684-688; Ryan et al. (2001) Curr. Opin. Cell Biol., 13, 332-337; Zörnig et al. (2001) Biochem. Biophys. Acta, 1551, F1-F37.

The distinct morphological features that characterize cells undergoing apoptosis have given rise to a number of methods for assessing the onset and progress of apoptosis. One such feature of apoptotic cells that can be exploited for their detection is activation of a flippase, which results in externalization of phosphatidylserine, a phospholipid normally localized to the inner leaflet of the plasma membrane. Fadok et al. (1992) J. Immunol., 149, 4029-4035. Apoptotic cells bearing externalized phosphatidylserine can be detected by staining with a phosphatidylserine-binding protein, Annexin V, conjugated to a fluorescent dye. The characteristic DNA fragmentation that occurs during the apoptotic process can be detected by labeling the exposed 3'-OH ends of the DNA fragments with fluorescein-labeled deoxynucleotides. Fluorescent dyes that bind nucleic acids, such as Hoescht 33258, can be used to detect chromatin condensation and nuclear fragmentation in apoptotic cells. The degree of apoptosis in a cell population can also be inferred from the extent of caspase proteolytic activity present in cellular extracts.

As a genetically defined process, apoptosis, like any other developmental program, can be disrupted by mutation. Alterations in the apoptotic pathways are believed to play a key role in a number of disease processes, including cancer. Wyllie et al. (1980) Int. Rev. Cytol., 68, 251-306; Thompson (1995) Science, 267, 1456-1462; Sen & D'Incalci (1992) FEBS Letters, 307, 122-127; McDonnell et al. (1995) Seminars in Cancer and Biology, 6, 53-60. Investigations into cancer development and progression have traditionally been focused on cellular proliferation. However, the important role that apoptosis plays in tumorigenesis has recently become apparent. In fact, much of what is now known about apoptosis has been learned using tumor models, since the control of apoptosis is invariably altered in some way in tumor cells. Bold et al. (1997) Surgical Oncology, 6, 133-142.

Apoptosis can be triggered during tumor development by a variety of signals. Extracellular signals include growth or survival factor depletion, hypoxia and ionizing radiation. Internal signals that can trigger apoptosis include DNA damage, shortening telomeres, and oncogenic mutations that produce inappropriate proliferative signals. Lowe & Lin (2000) Carcinogenesis, 21, 485-495. Ionizing radiation and nearly all cytotoxic chemotherapy agents used to treat malignancies are thought to act by triggering endogenous apoptotic mechanisms to induce cell death. Rowan & Fisher (1997) Leukemia, 11, 457-465; Kerr et al. (1994) Cancer, 73, 2013-2026; Martin & Schwartz (1997) Oncology Research, 9, 1-5.

Evidence would suggest that early in the progression of cancer, tumor cells are sensitive to agents (such as ionizing radiation or chemotherapeutic drugs) that induce apoptosis. However, as the tumor progresses, the cells develop resistance to apoptotic stimuli. Naik et al. (1996) Genes and Development, 10, 2105-2116. This may explain why early cancers respond better to treatment than more advanced lesions. The ability of late-stage cancers to develop resistance to chemotherapy and radiation therapy appears to be linked to alterations in the apoptotic pathway that limit the ability of tumor cells to respond to apoptotic stimuli. Reed et al. (1996) *Journal of Cellular Biology,* 60, 23-32; Meyn et al. (1996) *Cancer Metastasis Reviews,* 15, 119-131; Hannun (1997) *Blood,* 89, 1845-1853; Reed (1995) *Toxicology Letters,* 82-83, 155-158; Hickman (1996) *European Journal of Cancer,* 32A, 921-926. Resistance to chemotherapy has been correlated to overexpression of the anti-apoptotic gene bcl-2 and deletion or mutation of the pro-apoptotic bax gene in chronic lymphocytic leukemia and colon cancer, respectively.

The ability of tumor cells to successfully establish disseminated metastases also appears to involve alterations in the apoptotic pathway. Bold et al. (1997) *Surgical Oncology,* 6, 133-142. For example, mutations in the tumor suppressor gene p53 are thought to occur in 70% of tumors. Evan et al. (1995) *Curr. Opin. Cell Biol.,* 7, 825-834. Mutations that inactivate p53 limit the ability of cells to induce apoptosis in response to DNA damage, leaving the cell vulnerable to further mutations. Ko & Prives (1996) *Genes and Development,* 10, 1054-1072.

Therefore, apoptosis is intimately involved in the development and progression of neoplastic transformation and metastases, and a better understanding of the apoptotic pathways involved may lead to new potential targets for the treatment of cancer by the modulation of apoptotic pathways through gene therapy approaches. Bold et al. (1997) *Surgical Oncology,* 6, 133-142.

The present invention relates to cloning of an eIF-5A cDNA that is up regulated immediately before the induction of apoptosis. This apoptosis-specific eIF-5A is likely to be a suitable target for intervention in apoptosis-causing disease states since it appears to act at the level of post-transcriptional regulation of downstream effectors and transcription factors involved in the apoptotic pathway. Specifically, the apoptosis-specific eIF-5A appears to selectively facilitate the translocation of mRNAs encoding downstream effectors and transcription factors of apoptosis from the nucleus to the cytoplasm, where they are subsequently translated. The ultimate decision to initiate apoptosis appears to stem from a complex interaction between internal and external pro- and anti-apoptotic signals. Lowe & Lin (2000) *Carcinogenesis,* 21, 485-495. Through its ability to facilitate the translation of downstream apoptosis effectors and transcription factors, the apoptosis-related eIF-5A appears to tip the balance between these signals in favor of apoptosis.

As described previously, it is well established that anti-cancer agents induce apoptosis and that alterations in the apoptotic pathways can attenuate drug-induced cell death. Schmitt & Lowe (1999) *J. Pathol.,* 187, 127-137. For example, many anticancer drugs upregulate p53, and tumor cells that have lost p53 develop resistance to these drugs. However, nearly all chemotherapy agents can induce apoptosis independently of p53 if the dose is sufficient, indicating that even in drug-resistant tumors, the pathways to apoptosis are not completely blocked. Wallace-Brodeur & Lowe (1999) *Cell Mol. Life. Sci.,* 55, 64-75. This suggests that induction of apoptosis eIF-5A, even though it may not correct the mutated gene, may be able to circumvent the p53-dependent pathway and induce apoptosis by promoting alternative pathways.

Induction of apoptosis-related eIF-5A has the potential to selectively target cancer cells while having little or no effect on normal neighboring cells. This arises because mitogenic oncogenes expressed in tumor cells provide an apoptotic signal in the form of specific species of mRNA that are not present in normal cells. Lowe et al. (1993) *Cell,* 74, 954-967; Lowe & Lin (2000) *Carcinogenesis,* 21, 485-495. For example, restoration of wild-type p53 in p53-mutant tumor cells can directly induce apoptosis as well as increase drug sensitivity in tumor cell lines and xenographs. (Spitz et al., 1996; Badie et al. 1998).

The selectivity of apoptosis-eIF-5A arises from the fact that it selectively facilitates translation of mRNAs for downstream apoptosis effectors and transcription factors by mediating their translocation from the nucleus into the cytoplasm. Thus, for apoptosis eIF-5A to have an effect, mRNAs for these effectors and transcription factors have to be transcribed. Inasmuch as these mRNAs would be transcribed in cancer cells, but not in neighboring normal cells, it is to be expected that apoptosis eIF-5A would promote apoptosis in cancer cells but have minimal, if any, effect on normal cells. Thus, restoration of apoptotic potential in tumor cells with apoptosis-related eIF-5A may decrease the toxicity and side effects experienced by cancer patients due to selective targeting of tumor cells. Induction of apoptotic eIF-5A also has the potential to potentiate the response of tumor cells to anti-cancer drugs and thereby improve the effectiveness of these agents against drug-resistant tumors. This in turn could result in lower doses of anti-cancer drugs for efficacy and reduced toxicity to the patient.

Alternations in the apoptotic pathways are also believed to play a role in degeneration of retinal ganglion cells causing blindness due to glaucoma. Glaucoma describes a group of eye conditions in which increased intra-ocular pressure (IOP) leads to damage of the optic nerve and progressive blindness. Although glaucoma is currently managed by drugs or surgery to control IOP to reduce damage to the optic nerve or the use of neuro-protectors, there remains a need to protect retinal ganglion cells from degeneration by apoptosis in the glaucomatous eye.

Cytokines have also been implicated in the apoptotic pathway. Biological systems require cellular interactions for their regulation, and cross-talk between cells generally involves a large variety of cytokines. Cytokines are mediators that are produced in response to a wide variety of stimuli by many different cell types. Cytokines are pleiotropic molecules that can exert many different effects on many different cell types, but are especially important in regulation of the immune response and hematopoietic cell proliferation and differentiation. The actions of cytokines on target cells can promote cell survival, proliferation, activation, differentiation, or apoptosis depending on the particular cytokine, relative concentration, and presence of other mediators.

The use of anti-cytokines to treat autoimmune disorders (psoriasis, rheumatoid arthritis, Crohn's disease) is gaining popularity. The pro-inflammatory cytokines IL-1 and TNF play a large role in the pathology of these chronic disorders and anti-cytokine to therapies that reduce the biological activities of these two cytokines can provide therapeutic benefits (Dinarello and Abraham, 2002).

Interleukin 1 (IL-1) is an important cytokine that mediates local and systemic inflammatory reactions and which can synergize with TNF in the pathogenesis of many disorders, including vasculitis, osteoporosis, neurodegenerative disorders, diabetes, lupus nephritis, and autoimmune disorders such as rheumatoid arthritis. The importance of IL-1β in tumour angiogenesis and invasiveness was also recently demonstrated by the resistance of IL-1β knockout mice to metastases and angiogenesis when injected with melanoma cells (Voronov et al., 2003).

Interleukin 18 (IL-18) is a recently discovered member of the IL-1 family and is related by structure, receptors, and function to IL-1. IL-18 is a central cytokine involved in inflammatory and autoimmune disorders as a result of its ability to induce interferon-gamma (IFN-λ), TNF-α, and IL-1. IL-1β and IL-18 are both capable of inducing production of TNF-α, a cytokine known to contribute to cardiac dysfunction during myocardial ischemia (Maekawa et al., 2002). Inhibition of IL-18 by neutralization with an IL-18 binding protein was found to reduce ischemia-induced myocardial dysfunction in an ischemia/reperfusion model of suprafused human atrial myocardium (Dinarello, 2001). Neutralization of IL-18 using a mouse IL-18 binding protein was also able to decrease IFN-λ, TNF-α, and IL-1β transcript levels and reduce joint damage in a collagen-induced arthritis mouse model (Banda et al., 2003). A reduction of IL-18 production or availability may also prove beneficial to control metastatic cancer as injection of IL-18 binding protein in a mouse melanoma model successfully inhibited metastases (Carrascal et al., 2003). As a further indication of its importance as a pro-inflammatory cytokine, plasma levels of IL-18 were elevated in patients with chronic liver disease and increased levels were correlated with the severity of the disease (Ludwiczek et al., 2002). Similarly, IL-18 and TNF-α were elevated in the serum of diabetes mellitus patients with nephropathy (Moriwaki et al., 2003). Neuroinflammation following traumatic brain injury is also mediated by pro-inflammatory cytokines and inhibition of IL-18 by the IL-18 binding protein improved neurological recovery in mice following brain trauma (Yatsiv et al., 2002).

TNF-α, a member of the TNF family of cytokines, is a pro-inflammatory cytokine with pleiotropic effects ranging from co-mitogenic effects on hematopoietic cells, induction of inflammatory responses, and induction of cell death in many cell types. TNF-α is normally induced by bacterial lipopolysaccharides, parasites, viruses, malignant cells and cytokines and usually acts beneficially to protect cells from infection and cancer. However, inappropriate induction of TNF-α is a major contributor to disorders resulting from acute and chronic inflammation such as autoimmune disorders and can also contribute to cancer, AIDS, heart disease, and sepsis (reviewed by Aggarwal and Natarajan, 1996; Sharma and Anker, 2002). Experimental animal models of disease (i.e. septic shock and rheumatoid arthritis) as well as human disorders (i.e. inflammatory bowel diseases and acute graft-versus-host disease) have demonstrated the beneficial effects of blocking TNF-α (Wallach et al., 1999). Inhibition of TNF-α has also been effective in providing relief to patients suffering autoimmune disorders such as Crohn's disease (van Deventer, 1999) and rheumatoid arthritis (Richard-Miceli and Dougados, 2001). The ability of TNF-α to promote the survival and growth of B lymphocytes is also thought to play a role in the pathogenesis of B-cell chronic lymphocytic leukemia (B-CLL) and the levels of TNF-α being expressed by T cells in B-CLL was positively correlated with tumour mass and stage of the disease (Bojarska-Junak et al., 2002). Interleukin-1β (IL-1β) is a cytokine known to induce TNF-α production.

Deoxyhypusine synthase (DHS) and hypusine-containing eucaryotic translation initiation Factor-5A (eIF-5A) are known to play important roles in many cellular processes including cell growth and differentiation. Hypusine, a unique amino acid, is found in all examined eucaryotes and archaebacteria, but not in eubacteria, and eIF-5A is the only known hypusine-containing protein. Park (1988) J. Biol. Chem., 263, 7447-7449; Schümann & Klink (1989) System. Appl. Microbiol., 11, 103-107; Bartig et al. (1990) System. Appl. Microbiol., 13, 112-116; Gordon et al. (1987a) J. Biol. Chem., 262, 16585-16589. Active eIF-5A is formed in two post-translational steps: the first step is the formation of a deoxyhypusine residue by the transfer of the 4-aminobutyl moiety of spermidine to the α-amino group of a specific lysine of the precursor eIF-5A catalyzed by deoxyhypusine synthase; the second step involves the hydroxylation of this 4-aminobutyl moiety by deoxyhypusine hydroxylase to form hypusine.

The amino acid sequence of eIF-5A is well conserved between species, and there is strict conservation of the amino acid sequence surrounding the hypusine residue in eIf-5A, which suggests that this modification may be important for survival. Park et al. (1993) Biofactors, 4, 95-104. This assumption is further supported by the observation that inactivation of both isoforms of eIF-5A found to date in yeast, or inactivation of the DHS gene, which catalyzes the first step in their activation, blocks cell division. Schnier et al. (1991) Mol. Cell. Biol., 11, 3105-3114; Sasaki et al. (1996) FEBS Lett., 384, 151-154; Park et al. (1998) J. Biol. Chem., 273, 1677-1683. However, depletion of eIF-5A protein in yeast resulted in only a small decrease in total protein synthesis suggesting that eIF-5A may be required for the translation of specific subsets of mRNA's rather than for protein global synthesis. Kang et al. (1993), "Effect of initiation factor eIF-5A depletion on cell proliferation and protein synthesis," in Tuite, M. (ed.), Protein Synthesis and Targeting in Yeast, NATO Series H. The recent finding that ligands that bind eIF-5A share highly conserved motifs also supports the importance of eIF-5A. Xu & Chen (2001) J. Biol. Chem., 276, 2555-2561. In addition, the hypusine residue of modified eIF-5A was found to be essential for sequence-specific binding to RNA, and binding did not provide protection from ribonucleases.

In addition, intracellular depletion of eIF-5A results in a significant accumulation of specific mRNAs in the nucleus, indicating that eIF-5A may be responsible for shuttling specific classes of mRNAs from the nucleus to the cytoplasm. Liu & Tartakoff (1997) Supplement to Molecular Biology of the Cell, 8, 426a. Abstract No. 2476, 37th American Society for Cell Biology Annual Meeting. The accumulation of eIF-5A at nuclear pore-associated intranuclear filaments and its interaction with a general nuclear export receptor further suggest that eIF-5A is a nucleocytoplasmic shuttle protein, rather than a component of polysomes. Rosorius et al. (1999) J. Cell Science, 112, 2369-2380.

The first cDNA for eIF-5A was cloned from human in 1989 by Smit-McBride et al., and since then cDNAs or genes for eIF-5A have been cloned from various eukaryotes including yeast, rat, chick embryo, alfalfa, and tomato. Smit-McBride et al. (1989a) J. Biol. Chem., 264, 1578-1583; Schnier et al. (1991) (yeast); Sano, A. (1995) in Imahori, M. et al. (eds), Polyamines, Basic and Clinical Aspects, VNU Science Press, The Netherlands, 81-88 (rat); Rinaudo & Park (1992) FASEB J., 6, A453 (chick embryo); Pay et al. (1991) Plant Mol. Biol., 17, 927-929 (alfalfa); Wang et al. (2001) J. Biol. Chem., 276, 17541-17549 (tomato).

Expression of eIF-5A mRNA has been explored in various human tissues and mammalian cell lines. For example, changes in eIF-5A expression have been observed in human fibroblast cells after addition of serum following serum deprivation. Pang & Chen (1994) J. Cell Physiol., 160, 531-538. Age-related decreases in deoxyhypusine synthase activity and abundance of precursor eIF-5A have also been observed in senescing fibroblast cells, although the possibility that this reflects averaging of differential changes in isoforms was not determined. Chen & Chen (1997b) J. Cell Physiol., 170, 248-254.

Studies have shown that eIF-5A may be the cellular target of viral proteins such as the human immunodeficiency virus type 1 Rev protein and human T cell leukemia virus type 1 Rex protein. Ruhl et al. (1993) J. Cell Biol., 123, 1309-1320; Katahira et al. (1995) J. Virol., 69, 3125-3133. Preliminary studies indicate that eIF-5A may target RNA by interacting with other RNA-binding proteins such as Rev, suggesting that these viral proteins may recruit eIF-5A for viral RNA processing. Liu et al. (1997) Biol. Signals, 6, 166-174.

Thus, although eIF-5A and DHS are known, there remains a need in understanding how these proteins are involved in apoptotic pathways as well as cytokine stimulation to be able to modulate apoptosis and cytokine expression. The present invention fulfills this need.

SUMMARY OF INVENTION

The present invention relates to apoptosis specific eucaryotic initiation factor 5A (eIF-5A), referred to as apoptosis factor 5A1 or simply factor 5A1. The present invention also relates to apoptosis factor 5A1 nucleic acids and polypeptides and methods for inhibiting or suppressing apoptosis in cells using antisense nucleotides or siRNAs to inhibit expression of factor 5A 1. The invention also relates to suppressing or inhibiting expression of pro-inflammatory cytokines by inhibiting expression of apoptosis factor 5A1. Further, the present invention relates to inhibiting or suppressing expression of p53 by inhibiting expression of apoptosis factor 5A1. The present invention also relates to a method of increasing Bcl-2 expression by inhibiting or suppressing expression of apoptosis factor 5A1 using antisense nucleotides or siRNAs. The present invention also provides a method of inhibiting production of cytokines, especially TNF-α in human epithelial cells. In another embodiment of the present invention, suppressing expression of apoptosis-specific eIF-5A1 by the use of antisense oligonucleotides targeted at apoptosis-specific eIF-5A1 provides methods of preventing retinal ganglion cell death in a glaucomatous eye.

BRIEF DESCRIPTION OF THE DRAWINGS

FIG. 1 depicts the nucleotide sequence (SEQ ID NO: 11) and derived amino acid sequence (SEQ ID NO: 12) of the 3' end of rat apoptosis-specific eIF-5A.

FIG. 2 depicts the nucleotide sequence (SEQ ID NO: 15) and derived amino acid sequence (SEQ ID NO: 16) of the 5' end of rat apoptosis-specific eIF-5A cDNA.

FIG. 3 depicts the nucleotide sequence of rat corpus luteum apoptosis-specific eIF-5A full-length cDNA (SEQ ID NO: 1). The amino acid sequence is shown in SEQ ID NO: 2.

FIG. 4 depicts the nucleotide sequence (SEQ ID NO: 6) and derived amino acid sequence (SEQ ID NO: 7) of the 3' end of rat apoptosis-specific DHS cDNA.

FIG. 5 is an alignment of the full-length nucleotide sequence of rat corpus luteum apoptosis-specific eIF-5A cDNA (SEQ ID NO: 20) with the nucleotide sequence of human eIF-5A (SEQ ID NO: 3) (Accession number BC000751 or NM_001970, SEQ ID NO:3).

FIG. 6 is an alignment of the full-length nucleotide sequence of rat corpus luteum apoptosis-specific cDNA (SEQ ID NO: 20) with the nucleotide sequence of human eIF-5A (SEQ ID NO: 4) (Accession number NM_020390, SEQ ID NO:4).

FIG. 7 is an alignment of the full-length nucleotide sequence of rat corpus luteum apoptosis-specific eIF-5A cDNA (SEQ ID NO: 20) with the nucleotide sequence of mouse eIF-5A (Accession number BC003889). Mouse nucleotide sequence (Accession number BC003889) is SEQ ID NO:5.

FIG. 8 is an alignment of the derived full-length amino acid sequence of rat corpus luteum apoptosis-specific eIF-5A (SEQ ID NO: 2) with the derived amino acid sequence of human eIF-5A (SEQ ID NO: 21) (Accession number BC000751 or NM_001970).

FIG. 9 is an alignment of the derived full-length amino acid sequence of rat corpus luteum apoptosis-specific eIF-5A (SEQ ID NO: 2) with the derived amino acid sequence to of human eIF-5A (SEQ ID NO: 22) (Accession number NM_020390).

FIG. 10 is an alignment of the derived full-length amino acid sequence of rat corpus luteum apoptosis-specific eIF-5A (SEQ ID NO: 2) with the derived amino acid sequence of mouse eIF-5A (SEQ ID NO: 23) (Accession number BC003889).

FIG. 11 is an alignment of the partial-length nucleotide sequence of rat corpus luteum apoptosis-specific DHS cDNA (residues 1-453 of SEQ ID NO: 6) with the nucleotide sequence of human DHS (SEQ ID NO: 8) (Accession number BC000333, SEQ ID NO:8).

FIG. 27 illustrates detection of apoptosis as reflected by increased nuclear fragmentation when COS-7 cells were transiently transfected with pHM6 containing full-length rat apoptosis-specific eIF-5A in the sense orientation.

FIG. 29 illustrates detection of apoptosis as reflected by phosphatidylserine exposure when COS-7 cells were transiently transfected with pHM6 containing full-length rat apoptosis-specific eIF-5A in the sense orientation.

FIG. 38 is an alignment of human eIF-5A2 isolated from RKO cells (SEQ ID NO: 24) with the sequence of human eIF-5A2 (SEQ ID NO: 22) (Genbank accession number XM_113401). The consensus sequence is shown in SEQ ID NO: 28.

were measured and compared to the expression levels of the heart tissue before it was damaged by ischemia.

Figure 48:
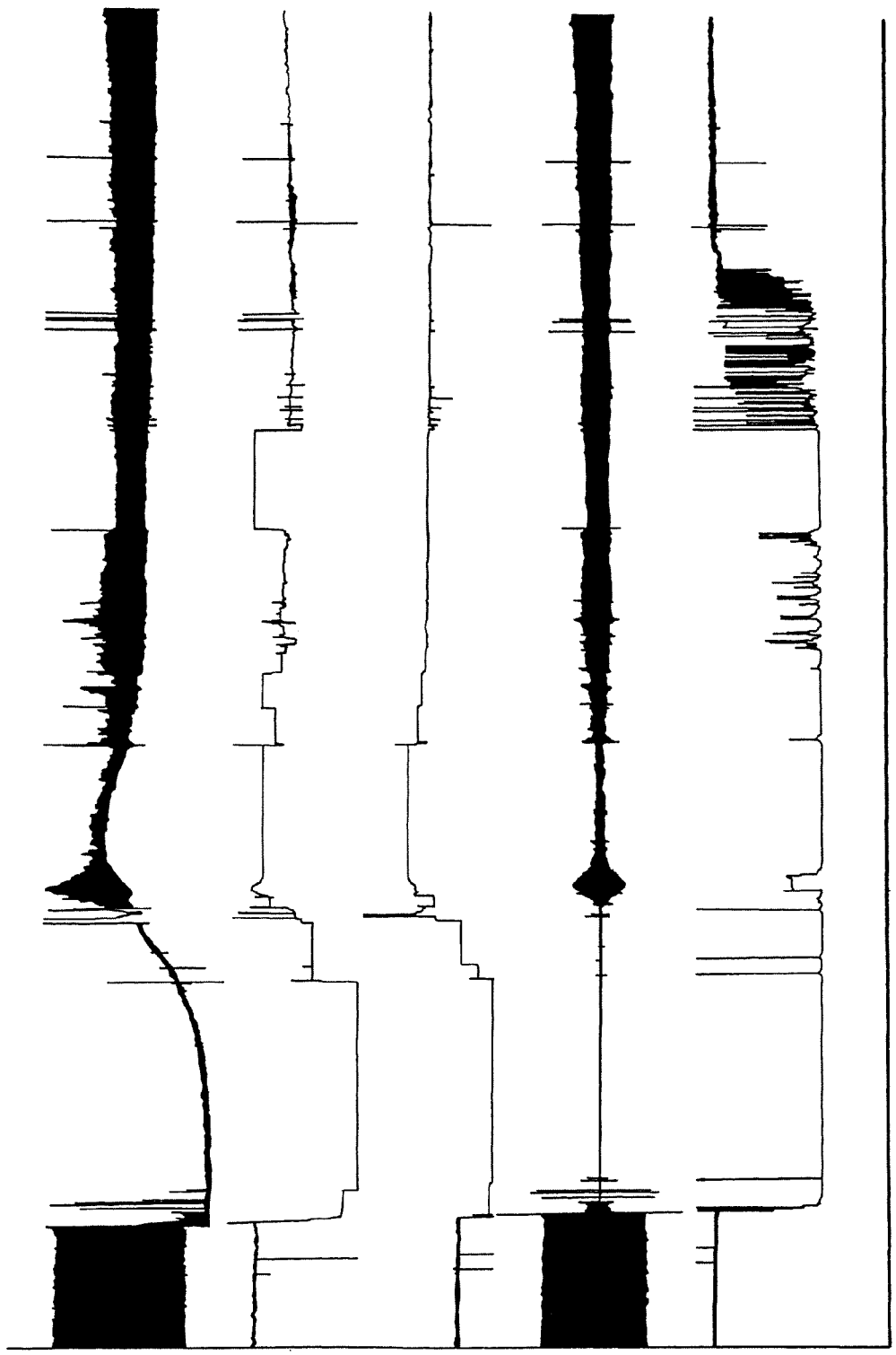

FIG. 48 shows EKGs of heart tissue before and after the ischemia was induced.

Figure 47:
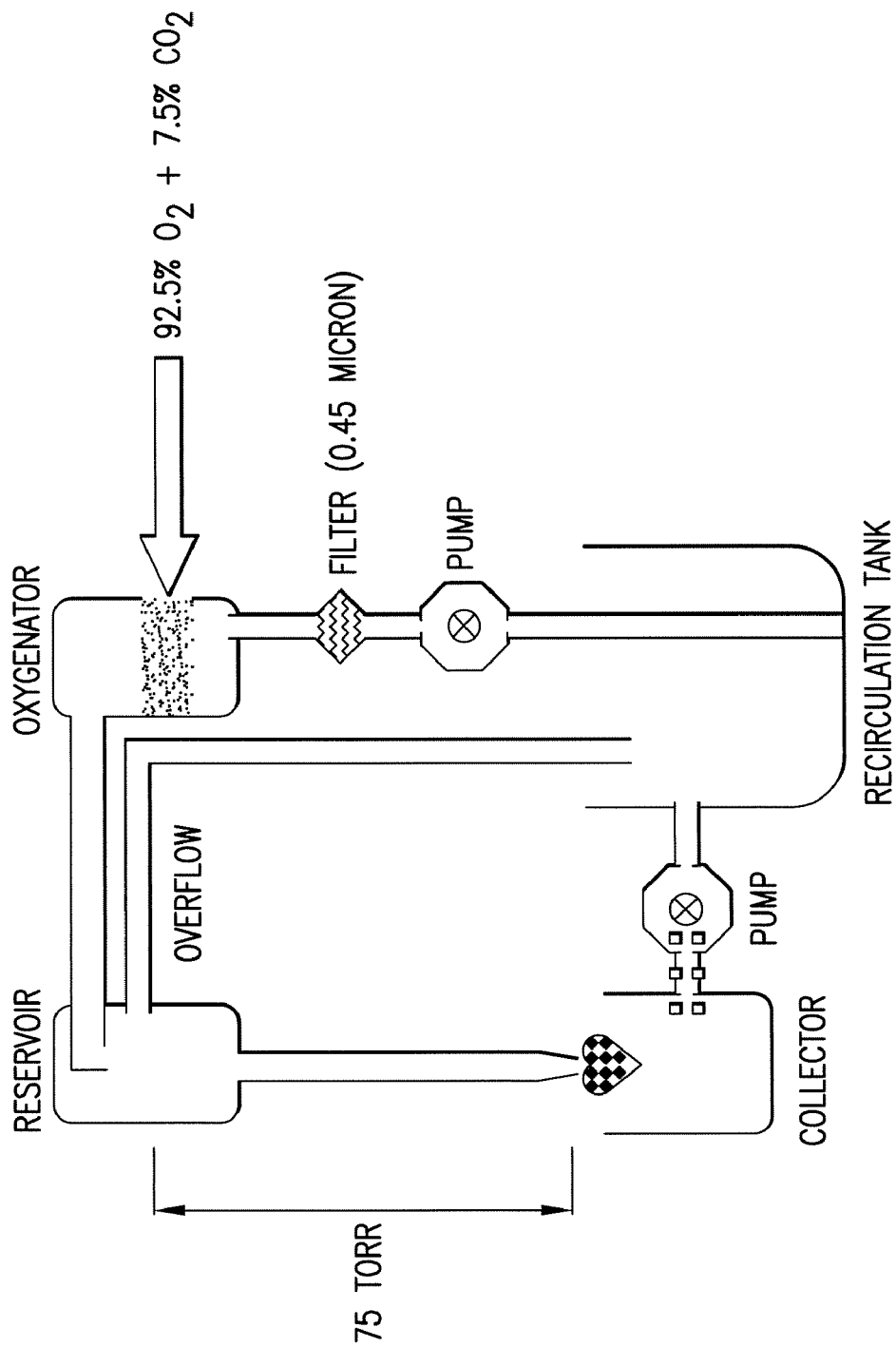
FIG. 47 depicts schematically an experiment performed on heart tissue. The heart tissue was exposed to normal oxygen levels and the expression levels of apoptosis-specific eIF-5A (eIF5a) and proliferating eIF-5A (eIF5b) measured. Later, the amount of oxygen delivered to the heart tissue was lowered, thus inducing hypoxia and ischemia, and ultimately, a heart attack in the heart tissue. The expression levels of apoptosis-specific eIF-5A (eIF5a) and proliferating eIF-5A (eIF5b)
Figure 49:
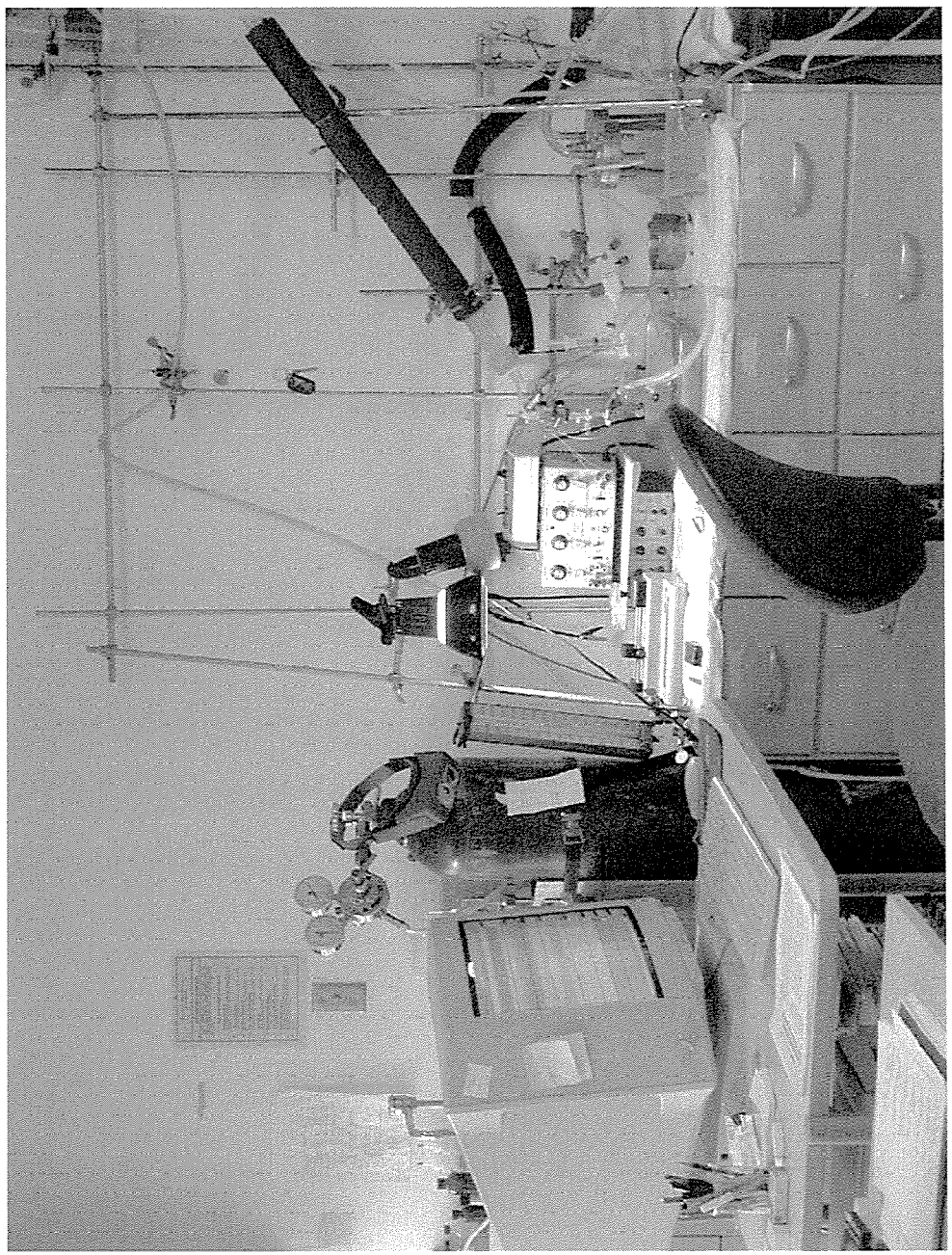

FIG. 49 shows the lab bench with the set up of the experiment depicted in FIG. 47.

Figure 50C:
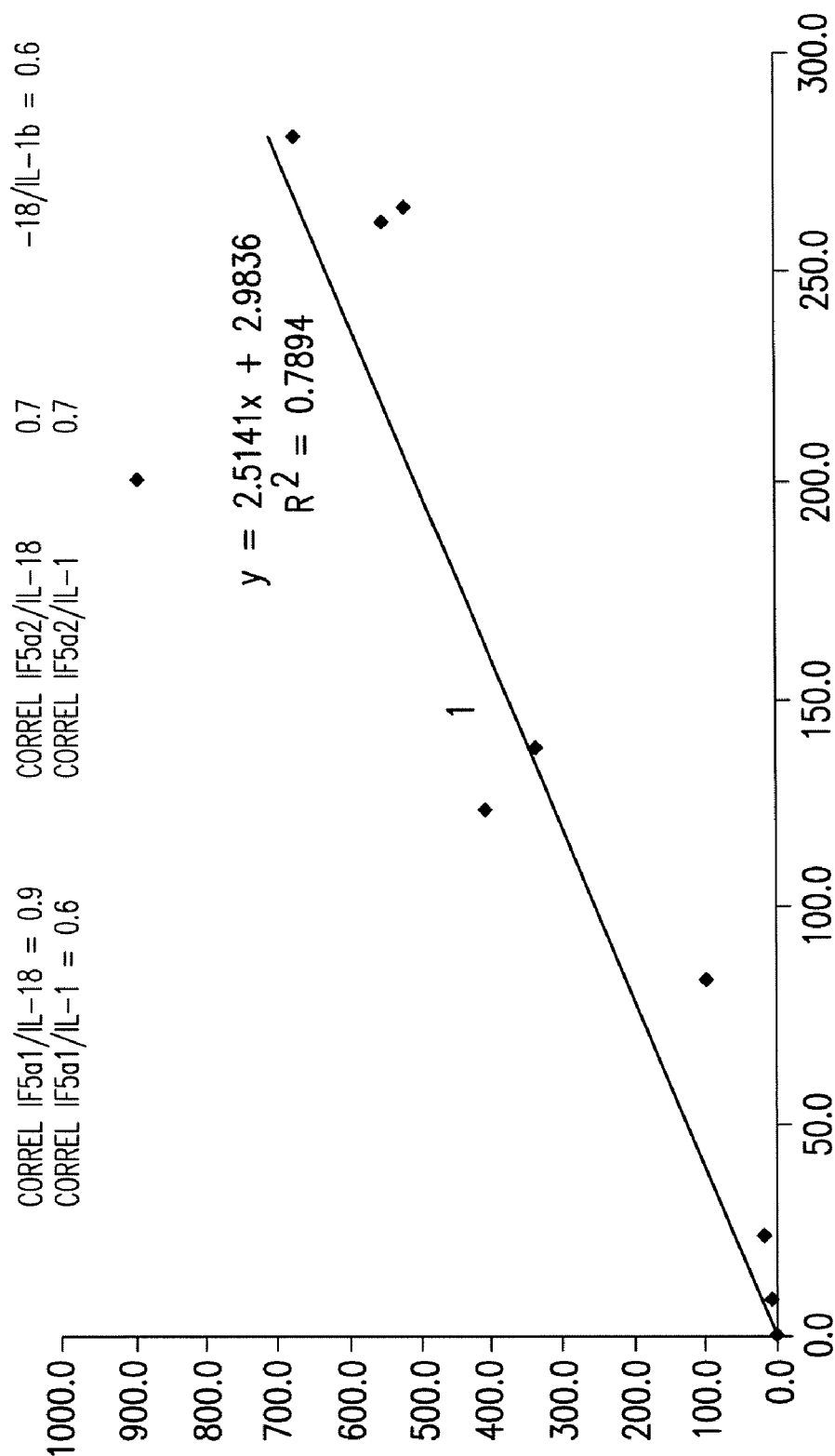
Figure 50D:
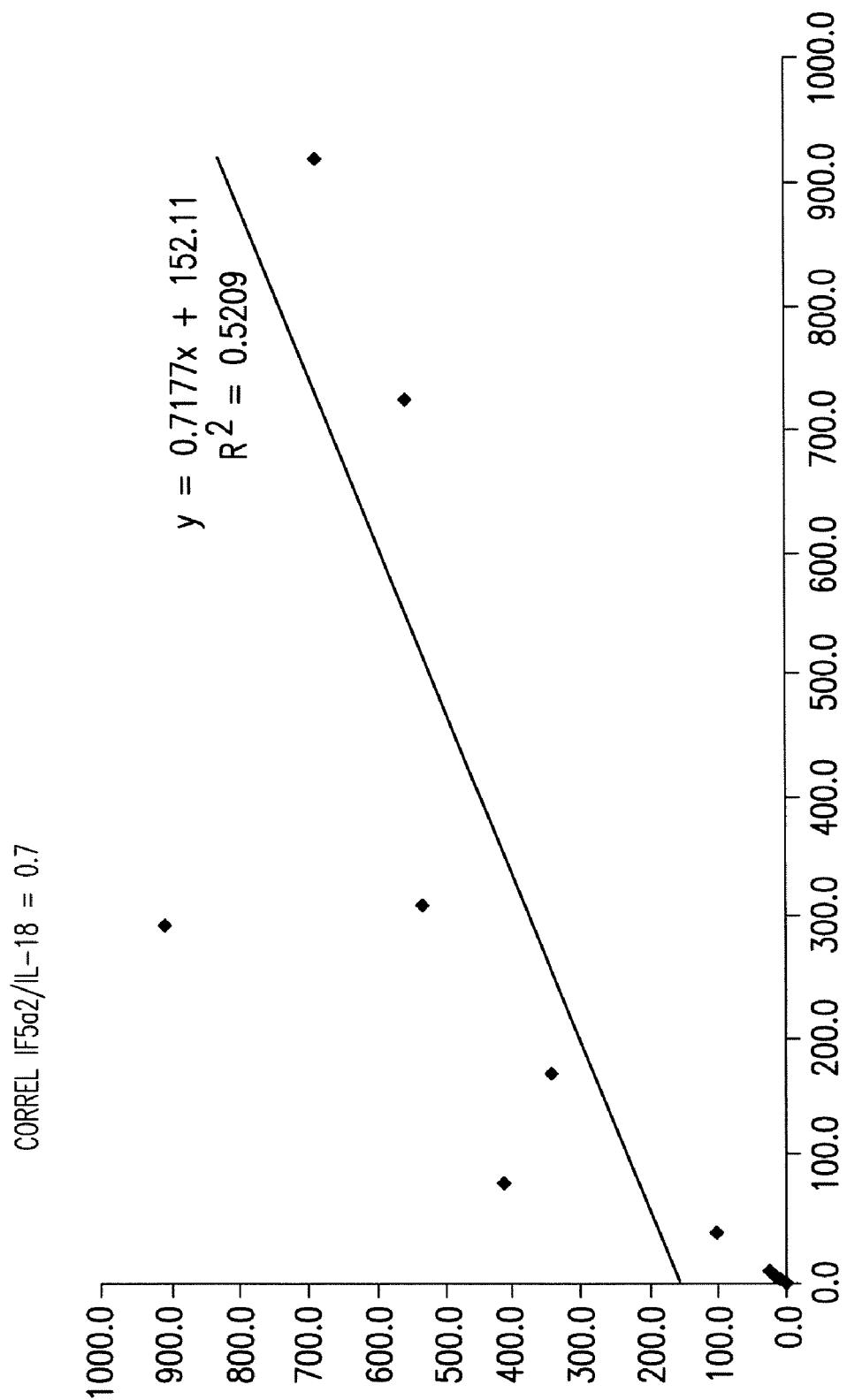
Figure 50E:
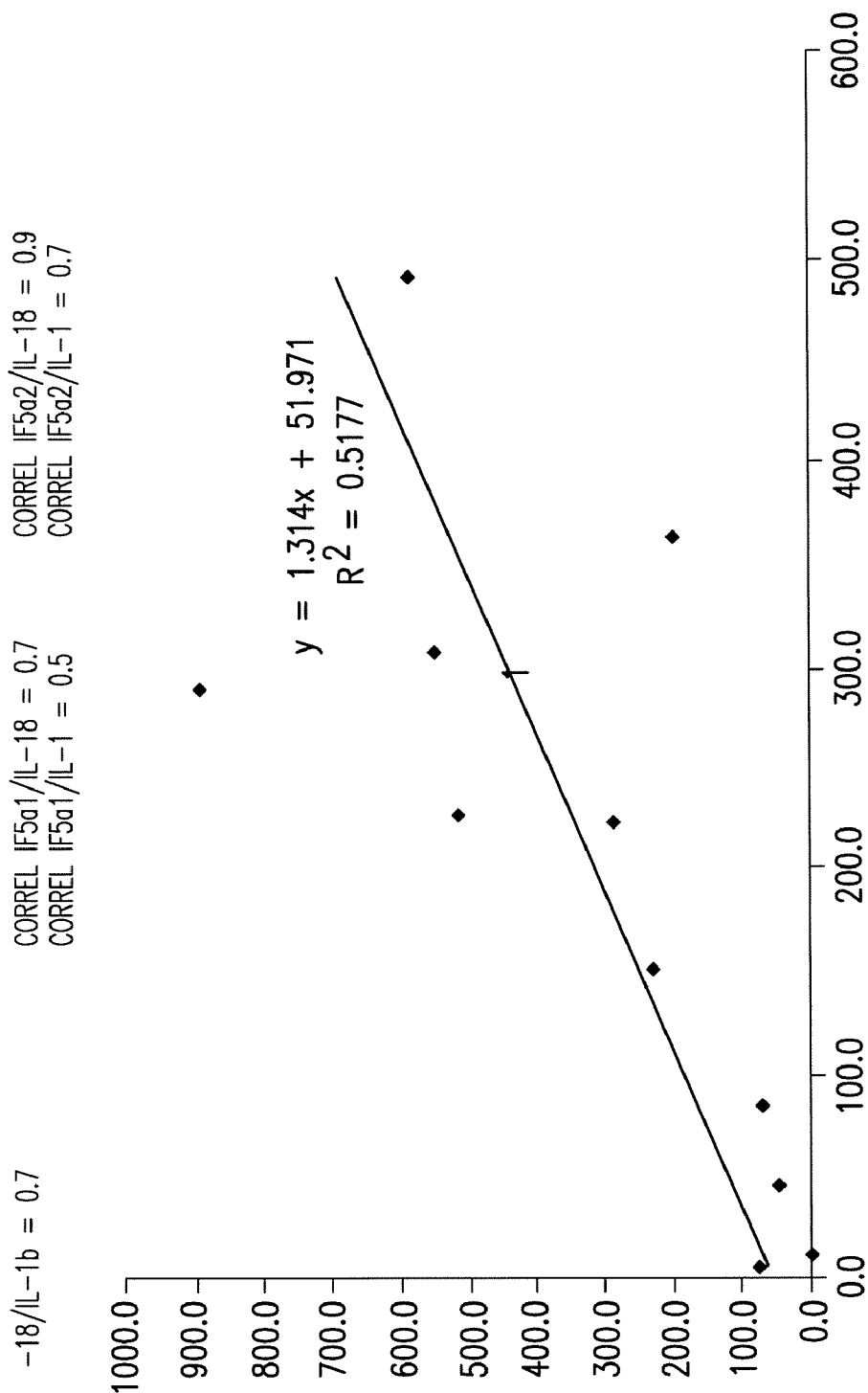
Figure 50F:
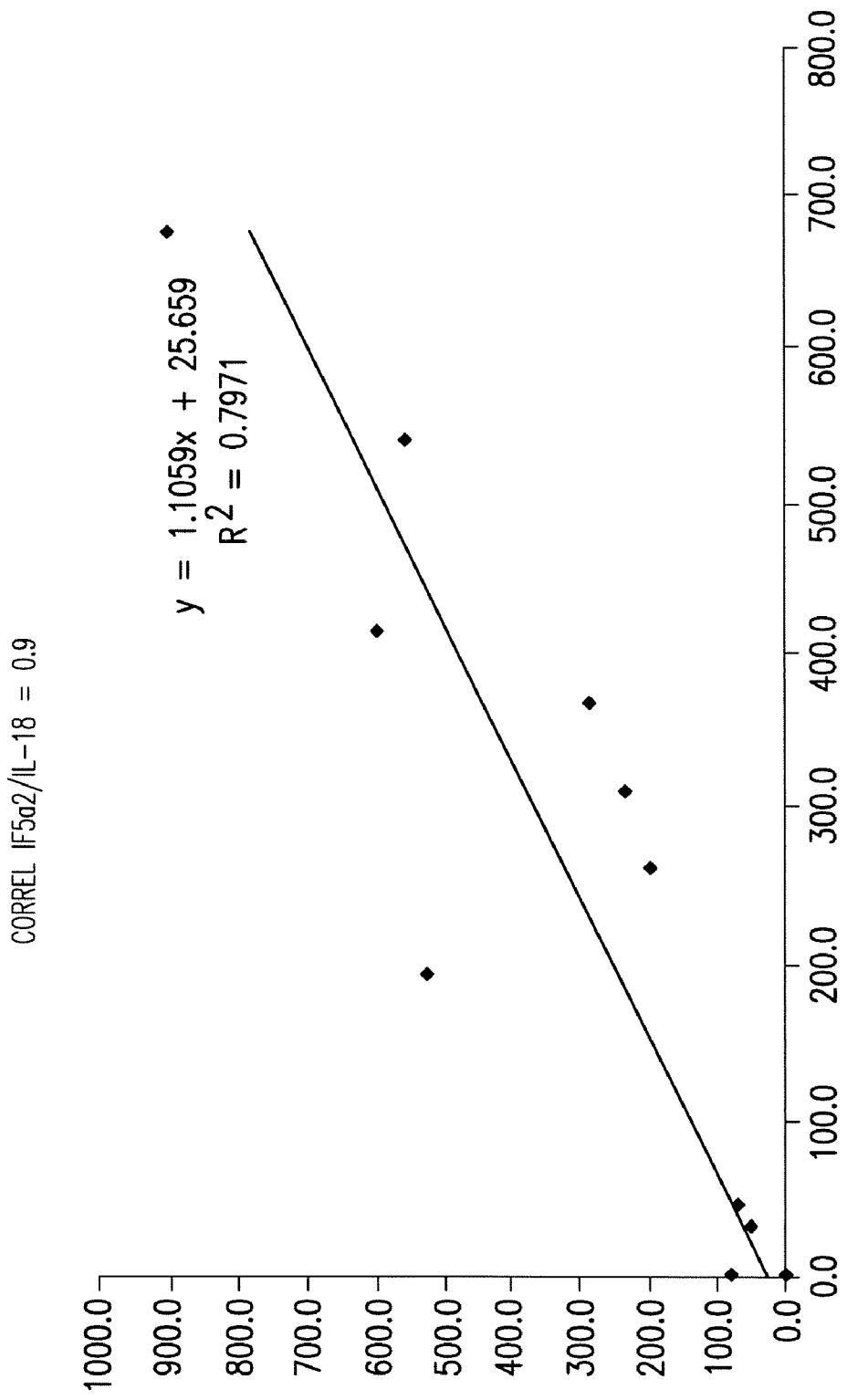

FIGS. 50A-F report patient data where the levels of Apoptosis Factor eIF-5a (also denoted as eIf-5a1 or on the chart as IF5a1) are correlated with levels of IL-1β and IL-18. FIG. 50A is a chart of data obtained from coronary artery bypass graft (CABG) patients. FIG. 50B is a chart of data obtained from valve replacement patients. FIG. 50C is a graph depicting the correlation of apoptosis factor eIF-5a (Factor 5a1) to IL-18 in CABG patients. FIG. 50D is a graph depicting the correlation of proliferating eIF-5a (Factor a2) to IL-18 in CABG patients. FIG. 50E is a graph depicting the correlation of apoptosis factor eIF-5a (Factor 5a1) to IL-18 in valve replacement patients. FIG. 50F is a graph depicting the correlation of proliferating eIF-5a (Factor a2) to IL-18 in valve replacement patients.

FIG. 51 is a chart of the patient's data from which patients data used in FIGS. 50A-F was obtained.

Figure 52:
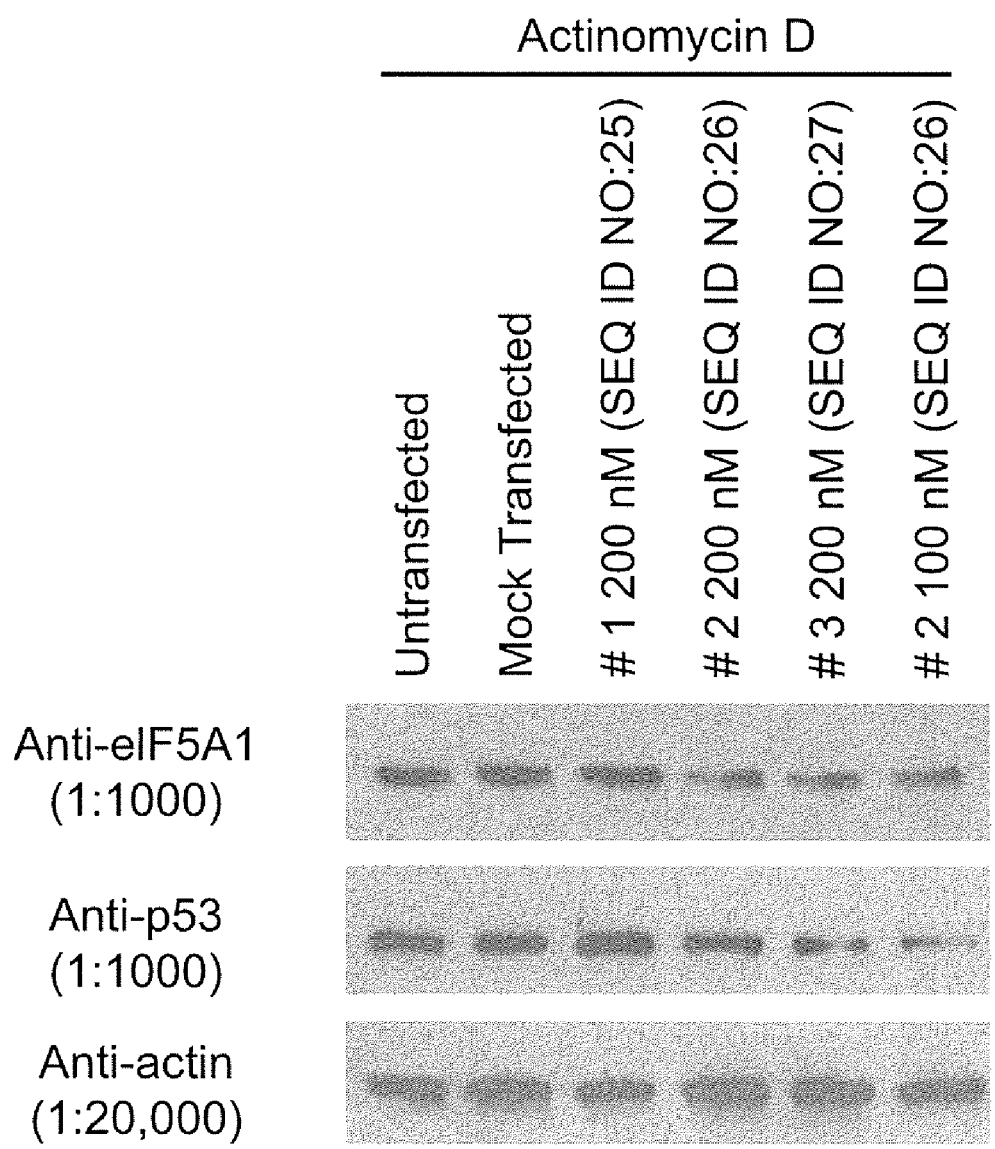

FIG. 52 shows the levels of protein produced by RKO cells after being treated with antisense oligo 1, 2 and 3 (to apoptosis factor 5A). The RKO cells produced less apoptosis factor 5A as well as less p53 after having been transfected with the antisense apoptosis factor 5A nucleotides.

Figure 53A:
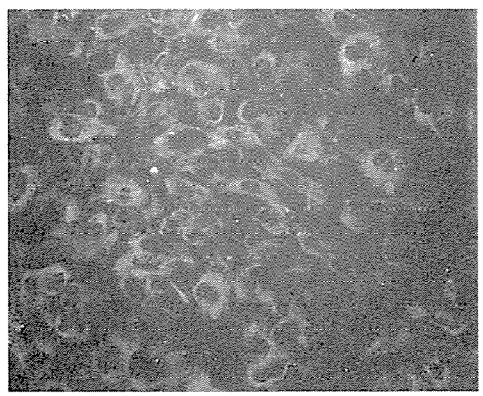
Figure 53B:
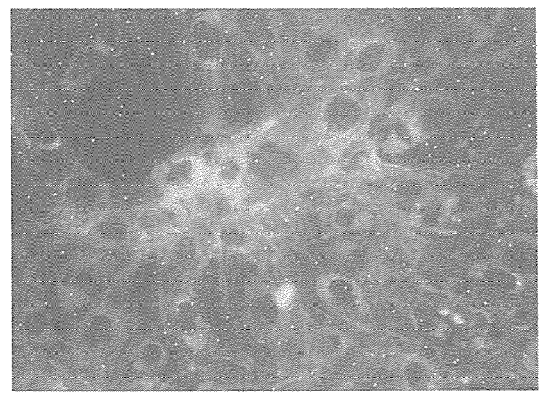
Figure 54:
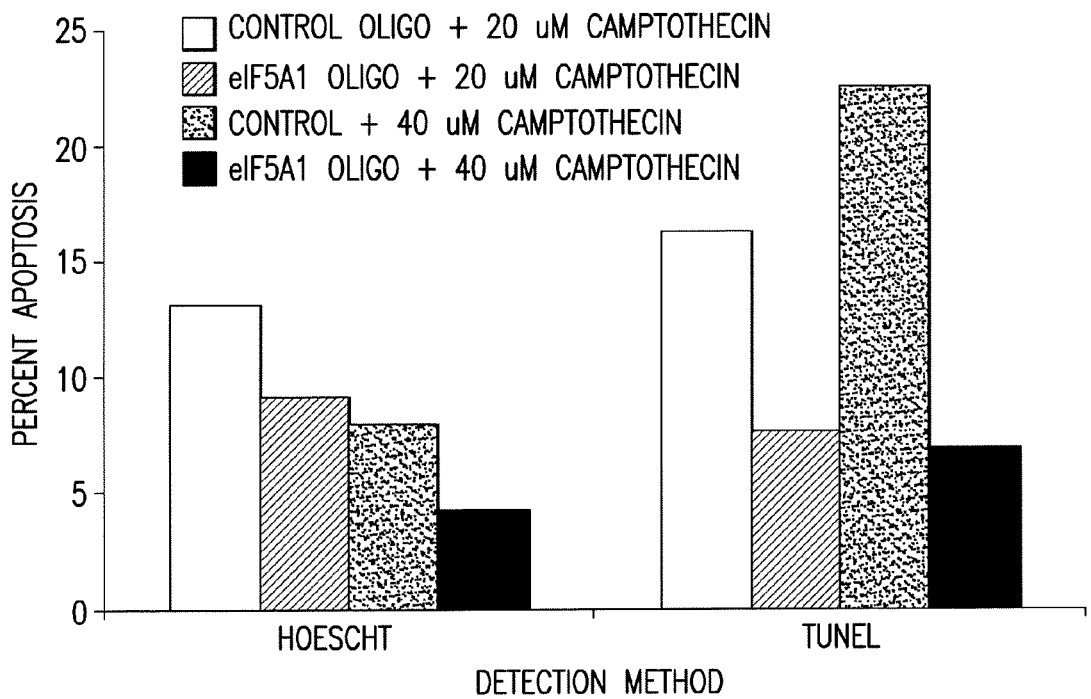
Figure 55:
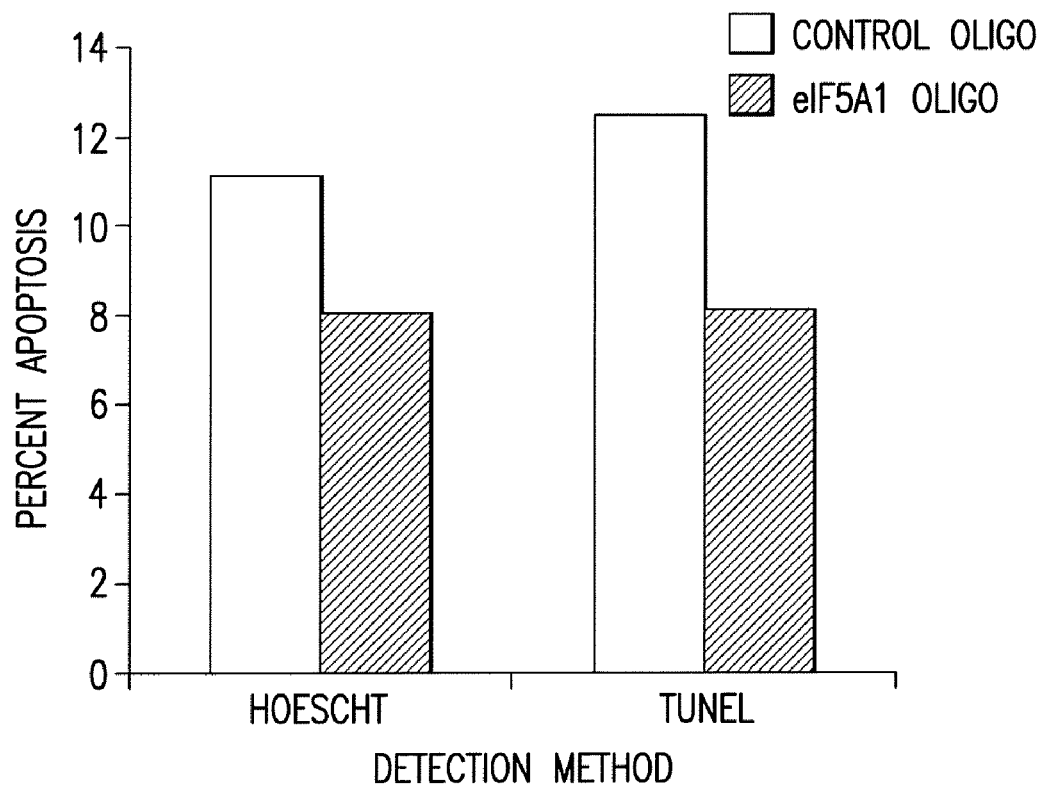
Figure 56:
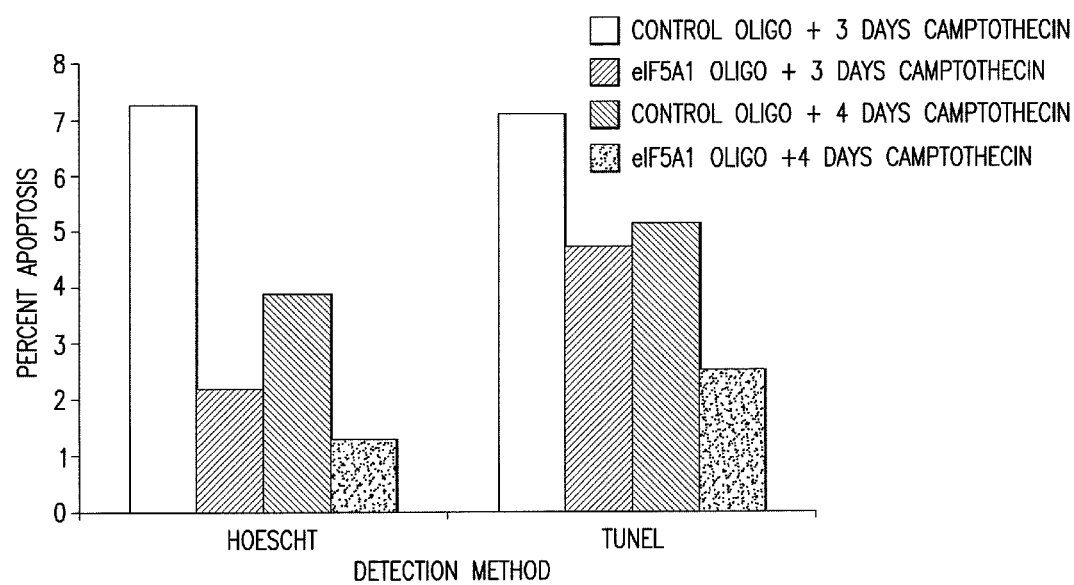
Figure 57:
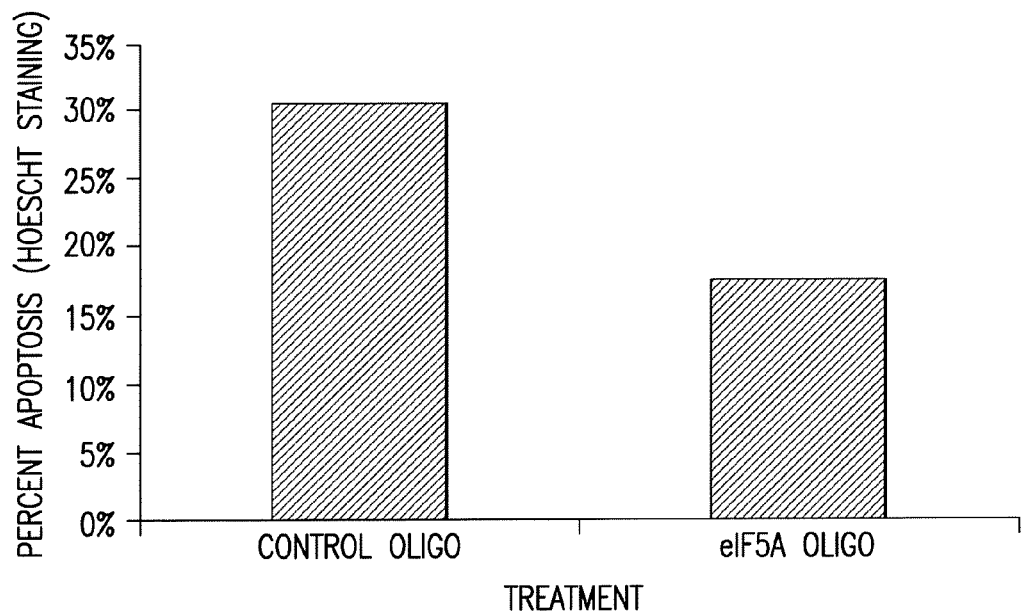
Figure 58:
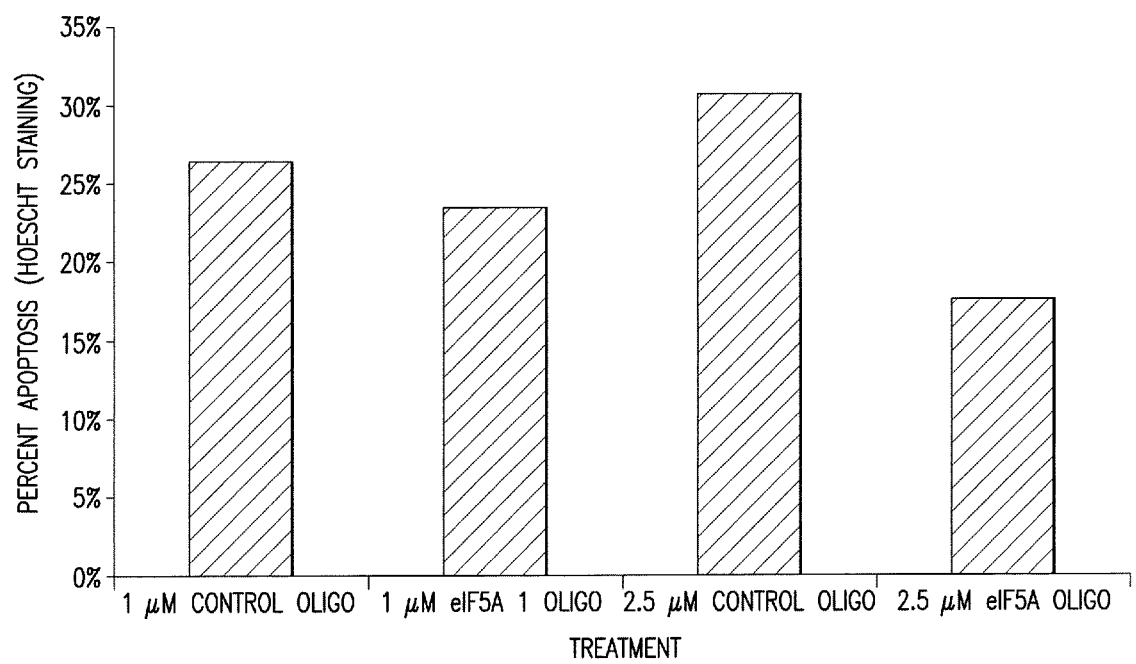

FIG. 53 shows uptake of the fluorescently labeled antisense oligonucleotide.

FIGS. 54-58 show a decrease in the percentage of cells undergoing apoptosis in the cells having been treated with antisense apoptosis factor 5A oligonucleotides as compared to cells not having been transfected with the antisense apoptosis factor 5A oligonucleotides.

Figure 59:
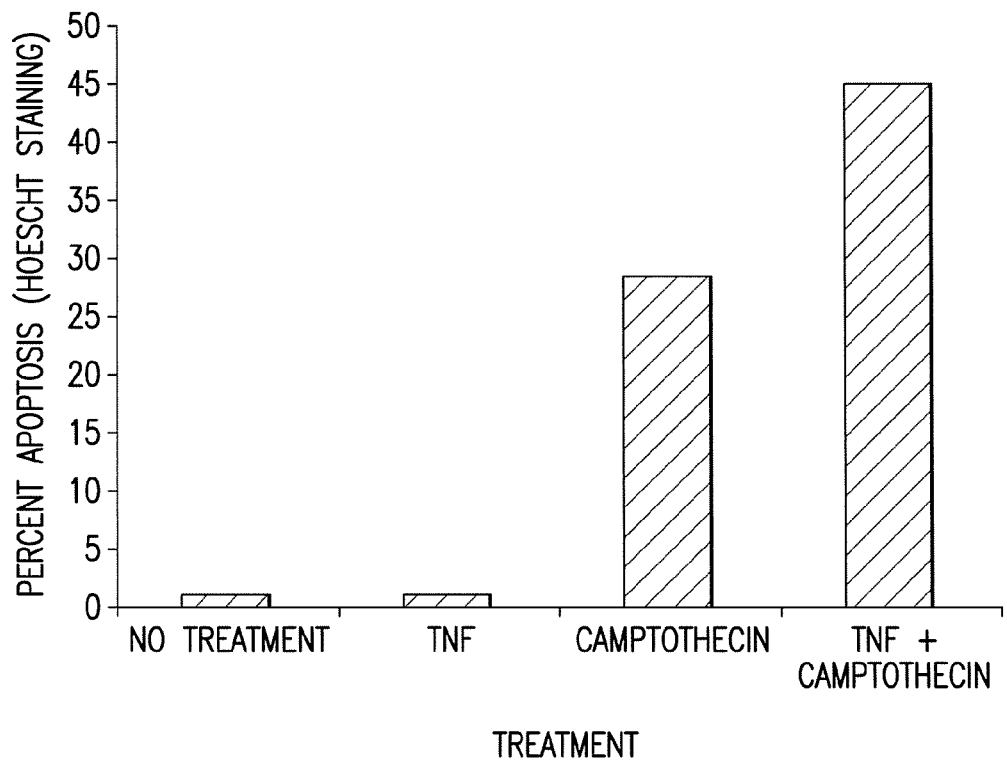

FIG. 59 shows that treating lamina cribrosa cells with TNF-α and/or camptothecin caused an increase in the number of cells undergoing apoptosis.

Figure 60:
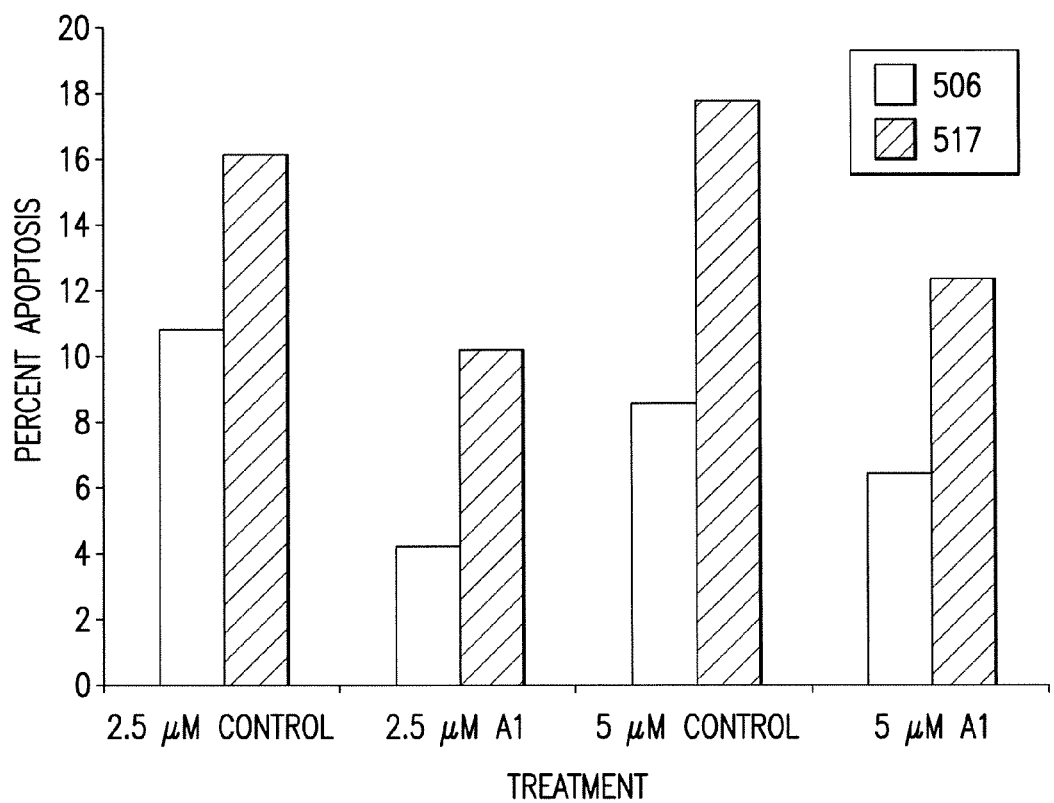
Figure 61:
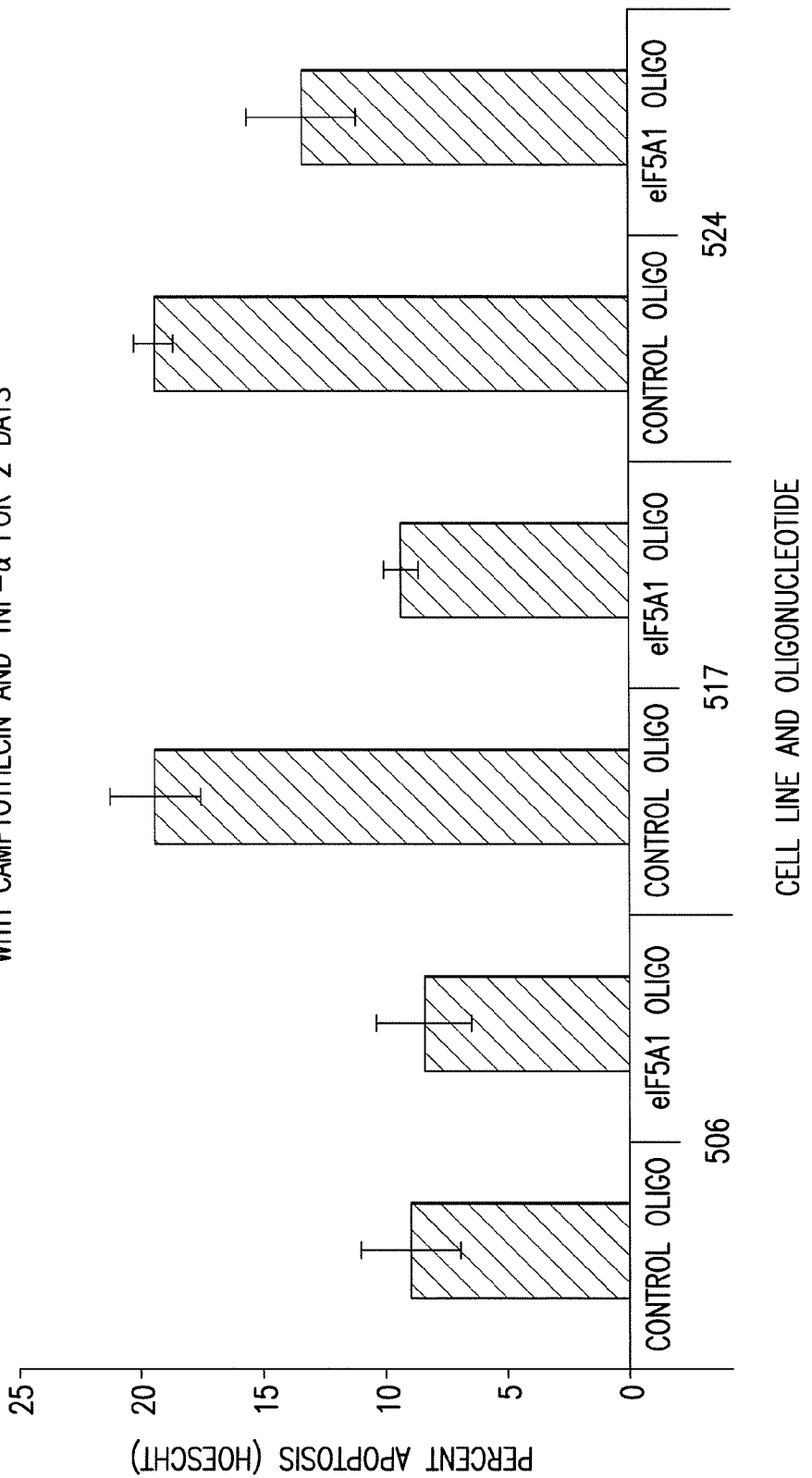

FIGS. 60 and 61 show a decrease in the percentage of cells undergoing apoptosis in the cells having being treated with antisense apoptosis factor 5A oligonucleotides as compared to cells not having been transfected with the antisense apoptosis factor 5A oligonucleotides.

Figure 62A:
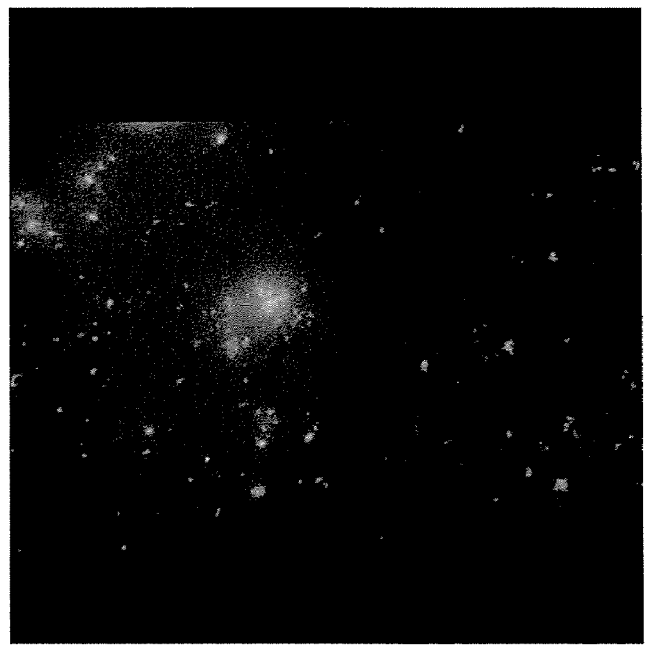
Figure 62B:
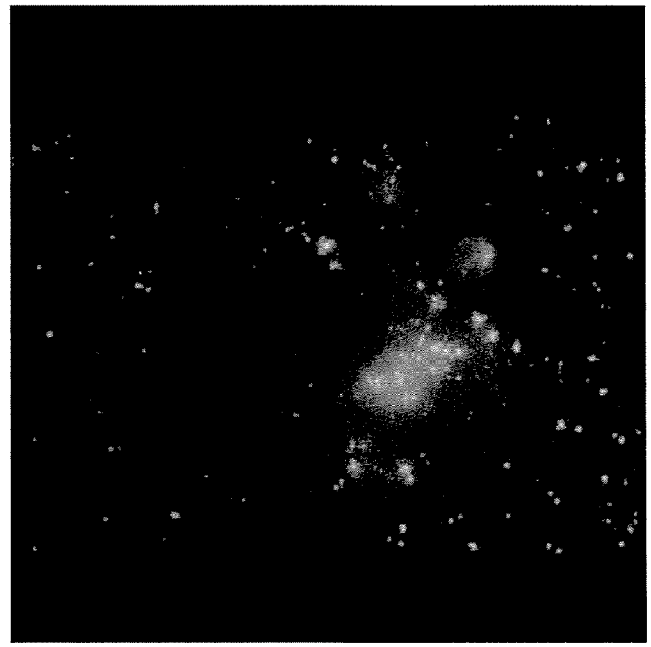

FIG. 62 shows that the lamina cribrosa cells uptake the labeled siRNA either in the presence of serum or without serum.

Figure 63:
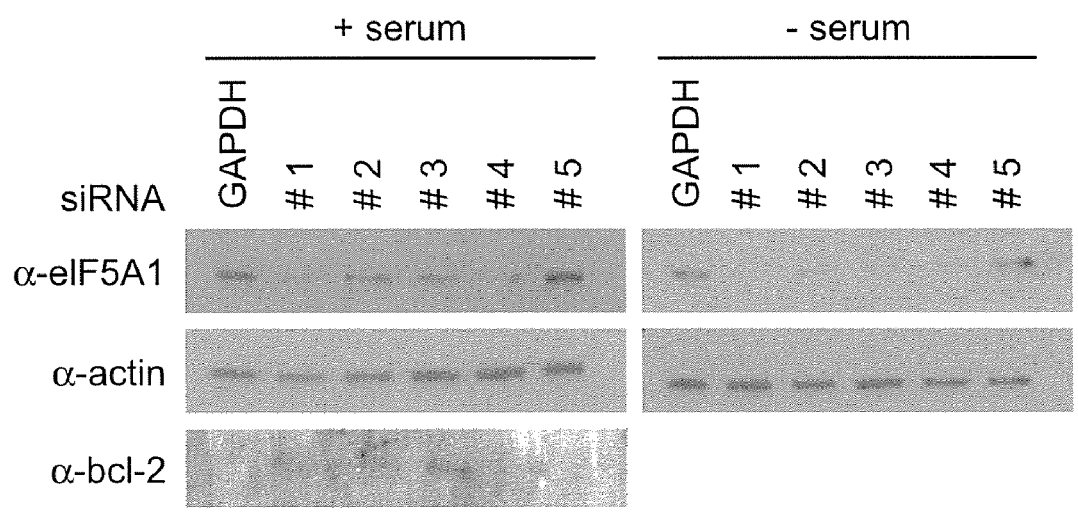

FIG. 63 shows that cells transfected with apoptosis factor 5a siRNA produced less apoptosis factor 5a protein and in addition, produced more Bcl-2 protein. A decrease in apoptosis factor 5A expression correlates with an increase in BCL-2 expression.

Figure 64:
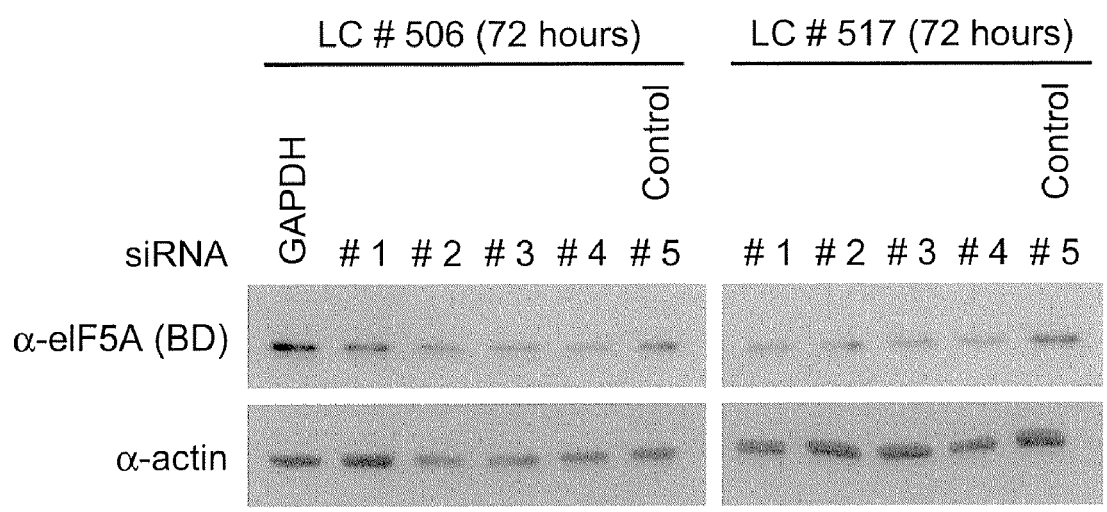

FIG. 64 shows that cells transfected with apoptosis factor 5a siRNA produced less apoptosis factor 5a protein.

Figure 65:
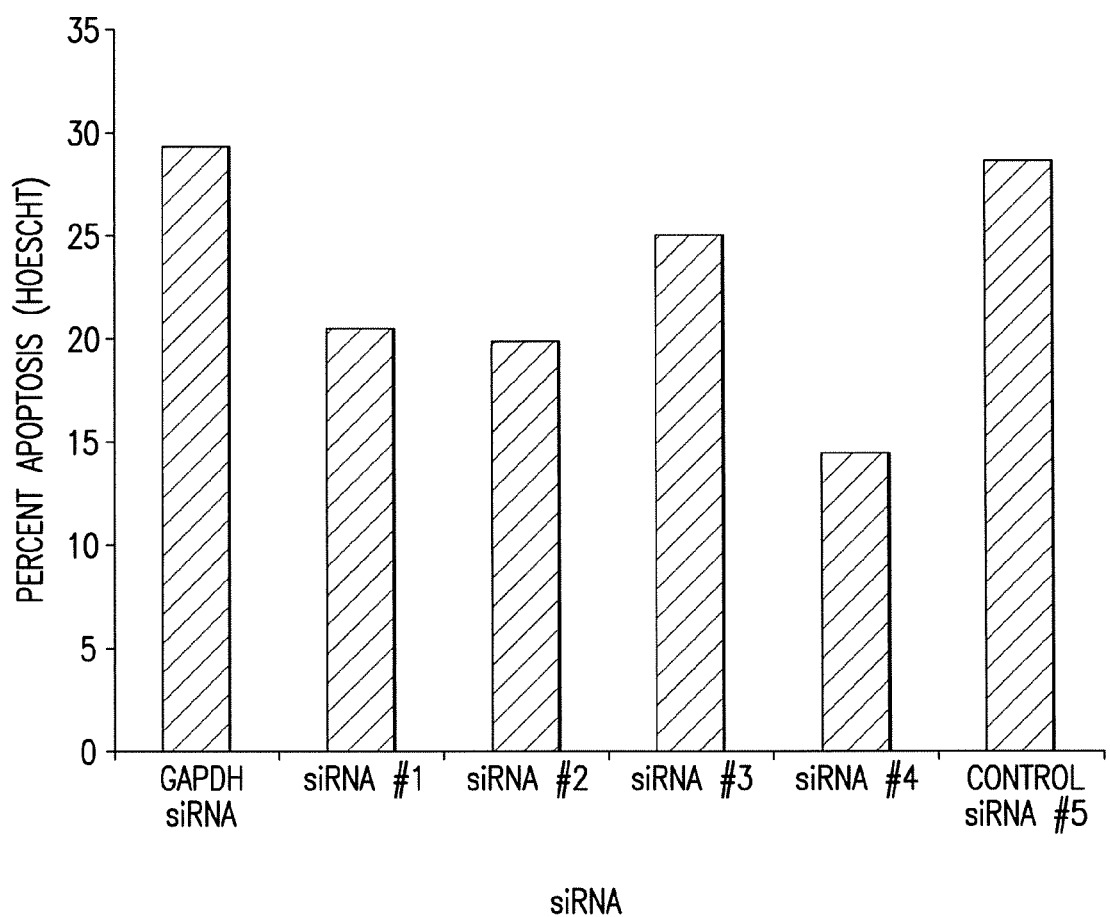
Figure 66:
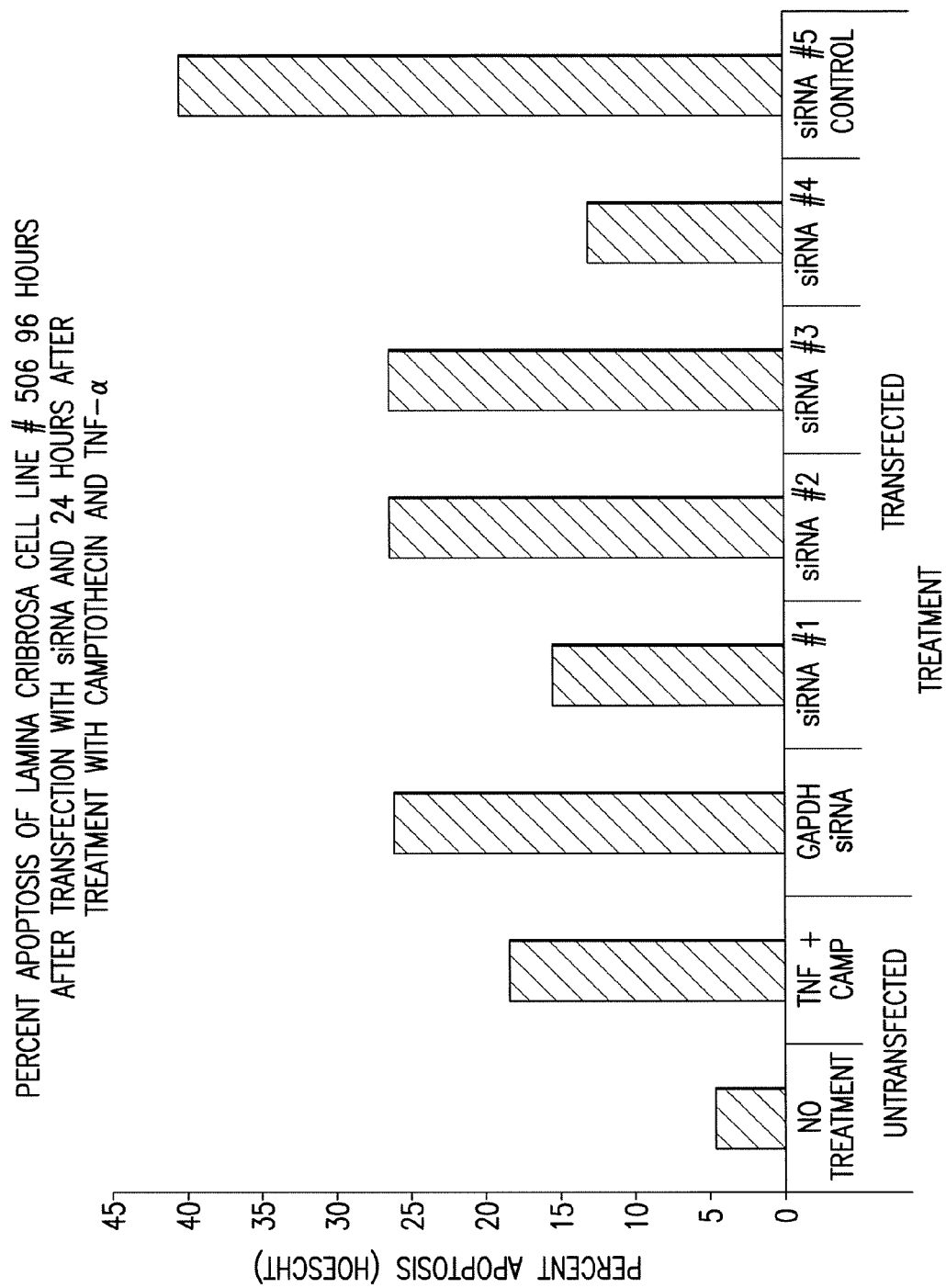
Figure 67:
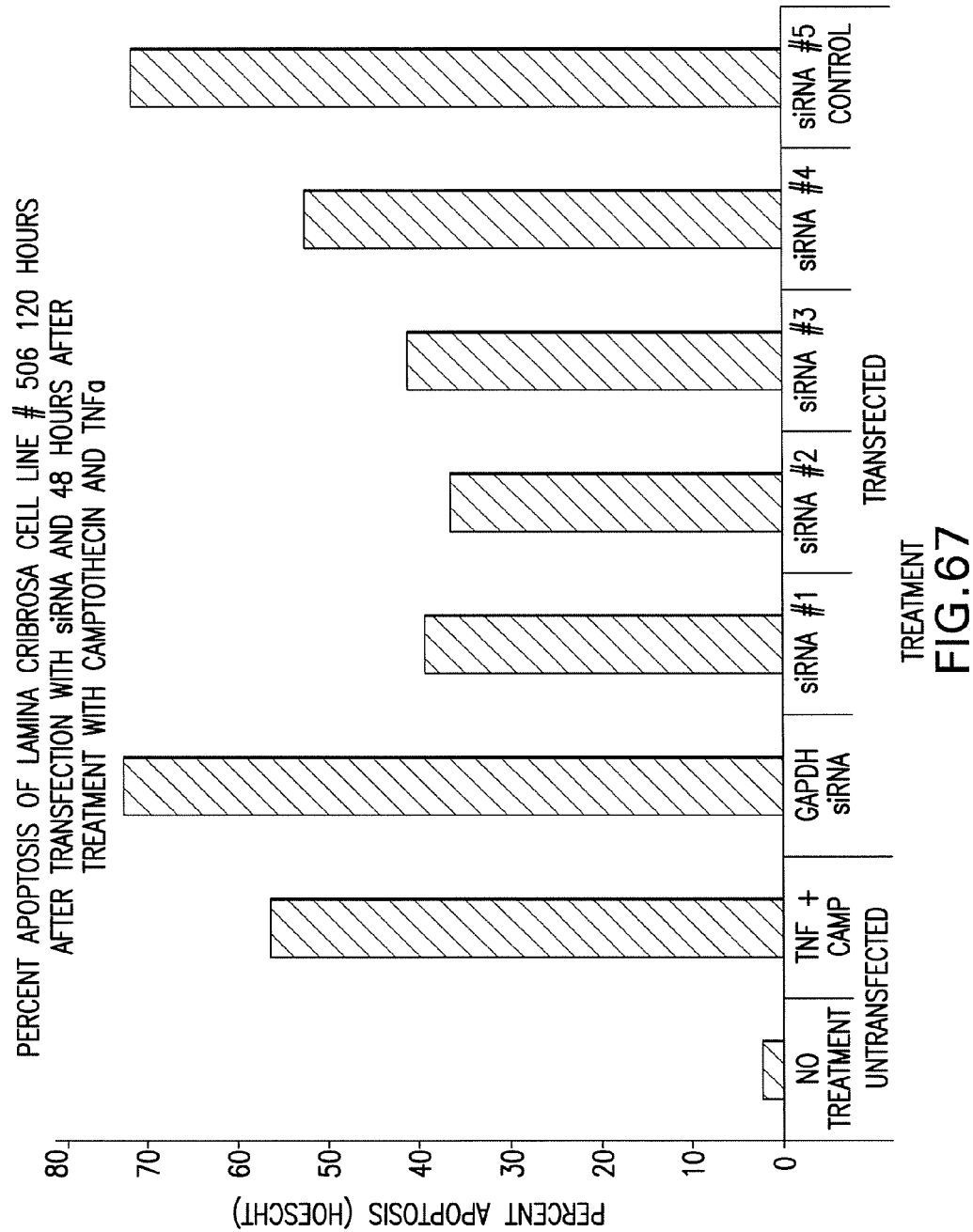

FIGS. 65-67 show that cells transfected with apoptosis factor 5a siRNA had a lower percentage of cells undergoing apoptosis after exposure to camptothecin and TNF-α.

Figure 68:
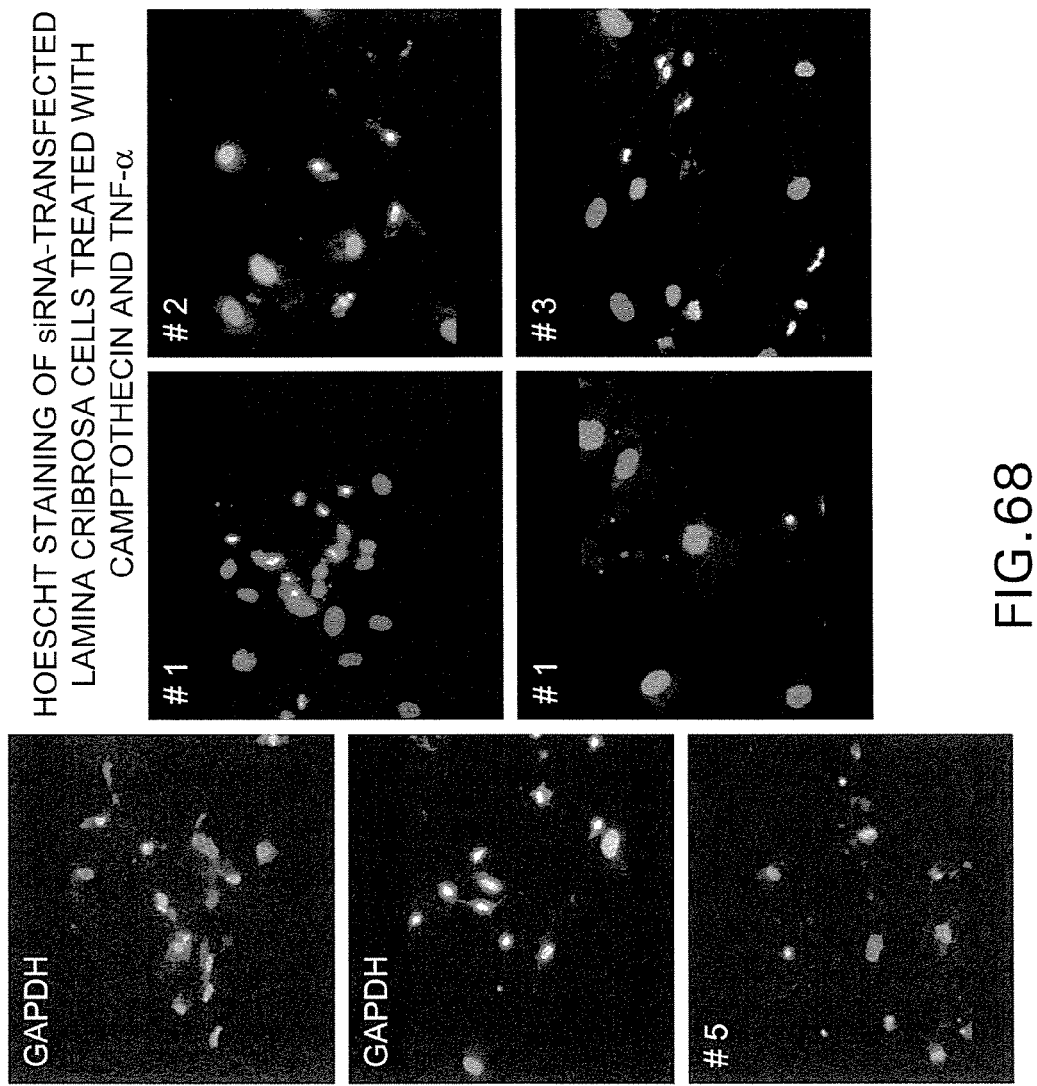

FIG. 68 are photographs of Hoescht-stained lamina cribrosa cell line #506 transfected with siRNA and treated with camptothecin and TNF-α from the experiment described in FIG. 67 and Example 13. The apoptosing cells are seen as more brightly stained cells. They have smaller nuclei because of chromatin condensing and are smaller and irregular in shape.

Figure 69:

FIG. 69 shows that IL-1 exposed HepG2 cells transfected with apoptosis factor 5A cells secreted less TNF-α than non-transfected cells.

FIG. 70 shows the sequence of human apoptosis factor 5a (SEQ ID NO:29) and the sequences of 5 siRNAs of the present invention (SEQ ID NO:30, 31, 32, 33 and 34).

FIG. 71 shows the sequence of human apoptosis factor 5a (SEQ ID NO: 29) and the sequences of 3 antisense polynucleotides of the present invention (SEQ ID NOS: 63-65, respectively in order of appearance) as well as the sequence of 3 target polynucleotides (SEQ ID NOS: 35-37, respectively in order of appearance).

FIG. 72 shows the binding position of three antisense oligonucleotides (SEQ ID NO:25-27, respectively in order of appearance) targeted against human eIF-5A1. The full-length nucleotide sequence is SEQ ID NO: 19.

FIG. 73a and b shows the nucleotide alignment (SEQ ID NO: 41 and 42, respectively in order of appearance) and amino acid alignment (SEQ ID NO: 43 and 22, respectively in order of appearance) of human eIF-5A1 (apoptosis factor 5A) against human eIF-5A2 (proliferating eIF-5A).

Figure 74A:
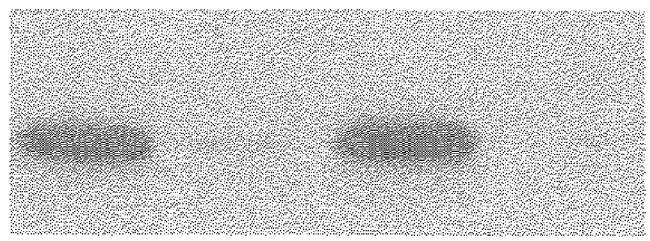
Figure 74B:
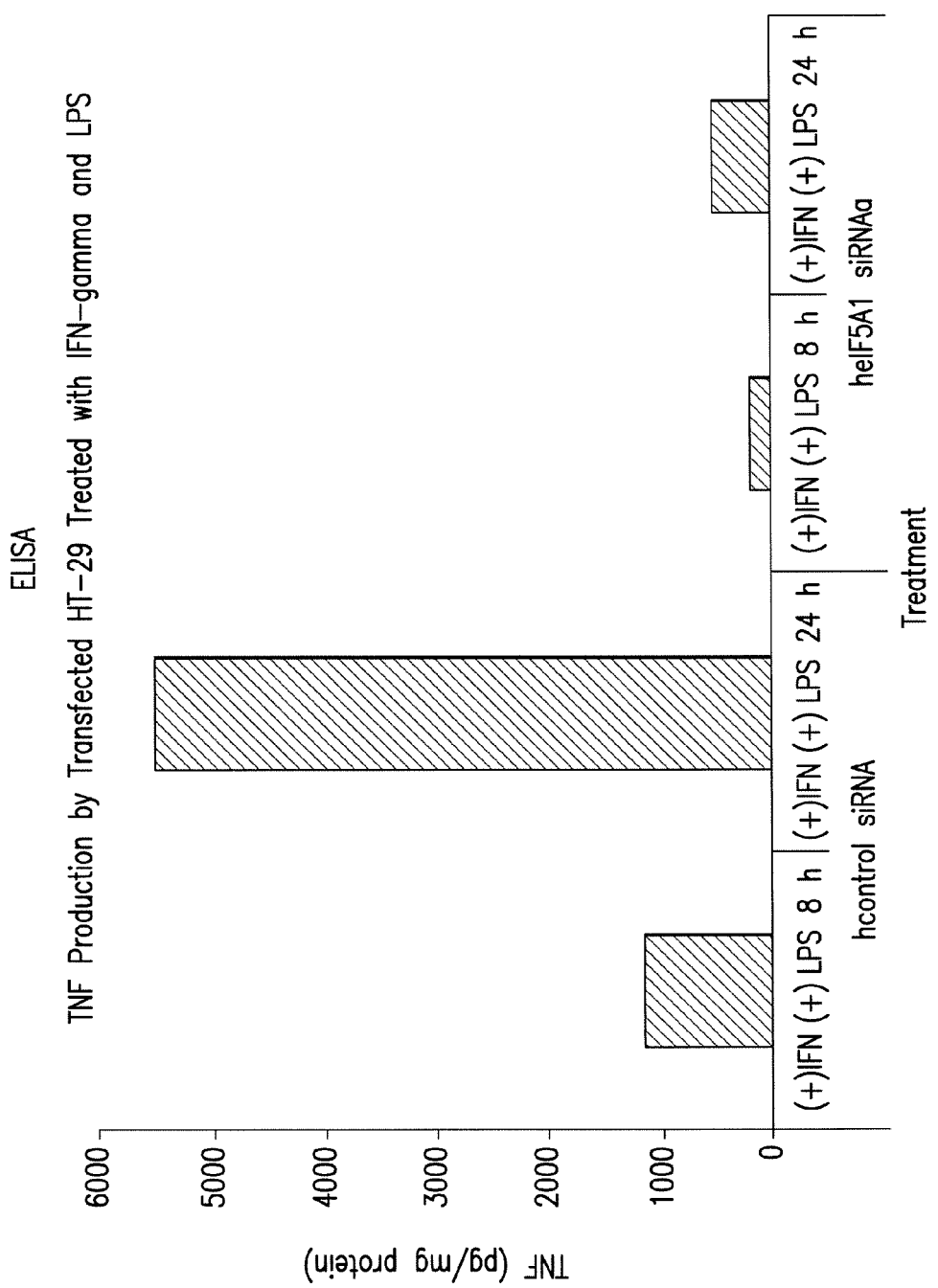

FIG. 74A provides a picture of a Western blot where siRNAs against eIF-5A1 have reduced if not inhibited the production of TNF-α in transfected HT-29 cells. FIG. 74B provides the results of an ELISA.

Figure 75:
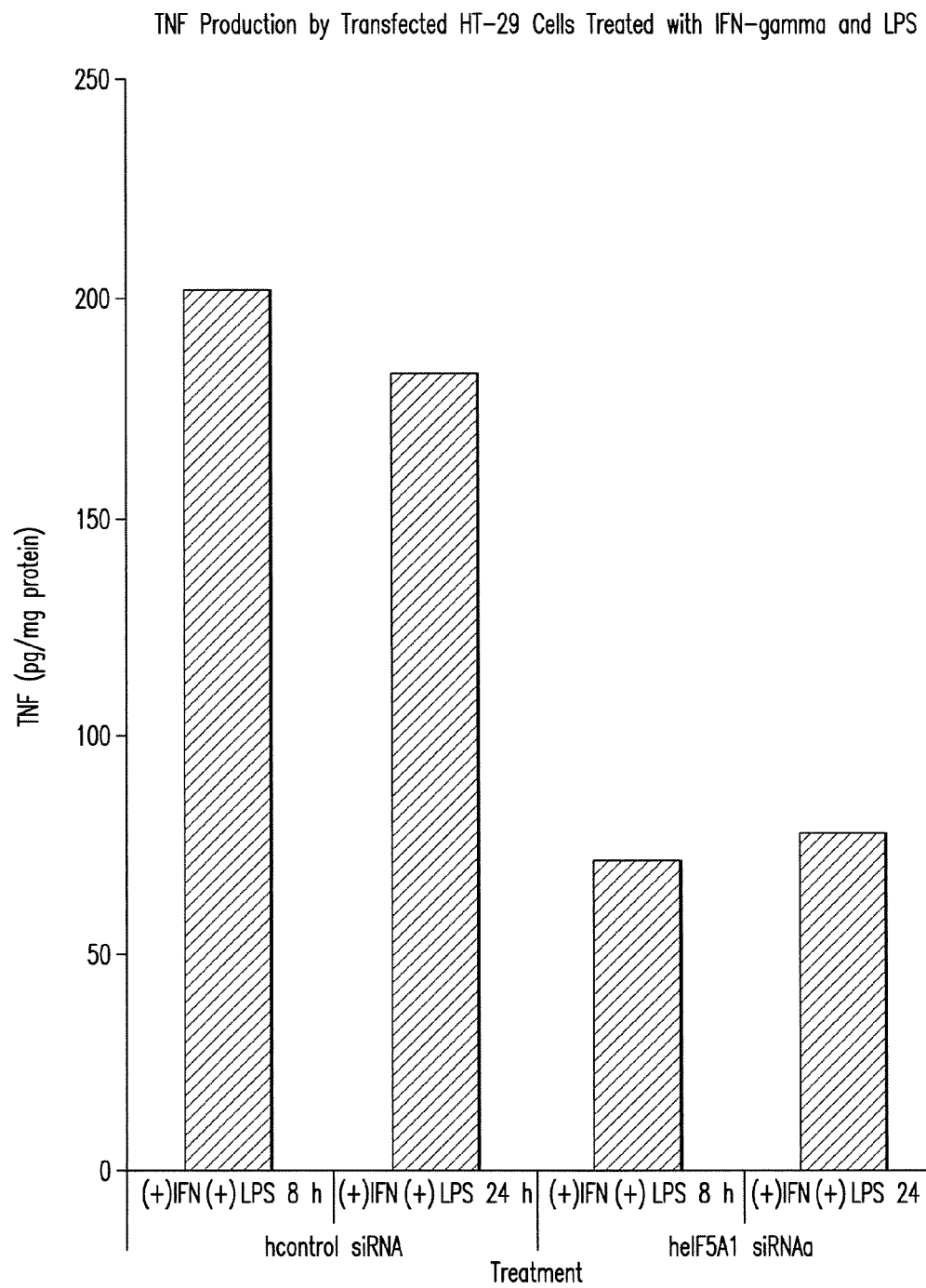

FIG. 75 provides the results of an ELISA. TNF-α production was reduced in cells treated with siRNAs against eIF-5A1 as compared to control cells.

Figure 76:
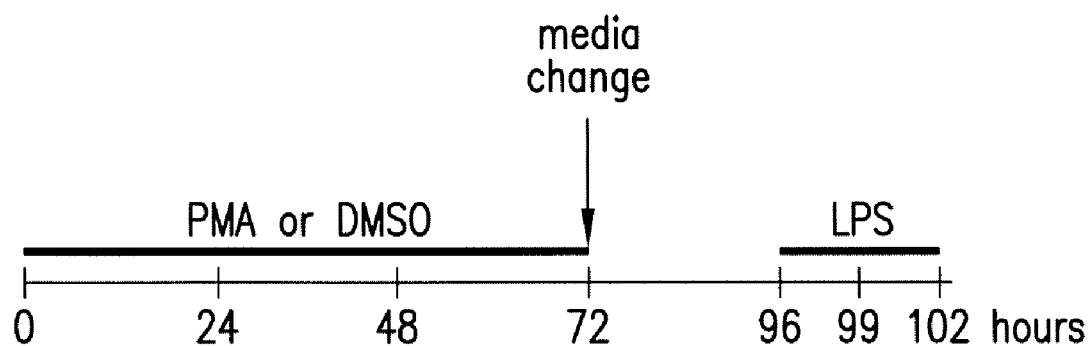

FIG. 76 shows the time course of the U-937 differentiation experiment. See Example 16.

Figure 77:
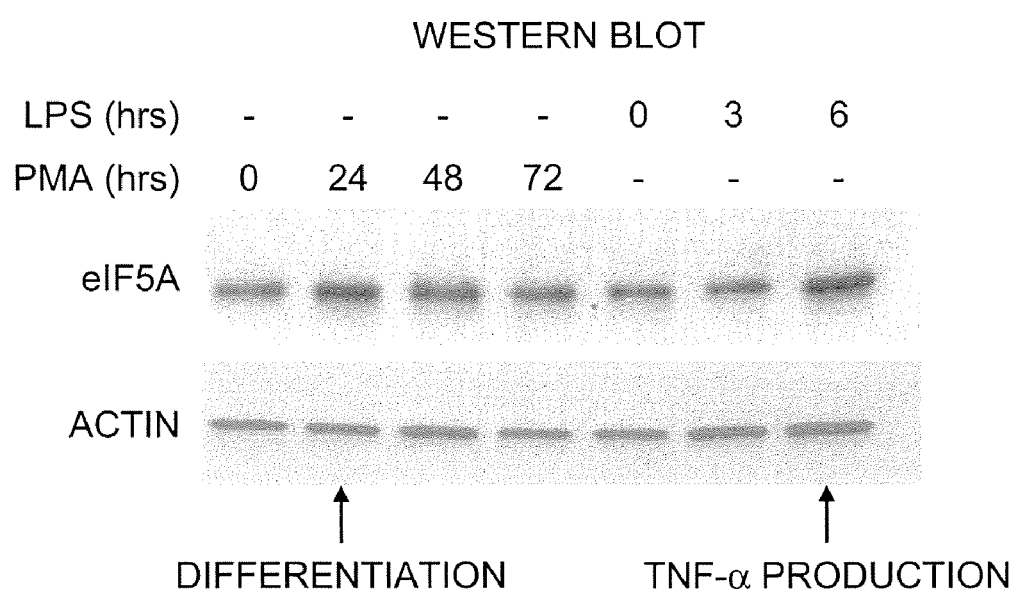

FIG. 77 shows the results of a Western blot showing that eIF-5A1 is up-regulated during monocyte differentiation and subsequent TNF-α secretion.

Figure 78:
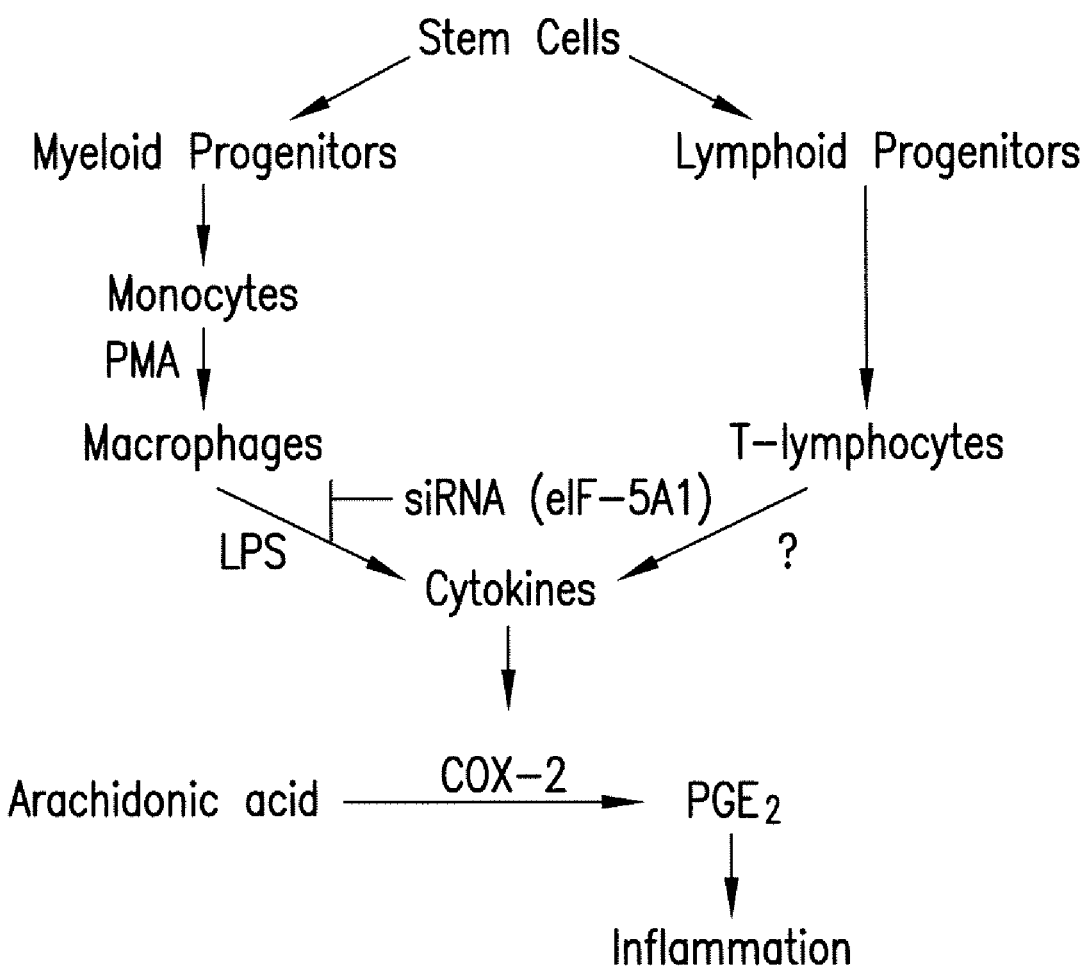

FIG. 78 depicts stem cell differentiation and the use of siRNAs against eIF-5A1 to inhibit cytokine production.

Figure 79:
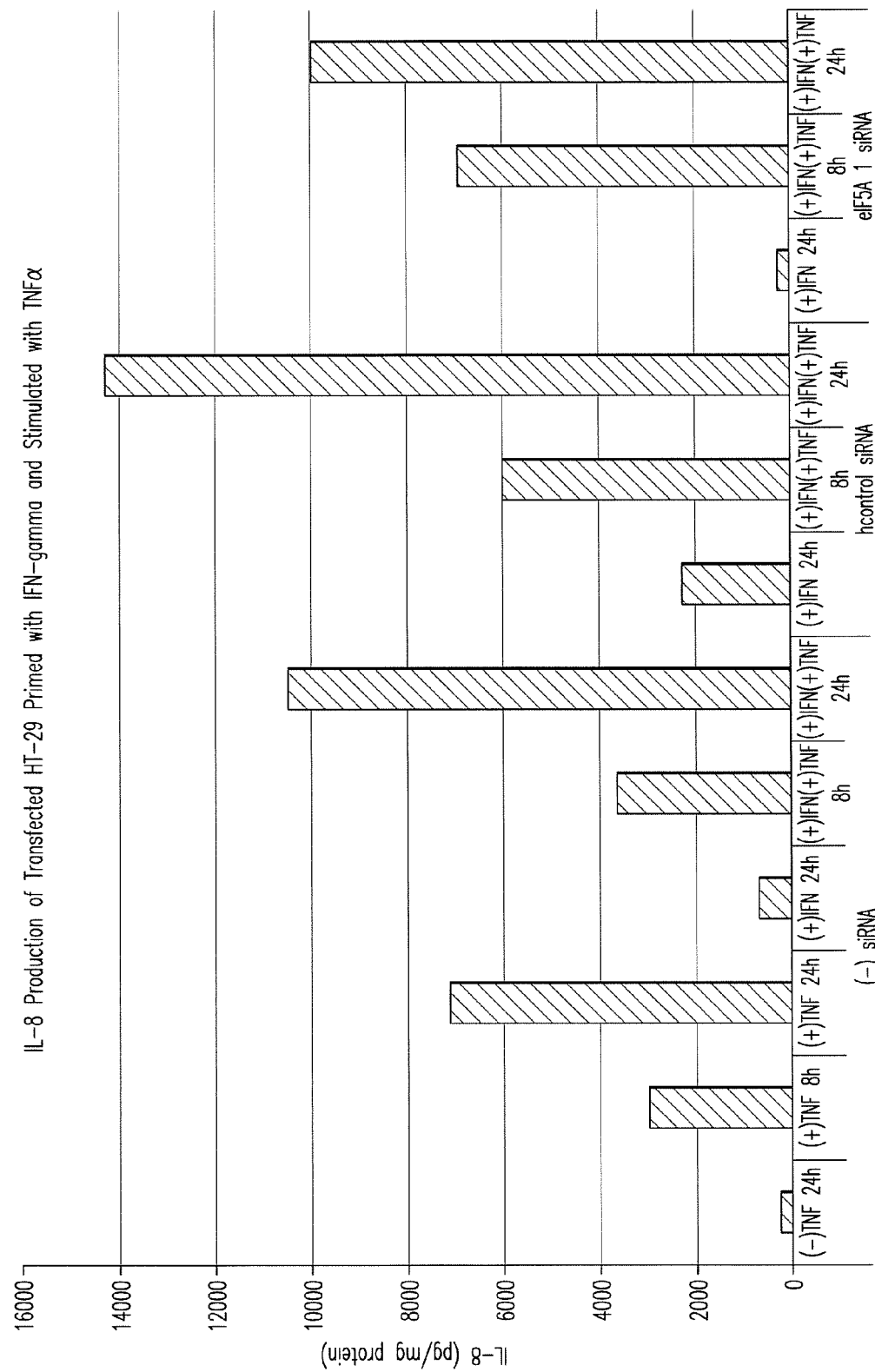

FIG. 79 is a bar graph showing that IL-8 is produced in response to TNF-alpha as well as in response to interferon. This graph shows that siRNA against eIF-5A blocked almost all IL-8 produced in response to interferon as well as a significant amount of the eIL-8 produced as a result of the combined treatment of interferon and TNF.

Figure 80:
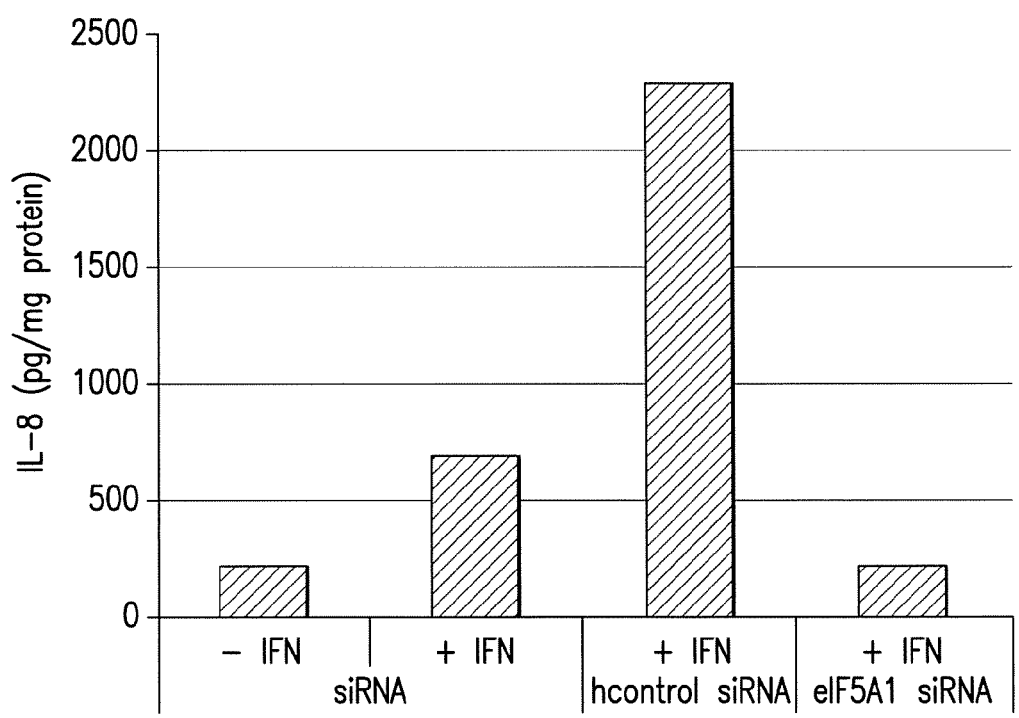

FIG. 80 is another bar graph showing that IL-8 is produced in response to TNF-alpha as well as in response to interferon. This graph shows that siRNA against eIF-5A blocked almost all IL-8 produced in response to interferon as well as a significant amount of the eIL-8 produced as a result of the combined treatment of interferon and TNF.

Figure 81:
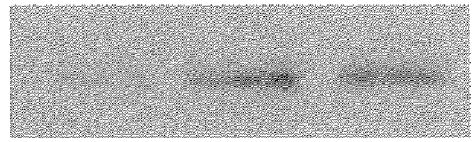
Figure 82A:
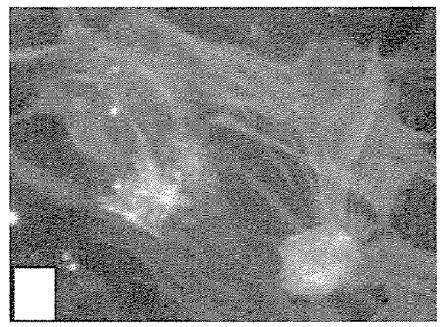
Figure 82B:
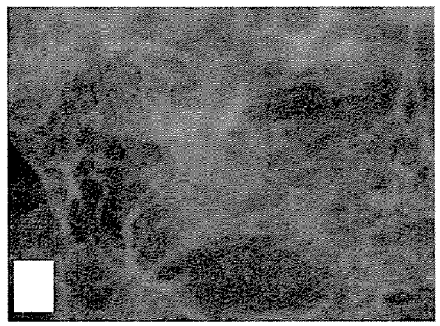
Figure 82C:
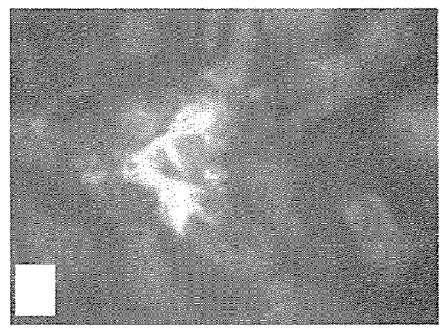
Figure 82D:

FIG. 81 is a western blot of HT-29 cells treated with IFN gamma for 8 and 24 hours. This blot shows upregulation (4 fold at 8 hours) of apoptosis eIF-5A in response to interferon gamma in HT-29 cells.

FIG. 82 is a characterization of lamina cribrosa cells by immunofluorescence. Lamina cribrosa cells (#506) isolated from the optic nerve head of an 83-year old male were characterized by immunofluorescence. Primary antibodies were a) actin; b) fibronectin; c) laminin; d) GFAP. All pictures were taken at 400 times magnification.

Figure 83:
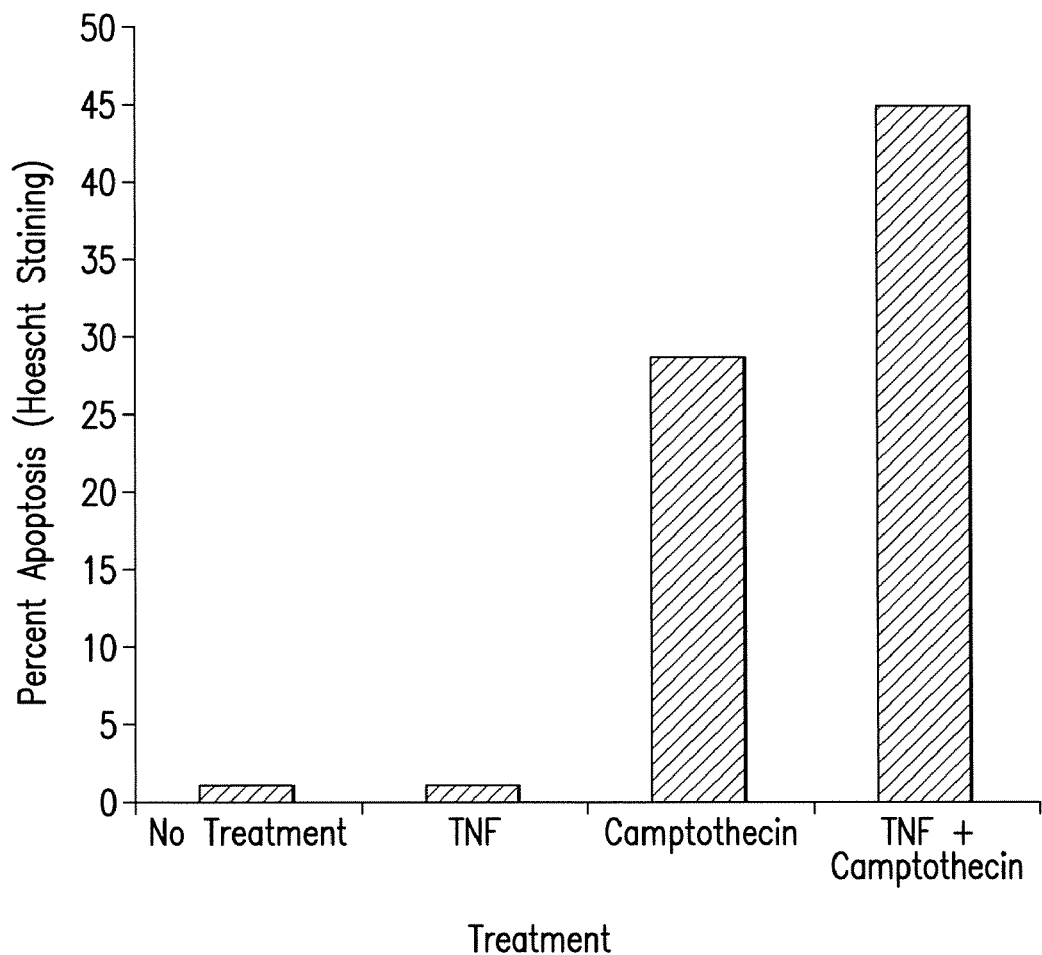

FIG. 83: Apoptosis of lamina cribrosa cell line #506 in response to treatment with camptothecin and TNF-α. Lamina cribrosa cell line #506 cells were seeded at 40,000 cells per well onto an 8-well culture slide. Three days later the confluent LC cells were treated with either 10 ng/ml TNF-α, 50 μM camptothecin, or 10 ng/ml TNF-α plus 50 camptothecin. An equivalent volume of DMSO, a vehicle control for camptothecin, was added to the untreated control cells. The cells were stained with Hoescht 33258 48 hours after treatment and viewed by fluorescence microscopy using a UV filter. Cells with brightly stained condensed or fragmented nuclei were counted as apoptotic.

FIG. 84: Expression of eIF-5A during camptothecin or TNF-α plus camptothecin treatment. Lamina cribrosa cell #506 cells were seeded at 40,000 cells per well onto a 24-well plate. Three days later the LC cells were treated with either 50 µM camptothecin or 10 ng/ml TNF-α plus 50 µM camptothecin and protein lysate was harvested 1, 4, 8, and 24 hours later. An equivalent volume of DMSO was added to control cells as a vehicle control and cell lysate was harvested 1 and 24 hours later. 5 µg of protein from each sample was separated by SDS-PAGE, transferred to a PVDF membrane, and Western blotted with anti-eIF-5A antibody. The bound antibody was detected by chemiluminescence and exposed to x-ray film. The membrane was then stripped and re-blotted with anti-β-actin as an internal loading control.

Figure 85:
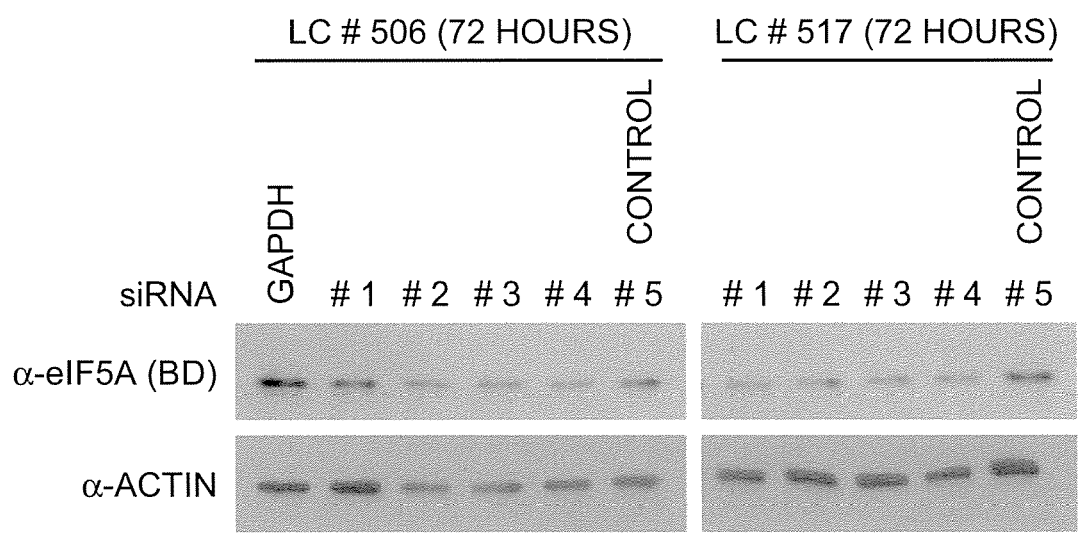

FIG. 85: Expression of eIF-5A in lamina cribosa cell lines #506 and #517 following transfection with siRNAs. Lamina cribrosa cell #506 and #517 cells were seeded at 10,000 cells per well onto a 24-well plate. Three days later the LC cells were transfected with either GAPDH siRNA, eIF-5A siRNAs #1-4, or control siRNA #5. Three days after transfection the protein lysate was harvested and 5 µg of protein from each sample was separated by SDS-PAGE, transferred to a PVDF membrane, and Western blotted with anti-eIF-5A antibody. The bound antibody was detected by chemiluminescence and exposed to x-ray film. The membrane was then stripped and re-blotted with anti-β-actin as an internal loading control.

Figure 86:
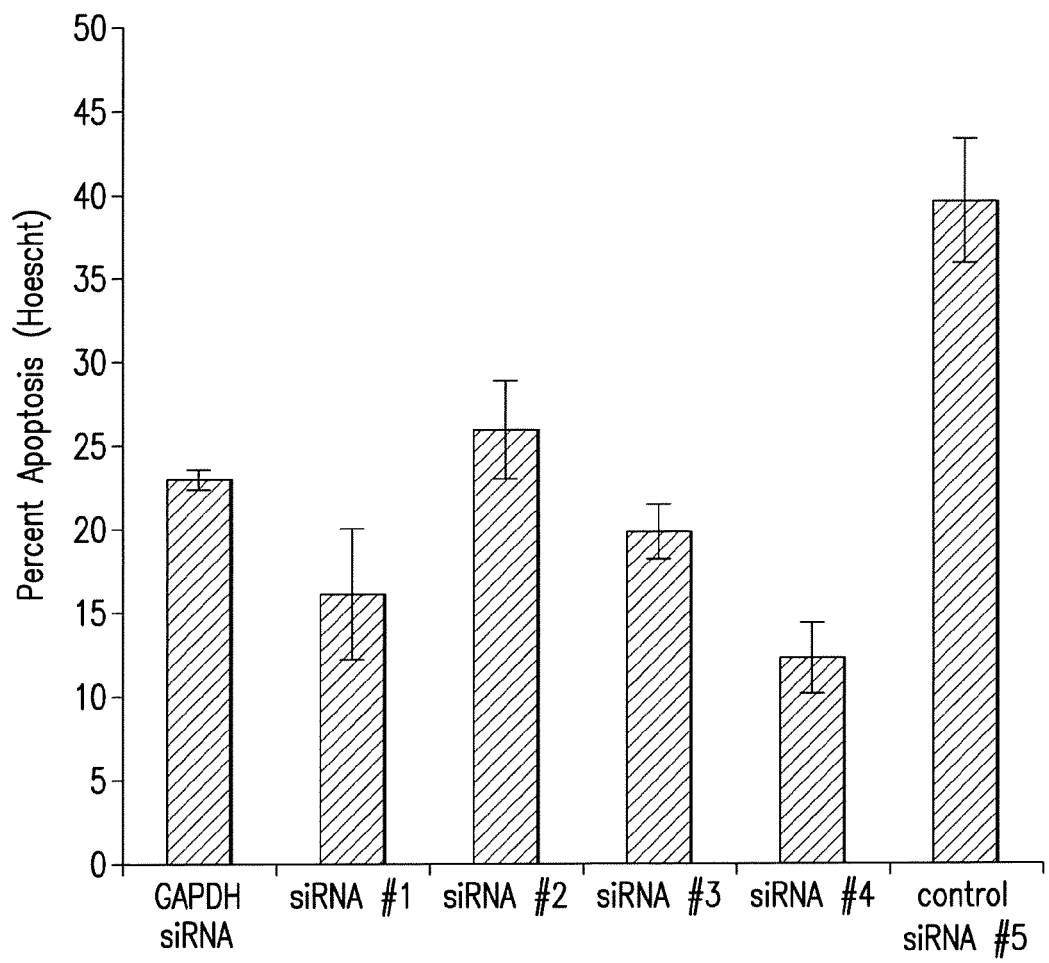

FIG. 86: Apoptosis of lamina cribosa cell line #506 cells transfected with eIF-5A siRNAs and treated with TNF-α and camptothecin. Lamina cribrosa cell line #506 cells were seeded at 7500 cells per well onto an 8-well culture slide. Three days later the LC cells were transfected with either GAPDH siRNA, eIF-5A siRNAs #1-4, or control siRNA #5. 72 hours after transfection, the transfected cells were treated with 10 ng/ml TNF-α plus 50 µM camptothecin. Twenty-four hours later the cells were stained with Hoescht 33258 and viewed by fluorescence microscopy using a UV filter. Cells with brightly stained condensed or fragmented nuclei were counted as apoptotic. This graph represents the average of n=4 independent experiments.

Figure 87:
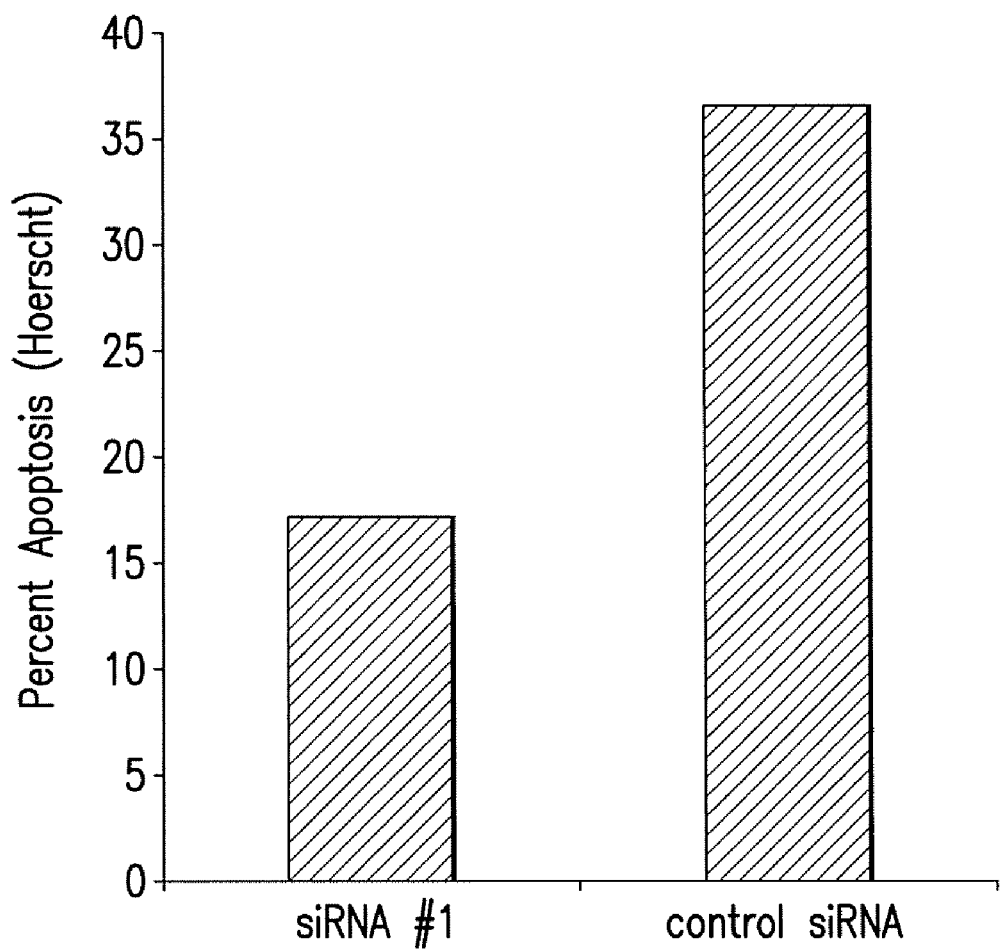

FIG. 87: Apoptosis of lamina cribosa cell line #517 cells transfected with eIF-5A siRNA #1 and treated with TNF-α and camptothecin. Lamina cribrosa cell line #517 cells were seeded at 7500 cells per well onto an 8-well culture slide. Three days later the LC cells were transfected with either eIF-5A siRNA #1 or control siRNA #5. 72 hours after transfection, the transfected cells were treated with 10 ng/ml TNF-α plus 50 µM camptothecin. Twenty-four hours later the cells were stained with Hoescht 33258 and viewed by fluorescence microscopy using a UV filter. Cells with brightly stained condensed or fragmented nuclei were counted as apoptotic. The results of two independent experiments are represented here.

FIG. 88: TUNEL-labeling of lamina cribosa cell line #506 cells transfected with eIF-5A siRNA #1 and treated with TNF-α and camptothecin. Lamina cribrosa cell line #506 cells were seeded at 7500 cells per well onto an 8-well culture slide. Three days later the LC cells were transfected with either eIF-5A siRNA #1 or control siRNA #5. 72 hours after transfection, the transfected cells were treated with 10 ng/ml TNF-α plus 50 µM camptothecin. Twenty-four hours later the cells were stained with Hoescht 33258 and DNA fragmentation was evaluated in situ using the terminal deoxynucleotidyl transferase-mediated dUTP-digoxigenin nick end labeling (TUNEL) method. Panel A represents the slide observed by fluorescence microscopy using a fluorescein filter to visualize TUNEL-labeling of the fragmented DNA of apoptotic cells. Panel B represents the same slide observed through a UV filter to visualize the Hoescht-stained nuclei. The results are representative of two independent experiments. All pictures were taken at 400 times magnification.

FIG. 89 depicts the design of siRNAs against eIF5-A1 (SEQ ID NO: 44-58, respectively in order of appearance). The siRNAs have the SEQ ID NO: 45, 48, 51, 54 and 56. The full-length nucleotide sequence is show in SEQ ID NO: 29.

DETAILED DESCRIPTION OF THE INVENTION

Several isoforms of eukaryotic initiation factor 5a (eIF-5A) have been isolated and present in published databanks. It was thought that these isoforms were functionally redundant. The present inventors have discovered that one isoform is upregulated immediately before the induction of apoptosis, which they have designated apoptosis factor 5A or factor 5A1 or eIF5-A1. The subject of the present invention is apoptosis factor 5A as well as DHS, which is involved in the activation of eIF-5A.

Apoptosis factor 5A is likely to be a suitable target for intervention in apoptosis-causing disease states since it appears to act at the level of post-transcriptional regulation of downstream effectors and transcription factors involved in the apoptotic pathway. Specifically, apoptosis factor 5A appears to selectively facilitate the translocation of mRNAs encoding downstream effectors and transcription factors of apoptosis from the nucleus to the cytoplasm, where they are subsequently translated. The ultimate decision to initiate apoptosis appears to stem from a complex interaction between internal and external pro- and anti-apoptotic signals. Lowe & Lin (2000) Carcinogenesis, 21, 485-495. Through its ability to facilitate the translation of downstream apoptosis effectors and transcription factors, the apoptosis factor 5A appears to tip the balance between these signals in favor of apoptosis.

Accordingly, the present invention provides a method of suppressing or reducing apoptosis in a cell by administering an agent that inhibits or reduces expression of either apoptosis factor 5A or DHS. One agent that can inhibit or reduce expression of apoptosis factor 5A or DHS is an antisense oligonucleotide.

Antisense oligonucleotides have been successfully used to accomplish both in vitro as well as in vivo gene-specific suppression. Antisense oligonucleotides are short, synthetic strands of DNA (or DNA analogs) that are antisense (or complimentary) to a specific DNA or RNA target. Antisense oligonucleotides are designed to block expression of the protein encoded by the DNA or RNA target by binding to the target and halting expression at the level of transcription, translation, or splicing. By using modified backbones that resist degradation (Blake et al., 1985), such as replacement of the phosphodiester bonds in the oligonucleotides with phosphorothioate linkages to retard nuclease degradation (Matzura and Eckstein, 1968), antisense oligonucleotides have been used successfully both in cell cultures and animal models of disease (Hogrefe, 1999).

Preferably, the antisense oligonucleotides of the present invention have a nucleotide sequence encoding a portion of an apoptosis factor 5A polypeptide or an apoptosis-specific DHS polypeptide. The inventors have transfected various cell lines with antisense nucleotides encoding a portion of an apoptosis factor 5A polypeptide as described below and measured the number of cells undergoing apoptosis. The cells that were transfected with the antisense oligonucleotides showed a decrease in the number of cells undergoing apoptosis as compared to like cells not having been transfected with the antisense oligos. FIGS. 54-58 show a decrease in the percentage of cells undergoing apoptosis in the cells having being treated with antisense apoptosis factor 5A oligonucleotides as compared to cells not having been transfected with the antisense apoptosis factor 5A oligonucleotides.

The present invention contemplates the use of many suitable nucleic acid sequences encoding an apoptosis factor 5A polypeptide or DHS polypeptide. For example, SEQ ID NOS: 1, 3, 4, 5, 11, 15, 19, 20, and 21 (apoptosis-factor 5A nucleic acid sequences), SEQ ID NOS:6 and 8 (apoptosis-specific DHS nucleic acid sequences), SEQ ID NOS:12 and 16 (apoptosis factor 5A sequences), and SEQ ID NO:7 (apoptosis-specific DHS polypeptide sequences), or portions thereof, provide suitable sequences. Other preferred apoptosis factor 5A antisense polynucleotide sequences include SEQ ID NO: 63-65. Additional antisense nucleotides include those that have substantial sequence identity to those enumerated above (i.e. 90% homology) or those having sequences that hybridize under highly stringent conditions to the enumerated SEQ ID NOs. Additionally, other suitable sequences can be found using the known sequences as probes according to methods known in the art.

The antisense oligonucleotides of the present invention may be single stranded, double stranded, DNA, RNA or a hybrid. The oligonucleotides may be modified by methods known in the art to increase stability, increase resistance to nuclease degradation or the like. These modifications are known in the art and include, but are not limited to modifying the backbone of the oligonucleotide, modifying the sugar moieties, or modifying the base. Also inclusive in these modifications are various DNA-RNA hybrids or constructs commonly referred to as "gapped" oligonucleotides.

The present invention provides other agents that can inhibit or reduce expression of apoptosis factor 5A or DHS. One such agent is siRNAs. Small Inhibitory RNAs (siRNA) have been emerging as a viable alternative to antisense oligonucleotides since lower concentrations are required to achieve levels of suppression that are equivalent or superior to those achieved with antisense oligonucleotides (Thompson, 2002). Long double-stranded RNAs have been used to silence the expression of specific genes in a variety of organisms such as plants, nematodes, and fruit flies. An RNase-III family enzyme called Dicer processes these long double stranded RNAs into 21-23 nucleotide small interfering RNAs which are then incorporated into an RNA-induced silencing complex (RISC). Unwinding of the siRNA activates RISC and allows the single-stranded siRNA to guide the complex to the endogenous mRNA by base pairing. Recognition of the endogenous mRNA by RISC results in its cleavage and consequently makes it unavailable for translation. Introduction of long double stranded RNA into mammalian cells results in a potent antiviral response which can be bypassed by use of siRNAs. (Elbashir et al., 2001). SiRNA has been widely used in cell cultures and routinely achieves a reduction in specific gene expression of 90% or more.

The use of siRNAs has also been gaining popularity in inhibiting gene expression in animal models of disease. A recent study that demonstrated that an siRNA against luciferase was able to block luciferase expression from a co-transfected plasmid in a wide variety of organs in postnatal mice using a hydrodynamic injection delivery technique (Lewis et al., 2002). An siRNA against Fas, a receptor in the TNF family, injected hydrodynamically into the tail vein of mice was able to transfect greater than 80% of hepatocytes and decrease Fas expression in the liver by 90% for up to 10 days after the last injection (Song et al., 2003). The Fas siRNA was also able to protect mice from liver fibrosis and fulminant hepatitis. The development of sepsis in mice treated with a lethal dose of lipopolysaccharide was inhibited by the use of an siRNA directed against TNF α (Sørensen et al., 2003). SiRNA has the potential to be a very potent drug for the inhibition of specific gene expression in vivo in light of their long-lasting effectiveness in cell cultures and in vivo, their ability to transfect cells in vivo, and their resistance to degradation in serum (Bertrand et al., 2002).

The present inventors have transfected cells with apoptosis factor 5A siRNAs and studied the effects on expression of apoptosis factor 5A. FIG. 64 shows that cells transfected with apoptosis factor 5a siRNA produced less apoptosis factor 5a protein. FIGS. 64-67 show that cells transfected with apoptosis factor 5A siRNAs have a lower percentage of cells undergoing apoptosis after exposure to camptothecin and TNF-α as compared to cells not having been transfected with apoptosis factor 5A siRNAs.

Preferred siRNAs include those that have SEQ ID NO: 30, 31, 32, 33, and 34. Additional siRNAs include those that have substantial sequence identity to those enumerated (i.e. 90% homology) or those having sequences that hybridize under highly stringent conditions to the enumerated SEQ ID NOs. FIG. 64 shows that cells transfected with apoptosis factor 5A siRNA produced less apoptosis factor 5A protein.

Many important human diseases are caused by abnormalities in the control of apoptosis. These abnormalities can result in either a pathological increase in cell number (e.g. cancer) or a damaging loss of cells (e.g. degenerative diseases). As non-limiting examples, the methods and compositions of the present invention can be used to prevent or treat the following apoptosis-associated diseases and disorders: neurological/neurodegenerative disorders (e.g., Alzheimer's, Parkinson's, Huntington's, Amyotrophic Lateral Sclerosis (Lou Gehrig's Disease), autoimmune disorders (e.g., rheumatoid arthritis, systemic lupus erythematosus (SLE), multiple sclerosis), Duchenne Muscular Dystrophy (DMD), motor neuron disorders, ischemia, heart ischemia, chronic heart failure, stroke, infantile spinal muscular atrophy, cardiac arrest, renal failure, atopic dermatitis, sepsis and septic shock, AIDS, hepatitis, glaucoma, diabetes (type 1 and type 2), asthma, retinitis pigmentosa, osteoporosis, xenograft rejection, and burn injury.

One such disease caused by abnormalities in the control of apoptosis is glaucoma. Apoptosis is a critical factor leading to blindness in glaucoma patients. Glaucoma is a group of eye conditions arising from damage to the optic nerve that results in progressive blindness. Apoptosis has been shown to be a direct cause of this optic nerve damage.

Early work in the field of glaucoma research has indicated that elevated IOP leads to interference in axonal transport at the level of the lamina cribosa (a perforated, collagenous connective tissue) that is followed by the death of retinal ganglion cells. Quigley and Anderson (1976) *Invest. Ophthalmol. Vis. Sci.,* 15, 606-16; Minckler, Bunt, and Klock, (1978) *Invest. Ophthalmol. Vis. Sci.,* 17, 33-50; Anderson and Hendrickson, (1974) *Invest. Ophthalmol. Vis. Sci.,* 13, 771-83; Quigley et al., (1980) *Invest. Ophthalmol. Vis. Sci.,* 19, 505-17. Studies of animal models of glaucoma and post-mortem human tissues indicate that the death of retinal ganglion cells in glaucoma occurs by apoptosis. Garcia-Valenzuela et. al., (1995) *Exp. Eye Res.,* 61, 33-44; Quigley et al., (1995) *Invest. Ophthalmol. Vis. Sci.,* 36, 774-786; Monard, (1998) In: Haefliger Flammer J (eds) *Nitric Oxide and Endothelin in the Pathogenesis of Glaucoma,* New York, N.Y., Lippincott-Raven, 213-220. The interruption of axonal transport as a result of increased IOP may contribute to retinal ganglion cell death by deprivation of trophic factors. Quigley, (1995) *Aust N Z J Ophthalmol,* 23(2), 85-91. Optic nerve head astrocytes in glaucomatous eyes have also been found to produce increased levels of some neurotoxic substances. For example, increased production of tumor necrosis factor-α (TNF-α) (Yan et al., (2000) *Arch. Ophthalmol.*, 118, 666-673), and nitric oxide synthase (Neufeld et al., (1997) *Arch. Ophthalmol.*, 115, 497-503), the enzyme which gives rise to nitric oxide, has been found in the optic nerve head of glaucomatous eyes. Furthermore, increased expression of the inducible form of nitric oxide synthase (iNOS) and TNF-α by activated retinal glial cells have been observed in rat models of hereditary retinal diseases. Cotinet et al., (1997) Glia, 20, 59-69; de Kozak et al., (1997) *Ocul. Immunol. Inflamm.*, 5, 85-94; Goureau et al., (1999) *J. Neurochem*, 72, 2506-2515. In the glaucomatous optic nerve head, excessive nitric oxide has been linked to the degeneration of axons of retinal ganglion cells. Arthur and Neufeld, (1999) *Surv Ophthalmol*, 43 (Suppl 1), S129-S135. Finally, increased production of TNF-α by retinal glial cells in response to simulated ischemia or elevated hydrostatic pressure has been shown to induce apoptosis in cocultured retinal ganglion cells. Tezel and Wax, (2000) *J. Neurosci.*, 20(23), 8693-8700.

Protecting retinal ganglion cells from degeneration by apoptosis is under study as a potential new treatment for blindness due to glaucoma. Antisense oligonucleotides have been used by several groups to target key proteins in the apoptotic process in order to protect retinal ganglion cells from apoptotic cell death. Antisense oligonucleotides are short, synthetic strands of DNA (or DNA analogs) that are antisense (or complimentary) to a specific DNA or RNA target. Antisense oligonucleotides are designed to block expression of the protein encoded by the DNA or RNA target by binding to the target and halting expression at the level of transcription, translation, or splicing. One of the hurdles to using antisense oligonucleotides as a drug is the rapid degradation of oligonucleotides in blood and in cells by nucleases. This problem has been addressed by using modified backbones that resist degradation (Blake et al., (1985) *Biochemistry*, 24, 6139-6145) such as replacement of the phosphodiester bonds in the oligonucleotides with phosphorothioate linkages to retard nuclease degradation. Matzura and Eckstein, (1968) *Eur. J. Biochem.*, 3, 448-452.

Antisense oligonucleotides have been used successfully in animal models of eye disease. In a model of transient global retinal ischemia, expression of caspase 2 was increased during ischemia, primarily in the inner nuclear and ganglion cell layers of the retina. Suppression of caspase using an antisense oligonucleotide led to significant histopathologic and functional improvement as determined by electroretinogram. Singh et al., (2001) *J. Neurochem.*, 77(2), 466-75. Another study demonstrated that, upon transection of the optic nerve, retinal ganglion cells upregulate the pro-apoptotic protein Bax and undergo apoptosis. Repeated injections of a Bax antisense oligonucleotide into the temporal superior retina of rats inhibited the local expression of Bax and increased the number of surviving retinal ganglion cells following transaction of the optic nerve. Isenmann et al., (1999) *Cell Death Differ.*, 6(7). 673-82.

Delivery of antisense oligonucleotides to retinal ganglion cells has been improved by encapsulating the oligonucleotides in liposomes, which were then coated with the envelope of inactivated hemagglutinating virus of Japan (HVJ; Sendai virus) by fusion (HVJ liposomes). Intravitreal injection into mice of FITC-labeled antisense oligonucleotides encapsulated in HVJ liposomes resulted in high fluorescence within 44% of the cells in the ganglion layer which lasted three days while fluorescence with naked FITC-labeled antisense oligonucleotide disappeared after one day. Hangai et al., (1998) *Arch Ophthalmol*, 116(7), 976.

A method of preventing or modulating apoptosis of the present invention is directed to modulating apoptosis in the cells of the eye, such as but not limited to, astrocytes, retinal ganglion, retinal glial cells and lamina cribosa. Death of retinal ganglion cells in glaucoma occurs by apoptosis. Thus, providing a method of inhibiting apoptosis in retinal ganglion cells or by protecting retinal ganglion cells from degeneration by apoptosis provides a novel treatment for prevention of blindness due to glaucoma.

The present invention provides a method for preventing retinal ganglion cell death in a glaucomatous eye, by suppressing expression of apoptosis-specific eIF-5A1. Inhibiting the expression of apoptosis-specific eIF-5A1 reduces apoptosis. Apoptosis-specific eIF-5A1 is a powerful gene that appears to regulate the entire apoptic process. Thus, controlling apoptosis in the optic nerve head indicates that blocking expression of apoptosis-specific eIF-5A1 provides a treatment for glaucoma.

Suppression of expression of apoptosis-specific eIF-5A1 is accomplished by administering antisense oligonucleotides targeted against human apoptosis-specific 5A1 to cells of the eye such as, but not limited to lamina crobosa, astrocytes, retinal ganglion, or retinal glial cells. Antisense oligonucleotides are as defined above, i.e. have a nucleotide sequence encoding at least a portion of an apoptosis-specific eIF-5A1 polypeptide. Antisense oligonucleotides targeted against human apoptosis-specific eIF-5A1 have a nucleotide sequence encoding at least a portion of human apoptosis-specific eIF-5A1 polypeptide. Preferred antisense oligonucleotides comprise SEQ ID NO:26 or 27 or oligonucleotides that bind to a sequence complementary to SEQ ID NO:26 or 27 under high stringency conditions.

Another embodiment of the invention provides a method of suppressing expression of apoptosis-specific eIF-5A1 in lamina cribosa cells, astrocyte cells, retinal ganglion cells or retinal glial cells. Antisense oligonucleotides, such as but not limited to, SEQ ID NO:26 and 27, targeted against human apoptosis-specific eIF-5A1 are administered to lamina cribosa cells, astrocyte cells, retinal ganglion cells or retinal glial cells. The cells may be human.

In addition to having a role in apoptosis, eIF-5A may also have a role in the immune response. The present inventors have discovered that apoptosis factor 5A levels correlate with elevated levels of two cytokines (Interleukin 1-beta "IL-1β" and interleukin 18 "IL-18") in ischemic heart tissue, thus further proving that apoptosis factor 5A is involved in cell death as it is present in ischemic heart tissue. Further, this apoptosis factor 5A/interleukin correlation has not been seen in non-ischemic heart tissue. See FIGS. 50A-F and 51. Using PCR measurements, levels of apoptosis factor 5A, proliferating eIF-5a (eIF-5A2—the other known isoform), IL-1β, and IL-18 were measured and compared in various ischemic heart tissue (from coronary bypass graft and valve (mitral and atrial valve) replacement patients).

The correlation of apoptosis eIF-5a to these potent interleukins further suggests that the inflammation and apoptosis pathways in ischemia may be controlled via controlling levels of apoptosis factor 5A. Further evidence that apoptosis factor 5A is involved in the immune response is suggested by the fact that human peripheral blood mononuclear cells (PBMCs) normally express very low levels of eIF-5A, but upon stimulation with T-lymphocyte-specific stimuli expression of eIF-5A increases dramatically (Bevec et al., 1994). This suggests a role for apoptosis factor 5A in T-cell proliferation and/or activation. Since activated T cells are capable of producing a wide variety of cytokines, it is also possible that apoptosis factor 5A may be required as a nucleocytoplasmic shuttle for cytokine mRNAs.

Another study looked at eIf-5A mRNA and cell surface marker expression in human peripheral blood mononuclear cells (PBMCs) and blood cell lines treated with various maturation stimulating agents (Bevec et al., Proc. Natl. Acad. Sci. USA, 91:10829-10833. (1994)). eIF-5A mRNA expression was induced in the PBMCs by numerous stimuli that also induced T-cell activation (Bevec et al., 1994). Higher levels of PBMC eIF 5A mRNA expression were observed in HIV-1 patients than in healthy donors. The authors of this study interpreted their results by suggesting that the eIF-5A mRNA was induced so that it could act as a nucleocytoplasmic shuttle for the important mRNAs necessary for T-cell activation and also for HIV-1 replication (Bevec et al., 1994). eIF-5A has been demonstrated to be a cellular binding factor for the HIV Rev protein and required for HIV replication (Ruhl et al. 1993).

Recent studies have suggested an important role for eIF-5A in the differentiation and activation of cells. When immature dendritic cells were induced to differentiate and mature, an induction of eIF-5A mRNA levels coincided with an elevation of CD83 protein expression (Kruse et al., J. Exp. Med. 191(9): 1581-1589 (2000)). Dendritic cells are antigen-presenting cells that sensitize helper and killer T cells to induce T cell-mediated immunity (Steinman, 1991). Immature dendritic cells lack the ability to stimulate T cells and require appropriate stimuli (i.e. inflammatory cytokines and/or microbial products) to mature into cells capable of activating T cells. The synthesis and surface expression of CD83 on mature dendritic cells is importantly involved in sensitizing helper and killer T cells and in inducing T cell-mediated immunity. When the immature dendritic cells were pretreated with an inhibitor (GC7) of hypusination and thus an inhibitor of eIF-5A activation, the surface expression of CD83 was prevented (Kruse et al., 2000). The authors of this study interpreted their results that the eIF-5A was essential for the nucleocytoplasmic translocation of the CD83 mRNA and that by blocking hypusination and thus eIF-5A, CD83 expression and dendritic cell maturation were blocked (Kruse et al., 2000).

In both of these studies (Bevec et al., 1994; Kruse et al., 2000) implicating a role for eIF-5A in the immune system, the authors did not specify or identify which isoform of eIF-5A they were examining, nor did they have a reason to. As briefly discussed above, humans are known to have two isoforms of eIF-5A, eIF-5A1 (apoptosis factor 5A1) and eIF-5A2, both encoded on separate chromosomes. Prior to the present inventors' discoveries it was believed that both of these isoforms were functionally redundant. The oligonucleotide described by Bevec et al. that was used to detect eIF-5A mRNA in stimulated PBMCs had 100% homology to human eIEF-5A1 and the study pre-dates the cloning of eIF-5A2. Similarly, the primers described by Kruse et al. that were used to detect eIF-5A by reverse transcription polymerase chain reaction during dendritic cell maturation had 100% homology to human eIF-5A1.

The present invention relates to controlling the expression of eIF-5A1 to control the rate of dendritic cell maturation and PBMC activation, which in turn may control the rate of T cell-mediated immunity. The present inventors studied the role of eIF-5A1 in the differentiation of monocytes into adherent macrophages using the U-937 cell line, as U-937 is known to express eIF-5A mRNA (Bevec et al., 1994). U-937 is a human monocyte cell line that grows in suspension and will become adherent and differentiate into macrophages upon stimulation with PMA. When PMA is removed by changing the media, the cells become quiescent and are then capable of producing cytokines (Barrios-Rodiles et al., J. Immunol. 163:963-969 (1999)). In response to lipopolysaccharide (LPS), a factor found on the outer membrane of many bacteria known to induce a general inflammatory response, the macrophages produce both TNF-α and IL-113 (Barrios-Rodiles et al., 1999). See FIG. 78 showing a chart of stem cell differentiation and the resultant production of cytokines. The U-937 cells also produce IL-6 and IL-10 following LPS-stimulation (Izeboud et al., J. Receptor & Signal Transduction Research, 19(1-4):191-202. (1999)).

Using U-937 cells, it was shown that eIF-5A1 is upregulated during monocyte differentiation and TNF-α secretion. See FIG. 77. Accordingly, one aspect of the invention provides for a method of inhibiting or delaying maturation of macrophages to inhibit or reduce the production of cytokines. This method involves providing an agent that is capable of reducing the expression of either DHS or eIF-5A1. By reducing or eliminating expression of DHS, eIF-5A1 activation will be reduced or eliminated. Since, eIF-5A1 is upregulated during monocyte differentiation and TNF-α secretion, it is believed that it is necessary for these events to occur. Thus, by reducing or eliminating activation of eIF-5A1 or by directly reducing or eliminating eIF-5A1 expression, monocyte differentiation and TNF-α secretion can be reduced or eliminated. Any agent capable of reducing the expression of DHS or eIF-5A1 may be used and includes, but is not limited to antisense oligonucleotides or siRNAs as described herein.

The present inventors have studied the ability of eIF-5A1 to promote translation of cytokines by acting as a nucleocytoplasmic shuttle for cytokine mRNAs in vitro using a cell line known to predictably produce cytokine(s) in response to a specific stimulus. Some recent studies have found that human liver cell lines can respond to cytokine stimulation by inducing production of other cytokines. HepG2 is a well characterized human hepatocellular carcinoma cell line found to be sensitive to cytokines. In response to IL-1β, HepG2 cells rapidly produce TNF-α mRNA and protein in a dose-dependent manner (Frede et al., 1996; Rowell et al., 1997; Wordemann et al., 1998). Thus, HepG2 cells were used as a model system to study the regulation of TNF-α production. The present inventors have shown that inhibition of eIF-5A1 expression in HepG2 cells caused the cells to produce less TNF-α after having been transfected with antisense nucleotides directed toward apoptosis factor 5A.

Thus one embodiment of the present invention provides a method for reducing levels of a cytokine in a cell. The method involves administering an agent to the cell capable of reducing expression of apoptosis factor 5A1. Reducing expression of apoptosis factor 5A1 causes a reduction in the expression of the cytokine, and thus leads to a decreased amount of the cytokine produced by cell. The cytokine is a preferably a pro-inflammatory cytokine, including, but not limited to IL-1, IL-18, IL-6 and TNF-α.

An agent capable of reducing expression of apoptosis factor 5A may be an antisense nucleotide having a sequence complementary to apoptosis factor 5A. Preferably the antisense nucleotide has a sequence selected from the group consisting of SEQ ID NO: 63-65 or is an antisense nucleotide that hybridizes under highly stringent conditions to a sequence selected from the group consisting of SEQ ID NO: 63-65.

An agent may also comprise a siRNA having a sequence complementary to apoptosis factor 5A. Preferably the siRNA has a sequence selected from the group consisting of SEQ ID NO: 30, 31, 32, and 33, or is a siRNA that hybridizes under highly stringent conditions to a sequence selected from the group consisting of SEQ ID NO: 30, 31, 32, and 33. FIGS. 65-67 show that cells transfected with apoptosis factor 5A siRNAs have a lower percentage of cells undergoing apoptosis after exposure to camptothecin and TNF-α. An agent may also comprise antisense DHS nucleotides.

The present invention is also directed to a polynucleotide having a sequence selected from the group consisting of SEQ ID NO: 63-65 or is an antisense nucleotide that hybridizes under highly stringent conditions to a sequence selected from the group consisting of SEQ ID NO: 63-65.

The present invention is also directed to a siRNA having a sequence selected from the group consisting of SEQ ID NO: 30, 31, 32, and 33 or is a siRNA that hybridizes under highly stringent conditions to a sequence selected from the group consisting of SEQ ID NO: 30, 31, 32, and 33.

The present invention is also directed to a method for reducing the expression of p53. This method involves administering an agent capable of reducing expression of apoptosis factor 5A, such as the antisense polynucleotides or the siRNAs described above. Reducing expression of apoptosis factor 5A1 reduces expression of p53 as shown in FIG. 52 and example 11.

The present invention is also directed to a method for increasing the expression of Bcl-2. This method entails administering an agent capable of reducing expression of apoptosis factor 5A. Preferred agents include the antisense oligonucleotides and siRNAs described above. Reducing of expression of apoptosis factor 5A1 increases expression of Bcl-2 as shown in FIG. 63 and example 13. FIG. 63 shows that cells transfected with apoptosis factor 5a siRNA produced less apoptosis factor 5A1 protein and in addition, produced more Bcl-2 protein. Decrease in apoptosis factor 5A1 expression correlates with an increase in BCL-2 expression.

The present invention also provides a method for reducing levels of TNF-alpha in a patient in need thereof comprising administering to said patient either the antisense polynucleotide or siRNAs described above. As demonstrated in FIG. 69 and example 14, cells transfected with antisense factor 5A oligonucleotides of the present invention produced less TNF-α after induction with IL-1 than cells not transfected with such antisense oligonucleotides.

The present invention provides for a method of reducing levels of TNF-alpha in human epithelial cells. As demonstrated in FIGS. 74A and B and FIG. 75 and example 15, reducing or inhibiting the expression of eIF-5A1 causes a decrease, if not complete inhibition of the production of TNF-alpha in a human epithelial cell line. siRNAs against eIF-5A1 were used to inhibit expression of eIF-5A1. This inhibition of expression not only reduced or inhibited the production of TNF-alpha, but it also protected the cells from cytokine-induced apoptosis. By reducing expression of eIF-5A1, the production of TNF-α is reduced. This dual effect provides a method of treating patients suffering from inflammatory bowel disorders such as Crohn's disease and ulcerative colitis, which are associated with an increased inflammation caused by TNF-α.

Thus, the present invention provides a method of treating pathological conditions characterized by an increased IL-1, TNF-alpha, IL-6 or IL-18 level comprising administering to a mammal having said pathological condition, an agent to reduce expression of apoptosis Factor 5A.

Known pathological conditions characterized by an increase in IL-1, TNF-alpha, or Il-6 levels include, but are not limited to, arthritis-rheumatoid and osteo arthritis, asthma, allergies, arterial inflammation, Crohn's disease, inflammatory bowel disease (ibd), ulcerative colitis, coronary heart disease, cystic fibrosis, diabetes, lupus, multiple sclerosis, graves disease, periodontitis, glaucoma & macular degeneration, ocular surface diseases including keratoconus, organ ischemia-heart, kidney, repurfusion injury, sepsis, multiple myeloma, organ transplant rejection, psoriasis and eczema.

As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological cross-reactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (1990) *J. Mol Biol.* 215:403-10. BLAST nucleotide searches can be performed with the NBLAST program. BLAST protein searches can be performed with the)(BLAST program to obtain amino acid sequences homologous to the proteins of the invention. To obtain gapped alignments for comparison purposes, Gapped BLAST can be utilized as described in Altschul et al. (1997) *Nucleic Acids Res.* 25(17):3389-3402. When utilizing BLAST and gapped BLAST programs, the default parameters of the respective programs (e.g., (BLAST and NBLAST) can be used.

The term "functional derivative" of a nucleic acid is used herein to mean a homolog or analog of the gene or nucleotide sequence. A functional derivative may retain at least a portion of the function of the given gene, which permits its utility in accordance with the invention. "Functional derivatives" of the apoptosis factor 5A polypeptide as described herein are fragments, variants, analogs, or chemical derivatives of apoptosis factor 5A that retain at least a portion of the apoptosis factor 5A activity or immunological cross reactivity with an antibody specific for apoptosis factor 5A. A fragment of the apoptosis factor 5A polypeptide refers to any subset of the molecule.

Functional variants can also contain substitutions of similar amino acids that result in no change or an insignificant change in function. Amino acids that are essential for function can be identified by methods known in the art, such as site-directed mutagenesis or alanine-scanning mutagenesis (Cunningham et al. (1989) Science 244:1081-1085). The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al. (1992) J. Mol. Biol. 224:899-904; de Vos et al. (1992) Science 255:306-312).

A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different animal genus or species. An "analog" refers to a non-natural molecule substantially similar to or functioning in relation to the entire molecule, a variant or a fragment thereof.

Variant peptides include naturally occurring variants as well as those manufactured by methods well known in the art. Such variants can readily be identified/made using molecular techniques and the sequence information disclosed herein. Further, such variants can readily be distinguished from other proteins based on sequence and/or structural homology to the eIF-5A or DHS proteins of the present invention. The degree of homology/identity present will be based primarily on whether the protein is a functional variant or non-functional variant, the amount of divergence present in the paralog family and the evolutionary distance between the orthologs.

Non-naturally occurring variants of the eIF-5A or DHS proteins of the present invention can readily be generated using recombinant techniques. Such variants include, but are not limited to deletions, additions and substitutions in the amino acid sequence of the proteins. For example, one class of substitutions are conserved amino acid substitution. Such substitutions are those that substitute a given amino acid in a protein by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, e.g. Sambrook, J. et al., Molecular Cloning: A Laboratory Manual, 2$^{nd}$ edition, Cold Spring Harbour Press, Cold Spring Harbor, N.Y., 1989.

The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SDS. Hybridization is carried out at about 68° C. for about 3 to 4 hours for fragments of cloned DNA and for about 12 to 16 hours for total eucaryotic DNA. For lower stringencies, the temperature of hybridization is reduced to about 42° C. below the melting temperature ($T_m$) of the duplex. The $T_m$ is known to be a function of the G-C content and duplex length as well as the ionic strength of the solution.

As used herein, the phrase "hybridizes to a corresponding portion" of a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridization under appropriate conditions. For example, a 100 nucleotide long sense molecule will recognize and hybridize to an approximately 100 nucleotide portion of a nucleotide sequence, so long as there is about 70% or more sequence similarity between the two sequences. It is to be understood that the size of the "corresponding portion" will allow for some mismatches in hybridization such that the "corresponding portion" may be smaller or larger than the molecule which hybridizes to it, for example 20-30% larger or smaller, preferably no more than about 12-15% larger or smaller.

In addition, functional variants of polypeptides can also contain substitution of similar amino acids that result in no change or an insignificant change in function. Amino acids that are essential for function can be identified by methods known in the art, such as site-directed mutagenesis or alanine-scanning mutagenesis (Cunningham et al., Science 244: 1081-1085 (1989)). The latter procedure introduces single alanine mutations at every residue in the molecule. The resulting mutant molecules are then tested for biological activity or in assays.

For example, an analog of apoptosis factor 5A refers to a non-natural protein or peptidomimetic substantially similar to either the entire protein or a fragment thereof. Chemical derivatives of apoptosis factor 5A contain additional chemical moieties not normally a part of the peptide or peptide fragment. Modifications can be introduced into peptide or fragment thereof by reacting targeted amino acid residues of the peptide with an organic derivatizing agent that is capable of reacting with selected side chains or terminal residues.

It is understood that the nucleic acids and polypeptides of the present invention, where used in an animal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The compositions of this invention can be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application.

Such compositions can be prepared in a manner well known in the pharmaceutical art. In making the composition the active ingredient will usually be mixed with a carrier, or diluted by a carrier, and/or enclosed within a carrier which can, for example, be in the form of a capsule, sachet, paper or other container. When the carrier serves as a diluent, it can be a solid, semi-solid, or liquid material, which acts as a vehicle, excipient or medium for the active ingredient. Thus, the composition can be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions, suspensions, sterile packaged powders and as a topical patch.

Having now generally described the invention, the same will be more readily understood through reference to the following examples, which are provided by way of illustration. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of conventional methods, such as those employed in the construction of vectors and plasmids, the insertion of nucleic acids encoding polypeptides into such vectors and plasmids, the introduction of plasmids into host cells, and the expression and determination thereof of genes and gene products can be obtained from numerous publication, including Sambrook, J. et al., (1989) Molecular Cloning: A Laboratory Manual, $2^{nd}$ ed., Cold Spring Harbor Laboratory Press. All references mentioned herein are incorporated in their entirety.

EXAMPLES

Example 1

Visualization of Apoptosis in Rat Corpus Luteum by DNA Laddering

The degree of apoptosis was determined by DNA laddering. Genomic DNA was isolated from dispersed corpus luteal cells or from excised corpus luteum tissue using the QIAamp DNA Blood Kit (Qiagen) according to the manufacturer's instructions. Corpus luteum tissue was excised before the induction of apoptosis by treatment with PGF-2α, 1 and 24 hours after induction of apoptosis. The isolated DNA was end-labeled by incubating 500 ng of DNA with 0.2 µCi [α-$^{32}$P]dCTP, 1 mM Tris, 0.5 mM EDTA, 3 units of Klenow enzyme, and 0.2 pM each of dATP, dGTP, and dTTP at room temperature for 30 minutes. Unincorporated nucleotides were removed by passing the sample through a 1 ml Sephadex G-50 column according to Sambrook et al. The samples were then resolved by Tris-acetate-EDTA (1.8%) gel electrophoresis. The gel was dried for 30 minutes at room temperature under vacuum and exposed to x-ray film at −80° C. for 24 hours.

Figure 16:
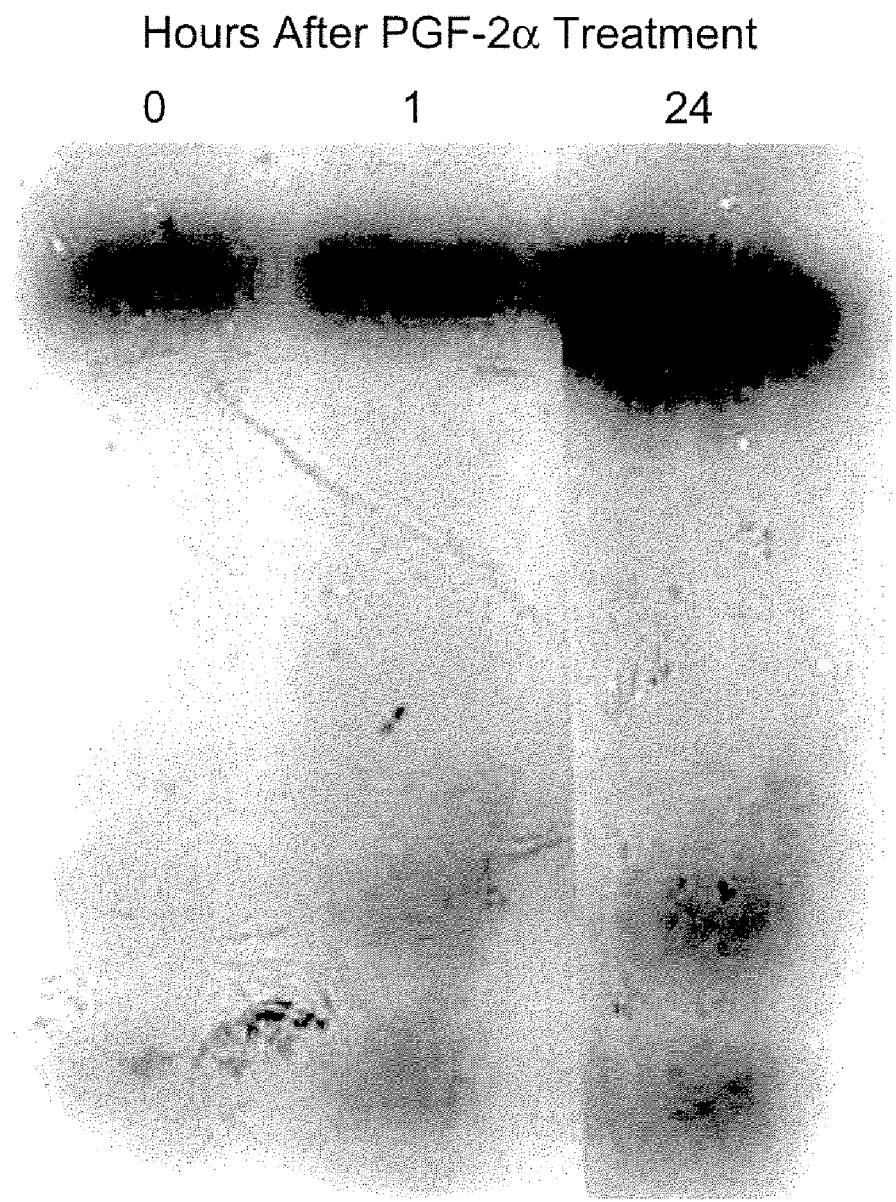
FIG. 16 depicts a DNA laddering experiment in which the degree of apoptosis in superovulated rat corpus lutea was examined after injection with PGF-2α.

In one experiment, the degree of apoptosis in superovulated rat corpus lutea was examined either 0, 1, or 24 hours after injection with PGF-2α. In the 0 hour control, the ovaries were removed without PGF-2α injection. Laddering of low molecular weight DNA fragments reflecting nuclease activity associated with apoptosis is not evident in control corpus luteum tissue excised before treatment with PGF-2α, but is discernible within 1 hour after induction of apoptosis and is pronounced by 24 hours after induction of apoptosis, which is shown in FIG. 16. In this figure, the top panel is an autoradiograph of the Northern blot probed with the $^{32}$P-dCTP-labeled 3'-untranslated region of rat corpus luteum apoptosis-specific DHS cDNA. The lower panel is the ethidium bromide stained gel of total RNA. Each lane contains 10 µg RNA. The data indicates that there is down-regulation of eIF-5A transcript following serum withdrawal.

Figure 17:
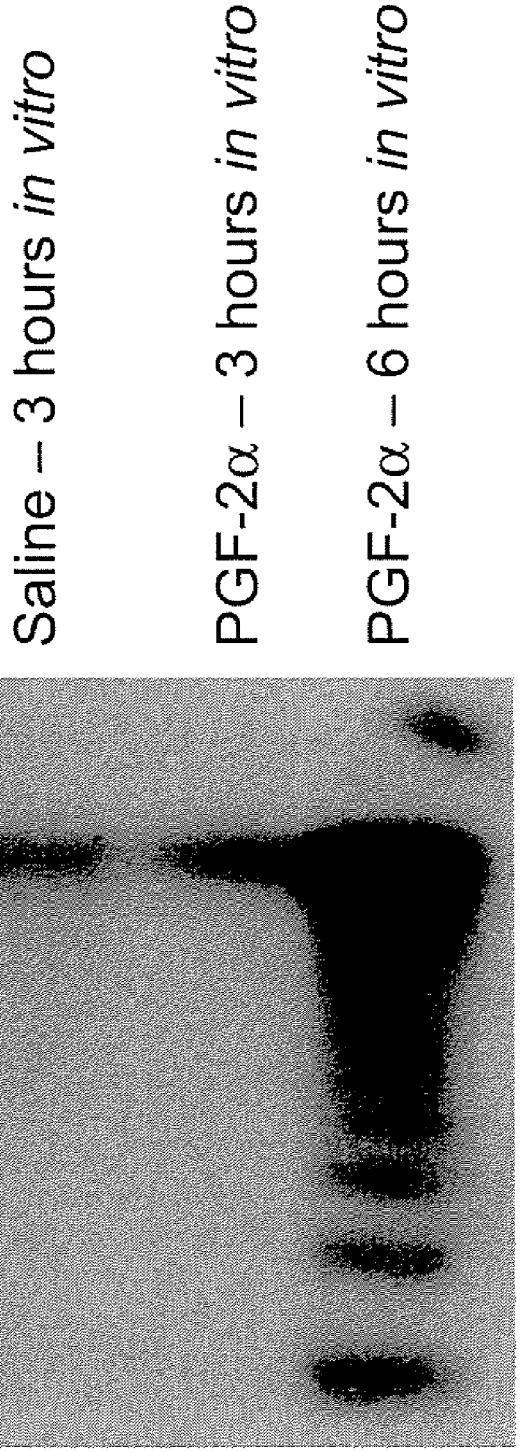
FIG. 17 is an agarose gel of genomic DNA isolated from apoptosing rat corpus luteum showing DNA laddering after treatment of rats with PGF F-2α.

In another experiment, the corresponding control animals were treated with saline instead of PGF-2α. Fifteen minutes after treatment with saline or PGF-2α, corpora lutea were removed from the animals. Genomic DNA was isolated from the corpora lutea at 3 hours and 6 hours after removal of the tissue from the animals. DNA laddering and increased end labeling of genomic DNA are evident 6 hours after removal of the tissue from the PGF-2α-treated animals, but not at 3 hours after removal of the tissue. See FIG. 17. DNA laddering reflecting apoptosis is also evident when corpora lutea are excised 15 minutes after treatment with PGF-2α and maintained for 6 hours under in vitro conditions in EBSS (Gibco). Nuclease activity associated with apoptosis is also evident from more extensive end labeling of genomic DNA.

Figure 18:
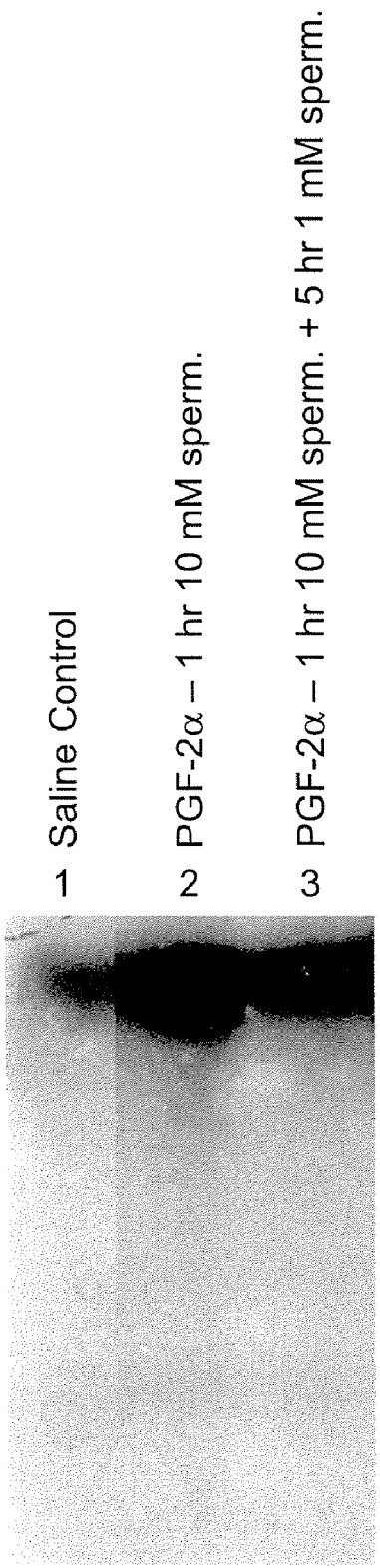
FIG. 18 depicts a DNA laddering experiment in which the degree of apoptosis in dispersed cells of superovulated rat corpora lutea was examined in rats treated with spermidine prior to exposure to prostaglandin F-2α (PGF-2α).

In another experiment, superovulation was induced by subcutaneous injection with 500 µg of PGF-2α. Control rats were treated with an equivalent volume of saline solution. Fifteen to thirty minutes later, the ovaries were removed and minced with collagenase. The dispersed cells from rats treated with PGF-2α were incubated in 10 mm glutamine+10 mm spermidine for 1 hour and for a further 5 hours in 10 mm glutamine without spermidine (lane 2) or in 10 mm glutamine+10 mm spermidine for 1 hour and for a further 5 hours in 10 mm glutamine+1 mm spermidine (lane 3). Control cells from rats treated with saline were dispersed with collagenase and incubated for 1 hour and a further 5 hours in glutamine only (lane 1). Five hundred nanograms of DNA from each sample was labeled with [$\alpha$-$^{32}$P]-dCTP using Klenow enzyme, separated on a 1.8% agarose gel, and exposed to film for 24 hours. Results are shown in FIG. 18.

Figure 19:
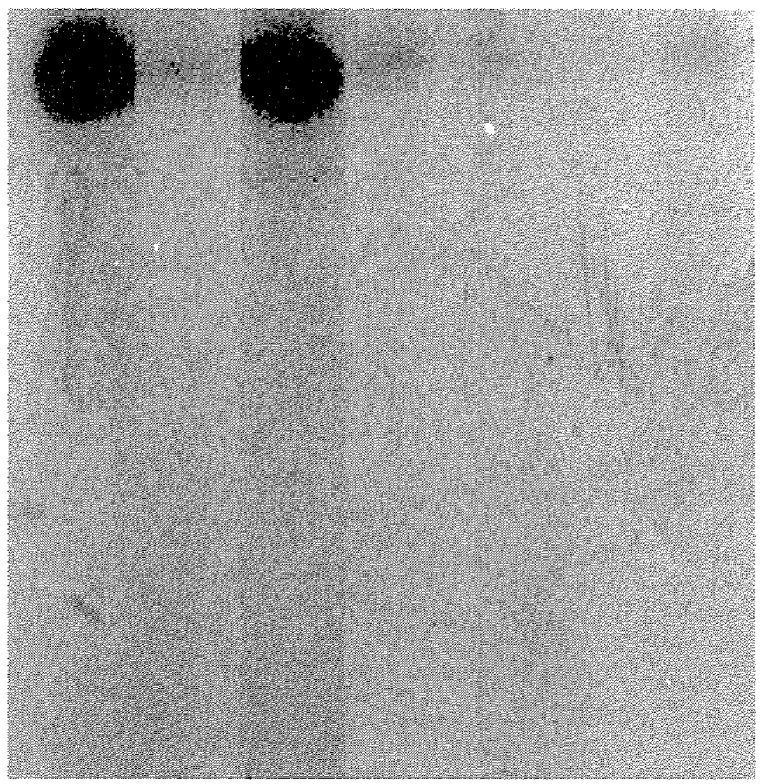
FIG. 19 depicts a DNA laddering experiment in which the degree of apoptosis in superovulated rat corpus lutea was examined in rats treated with spermidine and/or PGF-2α.

In yet another experiment, superovulated rats were injected subcutaneously with 1 mg/100 g body weight of spermidine, delivered in three equal doses of 0.333 mg/100 g body weight, 24, 12, and 2 hours prior to a subcutaneous injection with 500 μg PGF-2α. Control rats were divided into three sets: no injections, three injections of spermidine but no PGF-2α; and three injections with an equivalent volume of saline prior to PGF-2α treatment. Ovaries were removed front the rats either 1 hour and 35 minutes or 3 hours and 45 minutes after prostaglandin treatment and used for the isolation of DNA. Five hundred nanograms of DNA from each sample was labeled with [$\alpha$-$^{32}$P]-dCTP using Klenow enzyme, separated on a 1.8% agarose gel, and exposed to film for 24 hours: lane 1, no injections (animals were sacrificed at the same time as for lanes 3-5); lane 2, three injections with spermidine (animals were sacrificed at the same time as for lanes 3-5); lane 3, three injections with saline followed by injection with PGF-2α (animals were sacrificed 1 h and 35 min after treatment with PGF-2α); lane 4, three injections with spermidine followed by injection with PGF-2α (animals were sacrificed 1 h and 35 min after treatment with PGF-2α); lane 5, three injections with spermidine followed by injection with PGF-2α (animals were sacrificed 1 h and 35 min after treatment with PGF-2α); lane 6, three injections with spermidine followed by injection with PGF-2α (animals were sacrificed 3 h and 45 min after treatment with PGF-2α); lane 7, three injections with spermidine followed by injection with PGF-2α (animals were sacrificed 3 h and 45 min after treatment with PGF-2α). Results are shown in FIG. 19.

RNA Isolation

Total RNA was isolated from corpus luteum tissue removed from rats at various times after PGF-2α induction of apoptosis. Briefly, the tissue (5 g) was ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of Miracloth and centrifuged at 10,000 g at 4° C. for 30 minutes. The supernatant was then subjected to cesium chloride density gradient centrifugation at 11,200 g for 20 hours. The pelleted RNA was rinsed with 75% ethanol, resuspended in 600 ml DEPC-treated water and the RNA precipitated at −70° C. with 1.5 ml 95% ethanol and 60 ml of 3M NaOAc.

Genomic DNA Isolation and Laddering

Genomic DNA was isolated from extracted corpus luteum tissue or dispersed corpus luteal cells using the QIAamp DNA Blood Kit (Qiagen) according to the manufacturer's instructions. The DNA was end-labeled by incubating 500 ng of DNA with 0.2 μCi [$\alpha$-$^{32}$P]dCTP, 1 mM Tris, 0.5 mM EDTA, 3 units of Klenow enzyme, and 0.2 pM each of dATP, dGTP, and dTTP, at room temperature for 30 minutes. Unincorporated nucleotides were removed by passing the sample through a 1-ml Sephadex G-50 column according to the method described by Maniatis et al. The samples were then resolved by Tris-acetate-EDTA (2%) gel electrophoresis. The gel was dried for 30 minutes at room temperature under vacuum and exposed to x-ray film at −80° C. for 24 hours.

Plasmid DNA Isolation, DNA Sequencing

The alkaline lysis method described by Sambrook et al., supra, was used to isolate plasmid DNA. The full-length positive cDNA clone was sequenced using the dideoxy sequencing method. Sanger et al., Proc. Natl. Acad. Sci. USA, 74:5463-5467. The open reading frame was compiled and analyzed using BLAST search (GenBank, Bethesda, Md.) and sequence alignment was achieved using a BCM Search Launcher: Multiple Sequence Alignments Pattern-Induced Multiple Alignment Method (see F. Corpet, Nuc. Acids Res., 16:10881-10890, (1987). Sequences and sequence alignments are shown in FIGS. 5-11.

Northern Blot Hybridization of Rat Corpus Luteum RNA

Twenty milligrams of total RNA isolated from rat corpus luteum at various stages of apoptosis were separated on 1% denatured formaldehyde agarose gels and immobilized on nylon membranes. The full-length rat apoptosis-specific eIF-5A cDNA (SEQ ID NO:1) labeled with $^{32}$P-dCTP using a random primer kit (Boehringer) was used to probe the membranes $7\times10^7$. Alternatively, full length rat apoptosis-specific DHS cDNA (SEQ ID NO:6) labeled with $^{32}$P-dCTP using a random primer kit (Boehringer) was used to probe the membranes ($7\times10^7$ cpm). The membranes were washed once with 1×SSC, 0.1% SDS at room temperature and three times with 0.2×SSC, 0.1% SDS at 65° C. The membranes were dried and exposed to X-ray film overnight at −70° C.

Figure 12:
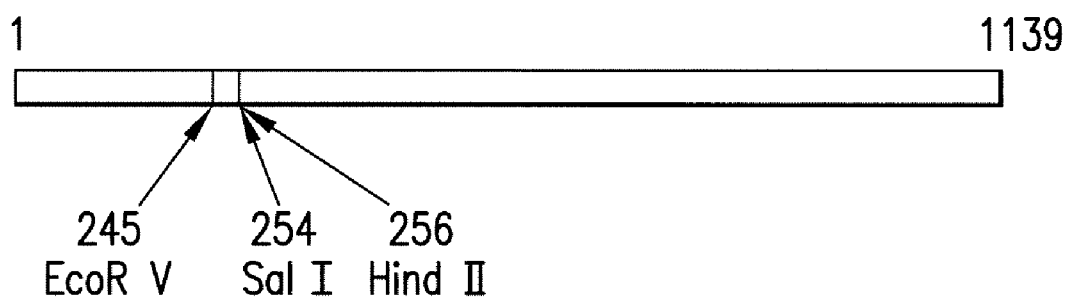
FIG. 12 is a restriction map of rat corpus luteum apoptosis-specific eIF-5A cDNA.
Figure 13:
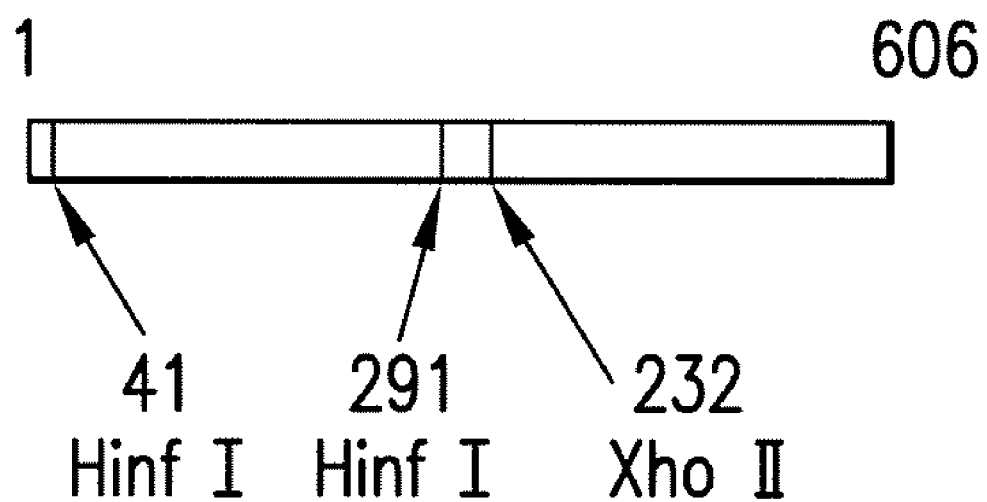
FIG. 13 is a restriction map of the partial-length rat apoptosis-specific DHS cDNA.
Figure 14:
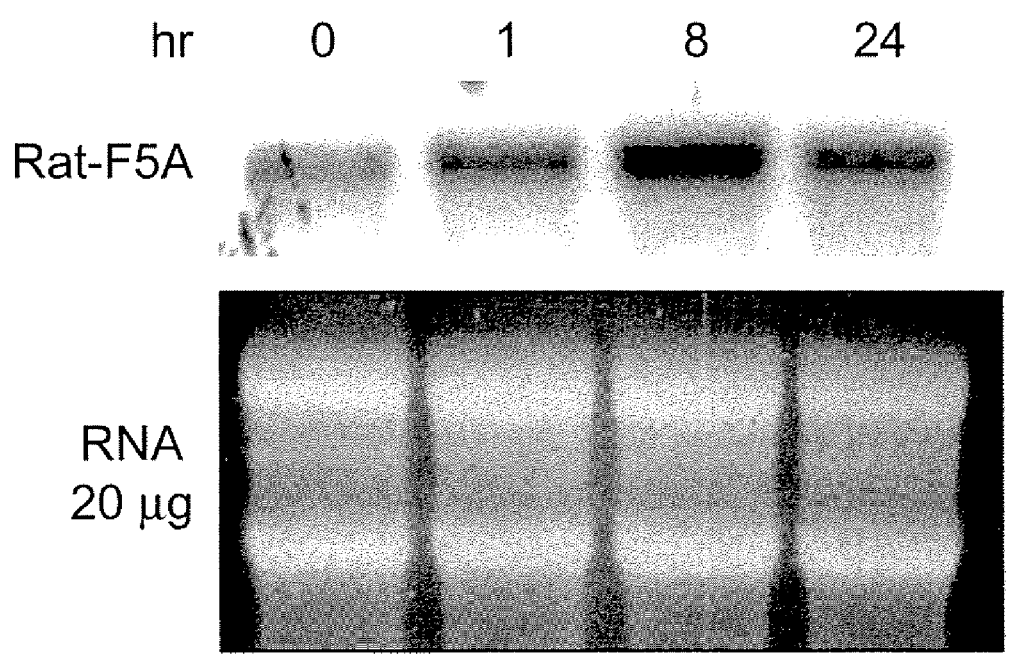
FIG. 14 is a Northern blot (top) and an ethidium bromide stained gel (bottom) of total RNA probed with the $^{32}$P-dCTP-labeled 3'-end of rat corpus luteum apoptosis-specific eIF-5A cDNA.
Figure 15:
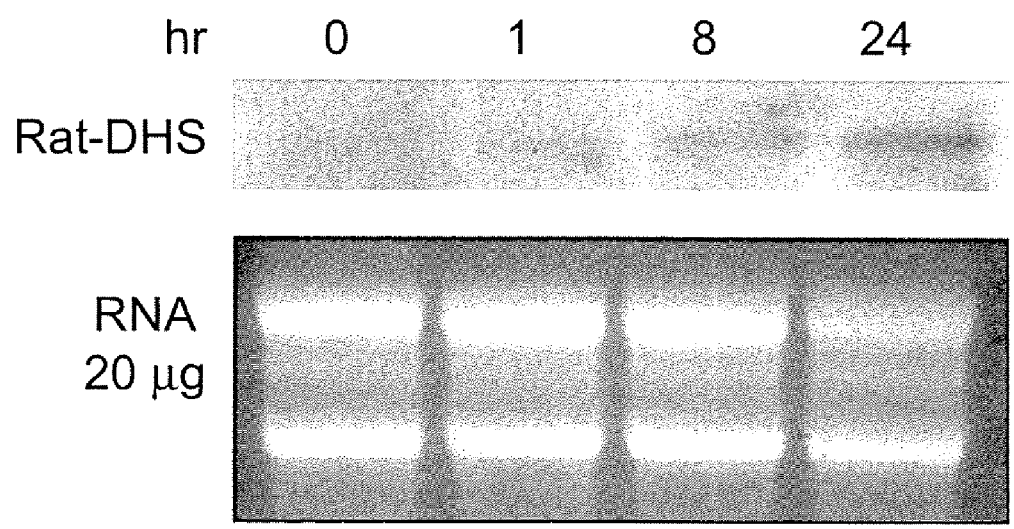
FIG. 15 is a Northern blot (top) and an ethidium bromide stained gel (bottom) of total RNA probed with the $^{32}$P-dCTP-labeled 3'-end of rat corpus luteum apoptosis-specific DHS cDNA.

As can be seen, eIF-5A and DHS are both upregulated in apoptosing corpus luteum tissue. Expression of apoptosis-specific eIF-5A is significantly enhanced after induction of apoptosis by treatment with PGF-2α—low at time zero, increased substantially within 1 hour of treatment, increased still more within 8 hours of treatment and increased slightly within 24 hours of treatment (FIG. 14). Expression of DHS was low at time zero, increased substantially within 1 hour of treatment, increased still more within 8 hours of treatment and increased again slightly within 24 hours of treatment (FIG. 15).

Generation of an Apoptosing Rat Corpus Luteum RT-PCR Product Using Primers Based on Yeast, Fungal and Human eIF-5A Sequences A partial-length apoptosis-specific eIF-5A sequence (SEQ ID NO:11) corresponding to the 3' end of the gene was generated from apoptosing rat corpus luteum RNA template by RT-PCR using a pair of oligonucleotide primers designed from yeast, fungal and human eIF-5A sequences. The upstream primer used to isolate the 3' end of the rat eIF-5A gene is a 20 nucleotide degenerate primer: 5' TCSA-ARACHGGNAAGCAYGG 3' (SEQ ID NO:9); wherein S is selected from C and G; R is selected from A and G; H is selected from A, T, and C; Y is selected from C and T; and N is any nucleic acid. The downstream primer used to isolate the 3' end of the rat eIF-5A gene contains 42 nucleotides: 5' GCGAAGCTTCCATGGCTCGAGTTTTTTTTTTTTTTT-TTTTTT 3' (SEQ ID NO:10). A reverse transcriptase polymerase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence of a 900 by fragment, which was subcloned into pBluescript™ (Stratagene Cloning Systems, LaJolla, Calif.) using blunt end ligation and sequenced (SEQ ID NO:11). The cDNA sequence of the 3' end is SEQ ID NO:11 and the amino acid sequence of the 3' end is SEQ ID NO:12. See FIGS. 1-2.

A partial-length apoptosis-specific eIF-5A sequence (SEQ ID NO:15) corresponding to the 5' end of the gene and overlapping with the 3' end was generated from apoptosing rat corpus luteum RNA template by RT-PCR. The 5' primer is a 24-mer having the sequence, 5' CAGGTCTAGAGTTG- GAATCGAAGC 3' (SEQ ID NO:13), that was designed from human eIF-5A sequences. The 3' primer is a 30-mer having the sequence, 5' ATATCTCGAGCCTTGATTGCAA-CAGCTGCC 3' (SEQ ID NO:14) that was designed according to the 3' end RT-PCR fragment. A reverse transcriptase-polymerase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence a 500 by fragment, which was subcloned into pBluescript™ (Stratagene Cloning Systems, LaJolla, Calif.) using XbaI and XhoI cloning sites present in the upstream and downstream primers, respectively, and sequenced (SEQ ID NO:15). The cDNA sequence of the 5' end is SEQ ID NO:15, and the amino acid sequence of the 5' end is SEQ ID NO:16. See FIG. 2.

The sequences of the 3' and 5' ends of the rat apoptosis-specific eIF-5A (SEQ ID NO:11 and SEQ ID NO:15, respectively) overlapped and gave rise to the full-length cDNA sequence (SEQ ID NO:1). This full-length sequence was aligned and compared with sequences in the GeneBank data base. See FIGS. 1-2. The cDNA clone encodes a 154 amino acid polypeptide (SEQ ID NO:2) having a calculated molecular mass of 16.8 KDa. The nucleotide sequence, SEQ ID NO:1, for the full length cDNA of the rat apoptosis-specific corpus luteum eIF-5A gene obtained by RT-PCR is depicted in FIG. 3 and the corresponding derived amino acid sequence is SEQ ID NO:9. The derived full-length amino acid sequence of eIF-5A was aligned with human and mouse eIF-5a sequences. See FIG. 7-9.

Generation of an Apoptosing Rat Corpus Luteum RT-PCR Product Using Primers Based on a Human DHS Sequence A partial-length apoptosis-specific DHS sequence (SEQ ID NO:6) corresponding to the 3' end of the gene was generated from apoptosing rat corpus luteum RNA template by RT-PCR using a pair of oligonucleotide primers designed from a human DHS sequence. The 5' primer is a 20-mer having the sequence, 5' GTCTGTGTATTATTGGGCCC 3' (SEQ ID NO. 17); the 3' primer is a 42-mer having the sequence, 5' GCGAAGCTTCCATGGCTCGAGTTTT TTTTTTTTTTTTTTTT 3' (SEQ ID NO:18). A reverse transcriptase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence of a 606 by fragment, which was subcloned into pBluescript™ (Stratagene Cloning Systems, LaJolla, Calif.) using blunt end ligation and sequenced (SEQ ID NO:6). The nucleotide sequence (SEQ ID NO:6) for the partial length cDNA of the rat apoptosis-specific corpus luteum DHS gene obtained by RT-PCR is depicted in FIG. 4 and the corresponding derived amino acid sequence is SEQ ID NO. 7.

Isolation of Genomic DNA and Southern Analysis

Genomic DNA for southern blotting was isolated from excised rat ovaries. Approximately 100 mg of ovary tissue was divided into small pieces and placed into a 15 ml tube. The tissue was washed twice with 1 ml of PBS by gently shaking the tissue suspension and then removing the PBS using a pipette. The tissue was resuspended in 2.06 ml of DNA-buffer (0.2 M Tris-HCl pH 8.0 and 0.1 mM EDTA) and 240 µl of 10% SDS and 100 µl of proteinase K (Boehringer Manheim; 10 mg/ml) was added. The tissue was placed in a shaking water bath at 45° C. overnight. The following day another 100 µl of proteinase K (10 mg/ml) was added and the tissue suspension was incubated in a water-bath at 45° C. for an additional 4 hours. After the incubation the tissue suspension was extracted once with an equal volume of phenol:chloroform:iso-amyl alcohol (25:24:1) and once with an equal volume of chloroform:iso-amyl alcohol (24:1). Following the extractions 1/10th volume of 3M sodium acetate (pH 5.2) and 2 volumes of ethanol were added. A glass pipette sealed and formed into a hook using a Bunsen burner was used to pull the DNA threads out of solution and to transfer the DNA into a clean microcentrifuge tube. The DNA was washed once in 70% ethanol and air-dried for 10 minutes. The DNA pellet was dissolved in 500 µl of 10 mM Tris-HCl (pH 8.0), 10 µl of RNase A (10 mg/ml) was added, and the DNA was incubated for 1 hour at 37° C. The DNA was extracted once with phenol:chloroform:iso-amyl alcohol (25:24:1) and the DNA was precipitated by adding 1/10th volume of 3 M sodium acetate (pH 5.2) and 2 volumes of ethanol. The DNA was pelleted by centrifugation for 10 minutes at 13,000×g at 4° C. The DNA pellet was washed once in 70% ethanol and dissolved in 200 µl 10 mM Tris-HCl (pH 8.0) by rotating the DNA at 4° C. overnight.

For Southern blot analysis, genomic DNA isolated from rat ovaries was digested with various restriction enzymes that either do not cut in the endogenous gene or cut only once. To achieve this, 10 µg genomic DNA, 20 µl 10× reaction buffer and 100 U restriction enzyme were reacted for five to six hours in a total reaction volume of 200 µl. Digested DNA was loaded onto a 0.7% agarose gel and subjected to electrophoresis for 6 hours at 40 volts or overnight at 15 volts. After electrophoresis, the gel was depurinated for 10 minutes in 0.2 N HCl followed by two 15-minute washes in denaturing solution (0.5 M NaOH, 1.5 M NaCl) and two 15 minute washes in neutralizing buffer (1.5 M NaCl, 0.5 M Tris-HCl pH 7.4). The DNA was transferred to a nylon membrane, and the membrane was prehybridized in hybridization solution (40% formamide, 6×SSC, 5×Denhart's, solution (1×Denhart's solution is 0.02% Ficoll, 0.02% PVP, and 0.02% BSA), 0.5% SDS, and 1.5 mg of denatured salmon sperm DNA). A 700 by PCR fragment of the 3' UTR of rat eIF-5A cDNA (650 by of 3' UTR and 50 by of coding) was labeled with [a-32P]-dCTP by random priming and added to the membrane at $1 \times 10^6$ cpm/ml.

Similarly, a 606 by PCR fragment of the rat DHS cDNA (450 by coding and 156 by 3' UTR) was random prime labeled with [a-$^{32}$P]-dCTP and added at $1 \times 10^6$ cpm/ml to a second identical membrane. The blots were hybridized overnight at 42° C. and then washed twice with 2×SSC and 0.1% SDS at 42° C. and twice with 1×SSC and 0.1% SDS at 42° C. The blots were then exposed to film for 3-10 days.

Figure 20:
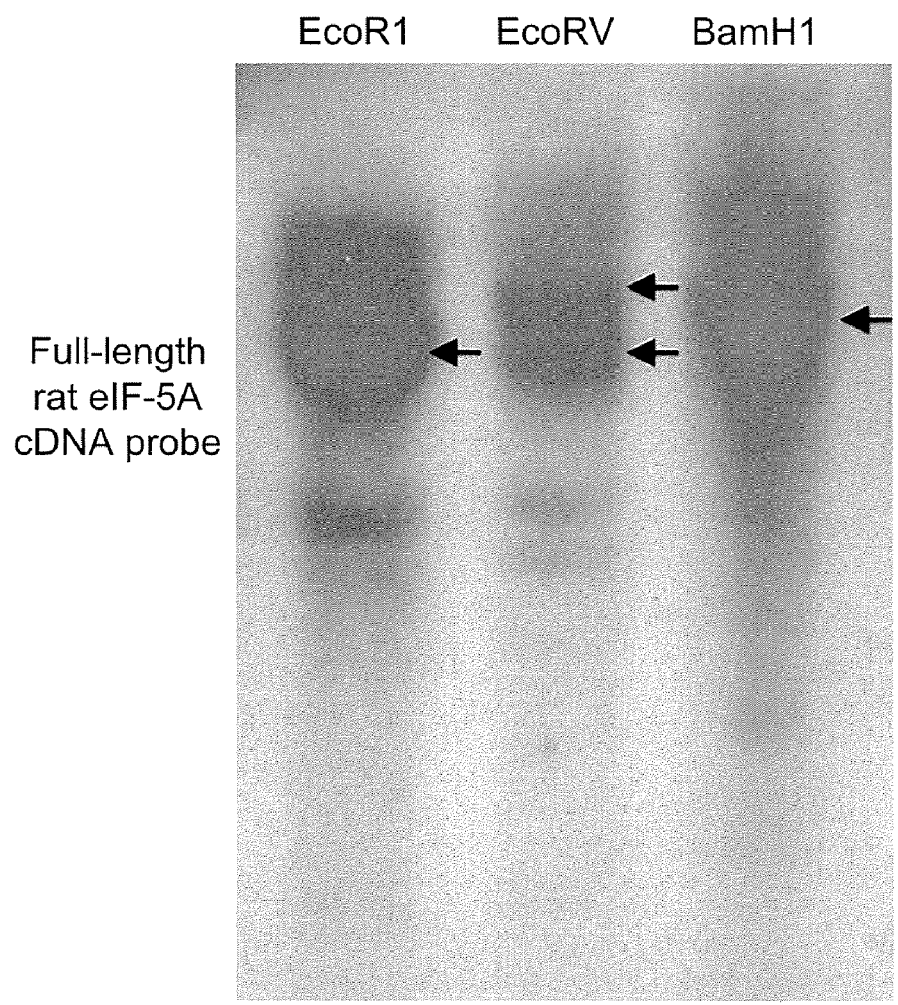
FIG. 20 is a Southern blot of rat genomic DNA probed with $^{32}$P-dCTP-labeled partial-length rat corpus luteum apoptosis-specific eIF-5A cDNA.

Rat corpus genomic DNA was cut with restriction enzymes as indicated on FIG. 20 and probed with $^{32}$P-dCTP-labeled eIF-5A cDNA. Hybridization under high stringency conditions revealed hybridization of the full-length cDNA probe to several restriction fragments for each restriction enzyme digested DNA sample, indicating the presence of several isoforms of eIF-5A. Of particular note, when rat genomic DNA was digested with EcoRV, which has a restriction site within the open reading frame of apoptosis-specific eIF-5A, two restriction fragments of the apoptosis-specific isoform of eIF-5A were detectable in the Southern blot. The two fragments are indicated with double arrows in FIG. 20. The restriction fragment corresponding to the apoptosis-specific isoform of eIF-5A is indicated by a single arrow in the lanes labeled EcoR1 and BamH1, restriction enzymes for which there are no cut sites within the open reading frame. These results suggest that the apoptosis-specific eIF-5A is a single copy gene in rat. As shown in FIGS. 5 through 13, the eIF-5A gene is highly conserved across species, and so it would be expected that there is a significant amount of conservation between isoforms within any species.

Figure 21:
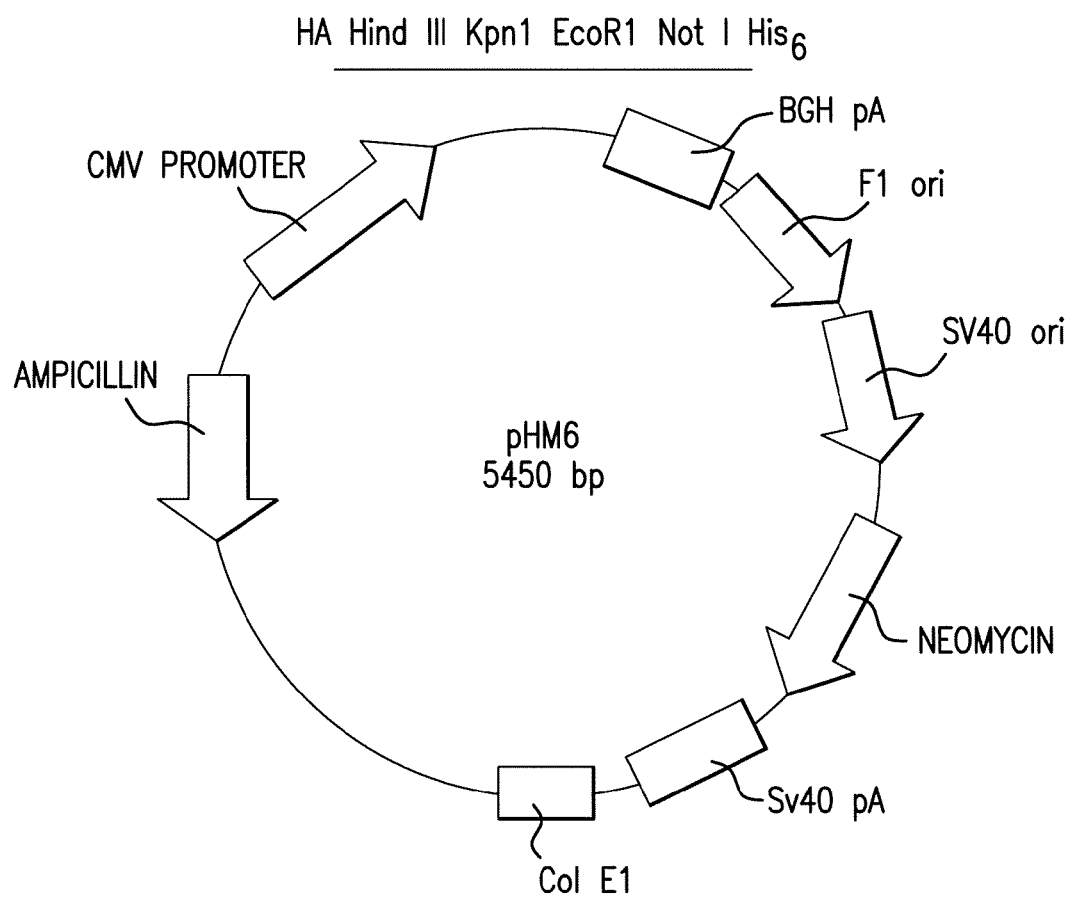
FIG. 21 depicts pHM6, a mammalian epitope tag expression vector (Roche Molecular Biochemicals).

FIG. 21 shows a Southern blot of rat genomic DNA probed with $^{32}$P-dCTP-labeled partial-length rat corpus luteum apoptosis-specific DHS cDNA. The genomic DNA was cut with EcoRV, a restriction enzyme that does not cut the partial-length cDNA used as a probe. Two restriction fragments are evident indicating that there are two copies of the gene or that the gene contains an intron with an EcoRV site.

Example 2

The present example demonstrates modulation of apoptosis with apoptosis factor 5A and DHS.

Culturing of COS-7 Cells and Isolation of RNA

COS-7, an African green monkey kidney fibroblast-like cell line transformed with a mutant of SV40 that codes for wild-type T antigen, was used for all transfection-based experiments. COS-7 cells were cultured in Dulbecco's Modified Eagle's medium (DMEM) with 0.584 grams per liter of L-glutamine, 4.5 g of glucose per liter, and 0.37% sodium bicarbonate. The culture media was supplemented with 10% fetal bovine serum (FBS) and 100 units of penicillin/streptomycin. The cells were grown at 37° C. in a humidified environment of 5% $CO_2$ and 95% air. The cells were subcultured every 3 to 4 days by detaching the adherent cells with a solution of 0.25% trypsin and 1 mM EDTA. The detached cells were dispensed at a split ratio of 1:10 in a new culture dish with fresh media.

COS-7 cells to be used for isolation of RNA were grown in 150-mm tissue culture treated dishes (Corning). The cells were harvested by detaching them with a solution of trypsin-EDTA. The detached cells were collected in a centrifuge tube, and the cells were pelleted by centrifugation at 3000 rpm for 5 minutes. The supernatant was removed, and the cell pellet was flash-frozen in liquid nitrogen. RNA was isolated from the frozen cells using the GenElute Mammalian Total RNA Miniprep kit (Sigma) according to the manufacturer's instructions.

Construction of Recombinant Plasmids and Transfection of COS-7 Cells

Recombinant plasmids carrying the full-length coding sequence of rat apoptosis eIF-5A in the sense orientation and the 3' untranslated region (UTR) of rat apoptosis eIF-5A in the antisense orientation were constructed using the mammalian epitope tag expression vector, pHM6 (Roche Molecular Biochemicals), which is illustrated in FIG. 21. The vector contains the following: CMV promoter—human cytomegalovirus immediate-early promoter/enhancer; HA—nonapeptide epitope tag from influenza hemagglutinin; BGH pA—Bovine growth hormone polyadenylation signal; f1 ori—f1 origin; SV40 ori—SV40 early promoter and origin; Neomycin—Neomycin resistance (G418) gene; SV40 pA—SV40 polyadenylation signal; Col E1—ColE1 origin; Ampicillin—Ampicillin resistance gene. The full-length coding sequence of rat apoptosis eIF-5A and the 3' UTR of rat apoptosis eIF-5A were amplified by PCR from the original rat eIF-5A RT-PCR fragment in pBluescript (SEQ ID NO:1). To amplify the full-length eIF-5A the primers used were as follows: Forward 5' GCCAAGCTTAATGGCAGATGATTT GG 3' (SEQ ID NO: 59) (Hind3) and Reverse 5' CT GAATTCCAGT TATTTTGCCATGG 3' (SEQ ID NO: 60) (EcoR1). To amplify the 3' UTR rat eIF-5A the primers used were as follows: forward 5' AATGAATTCCGCCATGAC-AGAGGAGGC 3' (SEQ ID NO: 61) (EcoR1) and reverse 5' GCGAAGCTTCCATGGCTCGAGTTTTTTTTTTTTTTT-TTTTTT 3' (SEQ ID NO: 62) (Hind3).

The full-length rat eIF-5A PCR product isolated after agarose gel electrophoresis was 430 by in length while the 3' UTR rat eIF-5A PCR product was 697 by in length. Both PCR products were subcloned into the Hind 3 and EcoR1 sites of pHM6 to create pHM6-full-length eIF-5A and pHM6-antisense 3'UTReIF-5A. The full-length rat eIF-5A PCR product was subcloned in frame with the nonapeptide epitope tag from influenza hemagglutinin (HA) present upstream of the multiple cloning site to allow for detection of the recombinant protein using an anti-[HA]-peroxidase antibody. Expression is driven by the human cytomegalovirus immediate-early promoter/enhancer to ensure high level expression in mammalian cell lines. The plasmid also features a neomycin-resistance (G418) gene, which allows for selection of stable transfectants, and a SV40 early promoter and origin, which allows episomal replication in cells expressing SV40 large T antigen, such as COS-7.

COS-7 cells to be used in transfection experiments were cultured in either 24 well cell culture plates (Corning) for cells to be used for protein extraction, or 4 chamber culture slides (Falcon) for cells to be used for staining. The cells were grown in DMEM media supplemented with 10% FBS, but lacking penicillin/streptomycin, to 50 to 70% confluency. Transfection medium sufficient for one well of a 24-well plate or culture slide was prepared by diluting 0.32 µg of plasmid DNA in 42.5 µl of serum-free DMEM and incubating the mixture at room temperature for 15 minutes. 1.6 µl of the transfection reagent, LipofectAMINE (Gibco, BRL), was diluted in 42.5 µl of serum-free DMEM and incubated for 5 minutes at room temperature. After 5 minutes the LipofectAMINE mixture was added to the DNA mixture and incubated together at room temperature for 30 to 60 minutes. The cells to be transfected were washed once with serum-free DMEM before overlaying the transfection medium and the cells were placed back in the growth chamber for 4 hours.

After the incubation, 0.17 ml of DMEM+20% FBS was added to the cells. The cells were then cultured for a further 40 hours before either being induced to undergo apoptosis prior to staining or harvested for Western blot analysis. As a control, mock transfections were also performed in which the plasmid DNA was omitted from the transfection medium.

Protein Extraction and Western Blotting

Protein was isolated for Western blotting from transfected cells by washing the cells twice in PBS (8 g/L NaCl, 0.2 g/L KCl, 1.44 g/L $Na_2HPO_4$, and 0.24 g/L $KH_2PO_4$) and then adding 150 µl of hot SDS gel-loading buffer (50 mM Tris-HCl pH 6.8, 100 mM dithiothreitol, 2% SDS, 0.1% bromophenol blue, and 10% glycerol). The cell lysate was collected in a microcentrifuge tube, heated at 95° C. for 10 minutes, and then centrifuged at 13,000×g for 10 minutes. The supernatant was transferred to a fresh microcentrifuge tube and stored at −20° C. until ready for use.

For Western blotting, 2.5 or 5 µg of total protein was separated on a 12% SDS-polyacrylamide gel. The separated proteins were transferred to a polyvinylidene difluoride membrane. The membrane was then incubated for one hour in blocking solution (5% skim milk powder, 0.02% sodium azide in PBS) and washed three times for 15 minutes in PBS-T (PBS+0.05% Tween-20). The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in PBS. The primary antibody was preincubated for 30 minutes in a solution of 5% milk in PBS prior to incubation with the membrane.

Several primary antibodies were used. An anti-[HA]-peroxidase antibody (Roche Molecular Biochemicals) was used at a dilution of 1:5000 to detect expression of the recombinant proteins. Since this antibody is conjugated to peroxidase, no secondary antibody was necessary, and the blot was washed and developed by chemiluminescence. The other primary antibodies that were used are monoclonal antibodies from Oncogene that recognize p53 (Ab-6), Bcl-2 (Ab-1), and c-Myc (Ab-2). The monoclonal antibody to p53 was used at a dilution of 0.1 µg/ml, and the monoclonal antibodies to Bcl-2 and c-Myc were both used at a dilution of 0.83 µg/ml. After incubation with primary antibody for 60 to 90 minutes, the membrane was washed 3 times for 15 minutes in PBS-T. Secondary antibody was then diluted in 1% milk in PBS and incubated with the membrane for 60 to 90 minutes. When p53 (Ab-6) was used as the primary antibody, the secondary antibody used was a goat anti-mouse IgG conjugated to alkaline phosphatase (Rockland) at a dilution of 1:1000. When Bcl-2 (Ab-1) and c-Myc (Ab-2) were used as the primary antibody, a rabbit anti-mouse IgG conjugated to peroxidase (Sigma) was used at a dilution of 1:5000. After incubation with the secondary antibody, the membrane was washed 3 times in PBS-T.

Two detection methods were used to develop the blots, a colorimetric method and a chemiluminescent method. The colorimetric method was used only when p53 (Ab-6) was used as the primary antibody in conjunction with the alkaline phosphatase-conjugated secondary antibody. Bound antibody was visualized by incubating the blot in the dark in a solution of 0.33 mg/mL nitro blue tetrazolium, 0.165 mg/mL 5-bromo-4-chloro-3-indolyl phosphate, 100 mM NaCl, 5 mM $MgCl_2$, and 100 mM Tris-HO (pH 9.5). The color reaction was stopped by incubating the blot in 2 mM EDTA in PBS. A chemiluminescent detection method was used for all other primary antibodies, including anti-[HA]-peroxidase, Bcl-2 (Ab-1), and c-Myc (Ab-2). The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 10 minutes.

Induction of Apoptosis in COS 7 Cells

Figure 22:
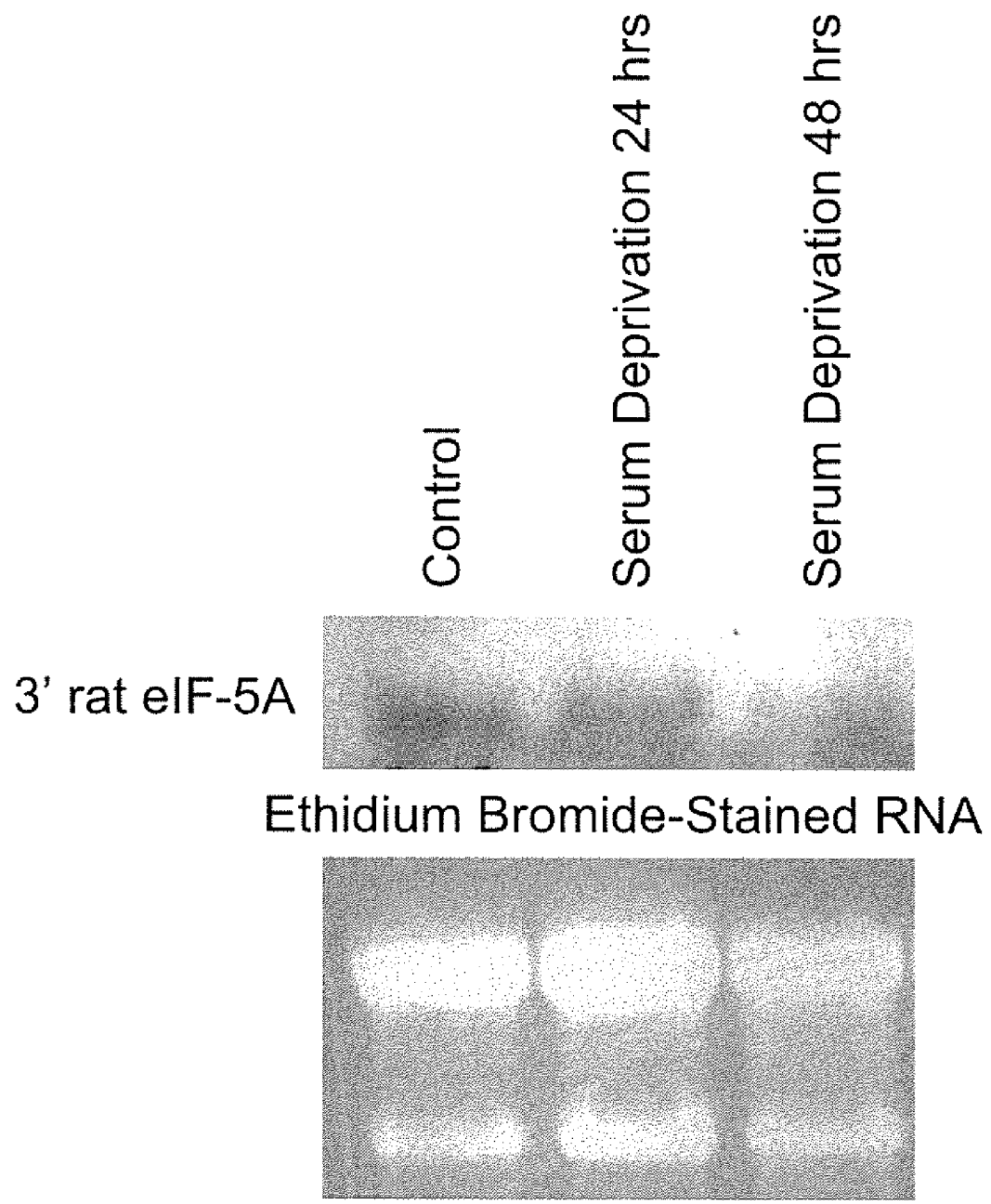
FIG. 22 is a Northern blot (top) and ethidium bromide stained gel (bottom) of total RNA isolated from COS-7 cells after induction of apoptosis by withdrawal of serum probed with the $^{32}$P-dCTP-labeled 3'-untranslated region of rat corpus luteum apoptosis-specific DHS cDNA.

Two methods were used to induce apoptosis in transfected COS-7 cells, serum deprivation and treatment with Actinomycin D, *streptomyces* sp (Calbiochem). For both treatments, the medium was removed 40 hours post-transfection. For serum starvation experiments, the media was replaced with serum- and antibiotic-free DMEM. Cells grown in antibiotic-free DMEM supplemented with 10% FBS were used as a control. For Actinomycin D induction of apoptosis, the media was replaced with antibiotic-free DMEM supplemented with 10% FBS and 1 µg/ml Actinomycin D dissolved in methanol. Control cells were grown in antibiotic-free DMEM supplemented with 10% FBS and an equivalent volume of methanol. For both methods, the percentage of apoptotic cells was determined 48 hours later by staining with either Hoescht or Annexin V-Cy3. Induction of apoptosis was also confirmed by Northern blot analyses, as shown in FIG. 22.

Hoescht Staining

The nuclear stain, Hoescht, was used to label the nuclei of transfected COS-7 cells in order to identify apoptotic cells based on morphological features such as nuclear fragmentation and condensation. A fixative, consisting of a 3:1 mixture of absolute methanol and glacial acetic acid, was prepared immediately before use. An equal volume of fixative was added to the media of COS-7 cells growing on a culture slide and incubated for 2 minutes. The media/fixative mixture was removed from the cells and discarded, and 1 ml of fixative was added to the cells. After 5 minutes the fixative was discarded, and 1 ml of fresh fixative was added to the cells and incubated for 5 minutes. The fixative was discarded, and the cells were air-dried for 4 minutes before adding 1 ml of Hoescht stain (0.5 µg/ml Hoescht 33258 in PBS). After a 10-minute incubation in the dark, the staining solution was discarded and the slide was washed 3 times for 1 minute with deionized water. After washing, 1 ml of McIlvaine's buffer (0.021 M citric acid, 0.058 M $Na_2HPO_4.7H_2O$; pH 5.6) was added to the cells, and they were incubated in the dark for 20 minutes. The buffer was discarded, the cells were air-dried for 5 minutes in the dark and the chambers separating the wells of the culture slide were removed. A few drops of Vectashield mounting media for fluorescence (Vector Laboratories) was added to the slide and overlaid with a coverslip. The stained cells were viewed under a fluorescence microscope using a UV filter. Cells with brightly stained or fragmented nuclei were scored as apoptotic.

Annexin V-Cy3 Staining

An Annexin V-Cy3 apoptosis detection kit (Sigma) was used to fluorescently label externalized phosphatidylserine on apoptotic cells. The kit was used according to the manufacturer's protocol with the following modifications. In brief, transfected COS-7 cells growing on four chamber culture slides were washed twice with PBS and three times with 1× Binding Buffer. 150 µl of staining solution (1 g/ml AnnCy3 in 1× Binding Buffer) was added, and the cells were incubated in the dark for 10 minutes. The staining solution was then removed, and the cells were washed 5 times with 1× Binding Buffer. The chamber walls were removed from the culture slide, and several drops of 1× Binding Buffer were placed on the cells and overlaid with a coverslip. The stained cells were analyzed by fluorescence microscopy using a green filter to visualize the red fluorescence of positively stained (apoptotic) cells. The total cell population was determined by counting the cell number under visible light.

Example 3

The present example demonstrates modulation of apoptosis with apoptosis factor 5A and DHS.

Figure 23:
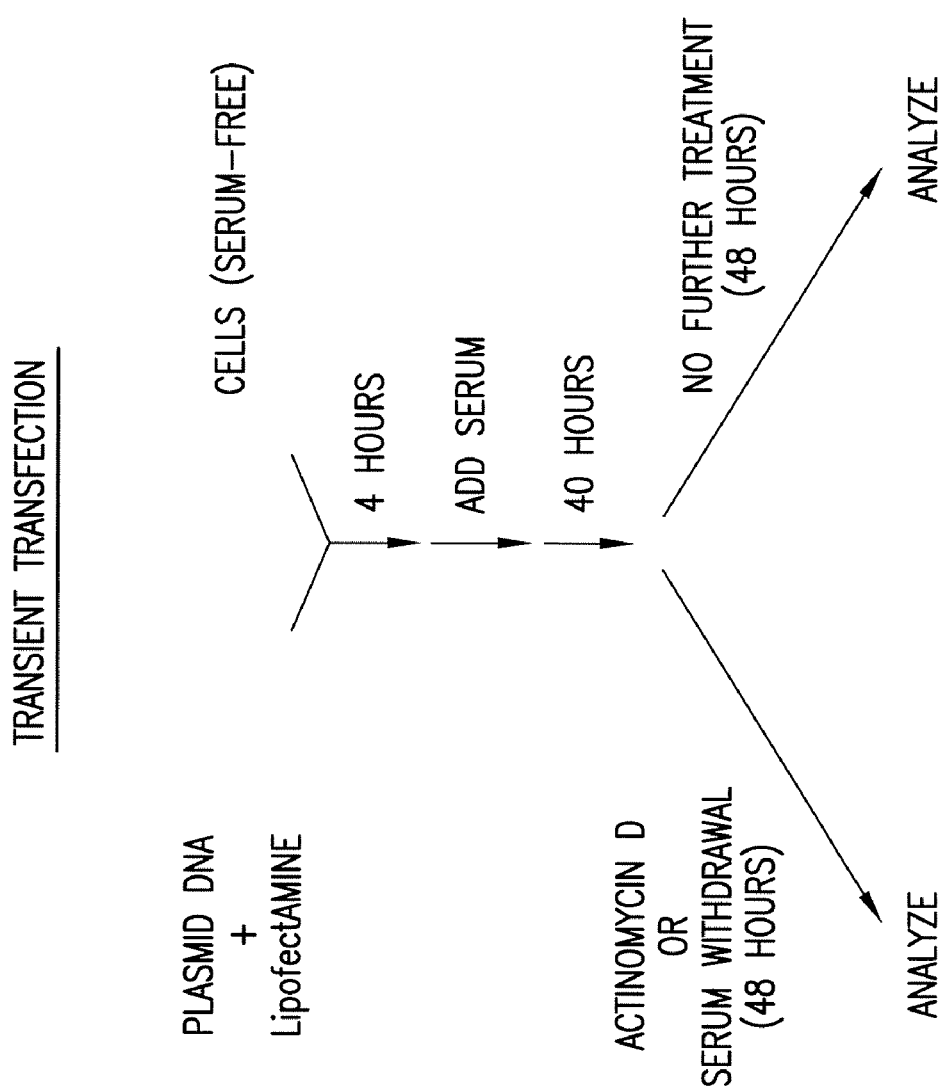
FIG. 23 is a flow chart illustrating the procedure for transient transfection of COS-7 cells.
Figure 24:
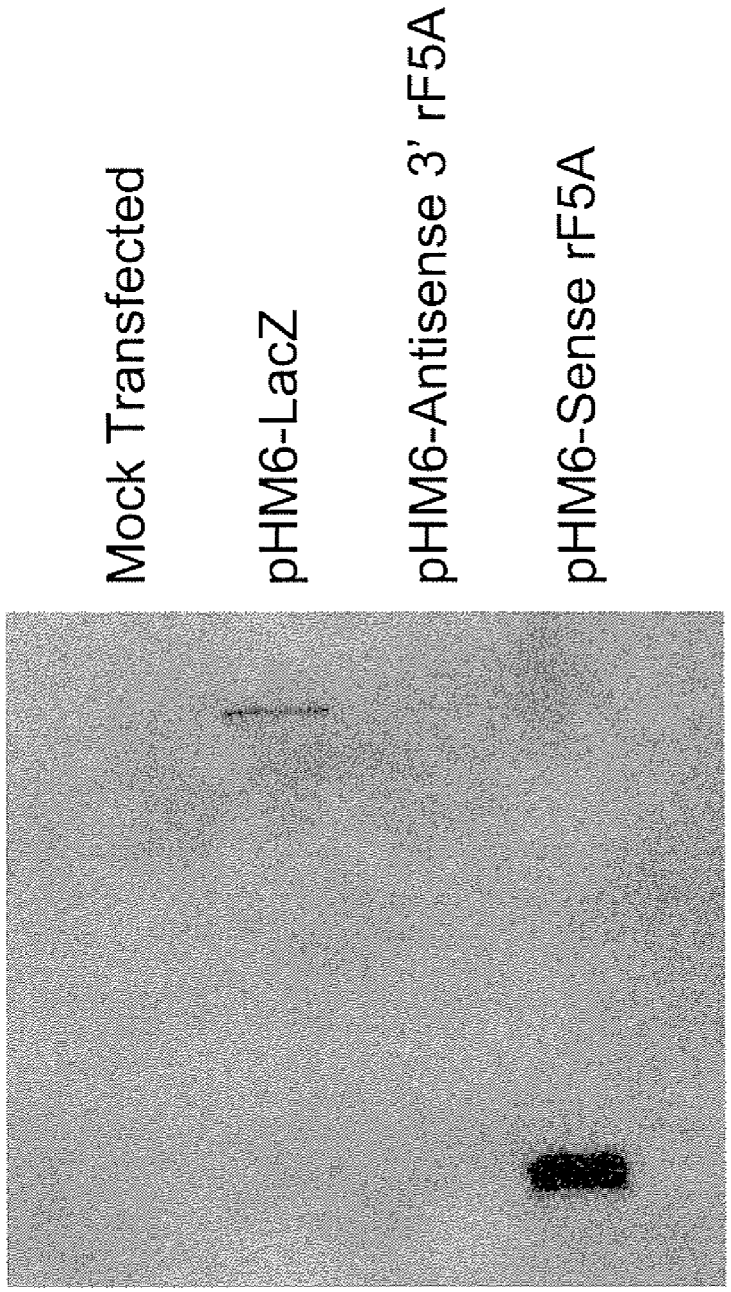
FIG. 24 is a Western blot of transient expression of foreign proteins in COS-7 cells following transfection with pHM6.

Using the general procedures and methods described in the previous examples, FIG. 23 is a flow chart illustrating the procedure for transient transfection of COS-7 cells, in which cells in serum-free medium were incubated in plasmid DNA in lipofectAMINE for 4 hours, serum was added, and the cells were incubated for a further 40 hours. The cells were then either incubated in regular medium containing serum for a further 48 hours before analysis (i.e. no further treatment), deprived of serum for 48 hours to induce apoptosis before analysis, or treated with actinomycin D for 48 hours to induce apoptosis before analysis.

FIG. 22 is a Western blot illustrating transient expression of foreign proteins in COS-7 cells following transfection with pHM6. Protein was isolated from COS-7 cells 48 hours after either mock transfection, or transfection with pHM6-LacZ, pHM6-Antisense 3' rF5A (pHM6-Antisense 3' UTR rat apoptosis eIF-5A), or pHM6-Sense rF5A (pHM6-Full length rat apoptosis eIF-5A). Five µg of protein from each sample was fractionated by SDS-PAGE, transferred to a PVDF membrane, and Western blotted with anti-[HA]-peroxidase. The bound antibody was detected by chemiluminescence and exposed to x-ray film for 30 seconds. Expression of LacZ (lane 2) and of sense rat apoptosis eIF-5A (lane 4) is clearly visible.

As described above, COS-7 cells were either mock transfected or transfected with pHM6-Sense rF5A (pHM6-Full length rat eIF-5A). Forty hours after transfection, the cells were induced to undergo apoptosis by withdrawal of serum for 48 hours. The caspase proteolytic activity in the transfected cell extract was measured using a fluorometric homogenous caspase assay kit (Roche Diagnostics). DNA fragmentation was also measured using the FragEL DNA Fragmentation Apoptosis Detection kit (Oncogene) which labels the exposed 3'-OH ends of DNA fragments with fluorescein-labeled deoxynucleotides.

Additional COS-7 cells were either mock transfected or transfected with pHM6-Sense rF5A (pHM6-Full length rat eIF-5A). Forty hours after transfection, the cells were either grown for an additional 48 hours in regular medium containing serum (no further treatment), induced to undergo apoptosis by withdrawal of serum for 48 hours or induced to undergo apoptosis by treatment with 0.5 µg/ml of Actinomycin D for 48 hours. The cells were either stained with Hoescht 33258, which depicts nuclear fragmentation accompanying apoptosis, or stained with Annexin V-Cy3, which depicts phosphatidylserine exposure accompanying apoptosis. Stained cells were also viewed by fluorescence microscopy using a green filter and counted to determine the percentage of cells undergoing apoptosis. The total cell population was counted under visible light.

Figure 25:
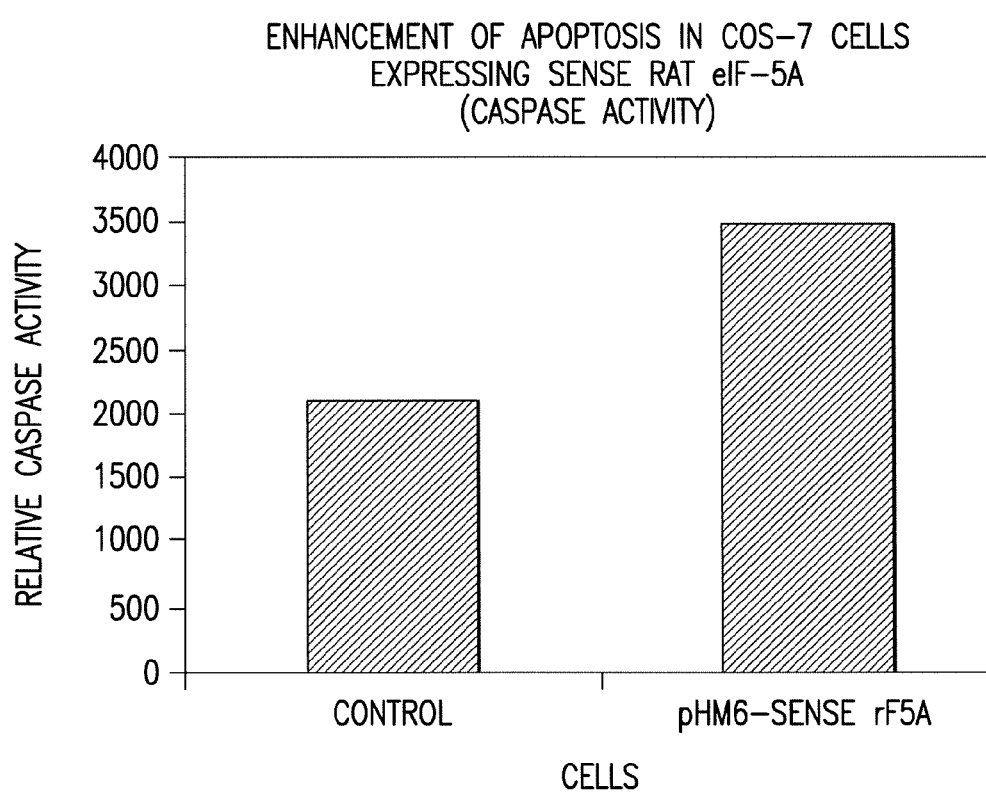
FIG. 25 illustrates enhanced apoptosis as reflected by increased caspase activity when COS-7 cells were transiently transfected with pHM6 containing full-length rat apoptosis-specific eIF-5A in the sense orientation.

FIG. 25 illustrates enhanced apoptosis as reflected by increased caspase activity when COS-7 cells were transiently transfected with pHM6 containing full-length rat apoptosis-induced eIF-5A in the sense orientation. Expression of rat apoptosis-induced eIF-5A resulted in a 60% increase in caspase activity.

Figure 26:
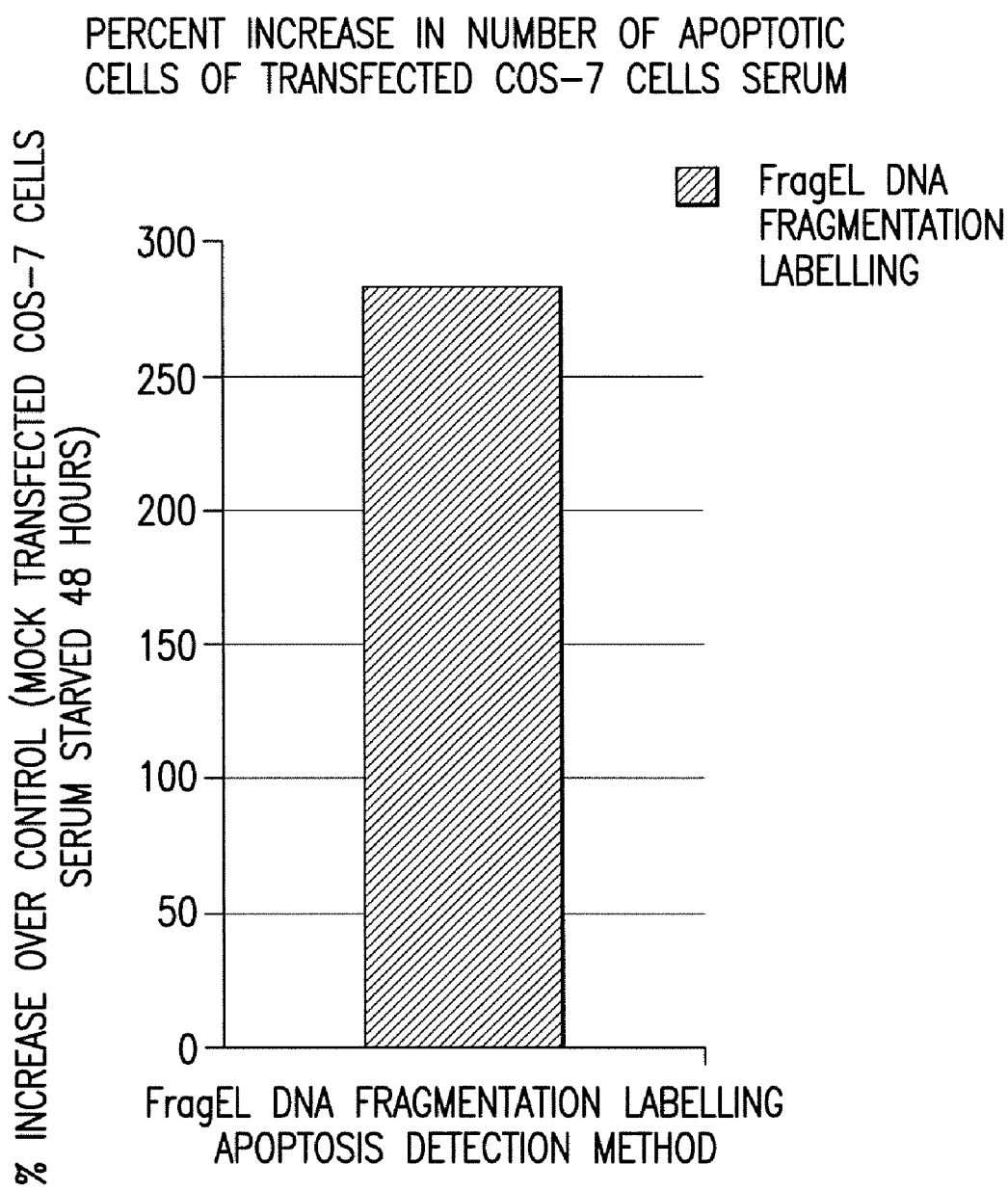
FIG. 26 illustrates enhanced apoptosis as reflected by increased DNA fragmentation when COS-7 cells were transiently transfected with pHM6 containing full-length rat apoptosis-specific eIF-5A in the sense orientation.
Figure 28:
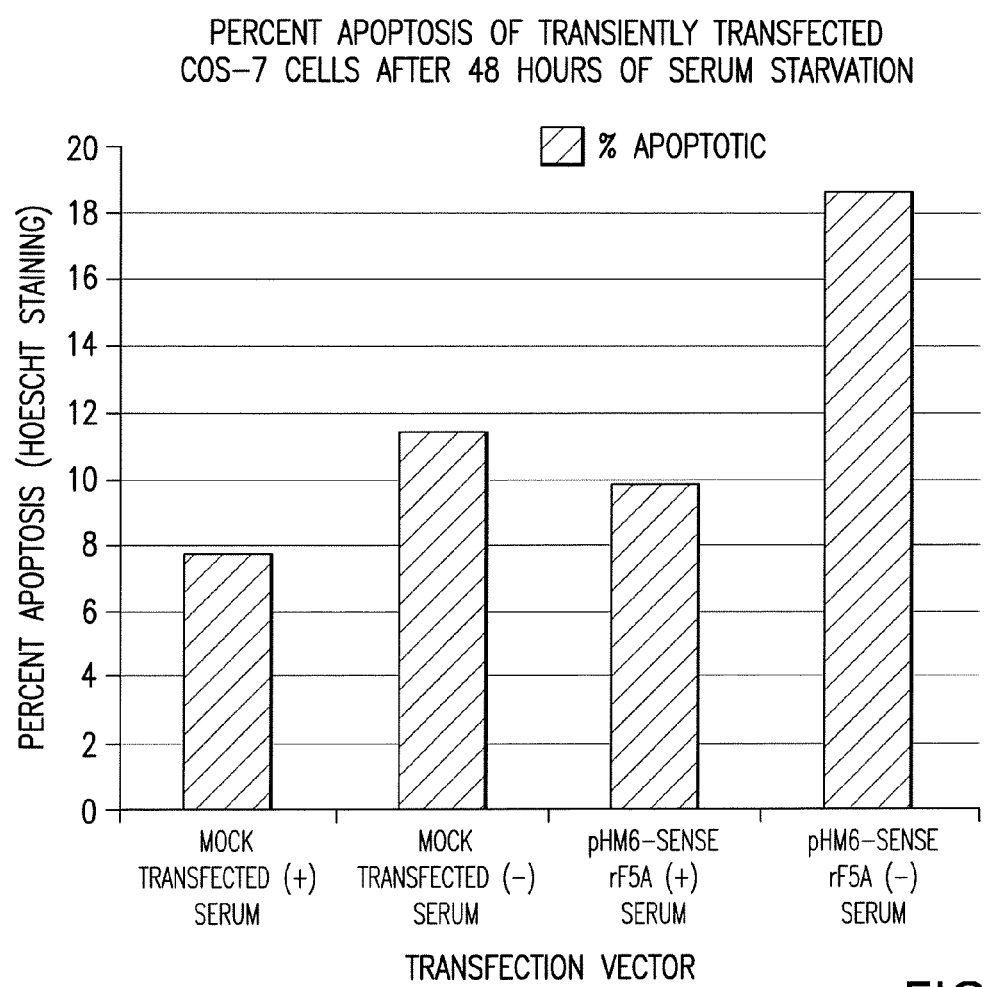
FIG. 28 illustrates enhanced apoptosis as reflected by increased nuclear fragmentation when COS-7 cells were transiently transfected with pHM6 containing full-length rat apoptosis-specific eIF-5A in the sense orientation.

FIG. 26 illustrates enhanced apoptosis as reflected by increased DNA fragmentation when COS-7 cells were transiently transfected with pHM6 containing full-length rat apoptosis-induced eIF-5A in the sense orientation. Expression of rat apoptosis-induced eIF-5A resulted in a 273% increase in DNA fragmentation. FIG. 27 illustrates detection of apoptosis as reflected by increased nuclear fragmentation when COS-7 cells were transiently transfected with pHM6 containing full-length rat apoptosis-induced eIF-5A in the sense orientation. There is a greater incidence of fragmented nuclei in cells expressing rat apoptosis-induced eIF-5A. FIG. 28 illustrates enhanced apoptosis as reflected by increased nuclear fragmentation when COS-7 cells were transiently transfected with pHM6 containing full-length rat apoptosis-induced eIF-5A in the sense orientation. Expression of rat apoptosis-induced eIF-5A resulted in a 27% and 63% increase in nuclear fragmentation over control in non-serum starved and serum starved samples, respectively.

Figure 30:
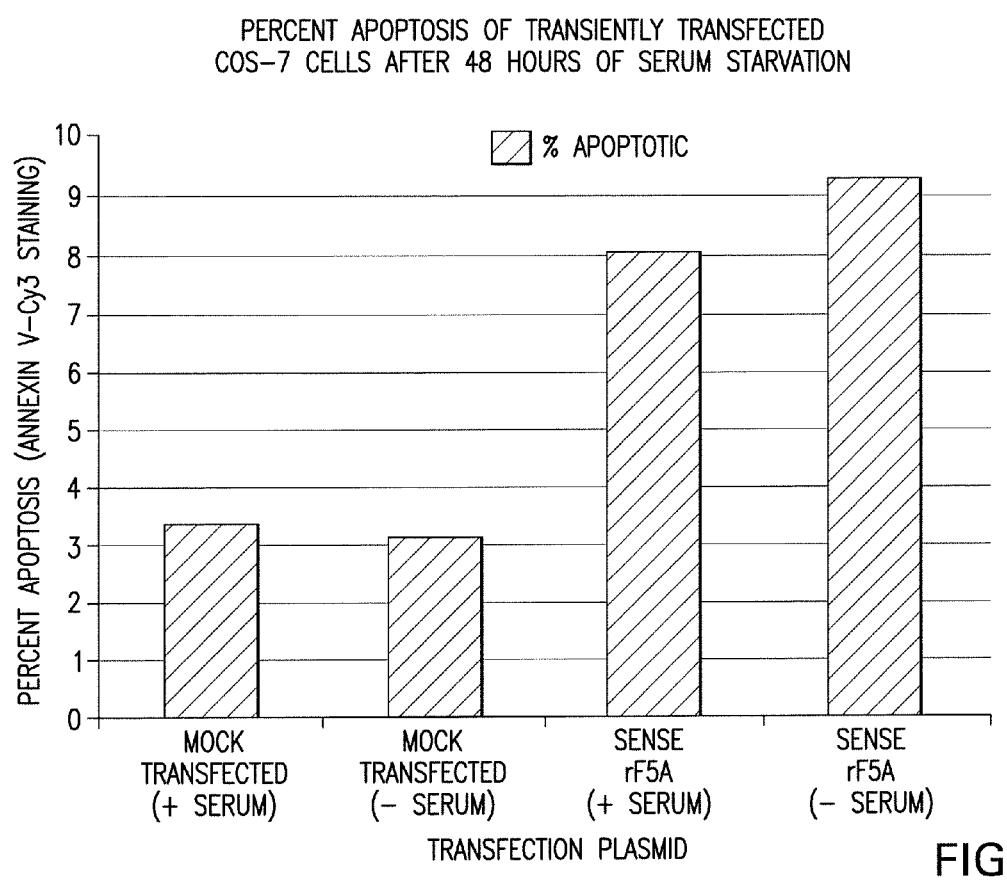
FIG. 30 illustrates enhanced apoptosis as reflected by increased phosphatidylserine exposure when COS-7 cells were transiently transfected with pHM6 containing full-length rat apoptosis-specific eIF-5A in the sense orientation.

FIG. 29 illustrates detection of apoptosis as reflected by phosphatidylserine exposure when COS-7 cells were transiently transfected with pHM6 containing full-length rat apoptosis-induced eIF-5A in the sense orientation. FIG. 30 illustrates enhanced apoptosis as reflected by increased phosphatidylserine exposure when COS-7 cells were transiently transfected with pHM6 containing full-length rat apoptosis-induced eIF-5A in the sense orientation. Expression of rat apoptosis-induced eIF-5A resulted in a 140% and 198% increase in phosphatidylserine exposure over control, in non-serum starved and serum starved samples, respectively.

Figure 31:
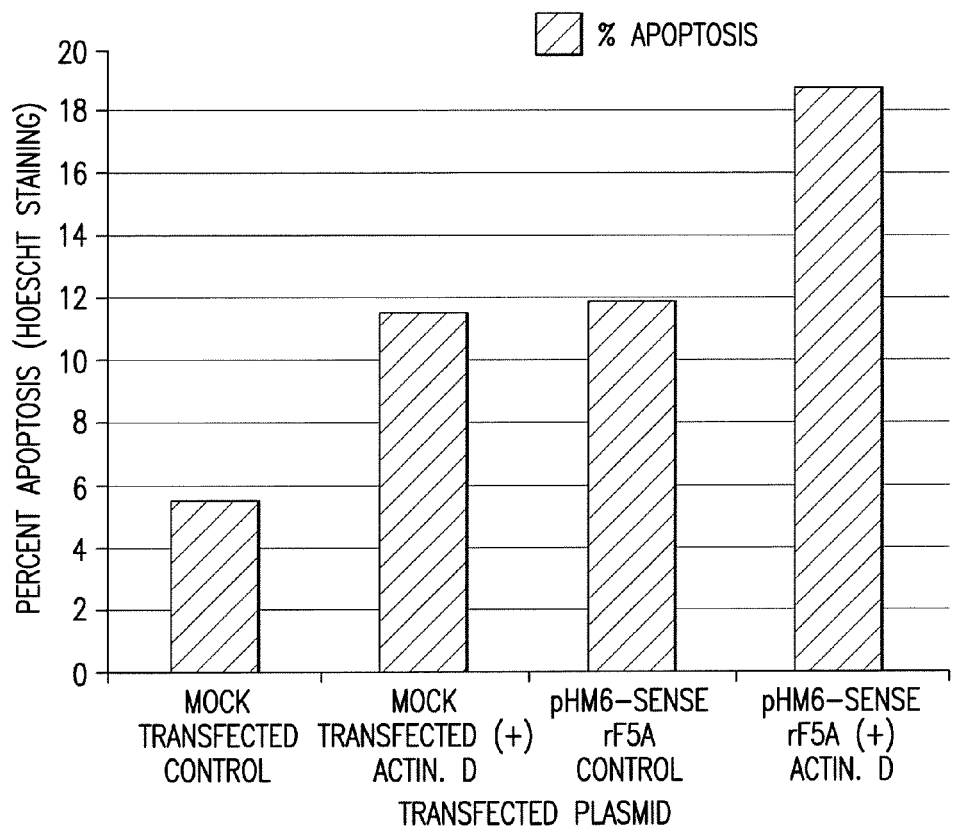
FIG. 31 illustrates enhanced apoptosis as reflected by increased nuclear fragmentation when COS-7 cells were transiently transfected with pHM6 containing full-length rat apoptosis-specific eIF-5A in the sense orientation.
Figure 32:
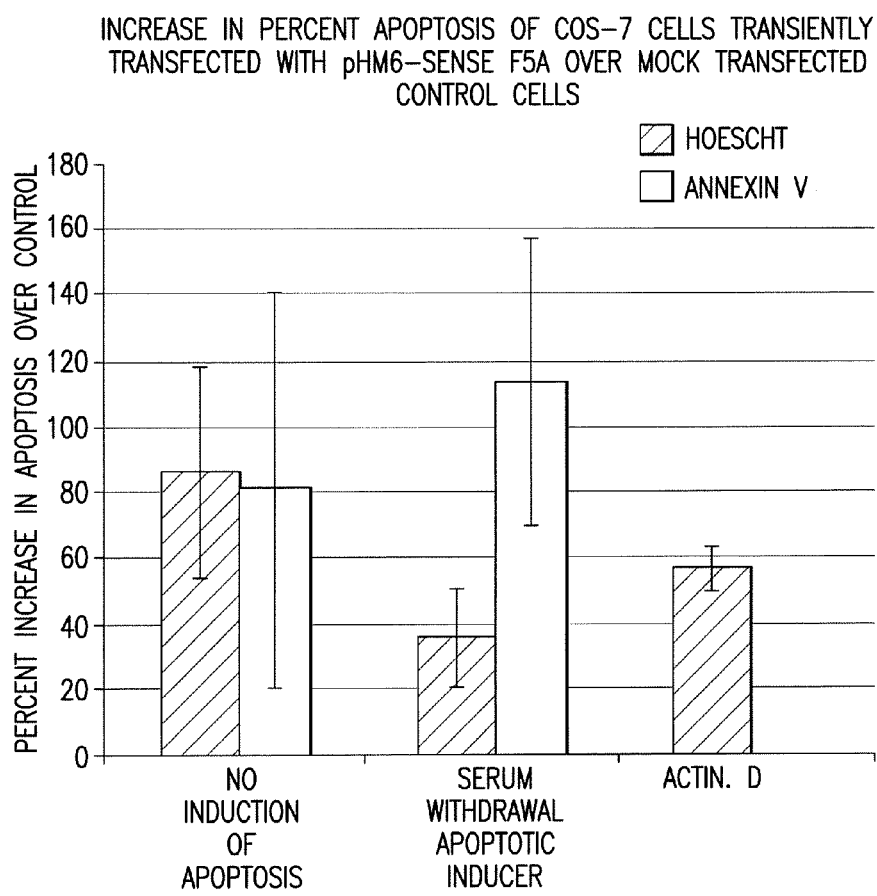
FIG. 32 illustrates enhanced apoptosis when COS-7 cells were transiently transfected with pHM6 containing full-length rat apoptosis-specific eIF-5A in the sense orientation.

FIG. 31 illustrates enhanced apoptosis as reflected by increased nuclear fragmentation when COS-7 cells were transiently transfected with pHM6 containing full-length rat apoptosis-induced eIF-5A in the sense orientation. Expression of rat apoptosis-induced eIF-5A resulted in a 115% and 62% increase in nuclear fragmentation over control in untreated and treated samples, respectively. FIG. 32 illustrates a comparison of enhanced apoptosis under conditions in which COS-7 cells transiently transfected with pHM6 containing full-length rat apoptosis-induced eIF-5A in the sense orientation were either given no further treatment or treatment to induce apoptosis.

Example 4

The present example demonstrates modulation of apoptotic activity following administration of apoptosis factor 5A and DHS.

COS-7 cells were either mock transfected, transfected with pHM6-LacZ or transfected with pHM6-Sense rF5A (pHM6-Full length rat eIF-5A) and incubated for 40 hours. Five µg samples of protein extract from each sample were fractionated by SDS-PAGE, transferred to a PVDF membrane, and Western blotted with a monoclonal antibody that recognizes Bcl-2. Rabbit anti-mouse IgG conjugated to peroxidase was used as a secondary antibody, and bound antibody was detected by chemiluminescence and exposure to x-ray film. Results are shown in FIG. 32. Less Bcl-2 is detectable in cells transfected with pHM6-Sense rF5A than in those transfected with pHM6-LacZ; therefore, Bcl-2 is down-regulated.

Additional COS-7 cells were either mock transfected, transfected with pHM6-antisense 3' rF5A (pHM6-antisense 3' UTR of rat apoptosis-specific eIF-5A) or transfected with pHM6-Sense rF5A (pHM6-Full length rat apoptosis-specific eIF-5A). Forty hours after transfection, the cells were induced to undergo apoptosis by withdrawal of serum for 48 hours. Five µg samples of protein extract from each sample were fractionated by SDS-PAGE, transferred to a PVDF membrane, and Western blotted with a monoclonal antibody that recognizes Bcl-2. Rabbit anti-mouse IgG conjugated to peroxidase was used as a secondary antibody, and bound antibody was detected by chemiluminescence and exposure to x-ray film.

Also additionally, COS-7 cells were either mock transfected, transfected with pHM6-LacZ or transfected with pHM6-Sense rF5A (pHM6-Full length rat eIF-5A) and incubated for 40 hours. Five µg samples of protein extract from each sample were fractionated by SDS-PAGE, transferred to a PVDF membrane, and Western blotted with a monoclonal antibody that recognizes p53. Goat anti-mouse IgG conjugated to alkaline phosphatase was used as a secondary antibody, and bound antibody was detected colorimetrically.

Finally, COS-7 cells were either mock transfected, transfected with pHM6-LacZ or transfected with pHM6-Sense rF5A (pHM6-Full length rat eIF-5A) and incubated for 40 hours. Five µg samples of protein extract from each sample were fractionated by SDS-PAGE, transferred to a PVDF membrane, and probed with a monoclonal antibody that recognizes p53. Corresponding protein blots were probed with anti-[HA]-peroxidase to determine the level of rat apoptosis-specific eIF-5A expression. Goat anti-mouse IgG conjugated to alkaline phosphatase was used as a secondary antibody, and bound antibody was detected by chemiluminescence.

Figure 33:
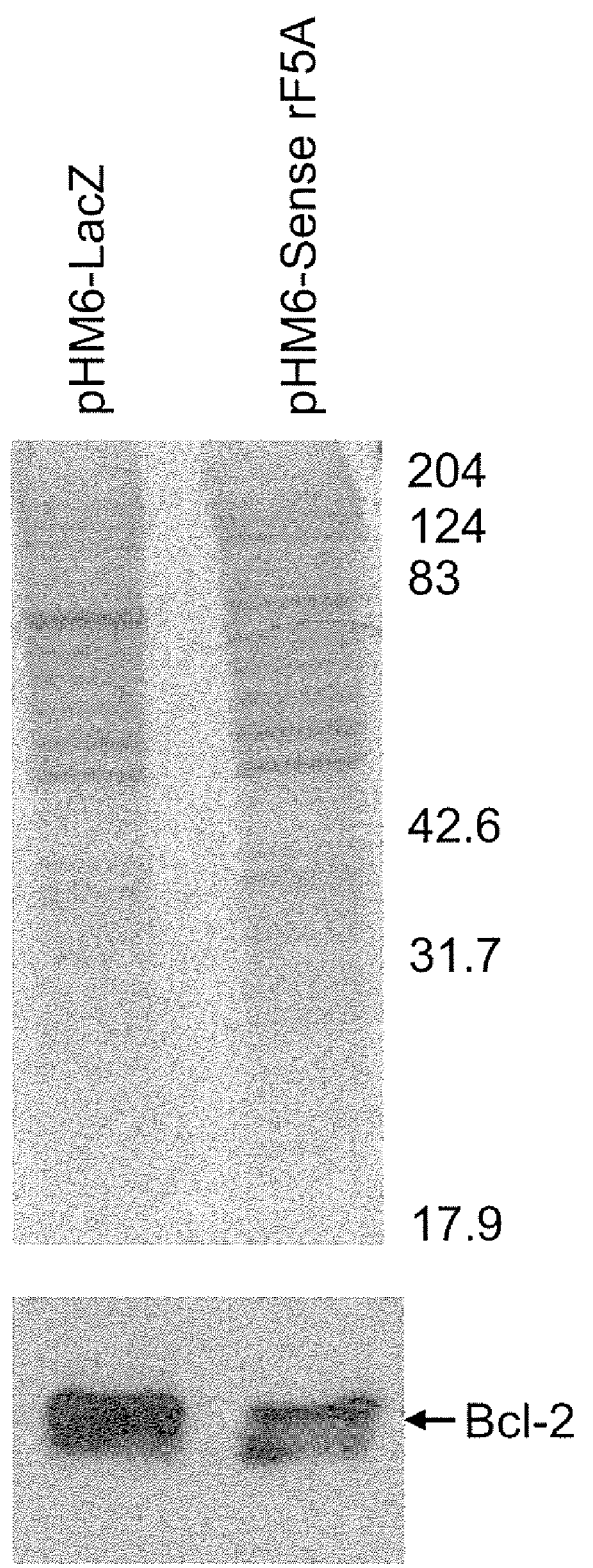
FIG. 33 illustrates down-regulation of Bcl-2 when COS-7 cells were transiently transfected with pHM6 containing full-length rat apoptosis-specific eIF-5A in the sense orientation. The top photo is the Coomassie-blue-stained protein blot; the bottom photo is the corresponding Western blot.

FIG. 33 illustrates downregulation of Bcl-2 when COS-7 cells were transiently transfected with pHM6 containing full-length rat apoptosis-induced eIF-5A in the sense orientation. The upper panel illustrates the Coomassie-blue-stained protein blot; the lower panel illustrates the corresponding Western blot. Less Bcl-2 is detectable in cells transfected with pHM6-Sense rF5A than in those transfected with pHM6-LacZ.

Figure 34:
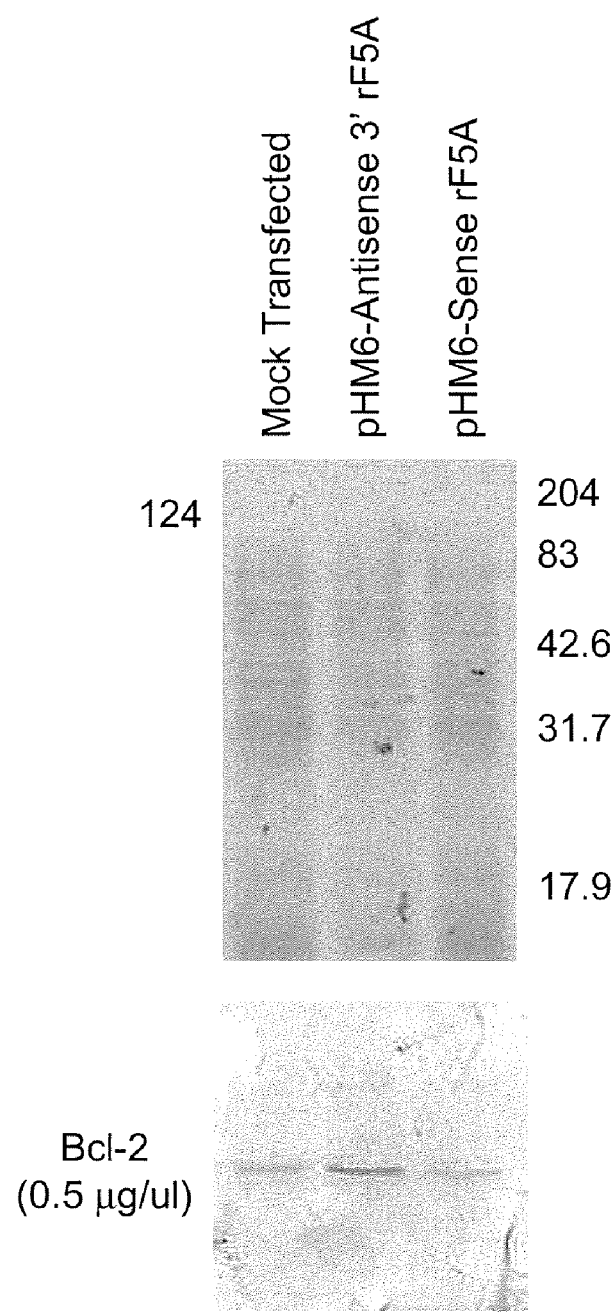
FIG. 34 is a Coomassie-blue-stained protein blot and the corresponding Western blot of COS-7 cells transiently transfected with pHM6 containing full-length rat apoptosis-specific eIF-5A in the antisense orientation using Bcl-2 as a probe.

FIG. 34 illustrates upregulation of Bcl-2 when COS-7 cells were transiently transfected with pHM6 containing full-length rat apoptosis-induced eIF-5A in the antisense orientation. The upper panel illustrates the Coomassie-blue-stained protein blot; the lower panel illustrates the corresponding Western blot. More Bcl-2 is detectable in cells transfected with pHM6-antisense 3' rF5A than in those mock transfected or transfected with pHM6-Sense rF5A.

Figure 35:
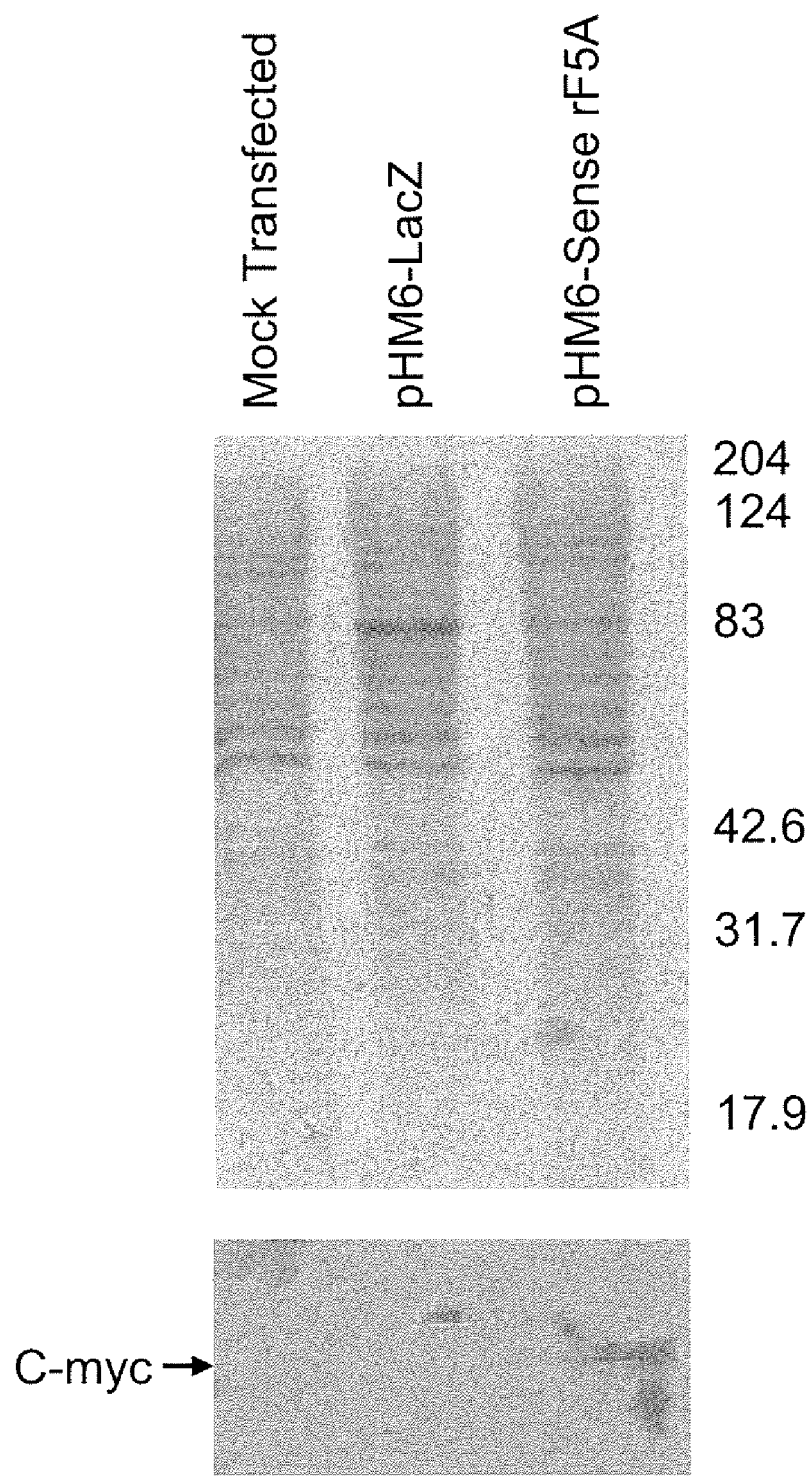
FIG. 35 is a Coomassie-blue-stained protein blot and the corresponding Western blot of COS-7 cells transiently transfected with pHM6 containing full-length rat apoptosis-specific eIF-5A in the sense orientation using c-Myc as a probe.

FIG. 35 illustrates upregulation of c-Myc when COS-7 cells were transiently transfected with pHM6 containing full-length rat apoptosis-induced eIF-5A in the sense orientation. The upper panel illustrates the Coomassie-blue-stained protein blot; the lower panel illustrates the corresponding Western blot. More c-Myc is detectable in cells transfected with pHM6-Sense rF5A than in those transfected with pHM6-LacZ or the mock control.

Figure 36:
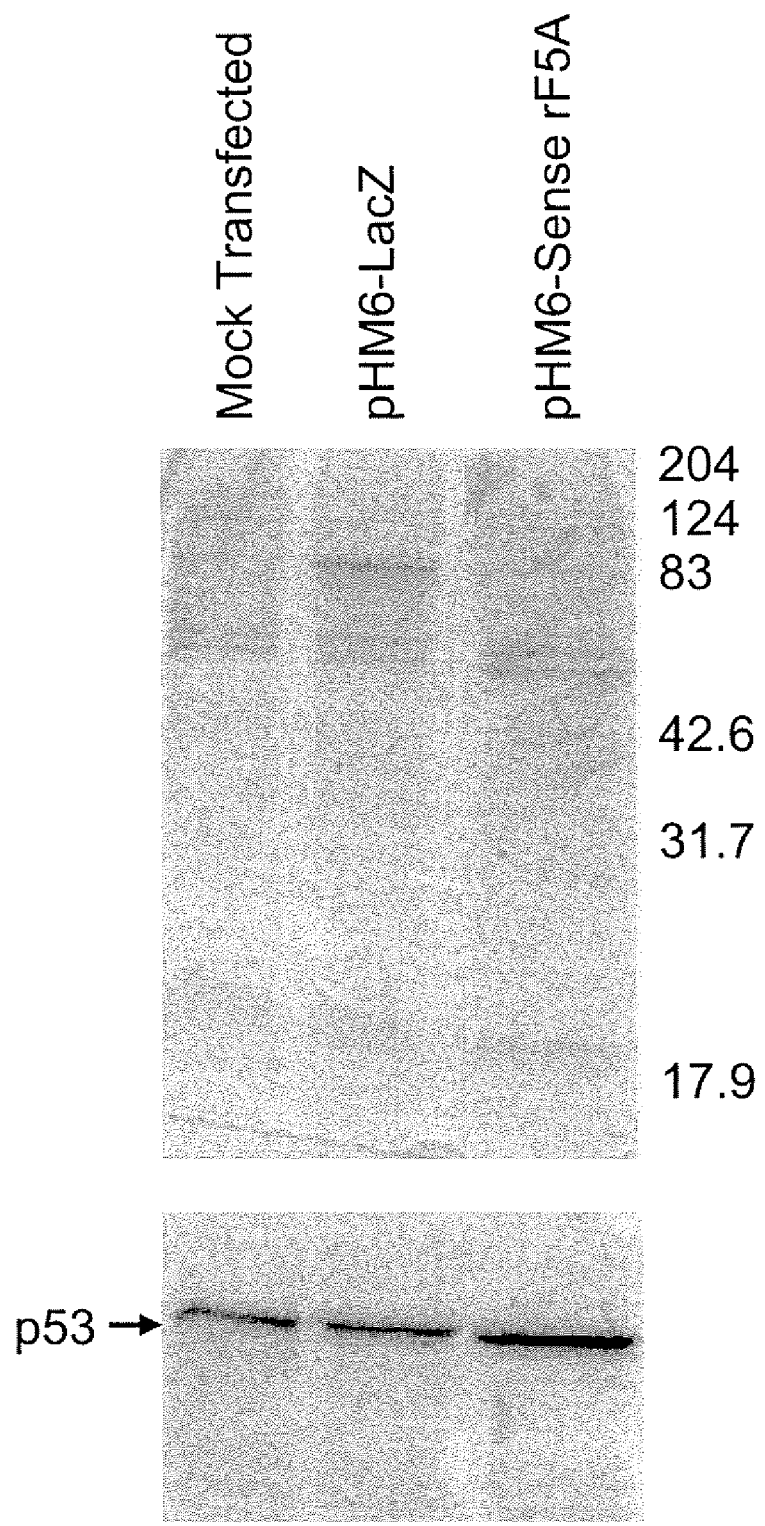
FIG. 36 is a Coomassie-blue-stained protein blot and the corresponding Western blot of COS-7 cells transiently transfected with pHM6 containing full-length rat apoptosis-specific eIF-5A in the sense orientation when p53 is used as a probe.

FIG. 36 illustrates upregulation of p53 when COS-7 cells were transiently transfected with pHM6 containing full-length rat apoptosis-induced eIF-5A in the sense orientation. The upper panel illustrates the Coomassie-blue-stained protein blot; the lower panel illustrates the corresponding Western blot. More p53 is detectable in cells transfected with pHM6-Sense rF5A than in those transfected with pHM6-LacZ or the mock control.

Figure 37B:
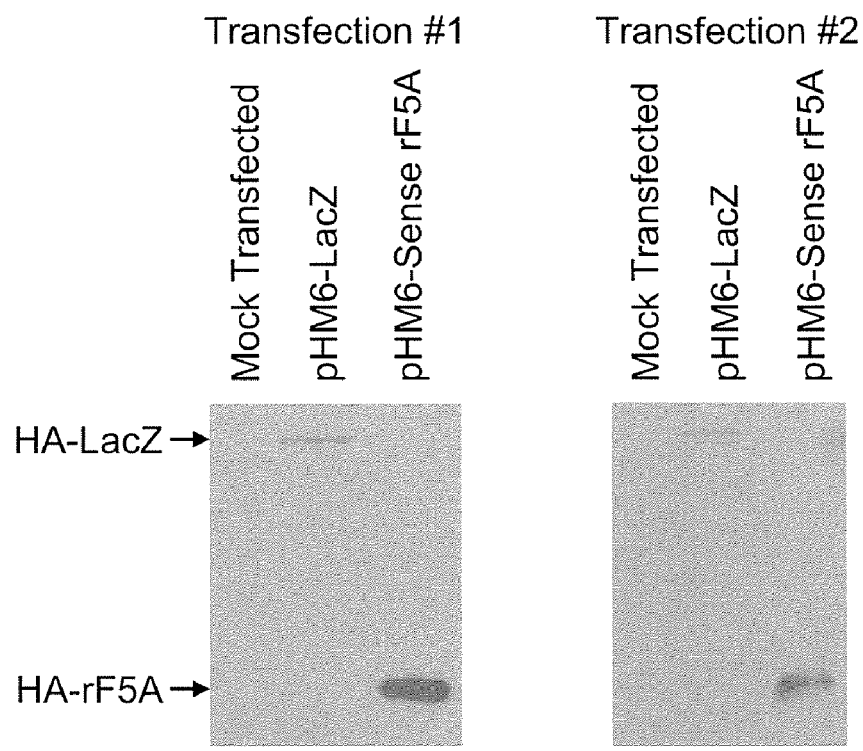
FIG. 37 is a Coomassie-blue-stained protein blot and the corresponding Western blot of expression of pHM6-full-length rat apoptosis-specific eIF-5A in COS-7 cells using an anti-[HA]-peroxidase probe and a Coomassie-blue-stained protein blot and the corresponding Western blot of expression of pHM6-full-length rat apoptosis-specific eIF-5A in COS-7 cells when a p53 probe is used.
Figure 37C:
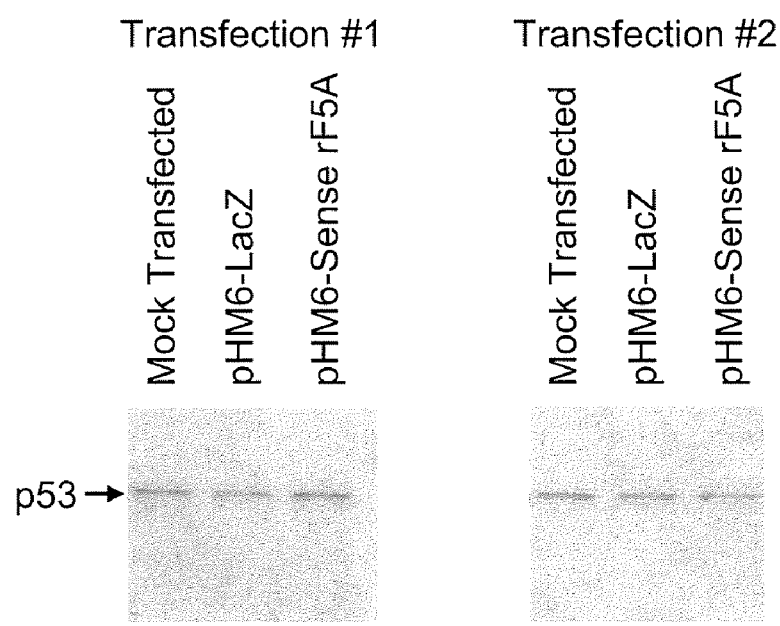
Figure 39:
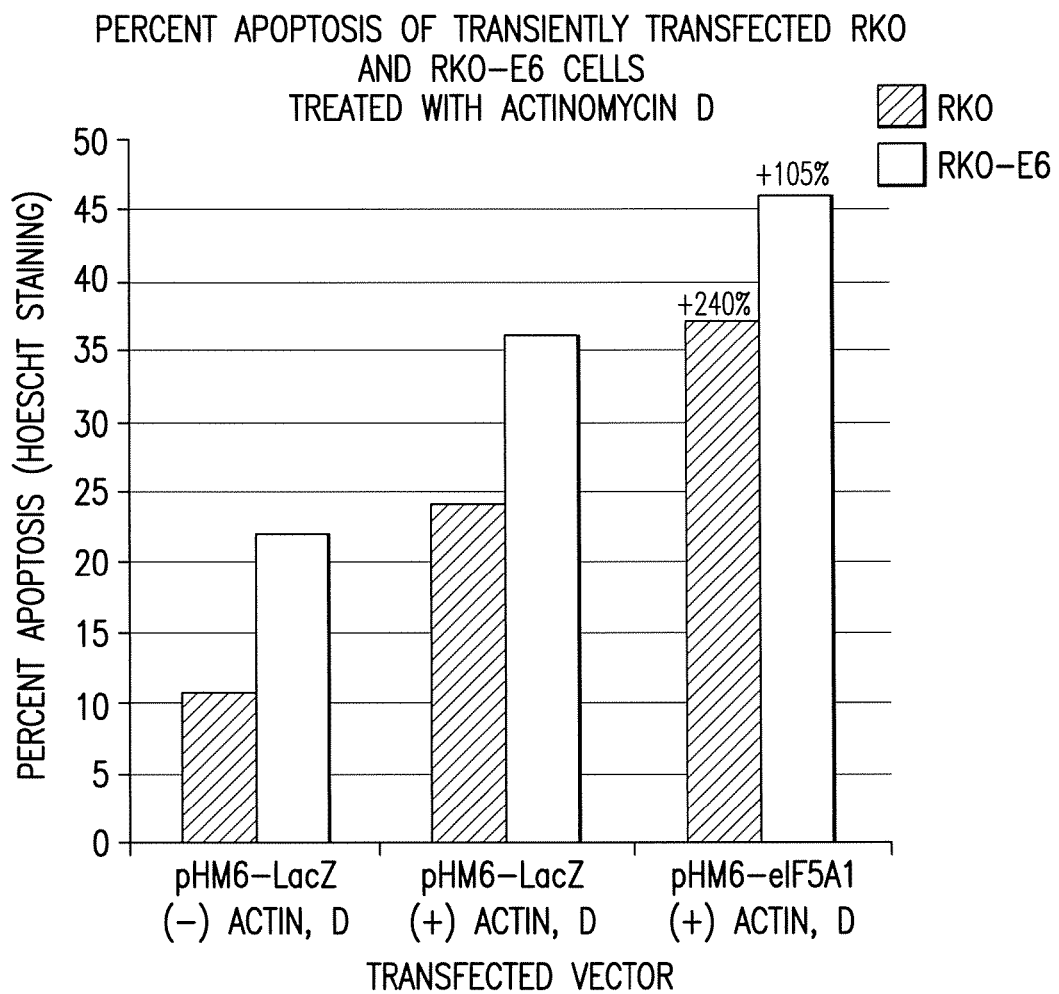
FIG. 39 is a graph depicting the percentage of apoptosis occurring in RKO and RKO-E6 cells following transient transfection. RKO and RKO-E6 cells were transiently transfected with pHM6-LacZ or pHM6-eIF-5A1. RKO cells treated with Actinomycin D and transfected with pHM6-eIF-5A1 showed a 240% increase in apoptosis relative to cells transfected with pHM6-LacZ that were not treated with Actinomycin D. RKO-E6 cells treated with Actinomycin D and transfected with pHM6-eIF-5A1 showed a 105% increase in apoptosis relative to cells transfected with pHM6-LacZ that were not treated with Actinomycin D.
Figure 40:
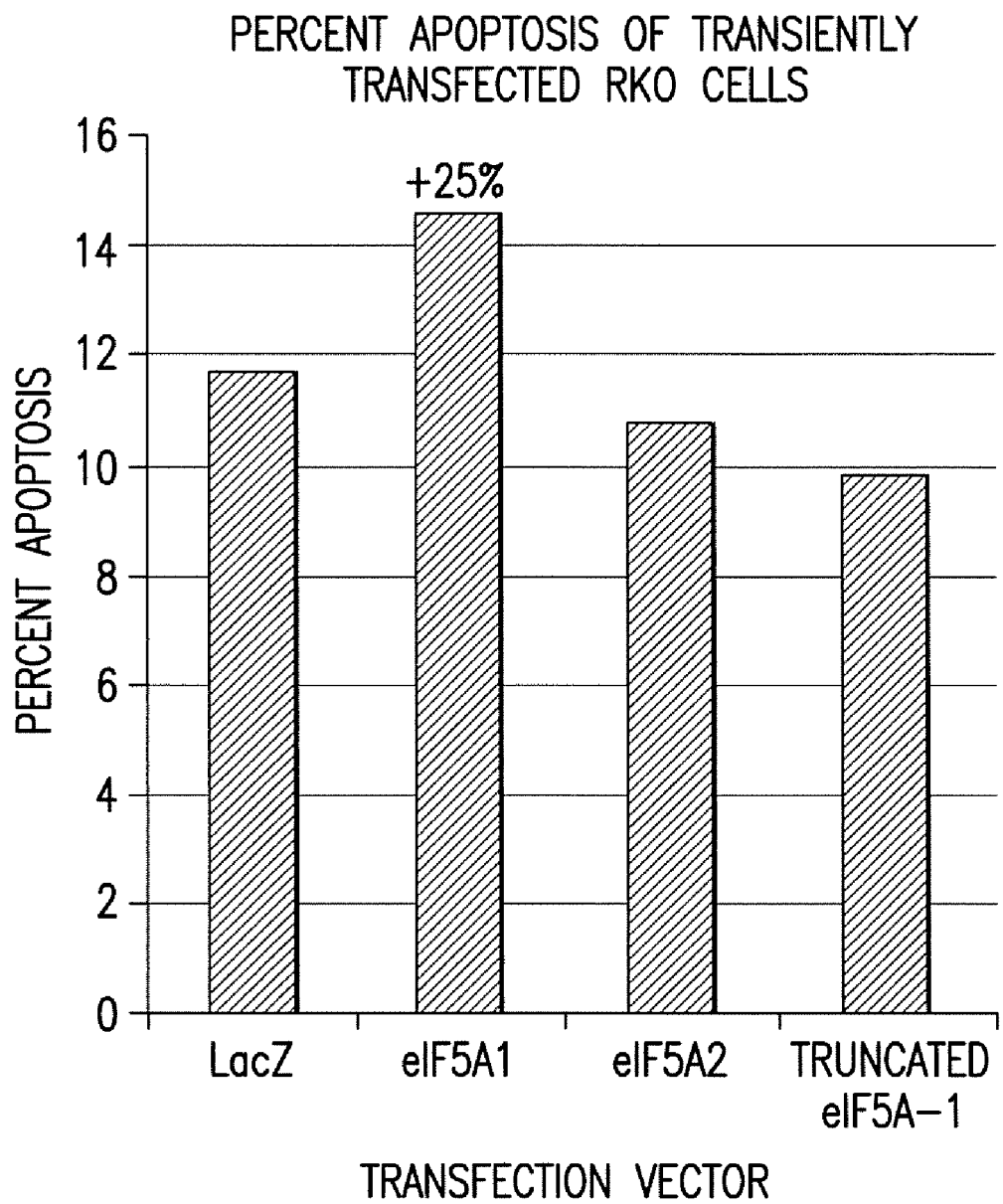
FIG. 40 is a graph depicting the percentage of apoptosis occurring in RKO cells following transient transfection. RKO cells were transiently transfected with pHM6-LacZ, pHM6-eIF-5A1, pHM6-eIF-5A2, or pHM6-truncated eIF-5A1. Cells transfected with pHM6-eIF-5A1 showed a 25% increase in apoptosis relative to control cells transfected with pHM6-LacZ. This increase was not apparent for cells transfected with pHM6-eIF-5A2 or pHM6-truncated eIF-5A1.
Figure 41:
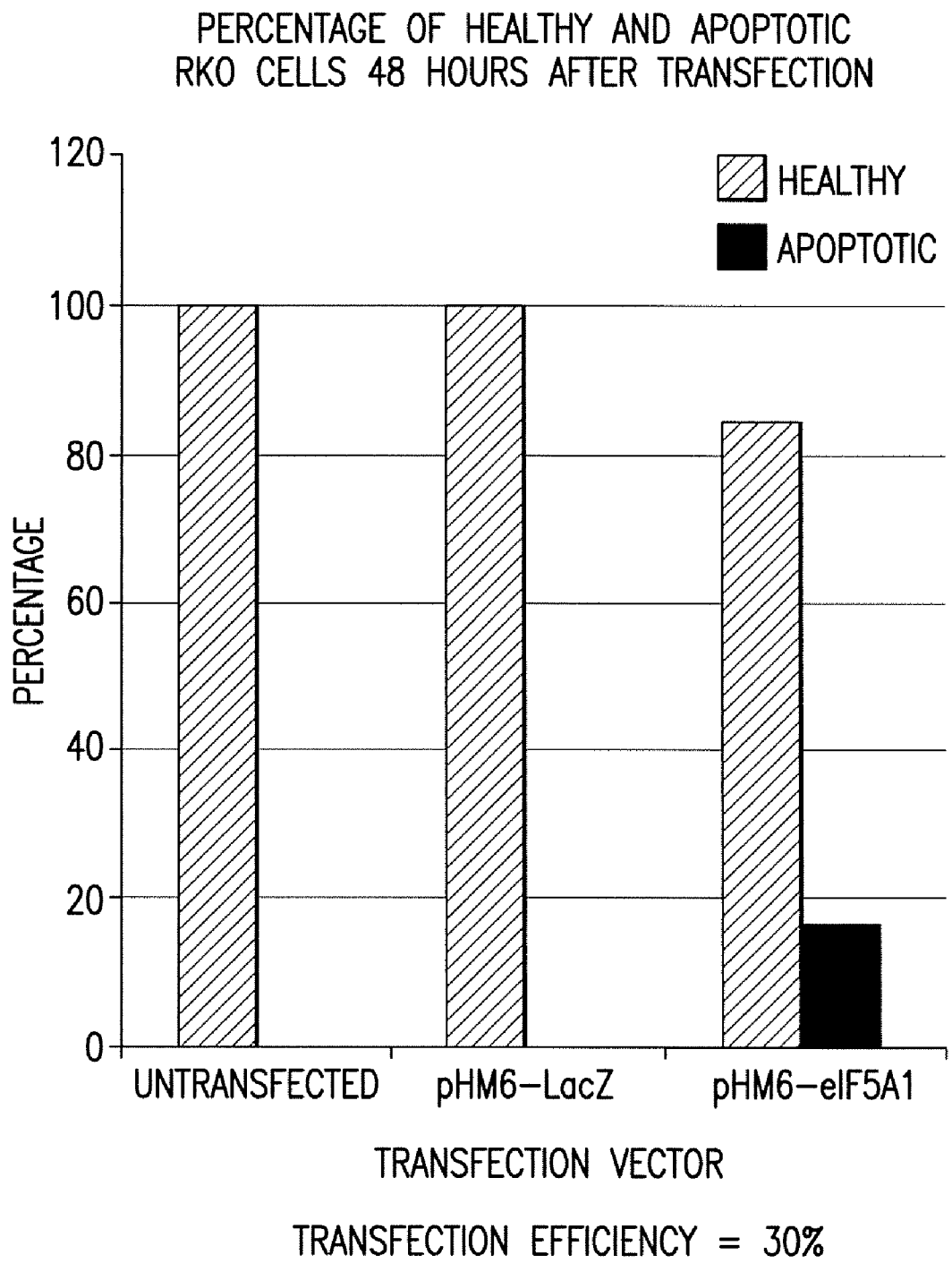
FIG. 41 is a graph depicting the percentage of apoptosis occurring in RKO cells following transient transfection. RKO cells were either left untransfected or were transiently transfected with pHM6-LacZ or pHM6-eIF-5A1. After correction for transfection efficiency, 60% of the cells transfected with pHM6-eIF-5A1 were apoptotic.
Figures 42A, 42B:
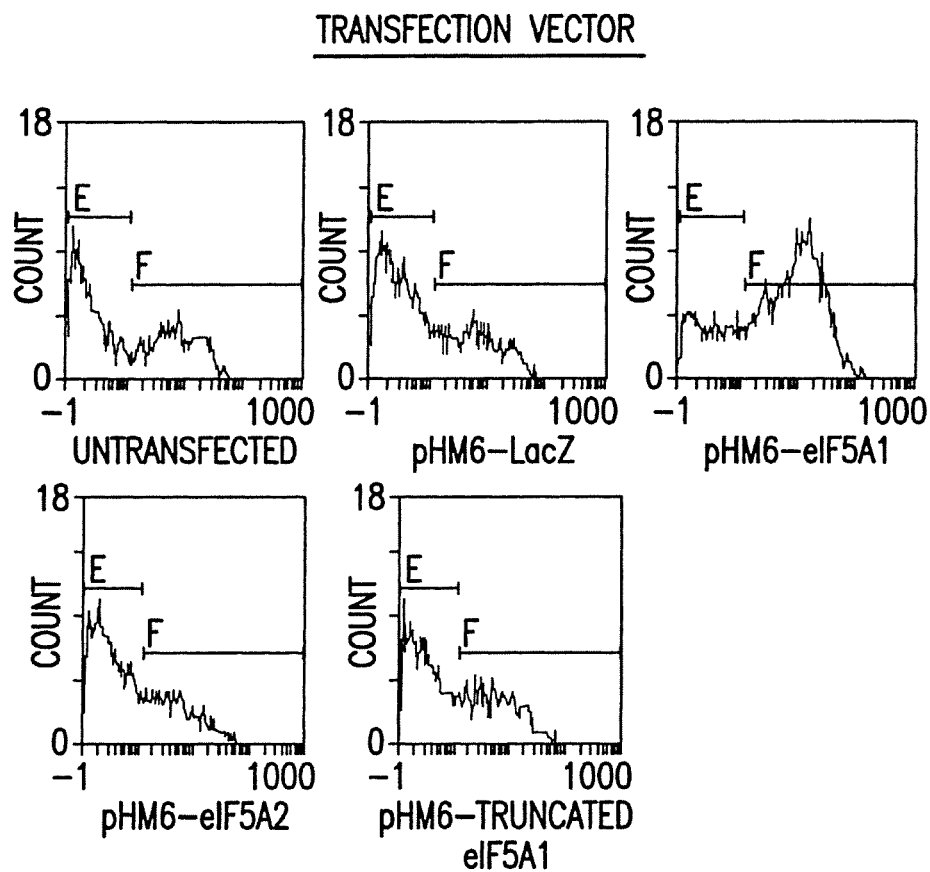
FIG. 42 provides the results of a flow cytometry analysis of RKO cell apoptosis following transient transfection. RKO cells were either left untransfected or were transiently transfected with pHM6-LacZ, pHM6-eIF-5A1, pHM6-eIF-5A2, or pHM6-truncated eIF-5A1. The table depicts the percentage of cells undergoing apoptosis calculated based on the area under the peak of each gate. After correction for background apoptosis in untransfected cells and for transfection efficiency, 80% of cells transfected with pHM6-eIF-5A1 exhibited apoptosis. Cells transfected with pHM6-LacZ, pHM6-eIF-5A2 or pHM6-truncated eIF-5A1 exhibited only background levels of apoptosis.
Figure 43:
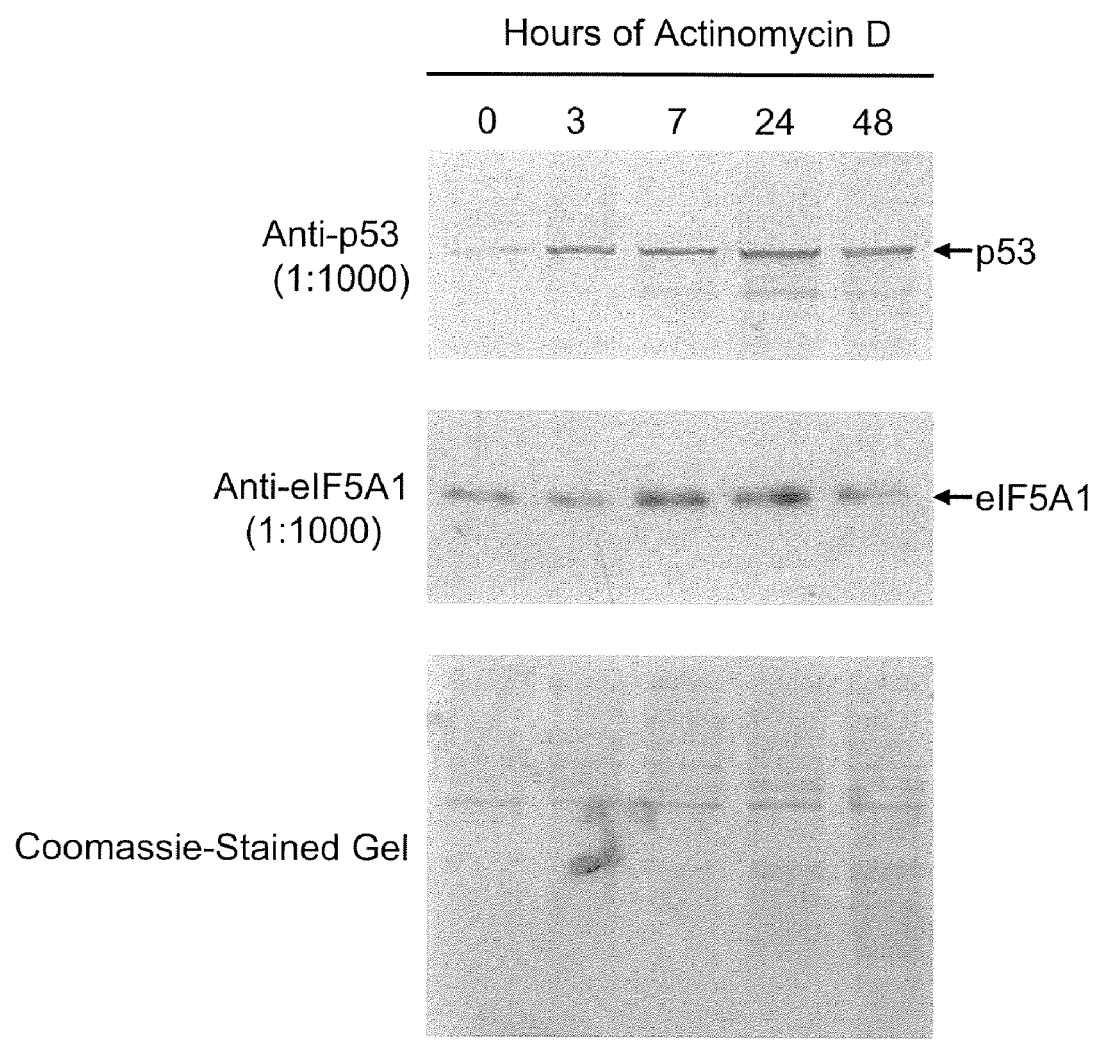
FIG. 43 provides Western blots of protein extracted from RKO cells treated with 0.25 μg/ml Actinomycin D for 0, 3, 7, 24, and 48 hours. The top panel depicts a Western blot using anti-p53 as the primary antibody. The middle panel depicts a Western blot using anti-eIF-5A1 as the primary antibody. The bottom panel depicts the membrane used for the anti-eIF-5A1 blot stained with Coomassie blue following chemiluminescent detection to demonstrate equal loading. p53 and eIF-5A1 are both upregulated by treatment with Actinomycin D.
Figure 44:
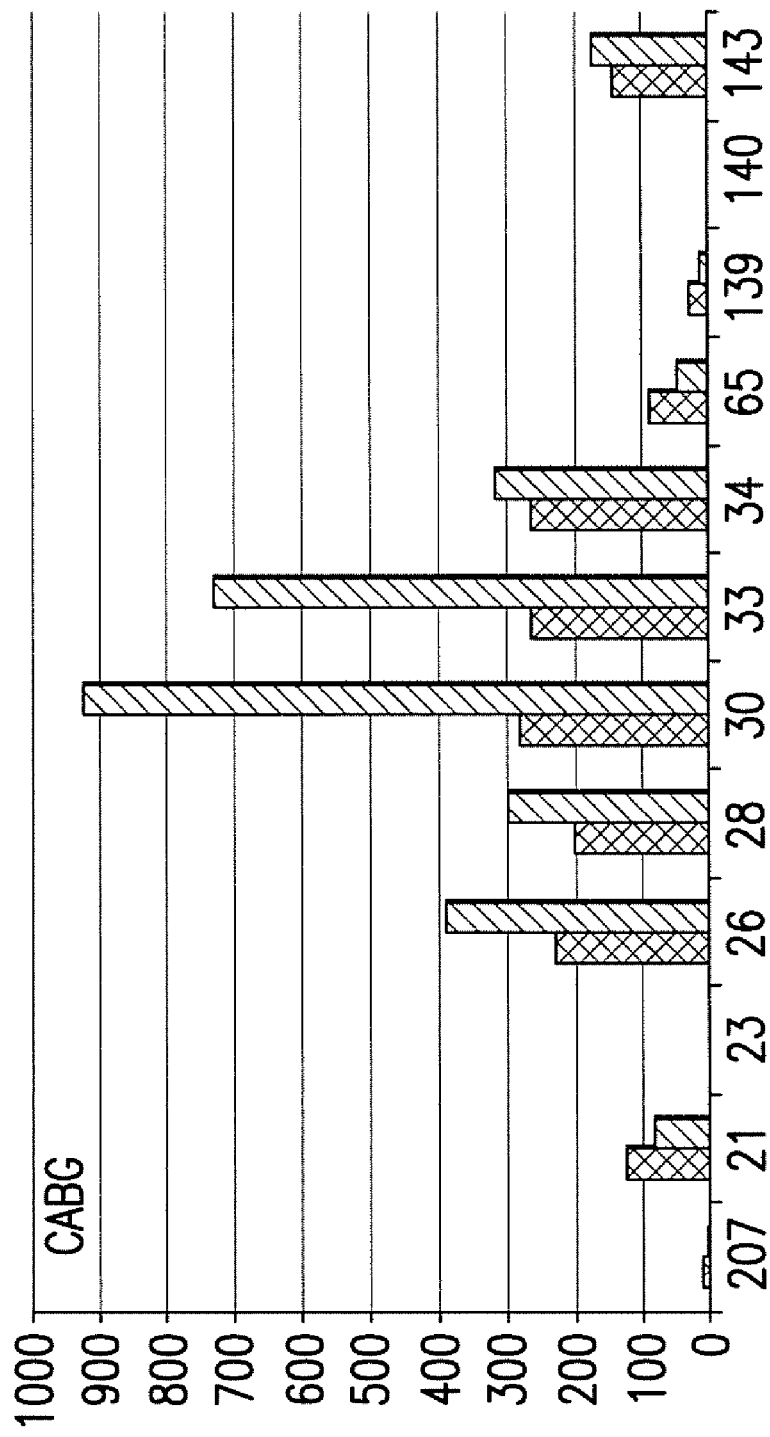
FIG. 44 is a bar graph showing that both apoptosis-specific eIF-5A (eIF-5A) and proliferation eIF-5A (eIF5b) are expressed in heart tissue. The heart tissue was taken from patients receiving coronary artery bypass grafts (CABG). Gene expression levels of eIF-5A (light gray bar) are compared to eIF5b (dark gray bar). The X-axis are patient identifier numbers. The Y-axis is pg/ng of 18s (picograms of message RNA over nanograms of ribosomal RNA 18S).
Figure 45:
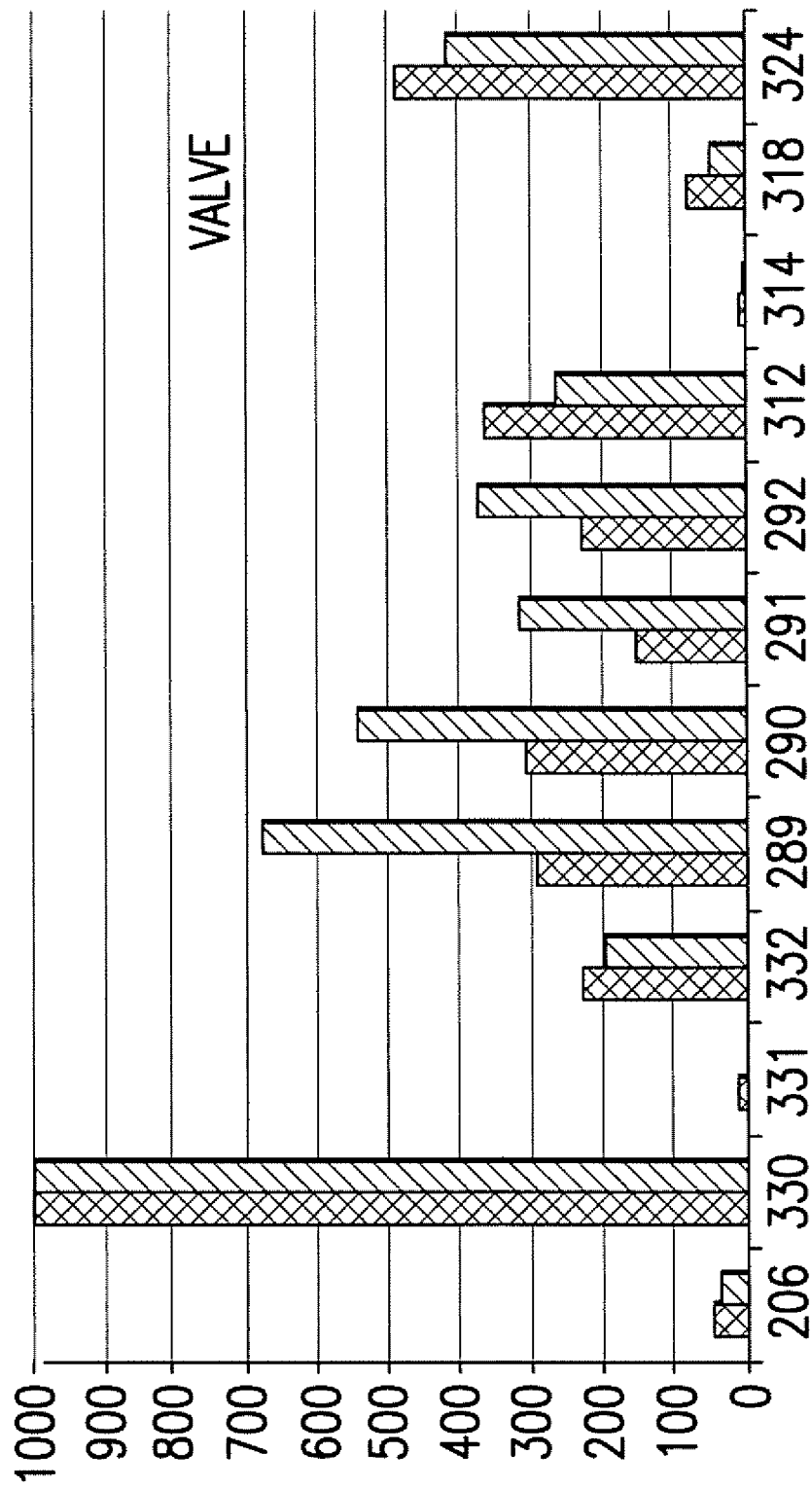
FIG. 45 is a bar graph showing that both apoptosis-specific (eIF5a) and proliferation eIF-5A (eIF5b) are expressed in heart tissue. The heart tissue was taken from patients receiving valve replacements. Gene expression levels of eIF5a (light gray bar) are compared to eIF5b (dark gray bar). The X-axis are patient identifier numbers. The Y-axis is pg/ng of 18s (picograms of message RNA over nanograms of ribosomal RNA 18S).

FIG. 37 illustrates the dependence of p53 upregulation upon the expression of pHM6-full length rat apoptosis-induced eIF-5A in COS-7 cells. In the Western blot probed with anti-[HA]-peroxidase, the upper panel illustrates the Coomassie-blue-stained protein blot and the lower panel illustrates the corresponding Western blot. More rat apoptosis-induced eIF-5A is detectable in the first transfection than in the second transfection. In the Western blot probed with anti-p53, the upper panel in A illustrates a corresponding Coomassie-blue-stained protein blot and the lower panel illustrates the Western blot with p53. For the first transfection, more p53 is detectable in cells transfected with pHM6-Sense rF5A than in those transfected with pHM6-LacZ or the mock control. For the second transfection in which there was less expression of rat apoptosis-induced eIF-5A, there was no detectable difference in levels of p53 between cells transfected with pHM6-Sense rF5A, pHM6-LacZ or the mock control.

Example 5

Figure 46:
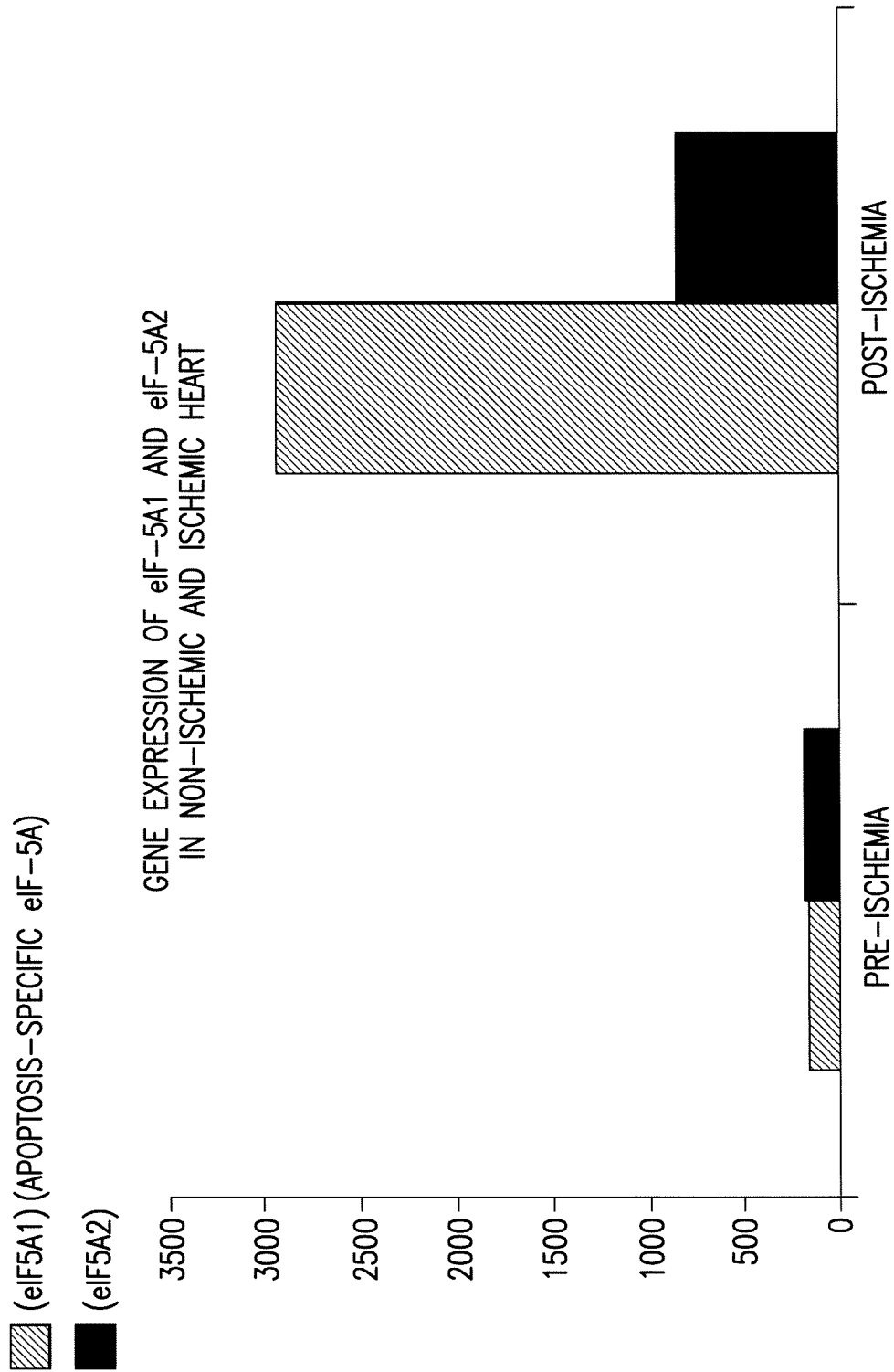
FIG. 46 is a bar graph showing the gene expression levels measured by real-time PCR of apoptosis-specific (eIf5a) versus proliferation eIF-5A (eIF5b) in pre-ischemia heart tissue and post ischemia heart tissue. The Y-axis is pg/ng of 18s (picograms of message RNA over nanograms of ribosomal RNA 18S).

FIG. 47 depicts an experiment run on heart tissue to mimic the beating of a human heart and the subsequent induced heart attack. FIG. 49 shows the laboratory bench set up. A slice of human heart tissue removed during valve replacement surgery to was hooked up to electrodes. A small weight was attached to the heart tissue for ease in measuring the strength of the heart beats. The electrodes provided an electrical stimulus to get the tissue to start beating. The levels of gene expression for both apoptosis-specific eIF-5A (eIF-5a) and proliferating eIF-5A (eIF-5b) were measured in the heart tissue before ischemia was induced. See FIG. 46. In the pre-ischemic heart tissue low levels of both eIF-5a and eIF-5b were produced and their levels were in relative balance. During this time, oxygen and carbon dioxide were delivered in a buffer to the heart at 92.5% and 7.5%, respectively. Later, the oxygen level was reduced and the nitrogen level was increased, to induce ischemia and finally a "heart attack." The heart tissue stopped beating. The oxygen levels were then returned to normal, the heart tissue was pulsed again with an electrical stimulus to start the heart beating again. After the "heart attack" the expression levels of apoptosis-specific eIF-5a and proliferating eIF-5A (eIF-5b) were again measured. This time, there was a significant increase in the level of expression of the apoptosis-specific eIF-5A levels, whereas the increase in the level of expression of proliferating eIF-5A (eIF-5b) was noticeably less. See FIG. 46.

After the "heart attack" the heart did not beat as strongly, as indicated by less compression/movement of the attached weight, thus indicating that the heart tissue cells were being killed rapidly due to the presence of apoptosis-specific eIF-5A.

The EKG results are depicted in FIG. 48. On the left side of the panels a normal heart beat is shown (the pre-ischemic heart tissue). After the "heart attack" (straight line), and the re-initiation of the heart beat, the EKG shows decreased activity due to muscle cell death. The EKG shows relative loss in strength of heart beat.

Example 6

Human Cell Line Culture Conditions

Human Lamina Cribrosa and Astrocyte Culture

Paired human eyes were obtained within 48 hours post mortem from the Eye Bank of Canada, Ontario Division. Optic nerve heads (with attached pole) were removed and placed in Dulbecco's modified Eagle's medium (DMEM) supplemented with antibiotic/antimycotic, glutamine, and 10% FBS for 3 hours. The optic nerve head (ONH) button was retrieved from each tissue sample and minced with fine dissecting scissors into four small pieces. Explants were cultured in 12.5 cm$^2$ plastic culture flasks in DMEM medium. Growth was observed within one month in viable explants. Once the cells reached 90% confluence, they were trypsinized and subjected to differential subculturing to produce lamina cribrosa (LC) and astrocyte cell populations. Specifically, LC cells were subcultured in 25 cm$^2$ flasks in DMEM supplemented with gentamycin, glutamine, and 10% FBS, whereas astrocytes were expanded in 25 cm$^2$ flasks containing EBM complete medium (Clonetics) with no FBS. FBS was added to astrocyte cultures following 10 days of subculture. Cells were maintained and subcultured as per this protocol.

Cell populations obtained by differential subculturing were characterized for identity and population purity using differential fluorescent antibody staining on 8 well culture slides. Cells were fixed in 10% formalin solution and washed three times with Dulbecco's Phosphate Buffered Saline (DPBS). Following blocking with 2% nonfat milk in DPBS, antibodies were diluted in 1% BSA in DPBS and applied to the cells in 6 of the wells. The remaining two wells were treated with only 1% bovine serum albumin (BSA) solution and no primary antibody as controls. Cells were incubated with the primary antibodies for one hour at room temperature and then washed three times with DPBS. Appropriate secondary antibodies were diluted in 1% BSA in DPBS, added to each well and incubated for 1 hour. Following washing with DPBS, the chambers separating the wells of the culture slide were removed from the slide, and the slide was immersed in double distilled water and then allowed to air-dry. Fluoromount (Vector Laboratories) was applied to each slide and overlayed by 22×60 mm coverglass slips.

Immunofluorescent staining was viewed under a fluorescent microscope with appropriate filters and compared to the control wells that were not treated with primary antibody. All primary antibodies were obtained from Sigma unless otherwise stated. All secondary antibodies were purchased from Molecular Probes. Primary antibodies used to identify LC cells were: anti-collagen I, anti-collagen IV, anti-laminin, anti-cellular fibronectin. Primary antibodies used to identify astrocytes were: anti-galactocerebroside (Chemicon International), anti-A2B5 (Chemicon International), anti-NCAM, anti-human Von willebrand Factor. Additional antibodies used for both cell populations included anti-glial fibrillary (GFAP) and anti-alpha-smooth muscle actin. Cell populations were determined to be comprised of LC cells if they stained positively for collagen I, collagen IV, laminin, cellular fibronectin, alpha smooth muscle actin and negatively for glial fibrillary (GFAP). Cell populations were determined to be comprised of astrocytes if they stained positively for NCAM, glial fibrillary (GFAP), and negatively for galactocerebroside, A2B5, human Von willebrand Factor, and alpha smooth muscle actin.

In this preliminary study, three sets of human eyes were used to initiate cultures. LC cell lines #506, #517, and #524 were established from the optic nerve heads of an 83-year old male, a 17-year old male, and a 26-year old female, respectively. All LC cell lines have been fully characterized and found to contain greater than 90% LC cells.

RKO Cell Culture

RKO (American Type Culture Collection CRL-2577), a human colon carcinoma cell line expressing wild-type p53, was used to test the antisense oligonucleotides for the ability to suppress eIF-5A1 protein expression. RKO were cultured in Minimum Essential Medium Eagle (MEM) with non-essential amino acids, Earle's salts, and L-glutamine. The culture media was supplemented with 10% fetal bovine serum (FBS) and 100 units of penicillin/streptomycin. The cells were grown at 37° C. in a humidified environment of 5% $CO_2$ and 95% air. The cells were subcultured every 3 to 4 days by detaching the adherent cells with a solution of 0.25% trypsin and 1 mM EDTA. The detached cells were dispensed at a split ratio of 1:10 to 1:12 into a new culture dish with fresh media.

HepG2 Cell Culture

HepG2, a human hepatocellular carcinoma cell line, was used to test the ability of an antisense oligo directed against human eIF-5A1 to block production of TNF-α in response to treatment with IL-1β. HepG2 cells were cultured in DMEM supplemented with gentamycin, glutamine, and 10% FBS and grown at 37° C. in a humidified environment of 5% $CO_2$ and 95% air.

Example 7

Induction of Apoptosis

Apoptosis was induced in RKO and lamina cribrosa cells using Actinomycin D, an RNA polymerase inhibitor, and camptothecin, a topoisomerase inhibitor, respectively. Actinomycin D was used at a concentration of 0.25 µg/ml and camptothecin was used at a concentration of 20, 40, or 50 Apoptosis was also induced in lamina cribrosa cells using a combination of camptothecin (50 µM) and TNF-α (10 ng/ml). The combination of camptothecin and TNF-α was found to be more effective at inducing apoptosis than either camptothecin or TNF-α alone.

Antisense Oligonucleotides

A set of three antisense oligonucleotides targeted against human eIF-5A1 were designed by, and purchased from, Molecula Research Labs. The sequence of the first antisense oligonucleotide targeted against human eIF-5A1 (#1) was 5' CCT GTC TCG AAG TCC AAG TC 3' (SEQ ID NO: 63). The sequence of the second antisense oligonucleotide targeted against human eIF-5A1 (#2) was 5' GGA CCT TGG CGT GGC CGT GC 3' (SEQ ID NO: 64). The sequence of the third antisense oligonucleotide targeted against human eIF-5A1 (#3) was 5' CTC GTA CCT CCC CGC TCT CC 3' (SEQ ID NO: 65). The control oligonucleotide had the sequence 5' CGT ACC GGT ACG GTT CCA GG 3' (SEQ ID NO: 66). A fluorescein isothiocyanate (FITC)-labeled antisense oligonucleotide (Molecula Research Labs) was used to monitor transfection efficiency and had the sequence 5' GGA CCT TGG CGT GGC CGT GCX 3' (SEQ ID NO: 67), where X is the FITC label. All antisense oligonucleotides were fully phosphorothioated.

Transfection of Antisense Oligonucleotides

The ability of the eIF-5A1 antisense oligonucleotides to block eIF-5A1 protein expression was tested in RKO cells. RKO cells were transfected with antisense oligonucleotides using the transfection reagent, Oligofectamine (Invitrogen). Twenty four hours prior to transfection, the cells were split onto a 24 well plate at 157,000 per well in MEM media supplemented with 10% FBS but lacking penicillin/streptomycin. Twenty four hours later the cells had generally reached a confluency of approximately 50%. RKO cells were either mock transfected, or transfected with 100 nM or 200 nM antisense oligonucleotide. Transfection medium sufficient for one well of an 24 well plate was prepared by diluting 0, 1.25, or 2.5 µl of a 20 µM stock of antisense oligonucleotide with serum-free MEM to a final volume of 42.5 µl and incubating the mixture at room temperature for 15 minutes. 1.5 µl of Oligofectamine was diluted in 6 µl of serum-free MEM and incubated for 7.5 minutes at room temperature. After 5 minutes the diluted Oligofectamine mixture was added to the DNA mixture and incubated together at room temperature for 20 minutes. The cells were washed once with serum-free MEM before adding 200 µl of MEM to the cells and overlaying 50 µl of transfection medium. The cells were placed back in the growth chamber for 4 hours. After the incubation, 125 µl of MEM+30% FBS was added to the cells. The cells were then cultured for a further 48 hours, treated with 0.25 µg/ml Actinomycin D for 24 hours, and then cell extract was harvested for Western blot analysis.

Transfection of lamina cribrosa cells was also tested using 100 and 200 nM antisense oligonucleotide and Oligofectamine using the same procedure described for RKO cells. However, effective transfection of lamina cribrosa cells was achieved by simply adding antisense oligonucleotide, diluted from 1 µM to 10 µM in serum-free media, to the cells for 24 hours and thereafter replacing the media with fresh antisense oligonucleotides diluted in serum-containing media every 24 hours for a total of two to five days.

The efficiency of antisense oligonucleotide transfection was optimized and monitored by performing transfections with an FITC-labeled antisense oligonucleotide having the same sequence as eIF-5A1 antisense oligonucleotide #2 but conjugated to FITC at the 3' end. RKO and lamina cribrosa cells were transfected with the FITC-labeled antisense oligonucleotide on an 8-well culture slide. Forty-eight hours later the cells were washed with PBS and fixed for 10 minutes in 3.7% formaldehyde in PBS. The wells were removed and mounting media (Vectashield) was added, followed by a coverslip. The cells were then visualized under UV light on a fluorescent microscope nucleus using a fluorescein filter (Green H546, filter set 48915) and cells fluorescing bright green were determined to have taken up the oligonucleotide.

Detection of Apoptosis

Following transfection of lamina cribosa cells with antisense oligonucleotides and induction of apoptosis with camptothecin, the percentage of cells undergoing apoptosis in cells treated with either control antisense oligonucleotide or antisense oligonucleotide eIF-5A1 SEQ ID NO:26 was determined. Two methods were used to detect apoptotic lamina cribosa cells—Hoescht staining and DeadEnd™ Fluorometric TUNEL. The nuclear stain, Hoescht, was used to label the nuclei of lamina cribosa cells in order to identify apoptotic cells based on morphological features such as nuclear fragmentation and condensation. A fixative, consisting of a 3:1 mixture of absolute methanol and glacial acetic acid, was prepared immediately before use. An equal volume of fixative was added to the media of cells growing on a culture slide and incubated for 2 minutes. The media/fixative mixture was removed from the cells and discarded and 1 ml of fixative was added to the cells. After 5 minutes the fixative was discarded and 1 ml of fresh fixative was added to the cells and incubated for 5 minutes. The fixative was discarded and the cells were air-dried for 4 minutes before adding 1 ml of Hoescht stain (0.5 µg/ml Hoescht 33258 in PBS). After a 10 minute incubation in the dark, the staining solution was discarded, the chambers separating the wells of the culture slide were removed, and the slide was washed 3 times for 1 minute with deionized water. After washing, a few drops of McIlvaine's buffer (0.021 M citric acid, 0.058 M $Na_2HPO_4.7H_2O$; pH 5.6) was added to the cells and overlaid with a coverslip. The stained cells were viewed under a fluorescent microscope using a UV filter. Cells with brightly stained or fragmented nuclei were scored as apoptotic. A minimum of 200 cells were counted per well.

The DeadEnd™ Fluorometric TUNEL (Promega) was used to detect the DNA fragmentation that is a characteristic feature of apoptotic cells. Following Hoescht staining, the culture slide was washed briefly with distilled water, and further washed by immersing the slide twice for 5 minutes in PBS (137 mM NaCl, 2.68 mM KCl, 1.47 mM $KH_2PO_4$, 8.1 mM $Na_2HPO_4$), blotting the slide on paper towel between washes. The cells were permeabilized by immersing them in 0.2% Triton X-100 in PBS for 5 minutes. The cells were then washed again by immersing the slide twice for 5 minutes in PBS and blotting the slide on paper towel between washes. 25 µl of equilibration buffer [200 mM potassium cacodylate (pH 6.6), 25 mM Tris-HCl (pH 6.6), 0.2 mM dithiothreitol, 0.25 mg/ml bovine serum albumin, and 2.5 mM cobalt chloride] was added per well and incubated for 5 to 10 minutes. During equilibration, 30 µl of reaction mixture was prepared for each well by mixing in a ratio of 45:5:1, respectively, equilibration buffer, nucleotide mix [50 µM fluorescein-12-dUTP, 100 µM dATP, 10 mM Tris-HCl (pH 7.6), and 1 mM EDTA], and terminal deoxynucleotidyl transferase enzyme (Tdt, 25 U/µl). After the incubation in equilibration buffer, 30 µl of reaction mixture was added per well and overlayed with a coverslip. The reaction was allowed to proceed in the dark at 37° C. for 1 hour. The reaction was terminated by immersing the slide in 2×SSC [0.3 M NaCl, and 30 mM sodium citrate (pH 7.0)] and incubating for 15 minutes. The slide was then washed by immersion in PBS three times for 5 minutes. The PBS was removed by sponging around the wells with a Kim wipe, a drop of mounting media (Oncogene research project, JA1750-4ML) was added to each well, and the slide was overlayed with a coverslip. The cells were viewed under a fluorescent microscope using a UV filter (UV-G 365, filter set 487902) in order to count the Hoescht-stained nuclei. Any cells with brightly stained or fragmented nuclei were scored as apoptotic. Using the same field of view, the cells were then viewed using a fluorescein filter (Green H546, filter set 48915) and any nuclei fluorescing bright green were scored as apoptotic. The percentage of apoptotic cells in the field of view was calculated by dividing the number of bright green nuclei counted using the fluorescein filter by the total number of nuclei counted under the UV filter. A minimum of 200 cells were counted per well.

FIGS. 54-57 depict the results of these studies. The percentage of apoptotic cells in samples having been transfected with apoptosis-specific eIF-5A1 is clearly much less than seen in cells having been transfected with the control oligonucleotide.

Protein Extraction and Western Blotting

Protein from transfected RKO cells was harvested for Western blot analysis by washing the cells with PBS, adding 40 µl of hot lysis buffer [0.5% SDS, 1 mM dithiothreitol, 50 mM Tris-HCl (pH 8.0)] per well. The cells were scraped and the resulting extract was transferred to a microfuge tube, boiled for 5 minutes, and stored at −20° C. The protein was quantitated using the Bio-Rad Protein Assay (Bio-Rad) according to the manufacturer's instructions.

For Western blotting 5 µg of total protein was separated on a 12% SDS-polyacrylamide gel. The separated proteins were transferred to a polyvinylidene difluoride membrane. The membrane was then incubated for one hour in blocking solution (5% skim milk powder in PBS) and washed three times for 15 minutes in 0.05% Tween-20/PBS. The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in 0.025% Tween-20/PBS. The primary antibody was preincubated for 30 minutes in a solution of 5% milk in 0.025% Tween-20/PBS prior to incubation with the membrane.

Several primary antibodies were used. A monoclonal antibody from Oncogene which recognizes p53 (Ab-6) and a polyclonal antibody directed against a synthetic peptide (amino-CRLPEGDLGKEIEQKYD-carboxy) (SEQ ID NO:68) homologous to the c-terminal end of human eIF-5A1 that was raised in chickens (Gallus Immunotech). An anti-β-actin antibody (Oncogene) was also used to demonstrate equal loading of protein. The monoclonal antibody to p53 was used at a dilution of 0.05 µg/ml, the antibody against eIF-5A1 was used at a dilution of 1:1000, and the antibody against actin was used at a dilution of 1:20,000. After incubation with primary antibody for 60 to 90 minutes, the membrane was washed 3 times for 15 minutes in 0.05% Tween-20/PBS. Secondary antibody was then diluted in 1% milk in 0.025% Tween-20/PBS and incubated with the membrane for 60 to 90 minutes. When p53 (Ab-6) was used as the primary antibody, the secondary antibody used was a rabbit anti-mouse IgG conjugated to peroxidase (Sigma) at a dilution of 1:5000. When anti-eIF-5A1 was used as the primary antibody, a rabbit anti-chicken IgY conjugated to peroxidase (Gallus Immunotech) was used at a dilution of 1:5000. The secondary antibody used with actin was a goat anti-mouse IgM conjugated to peroxidase (Calbiochem) used at a dilution of 1:5000. After incubation with the secondary antibody, the membrane was washed 3 times in PBS-T.

The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 30 minutes. The membrane was stripped by submerging the membrane in stripping buffer [100 mM 2-Mercaptoethanol, 2% SDS, and 62.5 mM Tris-HCl (pH 6.7)], and incubating at 50° C. for 30 minutes. The membrane was then rinsed in deionized water and washed twice for 10 minutes in large volumes of 0.05% Tween-20/PBS. Membranes were stripped and re-blotted up to three times.

Example 8

Construction of siRNA

Small inhibitory RNAs (siRNAs) directed against human eIF-5A1 were used to specifically suppress expression of eIF-5A1 in RKO and lamina cribrosa cells. Six siRNAs were generated by in vitro transcription using the Silencer™ siRNA Construction Kit (Ambion Inc.). Four siRNAs were generated against human eIF-5A1 (siRNAs #1 to #4) (SEQ ID NO:30-33). See FIG. 70. Two siRNAs were used as controls; an siRNA directed against GAPDH provided in the kit, and an siRNA (siRNA #5) (SEQ ID NO:34) which has the reverse sequence of the eIF-5A1-specific siRNA #1 (SEQ ID NO:30) but does not itself target eIF-5A1. The siRNAs were generated according to the manufacturer's protocol. In brief, DNA oligonucleotides encoding the desired siRNA strands were used as templates for T7 RNA polymerase to generate individual strands of the siRNA following annealing of a T7 promoter primer and a fill-in reaction with Klenow fragment. Following transcription reactions for both the sense and antisense strands, the reactions were combined and the two siRNA strands were annealed, treated with DNase and RNase, and then column purified. The sequence of the DNA oligonucleotides (T7 primer annealing site underlined) used to generate the siRNAs were: siRNA #1 antisense 5' AAAG-GAATGACTTCCAGCTGACCTGTCTC 3' (SEQ ID NO: 69) and siRNA #1 sense 5' AATCAGCTGGAAGTCAT-TCCTCCTGTCTC 3' (SEQ ID NO: 70); siRNA #2 antisense 5' AAGATCGTCGAGATGTCTACTCCTGTCTC 3' (SEQ ID NO: 71) and siRNA #2 sense 5' AAAGTAGACATCTC-GACGATCCCTGTCTC 3' (SEQ ID NO: 72); siRNA #3 antisense 5' AAGGTCCATCTGGTTGGTATTCCTGTCTC 3' (SEQ ID NO: 73) and siRNA #3 sense 5' AAAATAC-CAACCAGATGGACCCCTGTCTC 3' (SEQ ID NO: 74); siRNA #4 antisense 5' AAGCTGGACTCCTCCTACACA CCTGTCTC 3' (SEQ ID NO: 75) and siRNA #4 sense 5' AATGTGTAGGAGGAGTCCAGCCCTGTCTC 3' (SEQ ID NO: 76); siRNA #5 antisense 5' AAAGTCGACCTTCAG-TAAGGACCTGTCTC 3' (SEQ ID NO: 77) and siRNA #5 sense 5' AATCCTTACTGAAGGTCGACTCCTGTCTC 3' (SEQ ID NO: 78).

The Silencer™ siRNA Labeling Kit—FAM (Ambion) was used to label GAPDH siRNA with FAM in order to monitor the uptake of siRNA into RKO and lamina cribrosa cells. After transfection on 8-well culture slides, cells were washed with PBS and fixed for 10 minutes in 3.7% formaldehyde in PBS. The wells were removed and mounting media (Vectashield) was added, followed by a coverslip. Uptake of the FAM-labeled siRNA was visualized under a fluorescent microscope under UV light using a fluorescein filter. The GAPDH siRNA was labeled according to the manufacturer's protocol.
Transfection of siRNA RKO cells and lamina cribrosa cells were transfected with siRNA using the same transfection protocol. RKO cells were seeded the day before transfection onto 8-well culture slides or 24-well plates at a density of 46,000 and 105,800 cells per well, respectively. Lamina cribrosa cells were transfected when cell confluence was at 40 to 70% and were generally seeded onto 8-well culture slides at 7500 to 10,000 cells per well three days prior to transfection. Transfection medium sufficient for one well of an 8-well culture slide was prepared by diluting 25.5 pmoles of siRNA stock to a final volume of 21.2 µl in Opti-Mem (Sigma). 0.425 µl of Lipofectamine 2000 was diluted to a final volume of 21.2 µl in Opti-Mem and incubated for 7 to 10 minutes at room temperature. The diluted Lipofectamine 2000 mixture was then added to the diluted siRNA mixture and incubated together at room temperature for 20 to 30 minutes. The cells were washed once with serum-free media before adding 135 µl of serum-free media to the cells and overlaying the 42.4 µl of transfection medium. The cells were placed back in the growth chamber for 4 hours. After the incubation, 65 µl of serum-free media+ 30% FBS was added to the cells. Transfection of siRNA into cells to be used for Western blot analysis were performed in 24-well plates using the same conditions as the transfections in 8-well slides except that the volumes were increased by 2.3 fold.

Following transfection, RKO and lamina cribrosa cells were incubated for 72 hours prior to collection of cellular extract for Western blot analysis. In order to determine the effectiveness of the siRNAs directed against eIF-5A1 to block apoptosis, lamina cribrosa cells were treated with 50 µM of camptothecin (Sigma) and 10 ng/ml of TNF-α (Leinco Technologies) to induce apoptosis either 48 or 72 hours after transfection. The cells were stained with Hoescht either 24 or 48 hours later in order to determine the percentage of cells undergoing apoptosis.

Example 9

Detection of Apoptosis

Following transfection of lamina cribrosa cells with antisense oligonucleotides and induction of apoptosis with camptothecin, the percentage of cells undergoing apoptosis in cells treated with either control antisense oligonucleotide or antisense oligonucleotide eIF-5A1 #2 was determined. Two methods were used to detect apoptotic lamina cribrosa cells—Hoescht staining and DeadEnd™ Fluorometric TUNEL. The nuclear stain, Hoescht, was used to label the nuclei of lamina cribrosa cells in order to identify apoptotic cells based on morphological features such as nuclear fragmentation and condensation. A fixative, consisting of a 3:1 mixture of absolute methanol and glacial acetic acid, was prepared immediately before use. An equal volume of fixative was added to the media of cells growing on a culture slide and incubated for 2 minutes. The media/fixative mixture was removed from the cells and discarded and 1 ml of fixative was added to the cells. After 5 minutes the fixative was discarded and 1 ml of fresh fixative was added to the cells and incubated for 5 minutes. The fixative was discarded and the cells were air-dried for 4 minutes before adding 1 ml of Hoescht stain (0.5 µg/ml Hoescht 33258 in PBS). After a 10 minute incubation in the dark, the staining solution was discarded, the chambers separating the wells of the culture slide were removed, and the slide was washed 3 times for 1 minute with deionized water. After washing, a few drops of McIlvaine's buffer (0.021 M citric acid, 0.058 M $Na_2HPO_4.7H_2O$; pH 5.6) was added to the cells and overlaid with a coverslip. The stained cells were viewed under a fluorescent microscope using a UV filter. Cells with brightly stained or fragmented nuclei were scored as apoptotic. A minimum of 200 cells were counted per well.

The DeadEnd™ Fluorometric TUNEL (Promega) was used to detect the DNA fragmentation that is a characteristic feature of apoptotic cells. Following Hoescht staining, the culture slide was washed briefly with distilled water, and further washed by immersing the slide twice for 5 minutes in PBS (137 mM NaCl, 2.68 mM KCl, 1.47 mM $KH_2PO_4$, 8.1 mM Na$_2$HPO$_4$), blotting the slide on paper towel between washes. The cells were permeabilized by immersing them in 0.2% Triton X-100 in PBS for 5 minutes. The cells were then washed again by immersing the slide twice for 5 minutes in PBS and blotting the slide on paper towel between washes. 25 μl of equilibration buffer [200 mM potassium cacodylate (pH 6.6), 25 mM Tris-HCl (pH 6.6), 0.2 mM dithiothreitol, 0.25 mg/ml bovine serum albumin, and 2.5 mM cobalt chloride] was added per well and incubated for 5 to 10 minutes. During equilibration, 30 μl of reaction mixture was prepared for each well by mixing in a ratio of 45:5:1, respectively, equilibration buffer, nucleotide mix [50 μM fluorescein-12-dUTP, 100 μM dATP, 10 mM Tris-HCl (pH 7.6), and 1 mM EDTA], and terminal deoxynucleotidyl transferase enzyme (Tdt, 25 U/μl). After the incubation in equilibration buffer, 30 μl of reaction mixture was added per well and overlayed with a coverslip. The reaction was allowed to proceed in the dark at 37° C. for 1 hour. The reaction was terminated by immersing the slide in 2×SSC [0.3 M NaCl, and 30 mM sodium citrate (pH 7.0)] and incubating for 15 minutes. The slide was then washed by immersion in PBS three times for 5 minutes. The PBS was removed by sponging around the wells with a Kim wipe, a drop of mounting media (Oncogene research project, JA1750-4ML) was added to each well, and the slide was overlayed with a coverslip. The cells were viewed under a fluorescent microscope using a UV filter (UV-G 365, filter set 487902) in order to count the Hoescht-stained nuclei. Any cells with brightly stained or fragmented nuclei were scored as apoptotic. Using the same field of view, the cells were then viewed using a fluorescein filter (Green H546, filter set 48915) and any nuclei fluorescing bright green were scored as apoptotic. The percentage of apoptotic cells in the field of view was calculated by dividing the number of bright green nuclei counted using the fluorescein filter by the total number of nuclei counted under the UV filter. A minimum of 200 cells were counted per well.

Protein Extraction and Western Blotting

Protein from transfected RKO cells was harvested for Western blot analysis by washing the cells with PBS, adding 40 μl of hot lysis buffer [0.5% SDS, 1 mM dithiothreitol, 50 mM Tris-HCl (pH 8.0)] per well. The cells were scraped and the resulting extract was transferred to an eppendorf, boiled for 5 minutes, and stored at −20° C. The protein was quantitated using the Bio-Rad Protein Assay (Bio-Rad) according to the manufacturer's instructions.

For Western blotting 5 μg of total protein was separated on a 12% SDS-polyacrylamide gel. The separated proteins were transferred to a polyvinylidene difluoride membrane. The membrane was then incubated for one hour in blocking solution (5% skim milk powder in PBS) and washed three times for 15 minutes in 0.05% Tween-20/PBS. The membrane was stored overnight in PBS-T at 4° C. After being warmed to room temperature the next day, the membrane was blocked for 30 seconds in 1 μg/ml polyvinyl alcohol. The membrane was rinsed 5 times in deionized water and then blocked for 30 minutes in a solution of 5% milk in 0.025% Tween-20/PBS. The primary antibody was preincubated for 30 minutes in a solution of 5% milk in 0.025% Tween-20/PBS prior to incubation with the membrane.

Several primary antibodies were used. A monoclonal antibody from Oncogene which recognizes p53 (Ab-6; Oncogene), a monoclonal which recognizes human bcl-2 (Oncogene), and a polyclonal antibody directed against a synthetic peptide (amino-CRLPEGDLGKEIEQKYD-carboxy) (SEQ ID NO: 68) homologous to the c-terminal end of human eIF-5A1 that was raised in chickens (Gallus Immunotech). An anti-β-actin antibody (Oncogene) was also used to dem-onstrate equal loading of protein. The monoclonal antibody to p53 was used at a dilution of 0.05 μg/ml, the antibody against bcl-2 was used at a dilution of 1:3500, the antibody against eIF-5A1 was used at a dilution of 1:1000, and the antibody against actin was used at a dilution of 1:20,000. After incubation with primary antibody for 60 to 90 minutes, the membrane was washed 3 times for 15 minutes in 0.05% Tween-20/PBS. Secondary antibody was then diluted in 1% milk in 0.025% Tween-20/PBS and incubated with the membrane for 60 to 90 minutes. When p53 (Ab-6) was used as the primary antibody, the secondary antibody used was a rabbit anti-mouse IgG conjugated to peroxidase (Sigma) at a dilution of 1:5000. When anti-eIF-5A1 was used as the primary antibody, a rabbit anti-chicken IgY conjugated to peroxidase (Gallus Immunotech) was used at a dilution of 1:5000. The secondary antibody used with actin was a goat anti-mouse IgM conjugated to peroxidase (Calbiochem) used at a dilution of 1:5000. After incubation with the secondary antibody, the membrane was washed 3 times in PBS-T.

The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 30 minutes. The membrane was stripped by submerging the membrane in stripping buffer [100 mM 2-Mercaptoethanol, 2% SDS, and 62.5 mM Tris-HCl (pH 6.7)], and incubating at 50° C. for 30 minutes. The membrane was then rinsed in deionized water and washed twice for 10 minutes in large volumes of 0.05% Tween-20/PBS. Membranes were stripped and re-probed up to three times.

Example 10

Quantification of HepG2 TNF-α Production

HepG2 cells were plated at 20,000 cells per well onto 48-well plates. Seventy two hours later the media was removed and fresh media containing either 2.5 μM control antisense oligonucleotide or 2.5 μM antisense oligonucleotide eIF-5A1 #2 (SEQ ID NO:26) was added to the cells. Fresh media containing antisense oligonucleotides was added after twenty four hours. After a total of 48 hours incubation with the oligonucleotides, the media was replaced with media containing interleukin 1β (IL-1β, 1000 pg/ml; Leinco Technologies) and incubated for 6 hours. The media was collected and frozen (−20° C.) for TNF-α quantification. Additional parallel incubations with untreated cells (without antisense oligonucleotide and IL-1β) and cells treated with only IL-1β were used for controls. All treatments were done in duplicate. TNF-α released into the media was measured by ELISA assays (Assay Designs Inc.) according to the manufacturer's protocol.

Example 11

The following experiments show that antisense apoptosis factor 5A nucleotides were able to inhibit expression of apoptosis factor 5A as well as p53. RKO cells were either left untransfected, mock transfected, or transfected with 200 nM of antisense oligonucleotides eIF-5A1 #1, #2, or #3 (SEQ ID NO: 25, 26, and 27)/RKO cells were also transfected with 100 nM of antisense oligonucleotide eIF-5A1 #2 (SEQ ID NO:26). Forty-eight hours after transfection, the cells were treated with 0.25 μg/ml Actinomycin D. Twenty-four hours later, the cell extract was harvested and 5 μg of protein from each sample was separated on an SDS-PAGE gel, transferred to a PVDF membrane, and Western blotted with an antibody against eIF-5A1. After chemiluminescent detection, the membrane was stripped and reprobed with an antibody against p53. After chemiluminescent detection, the membrane was stripped again and reprobed with an antibody against actin. See FIG. 52 which shows the levels of protein produced by RKO cells after being treated with antisense oligo 1, 2 and 3 (to apoptosis factor 5A) (SEQ ID NO:25,26, and 27, respectively). The RKO cells produced less apoptosis factor 5A as well as less p53 after having been transfected with the antisense apoptosis factor 5A nucleotides.

Example 12

The following experiments show that antisense apoptosis factor 5A nucleotides were able to reduce apoptosis.

In one experiment, the lamina cribrosa cell line #506 was either (A) transfected with 100 nM of FITC-labeled antisense oligonucleotide using Oligofectamine transfection reagent or (B) transfected with 10 μM of naked FITC-labeled antisense oligonucleotide diluted directly in serum-free media. After 24 hours fresh media containing 10% FBS and fresh antisense oligonucleotide diluted to 10 μM was added to the cells. The cells, (A) and (B), were fixed after a total of 48 hours and visualized on a fluorescent microscope under UV light using a fluorescein filter. FIG. 53 shows uptake of the fluorescently labeled antisense oligonucleotide.

In another experiment, the lamina cribrosa cell line #506 was transfected with 10 μM of either the control antisense oligonucleotide or antisense oligonucleotide eIF-5A1 #2 (SEQ ID NO:26) for a total of 4 days. Forty-eight hours after beginning antisense oligonucleotide treatment, the cells were treated with either 20 μM or 40 μM camptothecin for 48 hours. Antisense oligonucleotide and camptothecin-containing media was changed daily. The percentage of apoptotic cells was determined by labeling the cells with Hoescht and TUNEL. See FIG. 54.

In another experiment, the lamina cribrosa cell line #506 was transfected with 10 μM of either the control antisense oligonucleotide or antisense oligonucleotide eIF-5A1 #2 (SEQ ID NO:26). Twenty-four hours later the media was changed and fresh antisense oligonucleotides were added. Forty-eight hours after beginning antisense oligonucleotide treatment, the antisense-oligonucleotides were removed and the cells were treated with 20 μM camptothecin for 3 days. The camptothecin-containing media was changed daily. The percentage of apoptotic cells was determined by labeling the cells with Hoescht and TUNEL. See FIG. 55.

In yet another experiment, the lamina cribrosa cell line #517 was transfected with 1 μM of either the control antisense oligonucleotide or antisense oligonucleotide eIF-5A1 #2 (SEQ ID NO:26) for a total of five days. Forty-eight hours after beginning antisense oligonucleotide treatment, the cells were treated with 20 μM camptothecin for either 3 or 4 days. Antisense oligonucleotide and camptothecin-containing media was changed daily. The percentage of apoptotic cells was determined by labeling the cells with Hoescht and TUNEL. See FIG. 56.

In another experiment, the lamina cribrosa cell line #517 was transfected with 2.5 μM of either the control antisense oligonucleotide or antisense oligonucleotide eIF-5A1 #2 (SEQ ID NO:26) for a total of five days. Forty-eight hours after beginning antisense oligonucleotide treatment, the cells were treated with 40 μM camptothecin for 3 days. Antisense oligonucleotide and camptothecin-containing media was changed daily. The percentage of apoptotic cells was determined by labeling the cells with Hoescht. See FIG. 57.

In another experiment, the lamina cribrosa cell line #517 was transfected with either 1 μM or 2.5 μM of either the control antisense oligonucleotide or antisense oligonucleotide eIF-5A1 #2 (SEQ ID NO:26) for a total of five days. Forty-eight hours after beginning antisense oligonucleotide treatment, the cells were treated with 40 μM camptothecin for 3 days. Antisense oligonucleotide and camptothecin-containing media was changed daily. The percentage of apoptotic cells was determined by labeling the cells with Hoescht. See FIG. 58.

In another experiment, the lamina cribrosa cell line #517 was left either untreated, or was treated with 10 ng/ml TNF-α, 50 μM camptothecin, or 10 ng/ml TNF-α and 50 μM camptothecin. The percentage of apoptotic cells was determined by labeling the cells with Hoescht. See FIG. 59.

In another experiment, the lamina cribrosa cell lines #506 and #517 were transfected with either 2.5 μM or 5 μM of either the control antisense oligonucleotide or antisense oligonucleotide eIF-5A1 #2 (SEQ ID NO:26) for a total of two days. Fresh media containing antisense oligonucleotides was added after 24 hours. Forty-eight hours after beginning antisense oligonucleotide treatment, the cells were treated with 50 μM camptothecin and 10 ng/ml TNF-α for 2 days. The percentage of apoptotic cells was determined by labeling the cells with Hoescht. See FIG. 60.

In another experiment, the lamina cribrosa cell lines #506, #517, and #524 were transfected with 2.5 μM of either the control antisense oligonucleotide or antisense oligonucleotide eIF-5A1 #2 (SEQ ID NO:26) for a total of two days. Fresh media containing antisense oligonucleotides was added after 24 hours. Forty-eight hours after beginning antisense oligonucleotide treatment, the cells were treated with 50 μM camptothecin and 10 ng/ml TNF-α for 2 days. The percentage of apoptotic cells was determined by labeling the cells with Hoescht. See FIG. 61.

Example 13

The following experiments show that cells transfected with siRNAs targeted against apoptosis factor 5A expressed less apoptosis factor 5A. The experiments also show that siRNAs targeted against apoptosis factor 5A were able to reduce apoptosis.

In one experiment, the lamina cribrosa cell line #517 was transfected with 100 nM of FAM-labeled siRNA using Lipofectamine 2000 transfection reagent either with serum (A) or without serum (B) during transfection. The cells, (A) and (B), were fixed after a total of 24 hours and visualized on a fluorescent microscope under UV light using a fluorescein filter. See FIG. 62.

In another experiment, RKO cells were transfected with 100 nM of siRNA either in the presence or absence of serum during the transfection. Six siRNAs were transfected, two control siRNAs (siRNA #5 (SEQ ID NO: 34) and one targeted against GAPDH) and four targeted against eIF-5A1 (siRNA #1 to #4) (SEQ ID NO:30-34). Seventy-two hours after transfection, the cell extract was harvested and 5 μg of protein from each sample was separated on an SDS-PAGE gel, transferred to a PVDF membrane, and Western blotted with an antibody against eIF-5A1. After chemiluminescent detection, the membrane was stripped and re-probed with an antibody against bcl-2. After chemiluminescent detection, the membrane was stripped again and re-probed with an antibody against actin. See FIG. 63.

In another experiment, lamina Cribrosa cell lines #506 and #517 were transfected with 100 nM of siRNA. Six siRNAs were transfected, two control siRNAs (siRNA #5 (SEQ ID NO:34) and one targeted against GAPDH) and four targeted against eIF-5A1 (siRNA #1 to #4) (SEQ ID NO:30-33). Seventy-two hours after transfection, the cell extract was harvested and 5 μg of protein from each sample was separated on an SDS-PAGE gel, transferred to a PVDF membrane, and Western blotted with an antibody against eIF-5A1. After chemiluminescent detection, the membrane was stripped and re-probed with an antibody against actin. See FIG. 64.

In another experiment, the lamina cribrosa cell line #506 was transfected with 100 nm of siRNA. Six siRNAs were transfected, two control siRNAs (siRNA #5 (SEQ ID NO:34) and one targeted against GAPDH) and four targeted against eIF-5A1 (siRNA #1 to #4) (SEQ ID NO:30-33). Forty-eight hours after transfection, the media was replaced with media containing 50 μM camptothecin and 10 ng/ml TNF-α. Twenty-four hours later, the percentage of apoptotic cells was determined by labeling the cells with Hoescht. See FIG. 65.

In another experiment, the lamina cribrosa cell line #506 was transfected with 100 nm of siRNA. Six siRNAs were transfected, two control siRNAs (siRNA #5 (SEQ ID NO:34) and one targeted against GAPDH) and four targeted against eIF-5A1 (siRNA #1 to #4) (SEQ ID NO:30-33). Seventy-two hours after transfection, the media was replaced with media containing 50 μM camptothecin and 10 ng/ml TNF-α. Twenty-four hours later, the percentage of apoptotic cells was determined by labeling the cells with Hoescht. See FIG. 66.

In another experiment, the lamina cribrosa cell line #506 was either left untransfected or was transfected with 100 nm of siRNA. Six siRNAs were transfected, two control siRNAs (siRNA #5 (SEQ ID NO:34) and one targeted against GAPDH) and four targeted against eIF-5A1 (siRNA #1 to #4) (SEQ ID NO:30-33). Seventy-two hours after transfection, the media was replaced with media containing 50 μM camptothecin and 10 ng/ml TNF-α. Fresh media was also added to the untransfected, untreated control cells. Forty-eight hours later, the percentage of apoptotic cells was determined by labeling the cells with Hoescht. See FIG. 67.

Photographs of Hoescht-stained lamina cribrosa cell line #506 transfected with siRNA and treated with camptothecin and TNF-α from the experiment described in FIG. 67 and example 13. See FIG. 68.

Example 14

This example shows that treating a human cell line with antisense oligonucleotides directed against apoptosis factor 5A causes the cells to produce less TNF-α.

HepG2 cells were treated with 2.5 μM of either the control antisense oligonucleotide or antisense oligonucleotide eIF-5A1 #2 for a total of two days. Fresh media containing antisense oligonucleotides was added after 24 hours. Additional cells were left untreated for two days. Forty-eight hours after the beginning of treatment, the cells were treated with IL-1β (1000 pg/ml) in fresh media for 6 hours. At the end of the experiment, the media was collected and frozen (−20° C.) for TNF-α quantification. TNF-α released into the media was measured using ELISA assays purchased from Assay Designs Inc. See FIG. 69.

Example 15

HT-29 cells (human colon adenocarcinoma) were transfected with either an siRNA against eIF-5A1 or with a control siRNA with the reverse sequence. The siRNA used is as follows:

```
Position 690 (3'UTR) % G/C = 48
5' AAGCUGGACUCCUCCUACACA 3'    (SEQ ID NO: 79)
```

The control siRNA used is as follows:

```
% G/C = 39
5' AAACACAUCCUCCUCAGGUCG 3'    (SEQ ID NO: 80)
```

After 48 hours the cells were treated with interferon-gamma (IFN-gamma) for 16 hours. After 16 hours the cells were washed with fresh media and treated with lipopolysaccharide (LPS) for 8 or 24 hours. At each time point (8 or 24 hours) the cell culture media was removed from the cells, frozen, and the TNF-alpha present in the media was quantitated by ELISA. The cell lysate was also harvested, quantitated for protein, and used to adjust the TNF-alpha values to pg/mg protein (to adjust for differences in cell number in different wells). The results of the Western blot and Elisa are provided in FIGS. 74 A and B. FIG. 75 contains the results of the same experiment except the cells were at a higher density.

Example 16

Tissue Culture Conditions of U-937 Cell Line

U-937 is a human monocyte cell line that grows in suspension and will become adherent and differentiate into macrophages upon stimulation with PMA (ATCC Number CRL-1593.2) (cells not obtained directly from ATCC). Cells were maintained in RPMI 1640 media with 2 mM L-glutamine, 1.5 g/L sodium bicarbonate, 4.5 g/L glucose, 10 mM HEPES, 1.0 mM sodium pyruvate and 10% fetal bovine serum in a 37° C. $CO_2$ (5%) incubator. Cells were split into fresh media (1:4 or 1:5 split ratio) twice a week and the cell density was always kept between 105 and 2×106 cells/ml. Cells were cultured in suspension in tissue culture-treated plastic T-25 flasks and experiments were conducted in 24-well plates.

Time Course Experiment

Two days before the start of an experiment, the cell density was adjusted to 3×105 cells/ml media. On the day of the experiment, the cells were harvested in log phase. The cell suspension was transferred to 15 ml tubes and centrifuged at 400×g for 10 mins at room temperature. The supernatant was aspirated and the cell pellet was washed/resuspended with fresh media. The cells were again centrifuged at 400×g for 10 mins, the supernatant was aspirated, and the cell pellet was finally resuspended in fresh media. Equal volumes of cell suspension and trypan blue solution (0.4% trypan blue dye in PBS) were mixed and the live cells were counted using a haemocytometer and a microscope. The cells were diluted to 4×105 cells/ml.

A 24-well plate was prepared by adding either PMA or DMSO (vehicle control) to each well. 1 ml of cell suspension was added to each well so that each well contained 400,000 cells, 0.1% DMSO+/−162 nM PMA. The cells were maintained in a 37° C. $CO_2$ (5%) incubator. Separate wells of cells were harvested at times 0, 24, 48, 72, 96, 99 and 102 h. See FIG. 76 for a summary of the experimental time points and additions.

The media was changed at 72 h. Since some cells were adherent and others were in suspension, care was taken to avoid disrupting the adherent cells. The media from each well was carefully transferred into corresponding microcentrifuge tubes and the tubes were centrifuged at 14,000×g for 3 min. The tubes were aspirated and the cell pellets were resuspended in fresh media (1 ml, (−) DMSO, (−) PMA), and returned to their original wells. The cells become quiescent in this fresh media without PMA. At 96 h, LPS (100 ng/ml) was added and cells were harvested at 3 h (99 h) and 6 h (102 h) later.

At the time points, the suspension cells and media were transferred from each well into microcentrifuge tubes. The cells were pelleted at 14,000×g for 3 min. The media (supernatant) was transferred to clean tubes and stored (−20° C.) for ELISA/cytokine analysis. The cells remaining in the wells were washed with PBS (1 ml, 37° C.) and this PBS was also used to wash the cell pellets in the corresponding microcentrifuge tubes. The cells were pelleted again at 14,000×g for 3 min. The cells were lysed with boiling lysis buffer (50 mM Tris pH 7.4 and 2% SDS). The adherent cells and the suspension cells from each well were pooled. The samples were boiled and then stored at −20° C.

Western Blotting

The protein concentration in each cell sample was determined by the BCA (bicinchoninic acid) method using BSA (bovine serum albumin) as the standard protein. Protein samples (5 µg total protein) were separated by 12% SDS-PAGE electrophoresis and transferred to PVDF membranes. The membranes were blocked with polyvinyl alcohol (1 µg/ml, 30 sec) and with 5% skim milk in PBS-t (1 h). The membranes were probed with a mouse monoclonal antibody raised against human eIF-5A (BD Biosciences cat #611976; 1:20,000 in 5% skim milk, 1 h). The membranes were washed 3×10 mins PBS-t. The secondary antibody was a horseradish peroxidase-conjugated antimouse antibody (Sigma, 1:5000 in 1% skim milk, 1 h). The membranes were washed 3×10 mins PBS-t. The protein bands were visualized by chemiluminescence (ECL detection system, Amersham Pharmacia Biotech).

To demonstrate that similar amounts of protein were loaded on each gel lane, the membranes were stripped and reprobed for actin. Membranes were stripped (100 mM 2-mercaptoethanol, 2% SDS, 62.5 mM Tris-HCl pH 6.7; 50° C. for 30 mins), washed, and then blocked as above. The membranes were probed with actin primary antibody (actin monoclonal antibody made in mouse; Oncogene, Ab-1; 1:20, 000 in 5% skim milk). The secondary antibody, washing, and detection were the same as above.

FIG. 77 shows that eIF-5A is upregulated during monocyte (U-397) differentiation and subsequent TNF-α secretion.

Example 17

Suppression of II-8 Production in Response to Interferon Gamma by eIF-5A siRNA

HT-29 (human colon adenocarcinoma) cells were transfected with siRNA directed to apoptosis eIF-5A. Approximately 48 hours after transfection the media was changed so that some of the test samples had media with interferon gamma and some of the samples had media without interferon gamma. 16 hours after interferon gamma addition, the cells were washed, and the media, with or without TNF-alpha, was placed on the cells. The media (used for ELISA detection of IL-8) and the cell lysate was harvested 8 or 24 hours later.

FIGS. 79 and 80 show that IL-8 is produced in response to TNF-alpha as well as in response to interferon. Priming the cells with interferon gamma prior to TNF treatment causes the cells to produce more IL-8 than either treatment alone. This may be due to the known upregulation of the TNF receptor 1 in response to interferon, so 'priming' the cells with interferon allows them to respond to TNF better since the cells have more receptors. siRNA against eIF-5A had no effect on IL-8 production in response to TNF alone (previous experiment) however, the siRNA blocked almost all IL-8 produced in response to interferon as well as a significant amount of the IL-8 produced as a result of the combined treatment of interferon and TNF. These results show that the by using siRNAs directed against apoptosis eIF-5A, the inventors have blocked the interferon signaling pathway leading to IL-8, but not the TNF pathway. FIG. 81 is a western showing upregulation (4 fold at 8 hours) of apoptosis eIF-5A in response to interferon gamma in HT-29 cells.

Example 18

Human Lamina Cribrosa Culture

Paired human eyes were obtained within 48 hours post mortem from the Eye Bank of Canada, Ontario Division. Optic nerve heads (with attached pole) were removed and placed in Dulbecco's modified Eagle's medium (DMEM) supplemented with antibiotic/antimycotic, glutamine, and 10% FBS for 3 hours. The optic nerve head (ONH) button was retrieved from each tissue sample and minced with fine dissecting scissors into four small pieces. Explants were cultured in 12.5 cm$^2$ plastic culture flasks in DMEM medium. Growth was observed within one month in viable explants. Once the cells reached 90% confluence, they were trypsinized and subjected to differential subculturing to produce lamina cribrosa (LC) and astrocyte cell populations. LC cells were enriched by subculture in 25 cm$^2$ flasks in DMEM supplemented with gentamycin, glutamine, and 10% FBS. Cells were maintained and subcultured as per this protocol.

The identity and population purity of cells populations obtained by differential subculturing was characterized using differential fluorescent antibody staining on 8 well culture slides. Cells were fixed in 10% formalin solution and washed three times with Dulbecco's Phosphate Buffered Saline (DPBS). Following blocking with 2% nonfat milk in DPBS, antibodies were diluted in 1% BSA in DPBS and applied to the cells in 6 of the wells. The remaining two wells were treated with only 1% bovine serum albumin (BSA) solution and only secondary antibody as controls. Cells were incubated with the primary antibodies for one hour at room temperature and then washed three times with DPBS. Appropriate secondary antibodies were diluted in 1% BSA in DPBS, added to each well and incubated for 1 hour. Following washing with DPBS, the slide was washed in water, air-dried, and overlayed with Fluoromount (Vector Laboratories). Immunofluorescent staining was viewed under a fluorescent microscope with appropriate filters and compared to the control wells that were not treated with primary antibody. All primary antibodies were obtained from Sigma unless otherwise stated. All secondary antibodies were purchased from Molecular Probes. Primary antibodies used to identify LC cells were: anti-collagen I, anti-collagen IV, anti-laminin, anti-cellular fibronectin, anti-glial fibrillary acidic protein (GFAP), and anti-alpha-smooth muscle actin. Cell populations were determined to be comprised of LC cells if they stained positively for collagen I, collagen to IV, laminin, cellular fibronectin, alpha smooth muscle actin and negatively for glial fibrillary (GFAP). In this study, two sets of human eyes were used to initiate cultures. LC cell lines #506 and #517 were established from the optic nerve heads of and 83-year old male and a 17-year old male, respectively. All LC cell lines have been fully characterized and found to contain greater than 90% LC cells.

Treatment of LC Cells

Apoptosis was induced in lamina cribrosa cells using a combination of 50 µM camptothecin (Sigma) and 10 ng/ml TNF-α (Leinco Technologies). The combination of camptothecin and TNF-α was found to be more effective at inducing apoptosis than either camptothecin or TNF-α alone.

Construction and Transfection of siRNAs

Small inhibitory RNAs (siRNAs) directed against human eIF-5A were used to specifically suppress expression of eIF-5A in lamina cribrosa cells. Six siRNAs were generated by in vitro transcription using the Silencer™ siRNA Construction Kit (Ambion Inc.). Four siRNAs were generated against human eIF-5A1 (siRNAs #1 to #4). Two siRNAs were used as controls; an siRNA directed against GAPDH provided in the kit, and an siRNA (siRNA #5), which had the reverse sequence of the eIF-5A-specific siRNA #1, but does not itself target eIF-5A. The siRNAs were generated according to the manufacturer's protocol. The eIF-5A and control siRNA targets had the following sequences: siRNA #1 5' AAAGGAATGACTTCCAGCTGA 3' (SEQ ID NO: 81); siRNA #2 5' AAGATCGTCGAGATGTCTACT 3' (SEQ ID NO: 82); siRNA #3 5' AAGGTCCATCTGGTTGGTATT 3' (SEQ ID NO: 83); siRNA #4 5' AAGCTGGACTCCTCCTACACA 3' (SEQ ID NO: 84); siRNA #5' AAAGTCGACCTTCAGTAAGGA 3' (SEQ ID NO: 85). Lamina cribrosa cells were transfected with siRNA using LipofectAMINE 2000. Lamina cribrosa cells were transfected when cell confluence was at 40 to 70% and were generally seeded onto 8-well culture slides at 7500 cells per well three days prior to transfection. Transfection medium sufficient for one well of an 8-well culture slide was prepared by diluting 25.5 pmoles of siRNA to a final volume of 21.2 µl in Opti-Mem (Sigma). 0.425 µl of Lipofectamine 2000 was diluted to a final volume of 21.2 µl in Opti-Mem and incubated for 7 to 10 minutes at room temperature. The diluted Lipofectamine 2000 mixture was then added to the diluted siRNA mixture and incubated together at room temperature for 20 to 30 minutes. The cells were washed once with serum-free media before adding 135 µl of serum-free media to the cells and overlaying 42.4 µl of transfection medium. The cells were placed back in the growth chamber for 4 hours. After the incubation, 65 µl of serum-free media plus 30% FBS was added to the cells. Transfection of siRNA into cells to be used for Western blot analysis were performed in 24-well plates using the same conditions as the transfections in 8-well slides except that the volumes were increased by 2.3 fold. Following transfection, lamina cribrosa cells were incubated for 72 hours prior to treatment with 50 µM of camptothecin (Sigma) and 10 ng/ml of TNF-α (Leinco Technologies) to induce apoptosis. Cell lysates were then harvested for Western blotting or the cells were examined for apoptosis Detection of Apoptotic Cells Transfected cells that had been treated with TNF-α and camptothecin for 24 hours were stained with Hoescht 33258 in order to determine the percentage of cells undergoing apoptosis. Briefly, cells were fixed with a 3:1 mixture of absolute methanol and glacial acetic acid and then incubated with Hoescht stain (0.5 µg/ml Hoescht 33258 in PBS). After a 10 minute incubation in the dark, the staining solution was discarded, the chambers separating the wells of the culture slide were removed, and the slide was washed 3 times for 1 minute with deionized water. After washing, a few drops of McIlvaine's buffer (0.021 M citric acid, 0.058 M $Na_2HPO_4.7H_2O$; pH 5.6) was added to the cells and overlaid with a coverslip. The stained cells were viewed under a fluorescent microscope using a UV filter. Cells with brightly stained or fragmented nuclei were scored as apoptotic. A minimum of 200 cells were counted per well. The DeadEnd™ Fluorometric TUNEL (Promega) was also used to detect the DNA fragmentation that is a characteristic feature of apoptotic cells. Following Hoescht staining, the culture slide was washed briefly with distilled water, and further washed by immersing the slide twice for 5 minutes in PBS (137 mM NaCl, 2.68 mM KCl, 1.47 mM $KH_2PO_4$, 8.1 mM $Na_2HPO_4$), blotting the slide on paper towel between washes. The cells were permeabilized by immersing them in 0.2% Triton X-100 in PBS for 5 minutes. The cells were then washed again by immersing the slide twice for 5 minutes in PBS and blotting the slide on paper towel between washes. 25 µl of equilibration buffer [200 mM potassium cacodylate (pH 6.6), 25 mM Tris-HCl (pH 6.6), 0.2 mM dithiothreitol, 0.25 mg/ml bovine serum albumin, and 2.5 mM cobalt chloride] was added per well and incubated for 5 to 10 minutes. During equilibration, 30 µl of reaction mixture was prepared for each well by mixing in a ratio of 45:5:1, respectively, equilibration buffer, nucleotide mix [50 µM fluorescein-12-dUTP, 100 µM dATP, 10 mM Tris-HCl (pH 7.6), and 1 mM EDTA], and terminal deoxynucleotidyl transferase enzyme (Tdt, 25 U/µl). After the incubation in equilibration buffer, 30 µl of reaction mixture was added per well and overlayed with a coverslip. The reaction was allowed to proceed in the dark at 37° C. for 1 hour. The reaction was terminated by immersing the slide in 2×SSC [0.3 M NaCl, and 30 mM sodium citrate (pH 7.0)] and incubating for 15 minutes. The slide was then washed by immersion in PBS three times for 5 minutes. The PBS was removed by sponging around the wells with a Kim wipe, a drop of mounting media (Oncogene research project, JA1750-4ML) was added to each well, and the slide was overlayed with a coverslip. The cells were viewed under a fluorescent microscope using a UV filter (UV-G 365, filter set 487902) in order to count the Hoescht-stained nuclei. Any cells with brightly stained or fragmented nuclei were scored as apoptotic. Using the same field of view, the cells were then viewed using a fluorescein filter (Green H546, filter set 48915) and any nuclei fluorescing bright green were scored as apoptotic. The percentage of apoptotic cells in the field of view was calculated by dividing the number of bright green nuclei counted using the fluorescein filter by the total number of nuclei counted under the UV filter. A minimum of 200 cells were counted per well.

Protein Extraction and Western Blot Analysis

Protein was isolated for Western blotting from lamina cribrosa cells growing on 24-well plates by washing the cells twice in PBS (8 g/L NaCl, 0.2 g/L KCl, 1.44 g/L $Na_2HPO_4$, and 0.24 g/L $KH_2PO_4$) and then adding 50 µl of lysis buffer [2% SDS, 50 mM Tris-HCl (pH 7.4)]. The cell lysate was collected in a microcentrifuge tube, boiled for 5 minutes and stored at −20° C. until ready for use. Protein concentrations were determined using the Bicinchoninic Acid Kit (BCA; Sigma). For Western blotting, 5 µg of total protein was separated on a 12% SDS-polyacrylamide gel. The separated proteins were transferred to a polyvinylidene difluoride membrane. The membrane was then incubated for one hour in blocking solution (5% skim milk powder, 0.02% sodium azide in PBS) and washed three times for 15 minutes in PBS-T (PBS+0.05% Tween-20). The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in PBS. The primary antibody was preincubated for 30 minutes in a solution of 5% milk in PBS prior to incubation with the membrane. The primary antibodies used were anti-eIF-5A (BD Transduction Laboratories) at 1:20,000 and anti-β-actin (Oncogene). The membranes were washed three times in PBS-T and incubated for 1 hour with the appropriate HRP-conjugated secondary antibodies diluted in 1% milk in PBS. The blot was washed and the ECL Plus Western blotting detection kit (Amersham Pharmacia Biotech) was used to detect the peroxidase-conjugated bound antibodies.

Results

Two lamina cribrosa (LC) cell lines were established from optic nerve heads obtained from male donors ranging in age from 83 years (#506) to 17 years (#517). The cells isolated from the human lamina cribrosa had the same broad, flat morphology with prominent nucleus observed in other studies (Lambert et al., 2001). Consistent with the characterizations of other groups, the LC cells showed immunoreactivity to alpha smooth muscle actin (FIG. 82a) as well as to a number of extracellular matrix proteins including cellular fibronectin (FIG. 82b), laminin (FIG. 82c), collagen I, and collagen IV (data not shown) (Clark et al., 1995; Hernandez et al., 1998; Hernandez and Yang, 2000; Lambert et al.; 2001). Negative immunoreactivity of the LC cells to glial fibrillary acidic protein (GFAP) was also observed consistent with previous findings (FIG. 82d) (Lambert et al., 2001). These findings support the identification of the isolated cells as being LC cells rather than optic nerve head astrocytes.

Since TNF-α is believed to play an important role during the glaucomatous process, the susceptibility of LC cells to the cytotoxic effects of TNF-α was examined. Confluent LC cells were exposed to either camptothecin, TNF-α, or a combination of camptothecin and TNF-α for 48 hours (FIG. 83). Hoescht staining revealed that TNF-α alone was not cytotoxic to LC cells. Treatment with camptothecin resulted in approximately 30% cell death of the LC cells. However, a synergistic increase in apoptosis was observed when LC cells were treated with both camptothecin and TNF-α, a treatment which resulted in the death of 45% of LC cells by 48 hours. These results indicate that LC cells are capable of responding to the cytotoxic effects of TNF-α when primed for apoptosis by camptothecin.

Figure 84A:
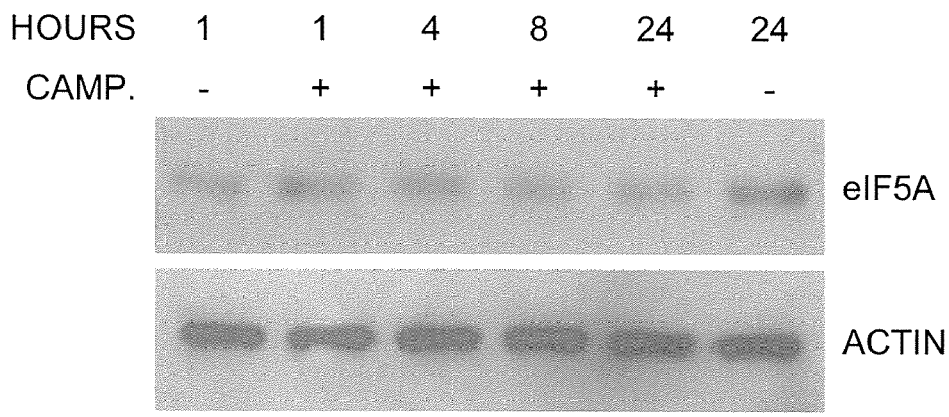
Figure 84B:
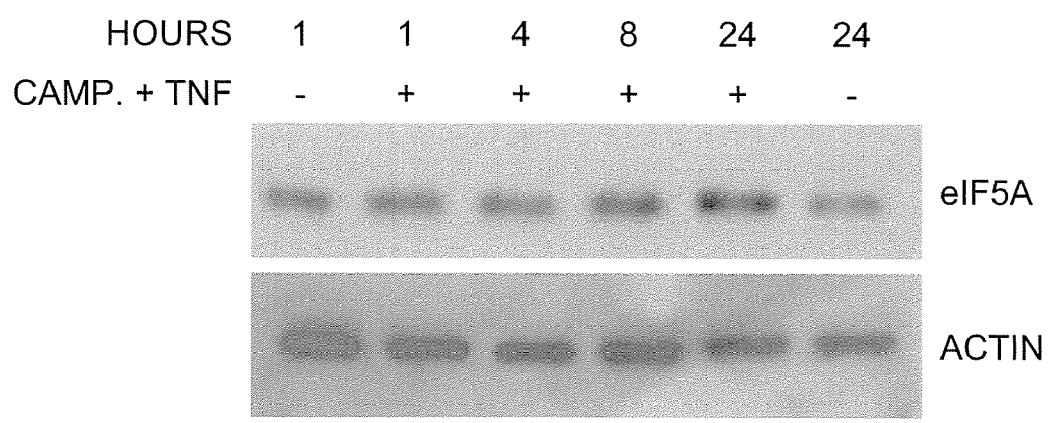

EIF-5A is a nucleocytoplasmic shuttle protein known to be necessary for cell division and recently suggested to also be involved during apoptosis. We examined the expression of eIF-5A protein in LC cells being induced to undergo apoptosis by either camptothecin, or camptothecin plus TNF-α. The expression of eIF-5A was not altered significantly upon treatment with camptothecin except perhaps to decrease slightly (FIG. 84A). However, a significant upregulation of eIF-5A protein was observed after 8 and 24 hours of camptothecin plus TNF-α treatment (FIG. 84B). These results indicate that eIF-5A expression is induced specifically by exposure to TNF-α and expression correlates to the induction of apoptosis. This points to a role for eIF-5A in the apoptotic pathway downstream of TNF-α receptor binding.

In order to examine the importance of eIF-5A expression during TNF-α-induced apoptosis in LC cells, a series of four siRNAs (siRNAs #1 to #4) targeting eIF-5A were designed and synthesized by in vitro transcription. To determine the effectiveness of the siRNAs in suppressing eIF-5A protein expression, LC cell lines #506 and #517 were transfected with each of the siRNAs and expression of eIF-5A protein in the cell lysate was examined 72 hours later (FIG. 85). For comparison, cells were also transfected with either an siRNA against GAPDH and/or a control siRNA (siRNA #5) having the same chemical composition as siRNA #1 but which does not recognize eIF-5A. All siRNAs directed against eIF-5A were capable of significantly suppressing eIF-5A expression in both LC cell lines (FIG. 85). The GAPDH siRNA was used as an additional control because, unlike the control siRNA #5 which simply has the reverse sequence of siRNA #1 and does not have a cellular target, it is an active siRNA capable of suppressing the expression of its target protein, GAPDH (data not shown). All four siRNAs against eIF-5A were also capable of protecting transfected LC cells (#506) from apoptosis induced by 24 hour treatment with TNF-α and camptothecin (FIG. 86). Using Hoescht staining to detect cell death, the siRNAs (siRNAs #1 to #4) were found to be able to reduce apoptosis of LC cells by 59% (siRNA #1), 35% (siRNA #2), 50% (siRNA #3), and 69% (siRNA #4). Interestingly, the siRNA against GAPDH was also able to reduce apoptosis of LC cells by 42% (FIG. 86). GAPDH is known to have cellular functions outside of its role as a glycolytic enzyme, including a proposed function during apoptosis of cerebellar neurons (Ishitani and Chuang, 1996; Ishitani et al., 1996a; Ishitani et al., 1996b). In a similar experiment we also demonstrated that siRNA #1 was able to reduce apoptosis of the LC line #517 by 53% in response to TNF-α and camptothecin indicating that eIF-5A siRNAs are protective for LC cells isolated from different optic nerve heads (FIG. 87). These results indicate that eIF-5A does have a function during apoptosis and may be an important intermediate in the pathway leading to TNF-α-induced apoptosis in LC cells.

In order to confirm that LC cells exposed to TNF-α and camptothecin were dying by classical apoptosis, DNA fragmentation was evaluated in situ using the terminal deoxynucleotidyl transferase-mediated dUTP-digoxigenin nick end labeling (TUNEL) method. LC cells (#506) were treated with TNF-α and camptothecin for 24 hours, 3 days after transfection with either an eIF-5A siRNA (siRNA #1) or a control siRNA (siRNA #5). The cells were also stained with Hoescht to facilitate visualization of the nuclei. 46% of LC cells transfected with the control siRNA were positive for TUNEL staining while only 8% of LC cells transfected with eIF-5A siRNA #1 were positively labeled indicating that the eIF-5A siRNA provided greater than 80% protection from apoptosis (FIG. 88). Similar results were obtained with eIF-5A siRNA #4 which provided greater than 60% protection from apoptosis relative to the control siRNA (data not shown).

The invention claimed is:

1. An siRNA for suppressing expression of apoptosis-specific eIF-5A1 wherein the siRNA targets SEQ ID NO:53 and wherein the siRNA is double-stranded for 19-25 nucleotides in length.

2. The siRNA of claim 1, wherein the siRNA has at least one single-stranded overhang region, with each single-stranded region comprising six or fewer nucleotides.

3. The siRNA of claim 2, wherein the siRNA has two single-stranded overhang regions.

4. The siRNA of claim 3, wherein each of the two single-stranded overhang regions comprise two nucleotides or less.

5. The siRNA of claim 4, wherein the double-stranded region on the siRNA is 19-21 nucleotides in length.

6. The siRNA of claim 5, wherein the double-stranded region on the siRNA is 21 nucleotides in length.

7. The siRNA of claim 6, wherein one strand of the siRNA has the nucleotide sequence of SEQ ID NO:54.

8. The siRNA of claim 6, wherein one strand of the siRNA has the nucleotide sequence of SEQ ID NO:55.

9. The siRNA of claim 5, wherein the double-stranded region on the siRNA is 19 nucleotides in length.

10. The siRNA of claim 9, wherein one strand of the siRNA has the nucleotide sequence of 5'-GCUGGACUCCUCCUACACA-3' (SEQ ID NO:86).

11. The siRNA of claim 9, wherein one strand of the siRNA has the nucleotide sequence of 5'-UGUGUAGGAGGAGUCCAGC-3' (SEQ ID NO:87).

* * * * *

SEQUENCE LISTING

```
<160> NUMBER OF SEQ ID NOS: 87

<210> SEQ ID NO 1
<211> LENGTH: 1139
<212> TYPE: DNA
<213> ORGANISM: Rattus rattus
<220> FEATURE:
<221> NAME/KEY: CDS
<222> LOCATION: (33)..(494)
```

<400> SEQUENCE: 1

```
caggtctaga gttggaatcg aagcctctta aa atg gca gat gat ttg gac ttc      53
                                    Met Ala Asp Asp Leu Asp Phe
                                     1               5 gag aca gga gat gca ggg gcc tca gcc acc ttc cca atg cag tgc tca     101
Glu Thr Gly Asp Ala Gly Ala Ser Ala Thr Phe Pro Met Gln Cys Ser
        10                  15                  20 gca tta cgt aag aat ggt ttt gtg gtc ctc aag ggc cgg cca tgt aag     149
Ala Leu Arg Lys Asn Gly Phe Val Val Leu Lys Gly Arg Pro Cys Lys
 25                  30                  35 atc gtc gag atg tct act tcg aag act ggc aag cat ggc cat gcc aag     197
Ile Val Glu Met Ser Thr Ser Lys Thr Gly Lys His Gly His Ala Lys
 40                  45                  50                  55 gtc cat ctg gtt ggt att gat att ttt act ggg aag aaa tat gaa gat     245
Val His Leu Val Gly Ile Asp Ile Phe Thr Gly Lys Lys Tyr Glu Asp
                 60                  65                  70 atc tgc ccg tcg act cat aac atg gat gtc ccc aac atc aaa agg aat     293
Ile Cys Pro Ser Thr His Asn Met Asp Val Pro Asn Ile Lys Arg Asn
                 75                  80                  85 gat ttc cag ctg att ggc atc cag gat ggg tac cta tcc ctg ctc cag     341
Asp Phe Gln Leu Ile Gly Ile Gln Asp Gly Tyr Leu Ser Leu Leu Gln
                 90                  95                 100 gac agt ggg gag gta cga gag gac ctt cgt ctg cct gag gga gac ctt     389
Asp Ser Gly Glu Val Arg Glu Asp Leu Arg Leu Pro Glu Gly Asp Leu
        105                 110                 115 ggc aag gag att gag cag aag tat gac tgt gga gaa gag atc ctg atc     437
Gly Lys Glu Ile Glu Gln Lys Tyr Asp Cys Gly Glu Glu Ile Leu Ile
120                 125                 130                 135 aca gtg ctg tcc gcc atg aca gag gag gca gct gtt gca atc aag gcc     485
Thr Val Leu Ser Ala Met Thr Glu Glu Ala Ala Val Ala Ile Lys Ala
                140                 145                 150 atg gca aaa taactggctt ccagggtggc ggtggtggca gcagtgatcc             534
Met Ala Lys atgagcctac agaggcccct ccccagctc tggctgggcc cttggctgga ctcctatcca    594
atttatttga cgttttattt tggttttcct caccccttca aactgtcggg agaccctgc    654
ccttcaccta gctcccttgg ccaggcatga gggagccatg gccttggtga agctacctgc   714
ctcttctctc gcagccctga tgggggaaag ggagtgggta ctgcctgtgg tttaggttcc   774
cctctccctt tttctttta attcaatttg gaatcagaaa gctgtggatt ctggcaaatg    834
gtcttgtgtc ctttatccca ctcaaaccca tctggtcccc tgttctccat agtccttcac   894
ccccaagcac cactgacaga ctggggacca gccccttcc ctgcctgtgt ctcttcccaa    954
accccctat aggggtgaca agaagaggag ggggggaggg gacacgatcc ctcctcaggc   1014
atctgggaag gccttgcccc catgggcttt acccttcct gtgggctttc tccctgacac   1074
atttgttaaa aatcaaacct gaataaaact acaagtttaa tatgaaaaaa aaaaaaaaa   1134
aaaaa                                                              1139
```

<210> SEQ ID NO 2
<211> LENGTH: 154
<212> TYPE: PRT
<213> ORGANISM: Rattus rattus

<400> SEQUENCE: 2

```
Met Ala Asp Asp Leu Asp Phe Glu Thr Gly Asp Ala Gly Ala Ser Ala
 1               5                  10                  15

Thr Phe Pro Met Gln Cys Ser Ala Leu Arg Lys Asn Gly Phe Val Val
             20                  25                  30
```

```
Leu Lys Gly Arg Pro Cys Lys Ile Val Glu Met Ser Thr Ser Lys Thr
         35                  40                  45
Gly Lys His Gly His Ala Lys Val His Leu Val Gly Ile Asp Ile Phe
     50                  55                  60
Thr Gly Lys Lys Tyr Glu Asp Ile Cys Pro Ser Thr His Asn Met Asp
 65                  70                  75                  80
Val Pro Asn Ile Lys Arg Asn Asp Phe Gln Leu Ile Gly Ile Gln Asp
                 85                  90                  95
Gly Tyr Leu Ser Leu Leu Gln Asp Ser Gly Glu Val Arg Glu Asp Leu
             100                 105                 110
Arg Leu Pro Glu Gly Asp Leu Gly Lys Glu Ile Glu Gln Lys Tyr Asp
         115                 120                 125
Cys Gly Glu Glu Ile Leu Ile Thr Val Leu Ser Ala Met Thr Glu Glu
     130                 135                 140
Ala Ala Val Ala Ile Lys Ala Met Ala Lys
145                 150
```

<210> SEQ ID NO 3
<211> LENGTH: 462
<212> TYPE: DNA
<213> ORGANISM: Homo sapiens

<400> SEQUENCE: 3

```
atggcagatg acttggactt cgagacagga gatgcagggg cctcagccac cttcccaatg     60
cagtgctcag cattacgtaa gaatggcttt gtggtgctca aaggccggcc atgtaagatc    120
gtcgagatgt ctacttcgaa gactggcaag cacggccacg ccaaggtcca tctggttggt    180
attgacatct ttactgggaa gaaatatgaa gatatctgcc cgtcaactca taatatggat    240
gtccccaaca tcaaaaggaa tgacttccag ctgattggca tccaggatgg gtacctatca    300
ctgctccagg acagcgggga ggtacgagag gaccttcgtc tccctgaggg agaccttggc    360
aaggagattg agcagaagta cgactgtgga gaagagatcc tgatcacggt gctgtctgcc    420
atgacagagg aggcagctgt tgcaatcaag gccatggcaa aa                       462
```

<210> SEQ ID NO 4
<211> LENGTH: 460
<212> TYPE: DNA
<213> ORGANISM: Homo sapiens

<400> SEQUENCE: 4

```
atggcagacg aaattgattt cactactgga gatgccgggg cttccagcac ttaccctatg     60
cagtgctcgg ccttgcgcaa aaacggcttc gtggtgctca aggacgacc atgcaaaata    120
gtggagatgt caacttccaa aactggaaag catggtcatg ccaaggttca ccttgttgga    180
attgatattt tcacgggcaa aaaatatgaa gatatttgtc cttctactca aacatggat    240
gttccaaata ttaagagaaa tgattatcaa ctgatatgca ttcaagatgg ttacctttcc    300
ctgctgacag aaactggtga agttcgtgag gatcttaaac tgccagaagg tgaactaggc    360
aaagaaatag gggaaaata caatgcaggt gaagatgtac aggtgtctgt catgtgtgca    420
atgagtgaag aatatgctgt agccataaaa ccctgcaaat                          460
```

<210> SEQ ID NO 5
<211> LENGTH: 462
<212> TYPE: DNA
<213> ORGANISM: Mus musculus

<400> SEQUENCE: 5

```
atggcagatg atttggactt cgagacagga gatgcagggg cctcagccac cttcccaatg      60
cagtgctcag cattacgtaa gaatggtttt gtggtgctca aaggccggcc atgtaagatc     120
gtcgagatgt ctacttcgaa gactggcaag catggccatg ccaaggtcca tctggttggc     180
attgacattt ttactgggaa gaaatatgaa gatatctgcc cgtcgactca taatatggat     240
gtccccaaca tcaaacggaa tgacttccag ctgattggca tccaggatgg gtacctatcc     300
ctgctccagg acagtgggga ggtacgagag gaccttcgtc tgcctgaagg agaccttggc     360
aaggagattg agcagaagta tgactgtgga gaagagatcc tgatcacagt gctgtctgcc     420
atgacagagg aggcagctgt tgcaatcaag gccatggcaa aa                        462
```

<210> SEQ ID NO 6
<211> LENGTH: 606
<212> TYPE: DNA
<213> ORGANISM: Rattus rattus
<220> FEATURE:
<221> NAME/KEY: CDS
<222> LOCATION: (1)..(453)

<400> SEQUENCE: 6

```
gct gtg tat tat tgg gcc cat aag aac cac ata cct gtg ctg agt cct       48
Ala Val Tyr Tyr Trp Ala His Lys Asn His Ile Pro Val Leu Ser Pro
 1               5                  10                  15 gca ctc aca gac ggc tca ctg ggt gac atg atc ttt ttc cat tcc tat       96
Ala Leu Thr Asp Gly Ser Leu Gly Asp Met Ile Phe Phe His Ser Tyr
             20                  25                  30 aaa aac cca ggc ttg gtc ctg gac atc gtt gaa gac ctg cgg ctc atc      144
Lys Asn Pro Gly Leu Val Leu Asp Ile Val Glu Asp Leu Arg Leu Ile
         35                  40                  45 aac atg cag gcc att ttc gcc aag cgc act ggg atg atc atc ctg ggt      192
Asn Met Gln Ala Ile Phe Ala Lys Arg Thr Gly Met Ile Ile Leu Gly
     50                  55                  60 gga ggc gtg gtc aag cac cac atc gcc aat gct aac ctc atg cgg aat      240
Gly Gly Val Val Lys His His Ile Ala Asn Ala Asn Leu Met Arg Asn
 65                  70                  75                  80 gga gct gac tac gct gtt tat atc aac aca gcc cag gag ttt gat ggc      288
Gly Ala Asp Tyr Ala Val Tyr Ile Asn Thr Ala Gln Glu Phe Asp Gly
                 85                  90                  95 tca gac tca gga gcc cgg cca gat gag gct gtc tcc tgg ggc aag atc      336
Ser Asp Ser Gly Ala Arg Pro Asp Glu Ala Val Ser Trp Gly Lys Ile
            100                 105                 110 cgg atg gat gca cag cca gta aag gtc tat gct gat gca tct ctg gtt      384
Arg Met Asp Ala Gln Pro Val Lys Val Tyr Ala Asp Ala Ser Leu Val
        115                 120                 125 ttc ccc ttg ctg gtg gct gag aca ttc gcc caa aag gca gat gcc ttc      432
Phe Pro Leu Leu Val Ala Glu Thr Phe Ala Gln Lys Ala Asp Ala Phe
    130                 135                 140 aga gct gag aag aat gag gac tgagcagatg ggtaaagacg gaggcttctg         483
Arg Ala Glu Lys Asn Glu Asp
145                 150 ccacaccttt atttattatt tgcataccaa cccctcctgg gccctctcct tggtcagcag     543
catcttgaga ataaatggcc tttttgttgg tttctgtaaa aaaggactt taaaaaaaaa      603
aaa                                                                   606
```

<210> SEQ ID NO 7
<211> LENGTH: 151
<212> TYPE: PRT
<213> ORGANISM: Rattus rattus

<400> SEQUENCE: 7

| Ala | Val | Tyr | Tyr | Trp | Ala | His | Lys | Asn | His | Ile | Pro | Val | Leu | Ser | Pro |
|---|---|---|---|---|---|---|---|---|---|---|---|---|---|---|---|
| 1 | | | | 5 | | | | | 10 | | | | | 15 | |

| Ala | Leu | Thr | Asp | Gly | Ser | Leu | Gly | Asp | Met | Ile | Phe | Phe | His | Ser | Tyr |
|---|---|---|---|---|---|---|---|---|---|---|---|---|---|---|---|
| | | | 20 | | | | | 25 | | | | | 30 | | |

| Lys | Asn | Pro | Gly | Leu | Val | Leu | Asp | Ile | Val | Glu | Asp | Leu | Arg | Leu | Ile |
|---|---|---|---|---|---|---|---|---|---|---|---|---|---|---|---|
| | | 35 | | | | | 40 | | | | | 45 | | | |

| Asn | Met | Gln | Ala | Ile | Phe | Ala | Lys | Arg | Thr | Gly | Met | Ile | Ile | Leu | Gly |
|---|---|---|---|---|---|---|---|---|---|---|---|---|---|---|---|
| | 50 | | | | | 55 | | | | | 60 | | | | |

| Gly | Gly | Val | Val | Lys | His | His | Ile | Ala | Asn | Ala | Asn | Leu | Met | Arg | Asn |
|---|---|---|---|---|---|---|---|---|---|---|---|---|---|---|---|
| 65 | | | | | 70 | | | | | 75 | | | | | 80 |

| Gly | Ala | Asp | Tyr | Ala | Val | Tyr | Ile | Asn | Thr | Ala | Gln | Glu | Phe | Asp | Gly |
|---|---|---|---|---|---|---|---|---|---|---|---|---|---|---|---|
| | | | | 85 | | | | | 90 | | | | | 95 | |

| Ser | Asp | Ser | Gly | Ala | Arg | Pro | Asp | Glu | Ala | Val | Ser | Trp | Gly | Lys | Ile |
|---|---|---|---|---|---|---|---|---|---|---|---|---|---|---|---|
| | | | 100 | | | | | 105 | | | | | 110 | | |

| Arg | Met | Asp | Ala | Gln | Pro | Val | Lys | Val | Tyr | Ala | Asp | Ala | Ser | Leu | Val |
|---|---|---|---|---|---|---|---|---|---|---|---|---|---|---|---|
| | | 115 | | | | | 120 | | | | | 125 | | | |

| Phe | Pro | Leu | Leu | Val | Ala | Glu | Thr | Phe | Ala | Gln | Lys | Ala | Asp | Ala | Phe |
|---|---|---|---|---|---|---|---|---|---|---|---|---|---|---|---|
| | 130 | | | | | 135 | | | | | 140 | | | | |

| Arg | Ala | Glu | Lys | Asn | Glu | Asp |
|---|---|---|---|---|---|---|
| 145 | | | | 150 | | |

<210> SEQ ID NO 8
<211> LENGTH: 453
<212> TYPE: DNA
<213> ORGANISM: Homo sapiens

<400> SEQUENCE: 8

```
tccgtgtatt actgggccca agaaccac atccctgtgt ttagtccgc acttacagac      60
ggctcgctgg gcgacatgat cttcttccat tcctacaaga acccgggcct ggtcctggac    120
atcgttgagg acctgaggct catcaacaca caggccatct tgccaagtg cactgggatg    180
atcattctgg gcgggggcgt ggtcaagcac acattgcca atgccaacct catgcggaac    240
ggggccgact acgctgttta catcaacaca gcccaggagt tgatggctc tgactcaggt    300
gcccgaccag acgaggctgt ctcctggggc aagatccggg tggatgcaca gcccgtcaag    360
gtctatgctg acgcctccct ggtcttcccc ctgcttgtgg ctgaaacctt tgcccagaag    420
atggatgcct tcatgcatga aagaacgag gac                                  453
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (12)
<223> OTHER INFORMATION: any nucleotide

<400> SEQUENCE: 9

```
tcsaarachg gnaagcaygg                                                 20
```

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gcgaagcttc catggctcga gttttttttt tttttttttt tt                      42

<210> SEQ ID NO 11
<211> LENGTH: 972
<212> TYPE: DNA
<213> ORGANISM: Rattus sp.
<220> FEATURE:
<221> NAME/KEY: CDS
<222> LOCATION: (1)..(327)

<400> SEQUENCE: 11

```
tcg aag acc ggt aag cac ggc cat gcc aag gtc cat ctg gtt ggt att      48
Ser Lys Thr Gly Lys His Gly His Ala Lys Val His Leu Val Gly Ile
  1               5                  10                  15 gat att ttt act ggg aag aaa tat gaa gat atc tgc ccg tcg act cat      96
Asp Ile Phe Thr Gly Lys Lys Tyr Glu Asp Ile Cys Pro Ser Thr His
             20                  25                  30 aac atg gat gtc ccc aac atc aaa agg aat gat ttc cag ctg att ggc    144
Asn Met Asp Val Pro Asn Ile Lys Arg Asn Asp Phe Gln Leu Ile Gly
         35                  40                  45 atc cag gat ggg tac cta tcc ctg ctc cag gac agt ggg gag gta cga    192
Ile Gln Asp Gly Tyr Leu Ser Leu Leu Gln Asp Ser Gly Glu Val Arg
     50                  55                  60 gag gac ctt cgt ctg cct gag gga gac ctt ggc aag gag att gag cag    240
Glu Asp Leu Arg Leu Pro Glu Gly Asp Leu Gly Lys Glu Ile Glu Gln
 65                  70                  75                  80 aag tat gac tgt gga gaa gag atc ctg atc aca gtg ctg tcc gcc atg    288
Lys Tyr Asp Cys Gly Glu Glu Ile Leu Ile Thr Val Leu Ser Ala Met
                 85                  90                  95 aca gag gag gca gct gtt gca atc aag gcc atg gca aaa taactggctt     337
Thr Glu Glu Ala Ala Val Ala Ile Lys Ala Met Ala Lys
            100                 105
```
ccagggtggc ggtggtggca gcagtgatcc atgagcctac agaggcccct cccccagctc    397
tggctgggcc cttggctgga ctcctatcca atttatttga cgttttattt tggttttcct    457
caccccttca aactgtcggg gagaccctgc ccttcaccta gctcccttgg ccaggcatga    517
gggagccatg gccttggtga agctacctgc ctcttctctc gcagccctga tgggggaaag    577
ggagtgggta ctgcctgtgg tttaggttcc cctctcccct tttcttttta attcaatttg    637
gaatcagaaa gctgtggatt ctggcaaatg gtcttgtgtc ctttatccca ctcaaaccca    697
tctggtcccc tgttctccat agtccttcac ccccaagcac cactgacaga ctggggacca    757 gccccttcc ctgcctgtgt ctcttcccaa acccctctat aggggtgaca agaagaggag    817
ggggggaggg gacacgatcc ctcctcaggc atctgggaag gccttgcccc catgggcttt    877
accctttcct gtgggctttc tccctgacac atttgttaaa aatcaaacct gaataaaact    937
acaagtttaa tatgaaaaaa aaaaaaaaaa aaaaa                              972

<210> SEQ ID NO 12
<211> LENGTH: 109
<212> TYPE: PRT
<213> ORGANISM: Rattus sp.

-continued

```
<400> SEQUENCE: 12

Ser Lys Thr Gly Lys His Gly His Ala Lys Val His Leu Val Gly Ile
 1               5                  10                  15

Asp Ile Phe Thr Gly Lys Lys Tyr Glu Asp Ile Cys Pro Ser Thr His
            20                  25                  30

Asn Met Asp Val Pro Asn Ile Lys Arg Asn Asp Phe Gln Leu Ile Gly
        35                  40                  45

Ile Gln Asp Gly Tyr Leu Ser Leu Leu Gln Asp Ser Gly Glu Val Arg
    50                  55                  60

Glu Asp Leu Arg Leu Pro Glu Gly Asp Leu Gly Lys Glu Ile Glu Gln
65                  70                  75                  80

Lys Tyr Asp Cys Gly Glu Glu Ile Leu Ile Thr Val Leu Ser Ala Met
                85                  90                  95

Thr Glu Glu Ala Ala Val Ala Ile Lys Ala Met Ala Lys
            100                 105

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
caggtctaga gttggaatcg aagc                                              24

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
atatctcgag ccttgattgc aacagctgcc                                        30

<210> SEQ ID NO 15
<211> LENGTH: 489
<212> TYPE: DNA
<213> ORGANISM: Rattus rattus
<220> FEATURE:
<221> NAME/KEY: CDS
<222> LOCATION: (33)..(485)

<400> SEQUENCE: 15
caggtctaga gttggaatcg aagcctctta aa atg gca gat gat ttg gac ttc        53
                                    Met Ala Asp Asp Leu Asp Phe
                                     1               5 gag aca gga gat gca ggg gcc tca gcc acc ttc cca atg cag tgc tca       101
Glu Thr Gly Asp Ala Gly Ala Ser Ala Thr Phe Pro Met Gln Cys Ser
         10                  15                  20 gca tta cgt aag aat ggt ttt gtg gtg ctc aag ggc cgg cca tgt aag       149
Ala Leu Arg Lys Asn Gly Phe Val Val Leu Lys Gly Arg Pro Cys Lys
     25                  30                  35 atc gtc gag atg tct act tcg aag act ggc aag cat ggc cat gcc aag       197
Ile Val Glu Met Ser Thr Ser Lys Thr Gly Lys His Gly His Ala Lys
 40                  45                  50                  55 gtc cat ctg gtt ggt att gat att ttt act ggg aag aaa tat gaa gat       245
Val His Leu Val Gly Ile Asp Ile Phe Thr Gly Lys Lys Tyr Glu Asp
                 60                  65                  70
```

```
atc tgc ccg tcg act cat aac atg gat gtc ccc aac atc aaa agg aat      293
Ile Cys Pro Ser Thr His Asn Met Asp Val Pro Asn Ile Lys Arg Asn
            75                  80                  85 gat ttc cag ctg att ggc atc cag gat ggg tac cta tcc ctg ctc cag      341
Asp Phe Gln Leu Ile Gly Ile Gln Asp Gly Tyr Leu Ser Leu Leu Gln
        90                  95                 100 gac agt ggg gag gta cga gag gac ctt cgt ctg cct gag gga gac ctt      389
Asp Ser Gly Glu Val Arg Glu Asp Leu Arg Leu Pro Glu Gly Asp Leu
    105                 110                 115 ggc aag gag att gag cag aag tat gac tgt gga gaa gag atc ctg atc      437
Gly Lys Glu Ile Glu Gln Lys Tyr Asp Cys Gly Glu Glu Ile Leu Ile
120                 125                 130                 135 aca gtg ctg tcc gcc atg aca gag gag gca gct gtt gca atc aag gct      485
Thr Val Leu Ser Ala Met Thr Glu Glu Ala Ala Val Ala Ile Lys Ala
            140                 145                 150 cgag                                                                 489

<210> SEQ ID NO 16
<211> LENGTH: 151
<212> TYPE: PRT
<213> ORGANISM: Rattus rattus

<400> SEQUENCE: 16

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala
145                 150

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gtctgtgtat tattgggccc                                                 20

<210> SEQ ID NO 18
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 18
gcgaagcttc catggctcga gtttttttttt tttttttttt tt                         42

<210> SEQ ID NO 19
<211> LENGTH: 1299
<212> TYPE: DNA
<213> ORGANISM: Homo sapiens

<400> SEQUENCE: 19
ggcacgaggg cggcggcggc ggtagaggcg gcggcggcgg cggcagcggg ctcggaggca       60
gcggttgggc tcgcggcgag cggacggggt cgagtcagtg cgttcgcgcg agttggaatc      120
gaagcctctt aaaatggcag atgacttgga cttcgagaca ggagatgcag gggcctcagc      180
caccttccca atgcagtgct cagcattacg taagaatggc tttgtggtgc tcaaaggccg      240
gccatgtaag atcgtcgaga tgtctacttc gaagactggc aagcacggcc acgccaaggt      300
ccatctggtt ggtattgaca tctttactgg gaagaaatat gaagatatct gcccgtcaac      360
tcataatatg gatgtcccca acatcaaaag gaatgacttc agctgattg catccagga       420 tgggtaccta tcactgctcc aggacagcgg ggaggtacga gaggaccttc gtctccctga      480
gggagacctt ggcaaggaga ttgagcagaa gtacgactgt ggagaagaga tcctgatcac      540
ggtgctgtct gccatgacag aggaggcagc tgttgcaatc aaggccatgg caaaataact      600
ggctcccagg atggcggtgg tggcagcagt gatcctctga acctgcagag gccccctccc      660
cgagcctggc ctggctctgg cccggtccta agctggactc ctcctacaca atttatttga      720
cgttttattt tggttttccc caccccctca atctgtcggg gagcccctgc ccttaccta      780 gctcccttgg ccaggagcga gcgaagctgt ggccttggtg aagctgccct cctcttctcc      840
cctcacacta cagccctggt gggggagaag ggggtgggtg ctgcttgtgg tttagtcttt      900
tttttttttt tttttttttt tttaaattca atctggaatc agaaagcggt ggattctggc      960
aaatggtcct tgtgccctcc ccactcatcc ctggtctggt ccctgttgc ccatagccct      1020 ttaccctgag caccacccca acagactggg gaccagcccc ctcgcctgcc tgtgtctctc     1080
cccaaacccc tttagatggg gagggaagag gaggagaggg gaggggacct gccccctcct     1140
caggcatctg ggagggccct gcccccatgg gctttaccct tccctgcggg ctctctcccc     1200
gacacatttg ttaaaatcaa acctgaataa aactacaagt ttaatatgaa aaaaaaaaa      1260 aaaaaaaaa aaaaaaaaaa aaaaaaaaaa aaaaaaaa                              1299

<210> SEQ ID NO 20
<211> LENGTH: 462
<212> TYPE: DNA
<213> ORGANISM: Rattus rattus

<400> SEQUENCE: 20
atggcagatg atttggactt cgagacagga gatgcagggg cctcagccac cttcccaatg       60
cagtgctcag cattacgtaa gaatggtttt gtggtgctca agggccggcc atgtaagatc      120
gtcgagatgt ctacttcgaa gactggcaag catggccatg ccaaggtcca tctggttggt      180
attgatattt ttactgggaa gaaatatgaa gatatctgcc cgtcgactca taacatggat      240
gtccccaaca tcaaaggaa tgatttccag ctgattggca tccaggatgg gtacctatcc       300
ctgctccagg acagtgggga ggtacgagag gaccttcgtc tgcctgaggg agaccttggc      360
```

```
aaggagattg agcagaagta tgactgtgga gaagagatcc tgatcacagt gctgtccgcc      420
atgacagagg aggcagctgt tgcaatcaag gccatggcaa aa                         462
```

<210> SEQ ID NO 21
<211> LENGTH: 154
<212> TYPE: PRT
<213> ORGANISM: Homo sapiens

<400> SEQUENCE: 21

```
Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150
```

<210> SEQ ID NO 22
<211> LENGTH: 153
<212> TYPE: PRT
<213> ORGANISM: Homo sapiens

<400> SEQUENCE: 22

```
Met Ala Asp Glu Ile Asp Phe Thr Thr Gly Asp Ala Gly Ala Ser Ser
1               5                   10                  15

Thr Tyr Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Tyr Gln Leu Ile Cys Ile Gln Asp
                85                  90                  95

Gly Tyr Leu Ser Leu Leu Thr Glu Thr Gly Glu Val Arg Glu Asp Leu
            100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
    130                 135                 140

Tyr Ala Val Ala Ile Lys Pro Cys Lys
145                 150
```

```
<210> SEQ ID NO 23
<211> LENGTH: 154
<212> TYPE: PRT
<213> ORGANISM: Mus musculus

<400> SEQUENCE: 23

Met Ala Asp Asp Leu Asp Phe Glu Thr Gly Asp Ala Gly Ala Ser Ala
 1               5                   10                  15

Thr Phe Pro Met Gln Cys Ser Ala Leu Arg Lys Asn Gly Phe Val Val
                20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
 65                 70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
130                 135                 140

Ala Ala Val Ala Ile Lys Ala Met Ala Lys
145                 150

<210> SEQ ID NO 24
<211> LENGTH: 153
<212> TYPE: PRT
<213> ORGANISM: Homo sapiens

<400> SEQUENCE: 24

Met Ala Asp Glu Ile Asp Phe Thr Thr Gly Asp Ala Gly Ala Ser Ser
 1               5                   10                  15

Thr Tyr Pro Met Gln Cys Ser Ala Leu Arg Lys Asn Gly Phe Val Val
                20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
 65                 70                  75                  80

Val Pro Asn Ile Lys Arg Asn Asp Tyr Gln Leu Ile Cys Ile Gln Asp
                85                  90                  95

Gly Cys Leu Ser Leu Leu Thr Glu Thr Gly Glu Val Arg Glu Asp Leu
            100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
130                 135                 140

Tyr Ala Val Ala Ile Lys Pro Cys Lys
145                 150

<210> SEQ ID NO 25
<211> LENGTH: 20
<212> TYPE: DNA
<213> ORGANISM: Homo sapiens
```

```
<400> SEQUENCE: 25
gacttggact tcgagacagg                                            20

<210> SEQ ID NO 26
<211> LENGTH: 19
<212> TYPE: DNA
<213> ORGANISM: Homo sapiens

<400> SEQUENCE: 26
gcacggccac gccaaggtc                                             19

<210> SEQ ID NO 27
<211> LENGTH: 20
<212> TYPE: DNA
<213> ORGANISM: Homo sapiens

<400> SEQUENCE: 27
ggacagcggg gaggtacgag                                            20

<210> SEQ ID NO 28
<211> LENGTH: 153
<212> TYPE: PRT
<213> ORGANISM: Artificial Sequence
<220> FEATURE:
<223> OTHER INFORMATION: Description of Artificial Sequence: Synthetic
      Consensus Sequence

<400> SEQUENCE: 28
```

Met Ala Asp Glu Ile Asp Phe Thr Thr Gly Asp Ala Gly Ala Ser Ser
 1               5                  10                  15

Thr Tyr Pro Met Gln Cys Ser Ala Leu Arg Lys Asn Gly Phe Val Val
                20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
 65                 70                  75                  80

Val Pro Asn Ile Lys Arg Asn Asp Tyr Gln Leu Ile Cys Ile Gln Asp
                85                  90                  95

Gly Cys Leu Ser Leu Leu Thr Glu Thr Gly Glu Val Arg Glu Asp Leu
            100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
    130                 135                 140

Tyr Ala Val Ala Ile Lys Pro Cys Lys
145                 150

```
<210> SEQ ID NO 29
<211> LENGTH: 1309
<212> TYPE: DNA
<213> ORGANISM: Homo sapiens

<400> SEQUENCE: 29
ggcacgaggg tagaggcggc ggcggcggcg gcagcgggct cggaggcagc ggttgggctc    60
gcggcgagcg gacggggtcg agtcagtgcg ttcgcgcgag ttggaatcga agcctcttaa   120
aatggcagat gacttggact tcgagacagg agatgcaggg gcctcagcca ccttcccaat   180
```

```
gcagtgctca gcattacgta agaatggctt tgtggtgctc aaaggccggc catgtaagat      240
cgtcgagatg tctacttcga agactggcaa gcacggccac gccaaggtcc atctggttgg      300
tattgacatc tttactggga agaaatatga agatatctgc ccgtcaactc ataatatgga      360
tgtccccaac atcaaaagga atgacttcca gctgattggc atccaggatg ggtacctatc      420
actgctccag gacagcgggg aggtacgaga ggaccttcgt ctccctgagg gagaccttgg      480
caaggagatt gagcagaagt acgactgtgg agaagagatc ctgatcacgg tgctgtctgc      540
catgacagag gaggcagctg ttgcaatcaa ggccatggca aaataactgg ctcccaggat      600
ggcggtggtg gcagcagtga tcctctgaac ctgcagaggc cccctccccg agcctggcct      660
ggctctggcc cggtcctaag ctggactcct cctacacaat ttatttgacg ttttatttt g      720 gttttcccca cccctcaat ctgtcgggga gccctgccc ttcacctagc tcccttggcc      780
aggagcgagc gaagctgtgg ccttggtgaa gctgccctcc tcttctcccc tcacactaca      840
gccctggtgg gggagaaggg ggtgggtgct gcttgtggtt tagtcttttt tttttttttt      900
tttttttttt aaattcaatc tggaatcaga aagcggtgga ttctggcaaa tggtccttgt      960
gccctcccca ctcatccctg gtctggtccc ctgttgccca tagcccttta ccctgagcac      1020
caccccaaca gactggggac cagccccctc gcctgcctgt gtctctcccc aaacccctt     1080 agatggggag ggaagaggag gagaggggag gggacctgcc ccctcctcag gcatctggga      1140
gggccctgcc cccatgggct ttacccttcc ctgcgggctc tctccccgac acatttgtta      1200
aaatcaaacc tgaataaaac tacaagttta atatgaaaaa aaaaaaaaaa aaaaaaaaa     1260 aaaaaaaaaa aaaaaaaaaa aaaaaaaaaa aaaaaaaaa aaaaaaaa                  1309

<210> SEQ ID NO 30
<211> LENGTH: 23
<212> TYPE: DNA
<213> ORGANISM: Homo sapiens

<400> SEQUENCE: 30
aaaggaatga cttccagctg att                                             23

<210> SEQ ID NO 31
<211> LENGTH: 23
<212> TYPE: DNA
<213> ORGANISM: Homo sapiens

<400> SEQUENCE: 31
aagatcgtcg agatgtctac ttc                                             23

<210> SEQ ID NO 32
<211> LENGTH: 23
<212> TYPE: DNA
<213> ORGANISM: Homo sapiens

<400> SEQUENCE: 32
aaggtccatc tggttggtat tga                                             23

<210> SEQ ID NO 33
<211> LENGTH: 23
<212> TYPE: DNA
<213> ORGANISM: Homo sapiens

<400> SEQUENCE: 33
aagctggact cctcctacac aat                                             23
```

<210> SEQ ID NO 34
<211> LENGTH: 23
<212> TYPE: DNA
<213> ORGANISM: Homo sapiens

<400> SEQUENCE: 34
aaagtcgacc ttcagtaagg att                                             23

<210> SEQ ID NO 35
<211> LENGTH: 20
<212> TYPE: DNA
<213> ORGANISM: Homo sapiens

<400> SEQUENCE: 35
gacttggact tcgagacagg                                                 20

<210> SEQ ID NO 36
<211> LENGTH: 20
<212> TYPE: DNA
<213> ORGANISM: Homo sapiens

<400> SEQUENCE: 36
gcacggccac gccaaggtcc                                                 20

<210> SEQ ID NO 37
<211> LENGTH: 19
<212> TYPE: DNA
<213> ORGANISM: Homo sapiens

<400> SEQUENCE: 37
ggacagcggg gaggtacga                                                  19

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 465
<212> TYPE: DNA
<213> ORGANISM: Homo sapiens

<400> SEQUENCE: 41
atggcagatg acttggactt cgagacagga gatgcagggg cctcagccac cttcccaatg      60
cagtgctcag cattacgtaa gaatggcttt gtggtgctca aaggccggcc atgtaagatc     120
gtcgagatgt ctacttcgaa gactggcaag cacggccacg ccaaggtcca tctggttggt    180
attgacatct ttactgggaa gaaatatgaa gatatctgcc cgtcaactca taatatggat    240
gtccccaaca tcaaaaggaa tgacttccag ctgattggca tccaggatgg gtacctatca    300
ctgctccagg acagcgggga ggtacgagag gaccttcgtc tccctgaggg agaccttggc    360

```
aaggagattg agcagaagta cgactgtgga gaagagatcc tgatcacggt gctgtctgcc    420
atgacagagg aggcagctgt tgcaatcaag gccatggcaa ataa                     465
```

<210> SEQ ID NO 42
<211> LENGTH: 462
<212> TYPE: DNA
<213> ORGANISM: Homo sapiens
<400> SEQUENCE: 42

```
atggcagacg aaattgattt cactactgga gatgccgggg cttccagcac ttaccctatg     60
cagtgctcgg ccttgcgcaa aaacggcttc gtggtgctca aggacgacc atgcaaaata    120 gtggagatgt caacttccaa aactggaaag catggtcatg ccaaggttca ccttgttgga   180
attgatattt tcacgggcaa aaaatatgaa gatatttgtc cttctactca caacatggat   240
gttccaaata ttaagagaaa tgattatcaa ctgatatgca ttcaagatgg ttacctttcc   300
ctgctgacag aaactggtga agttcgtgag gatcttaaac tgccagaagg tgaactaggc   360
aaagaaatag agggaaaata caatgcaggt gaagatgtac aggtgtctgt catgtgtgca   420
atgagtgaag aatatgctgt agccataaaa ccctgcaaat aa                      462
```

<210> SEQ ID NO 43
<211> LENGTH: 154
<212> TYPE: PRT
<213> ORGANISM: Homo sapiens
<400> SEQUENCE: 43

```
Met Ala Asp Asp Leu Asp Phe Glu Thr Gly Asp Ala Gly Ala Ser Ala
  1               5                  10                  15

Thr Phe Pro Met Gln Cys Ser Ala Leu Arg Lys Asn Gly Phe Val Val
             20                  25                  30

Leu Lys Gly Trp Pro Cys Lys Ile Val Glu Met Ser Ala Ser Lys Thr
         35                  40                  45

Gly Lys His Gly His Ala Lys Val His Leu Val Gly Ile Asp Ile Phe
     50                  55                  60

Thr Gly Lys Lys Tyr Glu Asp Ile Cys Pro Ser Thr His Asn Met Asp
 65                  70                  75                  80

Val Pro Asn Ile Lys Arg Asn Asp Phe Gln Leu Ile Gly Ile Gln Asp
                 85                  90                  95

Gly Tyr Leu Ser Leu Leu Gln Asp Ser Gly Glu Val Pro Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Leu Leu Ser Ala Met Thr Glu Glu
    130                 135                 140

Ala Ala Val Ala Ile Lys Ala Met Ala Lys
145                 150
```

<210> SEQ ID NO 44
<211> LENGTH: 21
<212> TYPE: DNA
<213> ORGANISM: Homo sapiens
<400> SEQUENCE: 44

```
aaaggaatga cttccagctg a                                               21
```

```
<210> SEQ ID NO 45
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 45
aaaggaauga cuuccagcug att                                              23

<210> SEQ ID NO 46
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 46
ucagcuggaa gucauuccuu utt                                              23

<210> SEQ ID NO 47
<211> LENGTH: 21
<212> TYPE: DNA
<213> ORGANISM: Homo sapiens

<400> SEQUENCE: 47
aagatcgtcg agatgtctac t                                                21

<210> SEQ ID NO 48
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 48
aagaucgucg agaugucuac utt                                              23

<210> SEQ ID NO 49
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 49
aguagacauc ucgacgaucu utt                                              23

<210> SEQ ID NO 50
<211> LENGTH: 21
<212> TYPE: DNA
<213> ORGANISM: Homo sapiens
```

```
<400> SEQUENCE: 50
aaggtccatc tggttggtat t                                              21

<210> SEQ ID NO 51
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 51
aagguccauc ugguugguau utt                                            23

<210> SEQ ID NO 52
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 52
aauaccaacc agauggaccu utt                                            23

<210> SEQ ID NO 53
<211> LENGTH: 21
<212> TYPE: DNA
<213> ORGANISM: Homo sapiens

<400> SEQUENCE: 53
aagctggact cctcctacac a                                              21

<210> SEQ ID NO 54
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 54
aagcuggacu ccuccuacac att                                            23

<210> SEQ ID NO 55
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 55
uguguaggag gaguccagcu utt                                            23
```

```
<210> SEQ ID NO 56
<211> LENGTH: 21
<212> TYPE: DNA
<213> ORGANISM: Homo sapiens

<400> SEQUENCE: 56
aaagtcgacc ttcagtaagg a                                              21

<210> SEQ ID NO 57
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 57
aaagucgacc uucaguaagg att                                            23

<210> SEQ ID NO 58
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic Oligonucleotide
<220> FEATURE:
<223> OTHER INFORMATION: Description of Artificial Sequence: Synthetic
      Oligonucleotide

<400> SEQUENCE: 58
uccuuacuga aggucgacuu utt                                            23

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 59
gccaagctta atggcagatg atttgg                                         26

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 60
ctgaattcca gttattttgc catgg                                          25

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 61
aatgaattcc gccatgacag aggaggc                                        27
```

```
<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 62
gcgaagcttc catggctcga gttttttttt tttttttttt tt                          42

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 63
cctgtctcga agtccaagtc                                                   20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 64
ggaccttggc gtggccgtgc                                                   20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 65
ctcgtacctc cccgctctcc                                                   20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 66
cgtaccggta cggttccagg                                                   20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 67
ggaccttggc gtggccgtgc                                                   20
```

```
<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      Oligonucleotide

<400> SEQUENCE: 68

Cys Arg Leu Pro Glu Gly Asp Leu Gly Lys Glu Ile Glu Gln Lys Tyr
 1               5                  10                  15
Asp

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 69
aaaggaatga cttccagctg acctgtctc                                      29

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 70
aatcagctgg aagtcattcc tcctgtctc                                      29

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 71
aagatcgtcg agatgtctac tcctgtctc                                      29

<210> SEQ ID NO 72
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 72
aaagtagaca tctcgacgat ccctgtctc                                      29

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 73
aaggtccatc tggttggtat tcctgtctc                                      29
```

```
<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 74
aaaataccaa ccagatggac ccctgtctc                                    29

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 75
aagctggact cctcctacac acctgtctc                                    29

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 76
aatgtgtagg aggagtccag ccctgtctc                                    29

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 77
aaagtcgacc ttcagtaagg acctgtctc                                    29

<210> SEQ ID NO 78
<211> LENGTH: 29
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 78
aatccttact gaaggtcgac tcctgtctc                                    29

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 79
aagcuggacu ccuccuacac a                                            21
```

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 80
aaacacaucc uccucagguc g    21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 81
aaaggaatga cttccagctg a    21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 82
aagatcgtcg agatgtctac t    21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 83
aaggtccatc tggttggtat t    21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 84
aagctggact cctcctacac a    21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic Oligonucleotide

<400> SEQUENCE: 85
aaagtcgacc ttcagtaagg a    21

```
<210> SEQ ID NO 86
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 86
gcuggacucc uccuacaca                                               19

<210> SEQ ID NO 87
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 87
uguguaggag gaguccagc                                               19
```